United States Patent
Xu et al.

(10) Patent No.: US 11,104,648 B2
(45) Date of Patent: Aug. 31, 2021

(54) PYRAZOLE DERIVATIVE

(71) Applicants: Zhejiang Research Institute of Chemical Industry Co., Ltd., Zhejiang (CN); Sinochem Lantian Co., Ltd., Zhejiang (CN)

(72) Inventors: Tianming Xu, Zhejiang (CN); Jiahua Xing, Zhejiang (CN); Liangkun Zhong, Zhejiang (CN); Dongsong Hu, Zhejiang (CN); Youchang Wei, Zhejiang (CN); Hongying Huang, Zhejiang (CN); Jiping Yu, Zhejiang (CN); Weili Peng, Zhejiang (CN)

(73) Assignees: ZHEJIANG RESEARCH INSTITUTE OF CHEMICAL INDUSTRY CO., LTD., Zhejiang (CN); SINOCHEM LANTIAN CO., LTD., Hangzhou (CN)

( * ) Notice: Subject to any disclaimer, the term of this patent is extended or adjusted under 35 U.S.C. 154(b) by 0 days.

(21) Appl. No.: 16/620,814

(22) PCT Filed: May 22, 2018

(86) PCT No.: PCT/CN2018/087840
§ 371 (c)(1),
(2) Date: Dec. 9, 2019

(87) PCT Pub. No.: WO2019/222912
PCT Pub. Date: Nov. 28, 2019

(65) Prior Publication Data
US 2020/0339515 A1    Oct. 29, 2020

(51) Int. Cl.
*C07D 231/12* (2006.01)
*C07D 231/16* (2006.01)
*A01N 43/56* (2006.01)

(52) U.S. Cl.
CPC .......... *C07D 231/16* (2013.01); *A01N 43/56* (2013.01); *C07D 231/12* (2013.01)

(58) Field of Classification Search
CPC ..... C07D 231/12; C07D 231/16; A01N 43/56
See application file for complete search history.

(56) References Cited

FOREIGN PATENT DOCUMENTS

| WO | WO-01/68580 A1 | 9/2001 | |
| WO | WO 2001/68589 A1 * | 9/2001 | ........... C07C 255/37 |

OTHER PUBLICATIONS

A machine generated English translation of WO 2001/68589 A1 (Sep. 20, 2001), Yagihara et al. (Year: 2001).*

* cited by examiner

*Primary Examiner* — Laura L Stockton
(74) *Attorney, Agent, or Firm* — Muncy, Geissler, Olds and Lowe, P.C.

(57) ABSTRACT

A pyrazole derivative having the following formula stru-1:

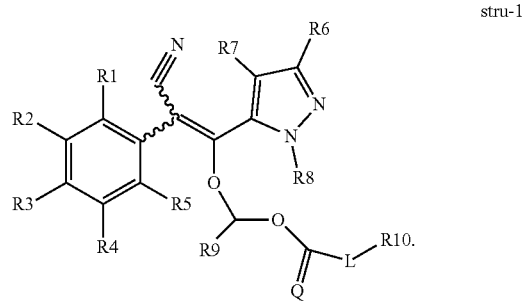

The pyrazole derivative is used for prevention and control of pests.

11 Claims, 1 Drawing Sheet

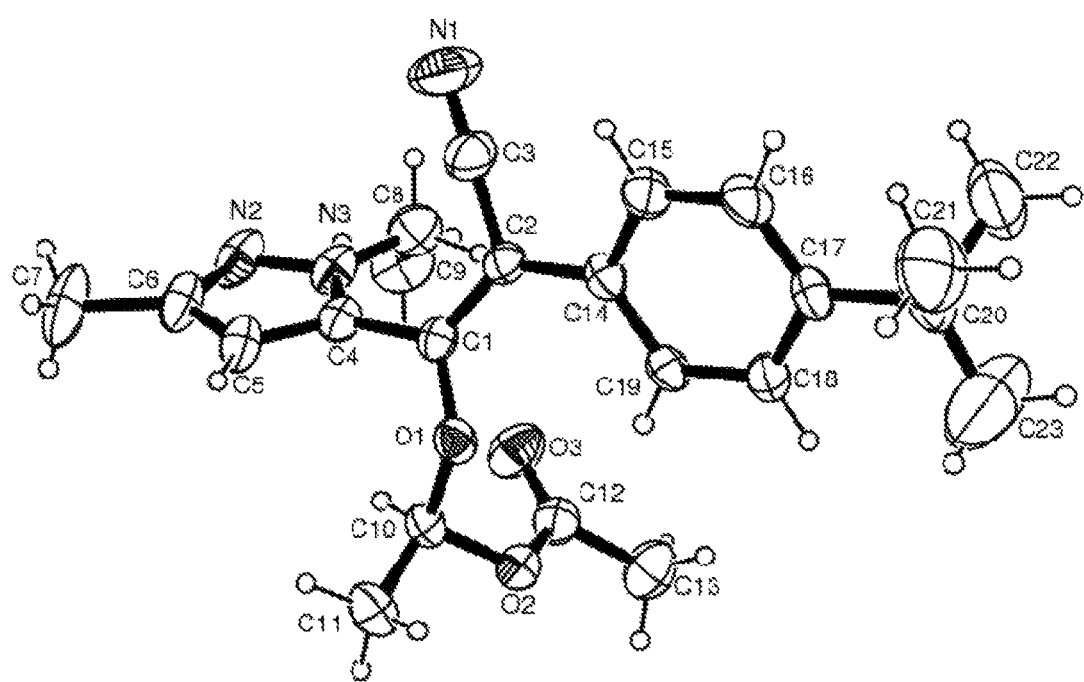

PYRAZOLE DERIVATIVE

FIELD OF THE INVENTION

The present invention relates to the field of agricultural insecticides and acaricides, and in particular to a pyrazole derivative.

BACKGROUND OF THE INVENTION

Presently, due to long-term use of pesticides, pests and insects produce resistance, resulting in a significant increase in the use of pesticides and serious damage to the environment. Therefore, it is required to continuously discover high-efficiency new pesticides with new mechanism of action, for example, new pesticides with higher activity against insects and pests, bacteria or acarids. Among the existing acaricide pesticides, most of pesticides can only control one of the three stages of eggs, nymphs and adult mites. It will be of significance if we can research and develop acaricides that have control effects on three stages of acarids.

The PCT Patent Application WO 01/68589 discloses heterocyclic acrylonitrile ether compounds, and the following compounds 8-1, 8-2, 8-3 and 8-4 are disclosed on page 71 in the Description.

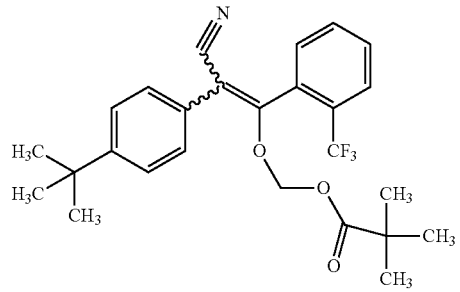

8-1

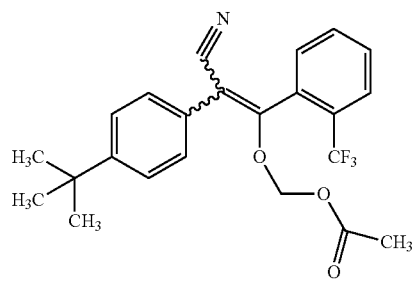

8-2

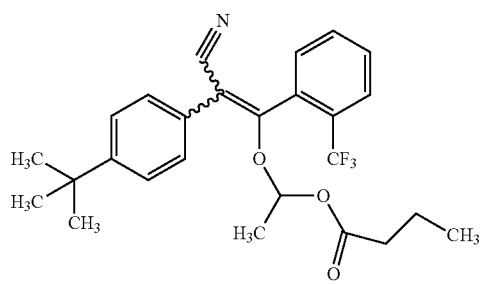

8-3

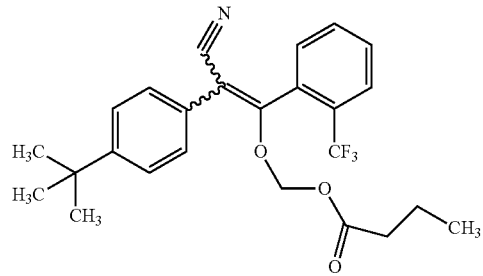

8-4

The pyrazole derivatives described herein are not disclosed in the prior art.

SUMMARY OF THE INVENTION

The present invention provides a pyrazole derivative having the following formula stru-1:

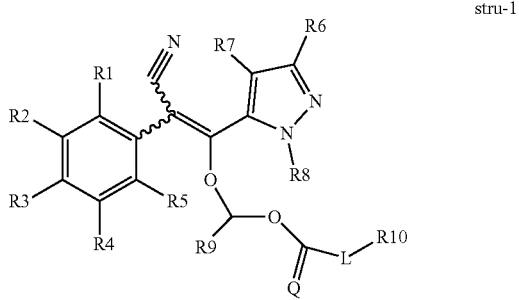

stru-1 wherein:

R1, R2, R3, R4, R5 are independently selected from hydrogen, halogen, nitro, nitrile, $C_1$-$C_{20}$ alkyl, $C_1$-$C_{20}$ haloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_{20}$ alkylsulfoxide, $C_1$-$C_{20}$ alkylsulfone, $C_1$-$C_{20}$ alkylsulfonate, $C_1$-$C_{20}$ alkyl carboxylic ester, $C_1$-$C_{20}$ alkyl acyl, $C_1$-$C_{20}$ haloalkyl acyl;

R6 is selected from hydrogen, halogen, nitro, nitrile, $C_1$-$C_{20}$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, phenyl substituted by at least one of hydrogen, halogen, nitro, cyano, $C_1$-$C_2$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one of hydrogen, halogen, nitro, cyano, $C_1$-$C_{20}$ alkyl, $C_1$-$C_{20}$ haloalkyl, $C_3$-$C_{20}$ cycloalkyl. $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone;

R7 is selected from hydrogen, halogen, nitro, nitrile, $C_1$-$C_{20}$ alkyl, $C_1$-$C_{20}$ haloalkyl, $C_1$-$C_2$ alkoxymethylene;

R8 is selected from hydrogen $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxymethylene, phenyl substituted by at least one of hydrogen, halogen, nitro, cyano, $C_1$-$C_{20}$ alkyl, $C_1$-$C_2$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one hydrogen, halogen, nitro, cyano $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_2$ haloalkoxy, $C_1$-$C_{20}$ alkylthio, $C_1$-$C_{20}$ haloalkylthio and $C_1$-$C_{20}$ alkylsulfone;

R9 is selected from hydrogen, halogen, nitro $C_1$-$C_{20}$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_{20}$ alkylsulfone, phenyl substituted by at least one of hydrogen, halogen, nitro, cyano, $C_1$-$C_2$ alkyl, $C_1$-$C_2$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone;

L is selected from oxygen, sulfur, methylene, nitrogen;

Q is selected from oxygen, sulfur;

R10 is selected from hydrogen, halogen, nitro, $C_1$-$C_{20}$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_{20}$ alkyl carboxylic ester, phenyl substituted by at least one of hydrogen, halogen, nitro, cyano, $C_1$-$C_2$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio and $C_1$-$C_{20}$ haloalkylthio, pyridyl, pyrazolyl, thienyl, furyl or thiazolyl substituted by at least one of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio and $C_1$-$C_{20}$ haloalkylthio.

In the pyrazole derivatives represented by the formula stru-1 provided in the present invention, substituents R1, R2, R3, R4, R5 are independently selected from hydrogen, halogen, nitro, nitrile, $C_1$-$C_{20}$ alkyl, $C_1$-$C_{20}$ haloalkyl, $C_2$-$C_{20}$ alkenyl, $C_2$-$C_2$a haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_2$ alkylsulfoxide, $C_1$-$C_{20}$ alkylsulfone, $C_1$-$C_2$ alkylsulfonate, $C_1$-$C_{20}$ alkyl carboxylic ester, $C_1$-$C_{20}$ alkyl acyl, $C_1$-$C_{20}$ haloalkyl acyl.

Preferably, the substituents R1, R2, R3, R4, R5 are independently selected from hydrogen, halogen, nitro, nitrile $C_1$-$C_{10}$ alkyl, $C_1$-$C_{10}$ haloalkyl, $C_2$-$C_{10}$ alkenyl, $C_2$-$C_{10}$ haloalkenyl, $C_2$-$C_{20}$ alkynyl, $C_2$-$C_{10}$ haloalkynyl, $C_1$-$C_{10}$ alkoxy, $C_1$-$C_{10}$ haloalkoxy, $C_1$-$C_{10}$ alkylthio, $C_1$-$C_{10}$ haloalkylthio, $C_1$-$C_{10}$ alkylsulfoxide, $C_1$-$C_{10}$ alkylsulfone, $C_1$-$C_{10}$ alkylsulfonate, $C_1$-$C_{10}$ alkyl carboxylic ester, $C_1$-$C_{10}$ alkyl acyl, $C_1$-$C_{10}$ haloalkyl acyl.

Further preferably, the substituents R1, R2, R3, R4, R5 are independently selected from hydrogen, halogen, nitro, nitrile, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfoxide, $C_1$-$C_6$ alkylsulfone, $C_1$-$C_6$ alkylsulfonate, $C_1$-$C_6$ alkyl carboxylic ester, $C_1$-$C_6$ alkyl acyl, $C_1$-$C_6$ haloalkyl acyl.

Still further preferably, the substituents R, R2, R3, R4, R5 are independently selected from hydrogen, fluorine, chlorine, bromine, nitro, nitrile, methyl, ethyl, isopropyl, tert-butyl, trifluoromethyl, methoxy, ethoxy, trifluoromethoxy, difluoromethoxy, difluoroethoxy, methylthio, trifluoromethylthio, trifluoroethylthio, methylsulfonyl, methylsulfonate.

In the pyrazole derivatives represented by the formula stru-1 provided in the present invention, the substituent R6 is selected from hydrogen, halogen, nitro, nitrile, $C_1$-$C_{20}$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_2$ haloalkylthio, phenyl substituted by at least one of hydrogen, halogen, nitro, cyano, $C_1$-$C_2$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one of hydrogen, halogen, nitro, cyano $C_1$-$C_2$ alkyl, $C_1$-$C_2$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone.

Preferably, the substituent R6 is selected from hydrogen, halogen, nitro, nitrile, $C_1$-$C_{10}$ alkyl, $C_1$-$C_{10}$ haloalkyl, $C_3$-$C_{10}$ cycloalkyl, $C_3$-$C_{10}$ halocycloalkyl, $C_2$-$C_{10}$ alkenyl, $C_2$-$C_{10}$ haloalkenyl, $C_2$-$C_{10}$ alkynyl, $C_2$-$C_{10}$ haloalkynyl, $C_1$-$C_{10}$ alkoxy, $C_1$-$C_{10}$ haloalkoxy, $C_1$-$C_{10}$ alkylthio, $C_1$-$C_{10}$ haloalkylthio, phenyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone, pyridyl, pyrazolyl, thienyl, furyl or thiazolyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone. The compound may be in the form of E, Z or a mixture of E and Z;

Further preferably, the substituent R6 is selected from hydrogen, halogen, nitro, nitrile, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, phenyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone, pyridyl, pyrazolyl, thienyl, furyl or thiazolyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone.

Still further preferably, the substituent R6 is selected from hydrogen, fluorine, chlorine, bromine, nitro, nitrile, methyl, ethyl, isopropyl, cyclopropyl, methoxy, ethoxy, trifluoromethyl, difluoromethyl, p-chlorophenyl, P-fluorophenyl.

In the pyrazole derivatives represented by the formula stru-1 provided in the present invention, substituent R7 is selected from hydrogen, halogen, nitro, nitrile, $C_1$-$C_{20}$ alkyl, $C_1$-$C_{20}$ haloalkyl, $C_1$-$C_{20}$ alkoxymethylene.

Preferably, the substituent R7 is selected from hydrogen, halogen, nitro, nitrile, $C_1$-$C_{10}$ alkyl, $C_1$-$C_{10}$ haloalkyl, $C_1$-$C_{10}$ alkoxymethylene.

Further preferably, the substituent R7 is selected from hydrogen, halogen, nitro, nitrile, $C_1$-$C_6$ alkyl, $C_1$-$C_6$ haloalkyl, $C_1$-$C_6$ alkoxymethylene.

Still further preferably, the substituent R7 is selected from hydrogen, halogen, nitro, nitrile, $C_1$-$C_5$ alkyl, $C_1$-$C_5$ haloalkyl, $C_1$-$C_5$ alkoxymethylene.

In the pyrazole derivatives represented by the formula stru-1 provided in the present invention, substituent R8 is selected from hydrogen, $C_1$-$C_2$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxymethylene, phenyl substituted by at least one of hydrogen, halogen, nitro, cyano, $C_1$-$C_{20}$ alkyl, $C_1$-$C_2$ haloalkyl, $C_3$-$C_2$ cycloalkyl, $C_3$-$C_{20}$ halocycloalkyl, $C_1$-$C_{20}$ alkoxy, $C_1$-$C_2$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one substituted pyridyl, pyrazolyl, thienyl, furyl or thiazolyl selected from the group consisting of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone.

Preferably, the substituent R8 is selected from hydrogen, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxymethylene, phenyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone, pyridyl, pyrazolyl, thienyl, furyl or thiazolyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone.

Further preferably, the substituent R8 is selected from hydrogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxymethylene, phenyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone, pyridyl, pyrazolyl, thienyl, furyl or thiazolyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone.

Still further preferably, the substituent R8 is selected from hydrogen, methyl, ethyl, monofluoromethyl, difluoromethyl, trifluoromethyl, methoxymethylene, ethoxymethylene.

In the pyrazole derivatives represented by the formula stru-1 provided in the present invention, substituent R9 is selected from hydrogen, halogen, nitro, $C_1$-$C_2$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_{20}$ alkylsulfone, phenyl substituted by at least one of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio, $C_1$-$C_{20}$ haloalkylthio and $C_1$-$C_{20}$ alkylsulfone, pyridyl, pyrazolyl, thienyl, furyl or thiazolyl substituted by at least one of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_2$ alkylthio, $C_1$-$C_{20}$ haloalkylthio and $C_1$-$C_{20}$ alkylsulfone.

Preferably, the substituent R9 is selected from hydrogen, halogen, nitro, $C_1$-$C_{10}$ alkyl, $C_1$-$C_{10}$ haloalkyl, $C_3$-$C_{10}$ cycloalkyl, $C_3$-$C_{10}$ halocycloalkyl, $C_2$-$C_{10}$ alkenyl, $C_2$-$C_{10}$ haloalkenyl, $C_2$-$C_{10}$ alkynyl, $C_2$-$C_{10}$ haloalkynyl, $C_1$-$C_{10}$ alkoxy, $C_1$-$C_{10}$ haloalkoxy, $C_1$-$C_{10}$ alkylthio, $C_1$-$C_{10}$ haloalkylthio, $C_1$-$C_{10}$ alkylsulfone, phenyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone, pyridyl, pyrazolyl, thienyl, furyl or thiazolyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio and $C_1$-$C_{10}$ alkylsulfone.

Further preferably, the substituent R9 is selected from hydrogen, halogen, nitro, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfone, phenyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone, pyridyl, pyrazolyl, thienyl, furyl or thiazolyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio and $C_1$-$C_6$ alkylsulfone.

Still further preferably, the substituent R9 is selected from hydrogen, fluorine, chlorine, bromine, nitro, methyl, ethyl, propyl, isopropyl, difluoromethyl, cyclopropyl, methylthiomethylene, phenyl, p-chlorophenyl, p-fluorophenyl, benzyl.

In the pyrazole derivatives represented by the formula stru-1 provided in the present invention, substituent L is selected from oxygen, sulfur, methylene, nitrogen.

Preferably, the substituent L is selected from oxygen, sulfur, methylene.

In the pyrazole derivatives represented by the formula stru-1 provided in the present invention, substituent Q is selected from oxygen, sulfur.

In the pyrazole derivatives represented by the formula stru-1 provided in the present invention, substituent R10 is selected from hydrogen, halogen, nitro, $C_1$-$C_{20}$ alkyl, $C_1$-$C_{20}$ haloalkyl, $C_3$-$C_{20}$ cycloalkyl, $C_3$-$C_{20}$ halocycloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_1$-$C_{20}$ alkoxy, $C_1$-$C_{20}$ haloalkoxy, $C_1$-$C_{20}$ alkylthio, $C_1$-$C_{20}$ haloalkylthio, $C_1$-$C_{20}$ alkyl carboxylic ester, phenyl substituted by at least one of hydrogen, halogen, nitro, cyano, $C_1$-$C_{20}$ alkyl, $C_1$-$C_{20}$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio and $C_1$-$C_{20}$ haloalkylthio, pyridyl, pyrazolyl, thienyl, furyl or thiazolyl substituted by at least one of hydrogen, halogen, nitro, cyano, $C_1$-$C_2$ alkyl, $C_1$-$C_2$ haloalkyl, $C_3$-$C_{20}$ cycloalkyl, $C_3$-$C_{20}$ halocycloalkyl, $C_1$-$C_{20}$ alkoxy, $C_1$-$C_{20}$ haloalkoxy, $C_1$-$C_{20}$ alkylthio and $C_1$-$C_{20}$ haloalkylthio.

Preferably, the substituent R10 is selected from hydrogen, halogen, nitro, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkenyl, $C_2$-$C_{10}$ haloalkenyl, $C_2$-$C_{10}$ alkynyl, $C_2$-$C_{10}$ haloalkynyl, $C_1$-$C_{10}$ alkoxy, $C_1$-$C_{10}$ haloalkoxy, $C_1$-$C_{10}$ alkylthio, $C_1$-$C_{10}$ haloalkylthio, $C_1$-$C_{10}$ alkyl carboxylic ester, phenyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{10}$ haloalkoxy, $C_1$-$C_{10}$ alkylthio and $C_1$-$C_{10}$ haloalkylthio, pyridyl, pyrazolyl, thienyl, furyl or thiazolyl substituted by at least one of hydrogen, halogen, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_{10}$ alkoxy, $C_1$-$C_{20}$ haloalkoxy, $C_1$-$C_{10}$ alkylthio and $C_1$-$C_{10}$ haloalkylthio.

Further preferably, the substituent R10 is selected from hydrogen, halogen, nitro, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkyl carboxylic ester, phenyl substituted by at least one of hydrogen, halogen, nitro, cyano, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio and $C_1$-$C_6$ haloalkylthio, pyridyl, pyrazolyl, thienyl, furyl or thiazolyl substituted by at least one of hydrogen, halogen, nitro, cyano, $C_1$-$C_6$ alkyl, $C_1$-$C_6$ haloalkyl, $C_3$-$C_6$ cycloalkyl, $C_1$-$C_6$ halocycloalkyl, $C_1$-$C_6$ alkoxy, $C_1$-$C_6$ haloalkoxy, $C_1$-$C_6$ alkylthio and $C_1$-$C_6$ haloalkylthio.

Still further preferably, the substituent R10 is selected from hydrogen, fluorine, chlorine, nitro, $C_1$-$C_6$ alkyl, $C_3$—C cycloalkyl, $C_3$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ methyl alkyl carboxylate. $C_1$-$C_6$ ethyl carboxylic acid ethyl ester, phenyl substituted by at least one of hydrogen, fluorine, chlorine, bromine, nitro, cyano, methyl, ethyl, trifluoromethyl, methoxy, ethoxy, trifluoroethoxy, and methylthio, pyridyl, pyrazolyl, thienyl, furyl or thiazolyl substituted by at least one of hydrogen, fluorine, chlorine, bromine, nitro, cyano, methyl, ethyl, trifluoromethyl, methoxy, ethoxy, trifluoroethoxy, and methylthio.

For the pyrazole derivatives represented by the formula stru-1 provided herein, as a preferred embodiment, in the formula stru-1:

R1, R2, R3, R4, R5 are independently selected from hydrogen, fluorine, chlorine, bromine, nitro, nitrile, methyl, ethyl, isopropyl, tert-butyl, trifluoromethyl, methoxy, ethoxy, trifluoromethoxy, difluoromethoxy, difluoroethoxy, methylthio, trifluoromethylthio, trifluoroethylthio, methylsulfonyl, methylsulfonate;

R6 is selected from hydrogen, fluorine, chlorine, bromine, nitro, nitrile, methyl, ethyl, isopropyl, cyclopropyl, trifluoromethyl, difluoromethyl, methoxy, ethoxy, p-chlorophenyl, p-fluorophenyl;

R7 is selected from hydrogen, halogen, nitro, nitrile, $C_1$-$C_5$ alkyl, $C_1$-$C_5$ haloalkyl, $C_1$-$C_5$ alkoxymethylene;

R8 is selected from methyl, ethyl;

R9 is selected from hydrogen, fluorine, chlorine, bromine, nitro, methyl, ethyl, propyl, isopropyl, difluoromethyl, cyclopropyl, methylthiomethylene, phenyl, p-chlorophenyl, p-fluorophenyl, benzyl:

L is selected from oxygen, sulfur, methylene:

Q is selected from oxygen, sulfur:

R10 is selected from hydrogen, fluorine, chlorine, nitro, $C_1$-$C_6$ alkyl, $C_3$-$C_6$ cycloalkyl, $C_3$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ methyl alkyl carboxylate. $C_1$-$C_6$, ethyl carboxylic acid ethyl ester, phenyl substituted by at least one of hydrogen, fluorine, chlorine, bromine, nitro, cyano, methyl, ethyl, trifluoromethyl, methoxy, ethoxy, trifluoroethoxy, and methylthio, pyridyl, pyrazolyl, thienyl, furyl or thiazolyl substituted by at least one of hydrogen, fluorine, chlorine, bromine, nitro, cyano, methyl, ethyl, trifluoromethyl, methoxy, ethoxy, trifluoroethoxy, and methylthio.

For the pyrazole derivatives represented by the formula stru-1 provided herein, as another preferred embodiment, in the formula stru-1:

R1, R2, R4, R5 are selected from hydrogen;

R3 is selected from t-butyl;

R6 is selected from hydrogen, fluorine, chlorine, bromine, nitro, nitrile, methyl, ethyl, isopropyl, cyclopropyl, trifluoromethyl, difluoromethyl, methoxy, ethoxy, p-chlorophenyl, p-fluorophenyl;

R7 is selected from hydrogen, halogen, nitro, nitrile, $C_1$-$C_5$ alkyl, $C_1$-$C_5$ haloalkyl, $C_1$-$C_5$ alkoxymethylene:

R8 is selected from methyl, ethyl;

R9 is selected from hydrogen, fluorine, chlorine, bromine, nitro, methyl, ethyl, propyl, isopropyl, difluoromethyl, cyclopropyl, methylthiomethylene, phenyl, p-chlorophenyl, p-fluorophenyl, benzyl:

L is selected from oxygen, sulfur, methylene:

Q is selected from oxygen, sulfur;

R10 is selected from hydrogen, fluorine, chlorine, nitro, $C_1$-$C_6$ alkyl, $C_3$-$C_6$ cycloalkyl, $C_3$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ methyl alkyl carboxylate, $C_1$-$C_6$ ethyl carboxylic acid ethyl ester, phenyl substituted by at least one of hydrogen, fluorine, chlorine, bromine, nitro, cyano, methyl, ethyl, methoxy, ethoxy, trifluoromethyl, trifluoroethoxy, and methylthio, pyridyl, pyrazolyl, thienyl, furyl or thiazolyl substituted by at least one of hydrogen, fluorine, chlorine, bromine, nitro, cyano, methyl, ethyl, methoxy, ethoxy, trifluoromethyl, trifluoroethoxy, and methylthio.

For pyrazole derivatives represented by the formula stru-1 provided herein, as the most preferred embodiment, the pyrazole derivatives are selected from at least one of the compounds represented by the following structural formula:

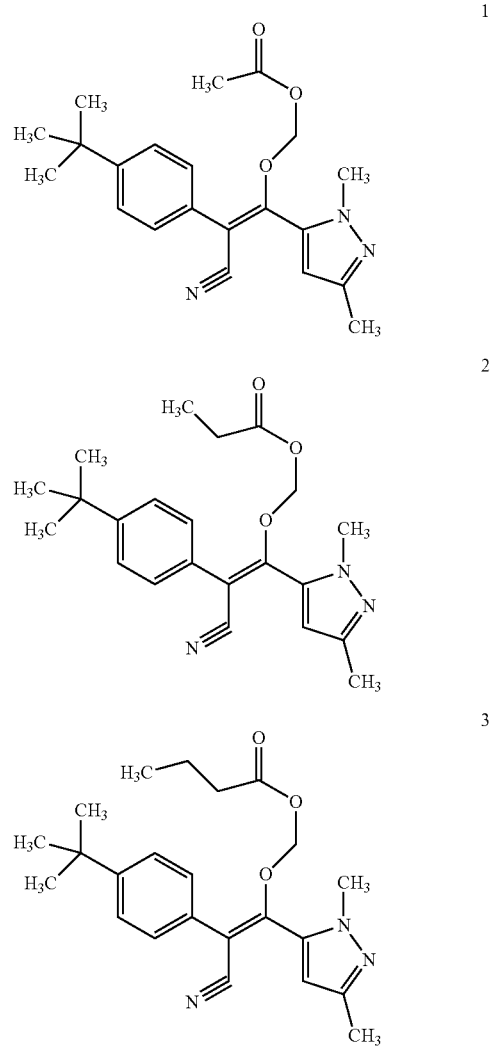

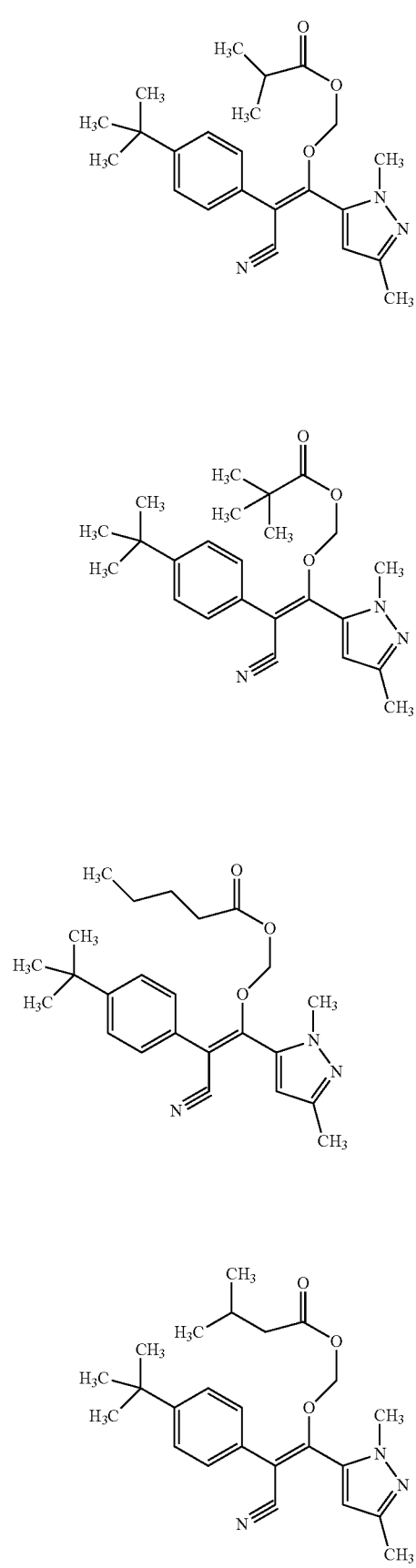
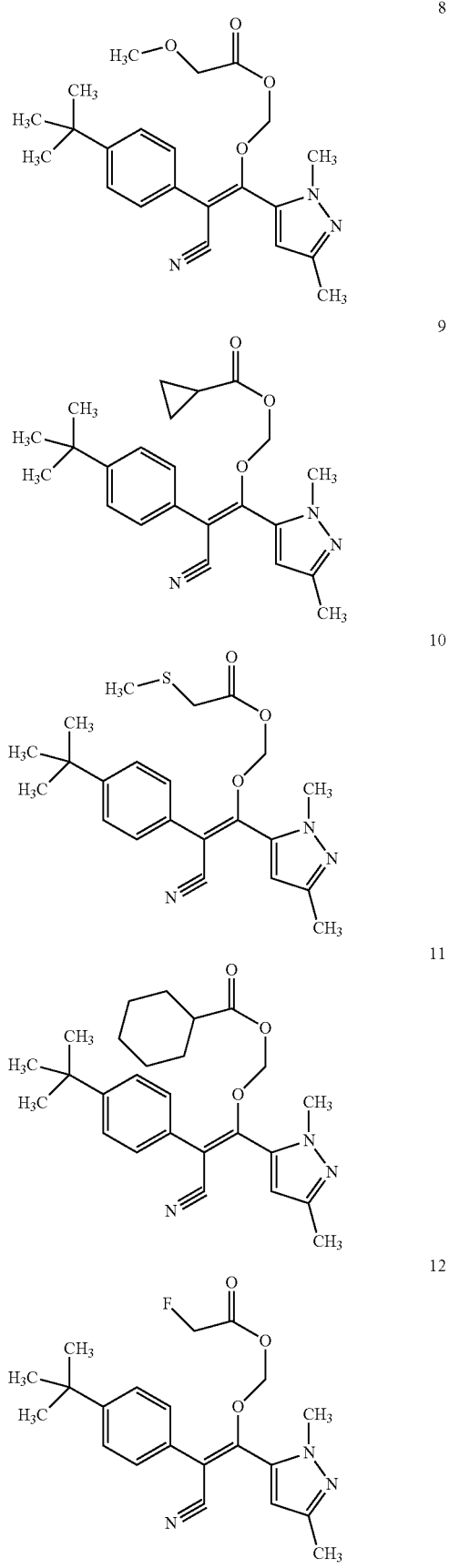

13
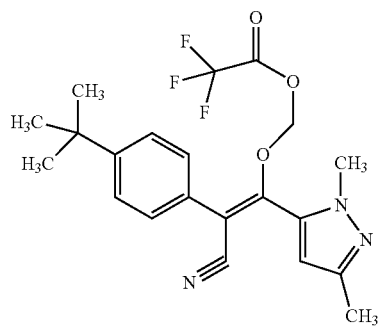
14
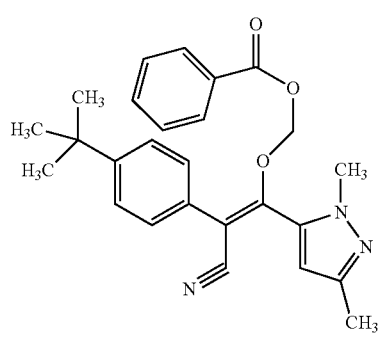
15
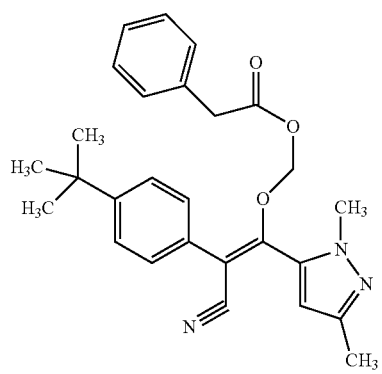
16
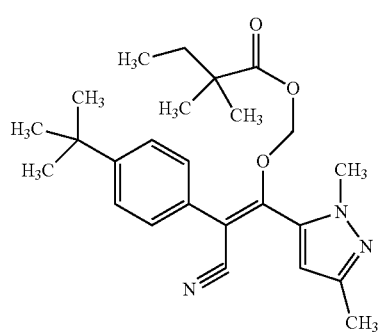
17
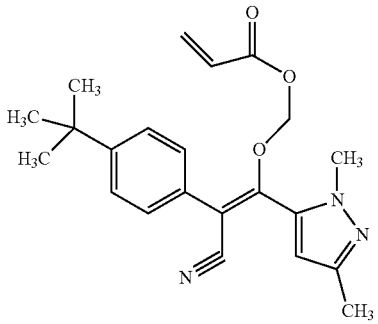
26
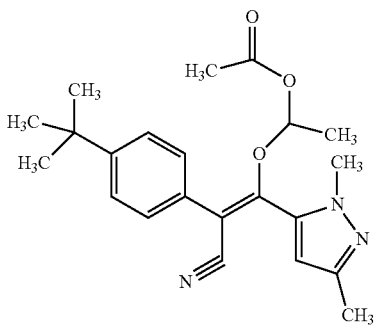
27
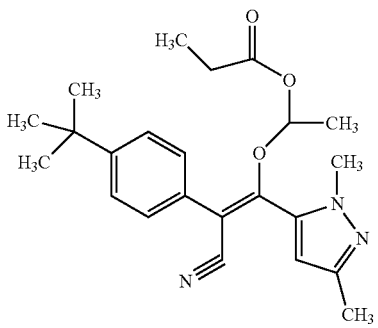
28
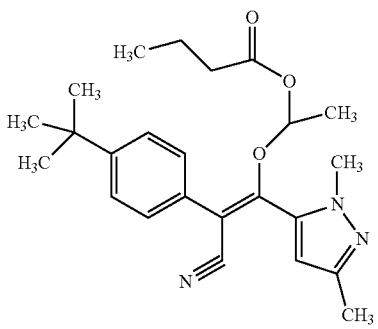
29
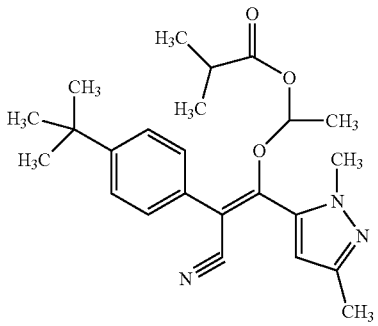

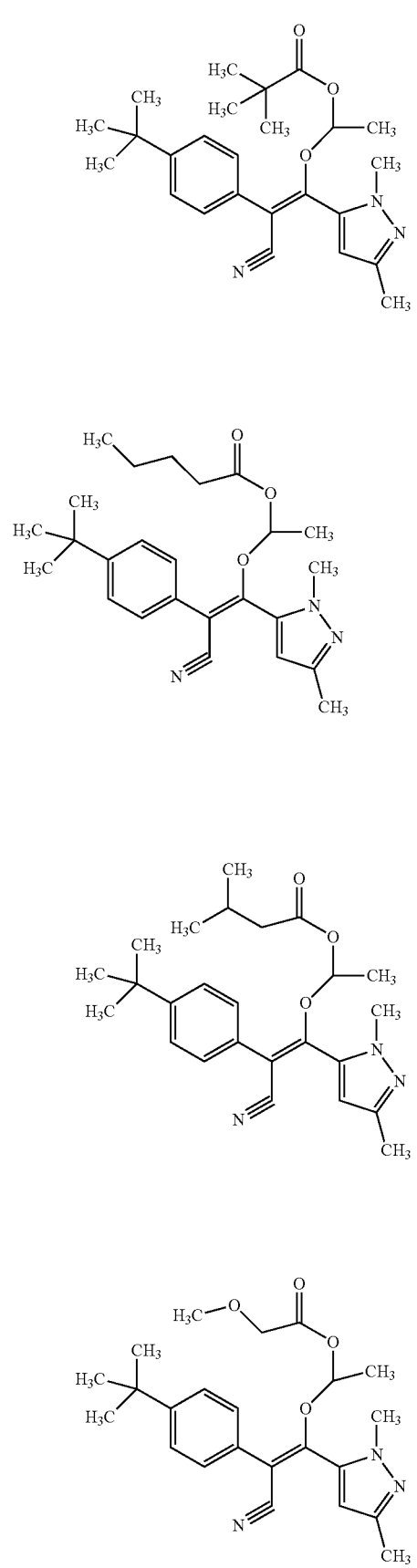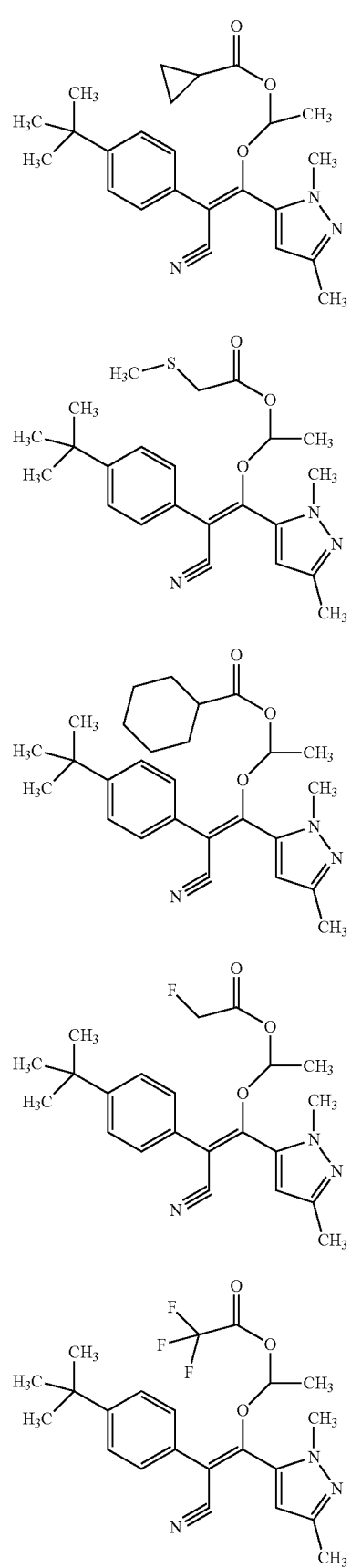

39
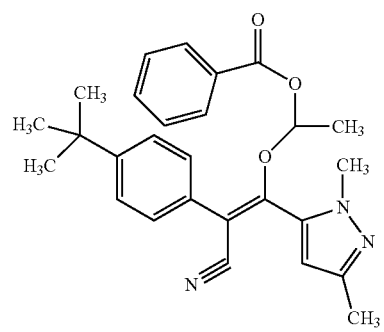
40
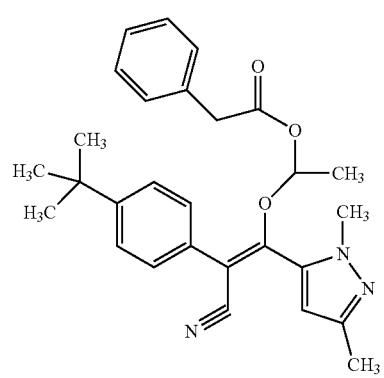
41
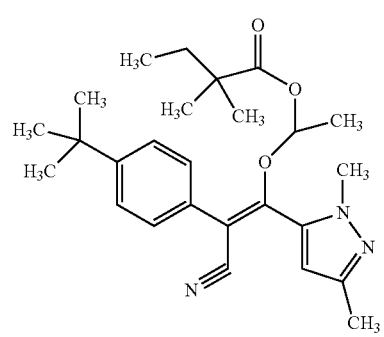
42
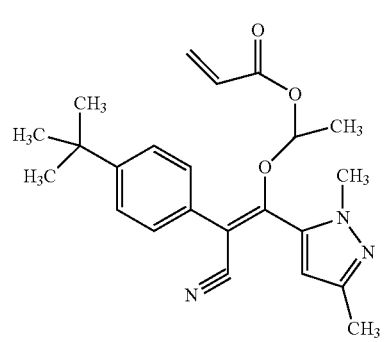
76
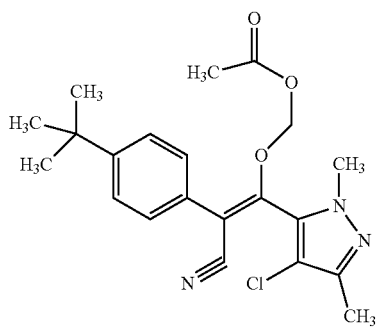
77
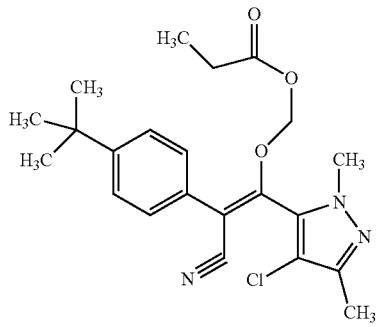
78
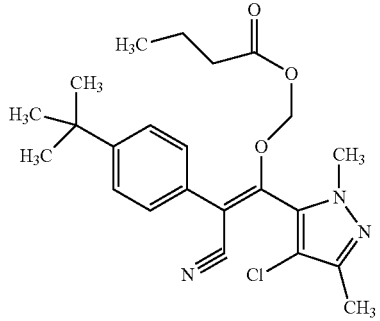
79
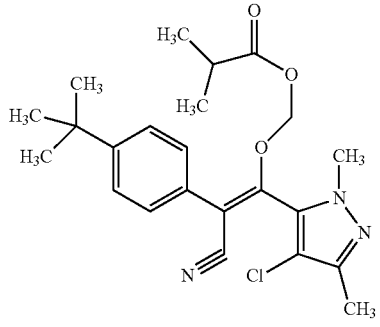
80
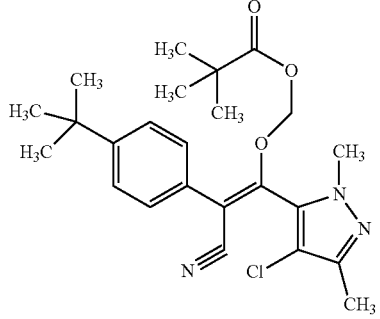

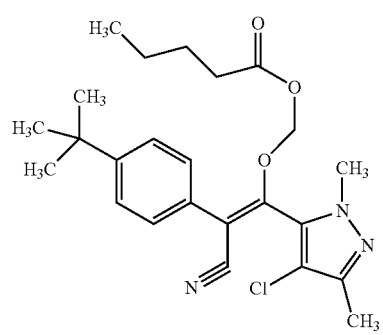
81
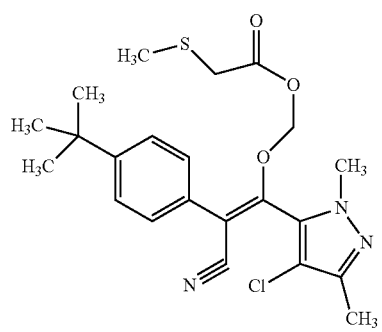
85
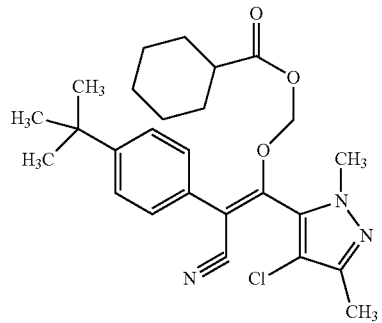
86

87

88

89

90
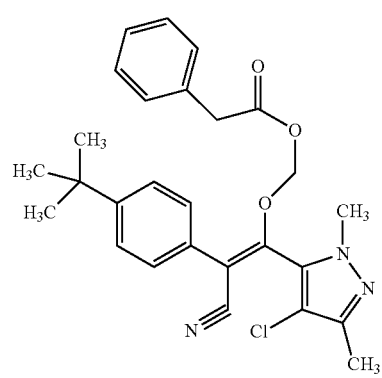
91
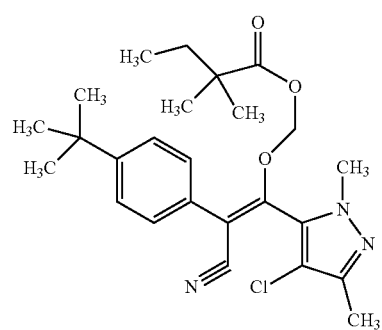
92
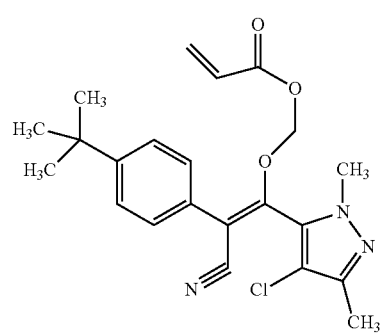
101
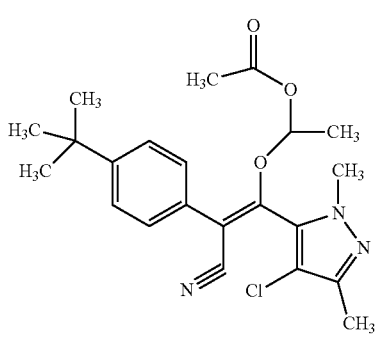
102
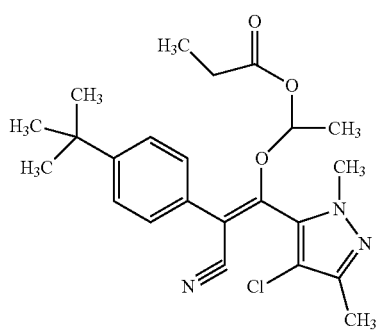
103
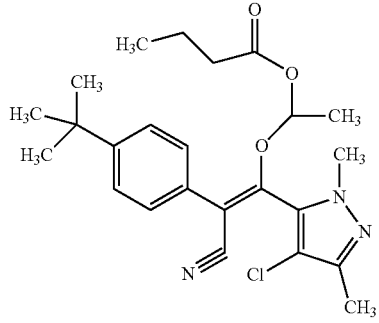
104
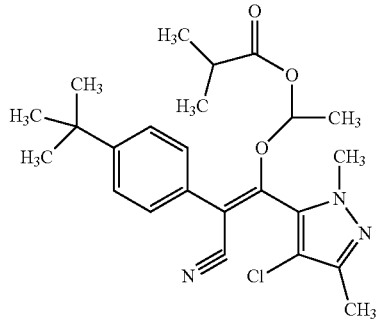
105
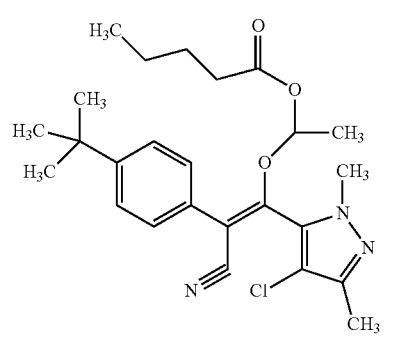
106

107
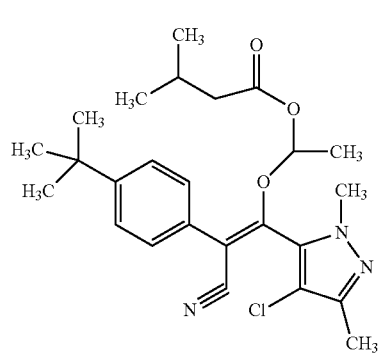
108
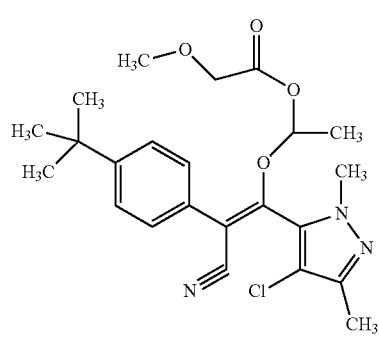
109
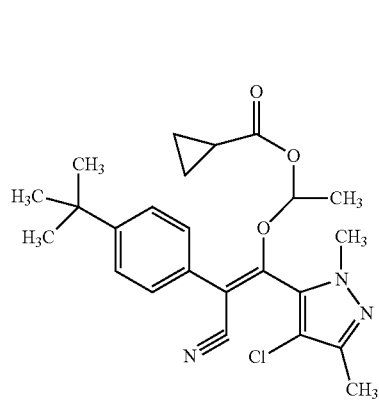
110
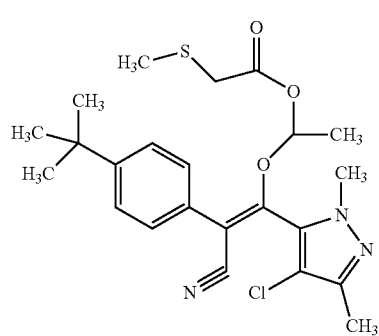
111
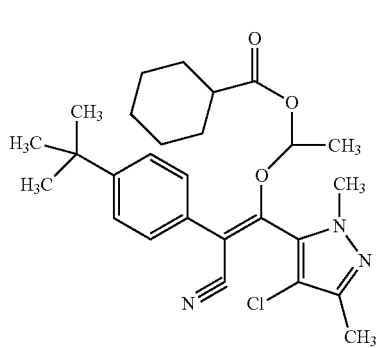
112
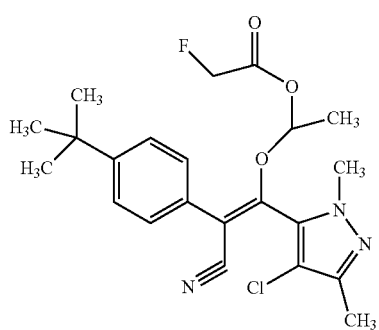
113
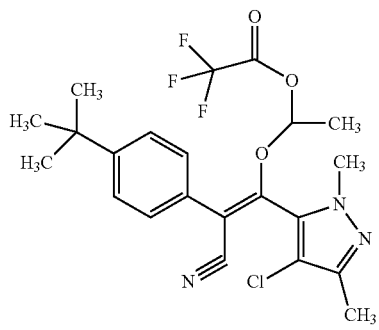
114
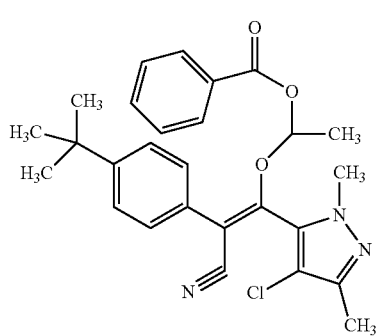

115
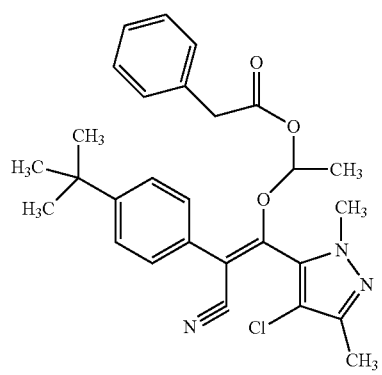
116
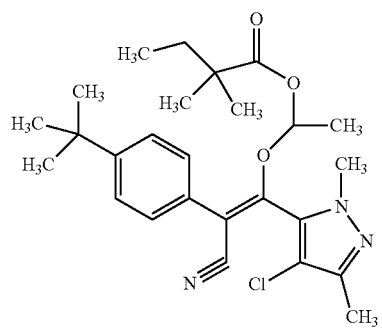
117
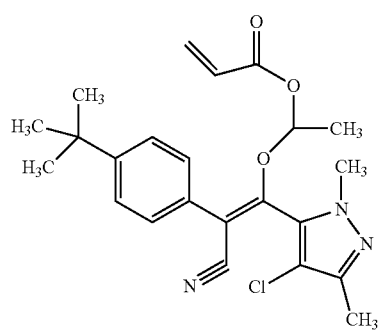
151
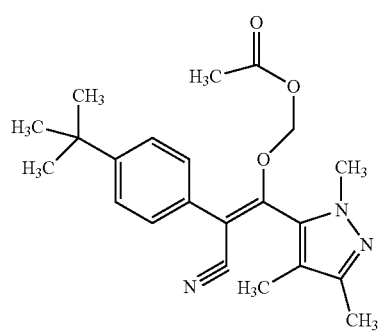
152
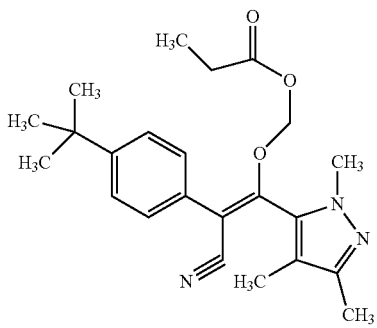
153
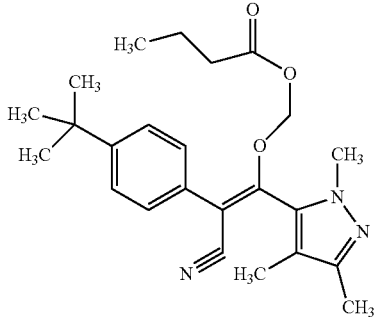
154
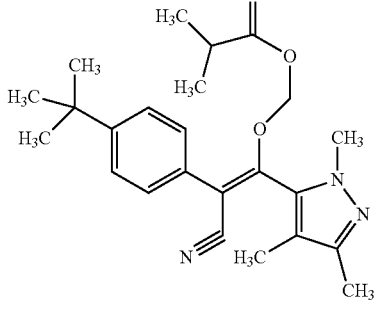
155
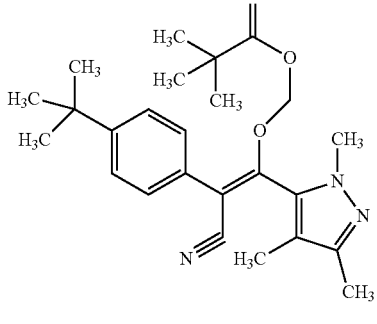
156
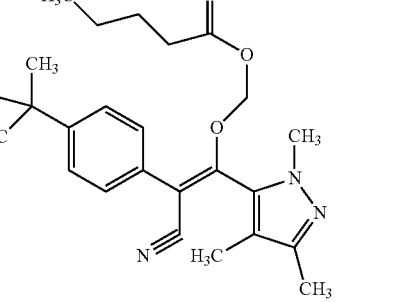

157 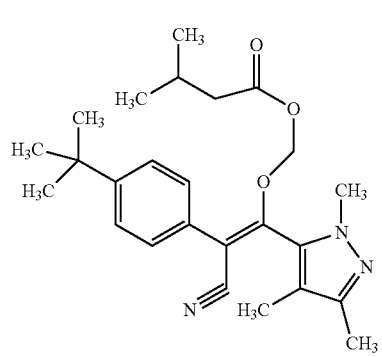
161 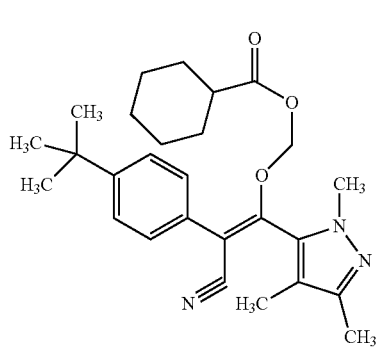
158 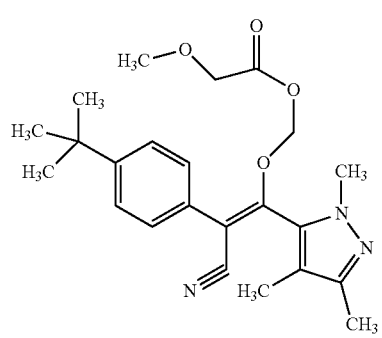
162
159 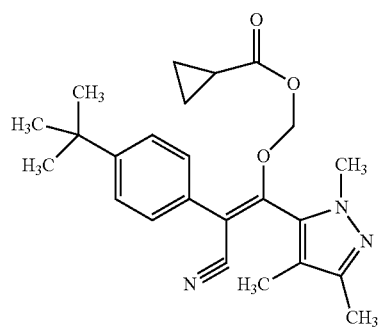
163 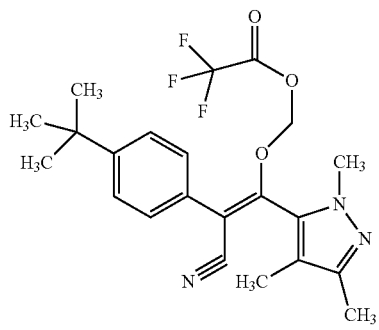
160 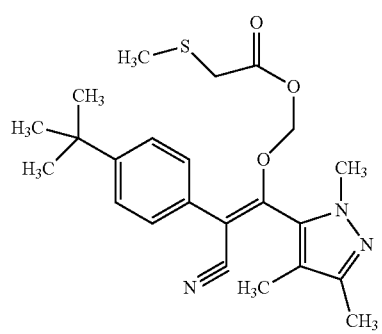
164 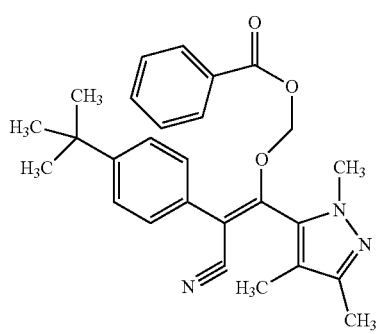

165
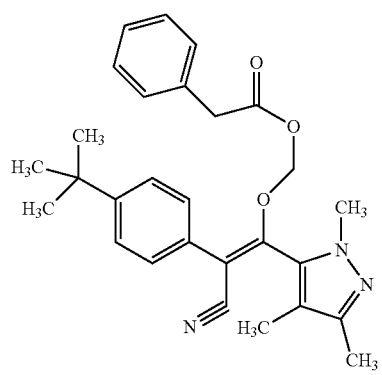
166
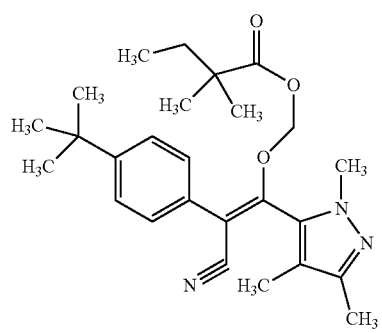
167
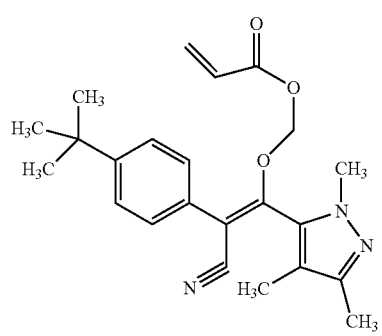
176
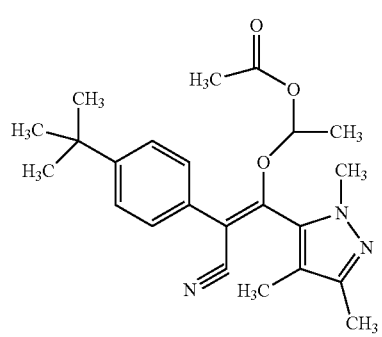
177
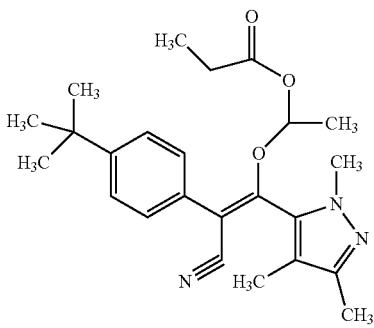
178
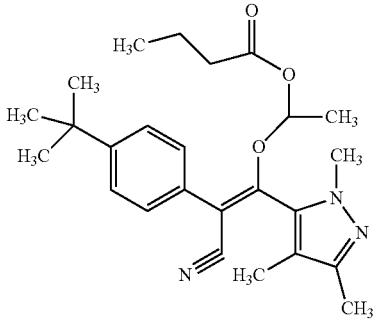
179
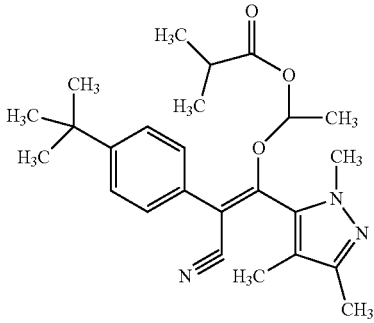
180
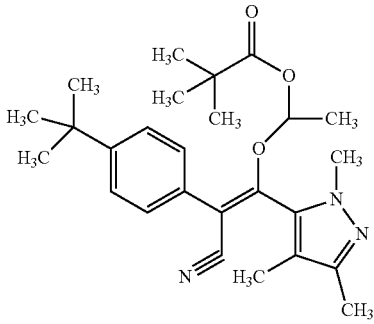
181
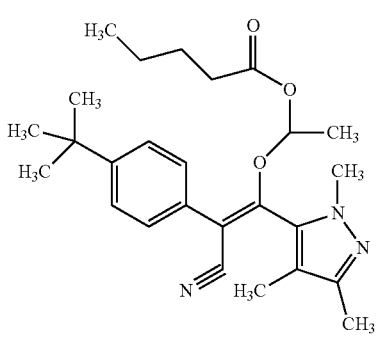

182 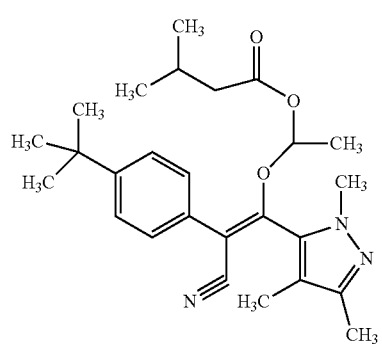
183 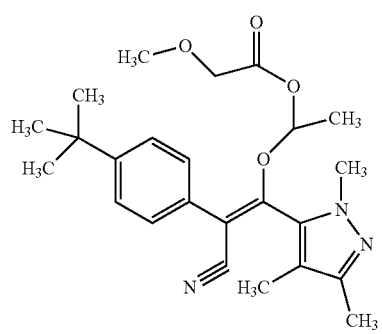
184 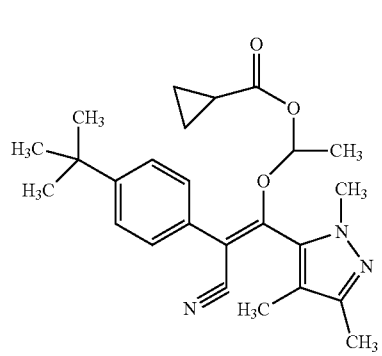
185 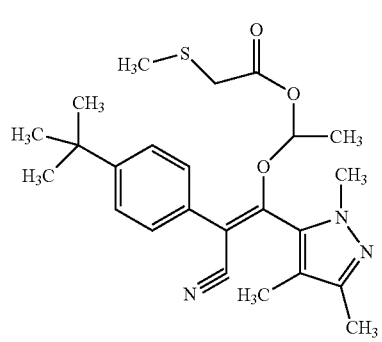
186 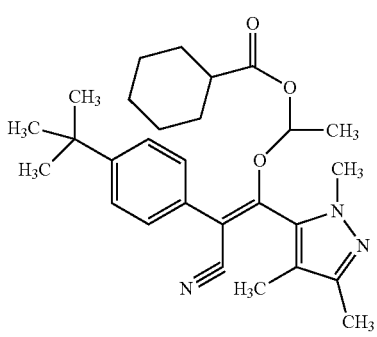
187 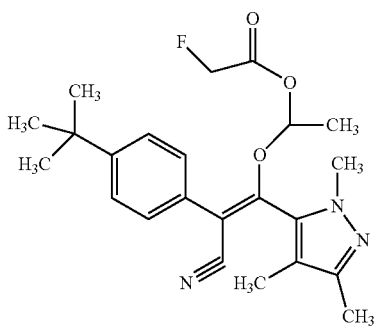
188 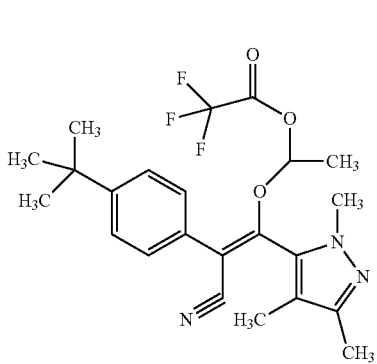
189 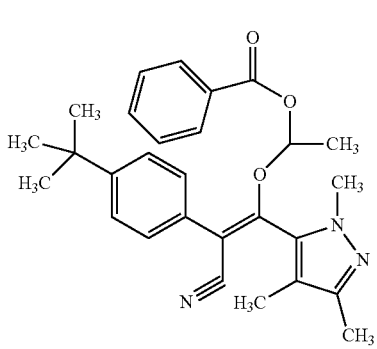

190
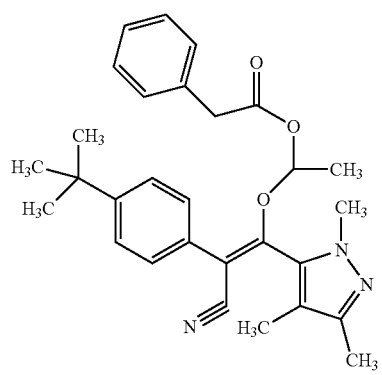
191
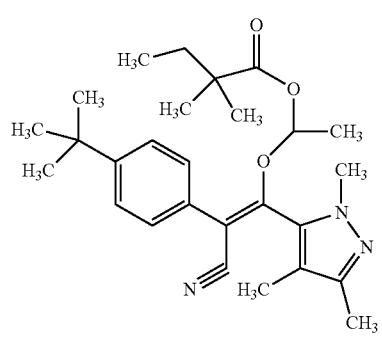
192
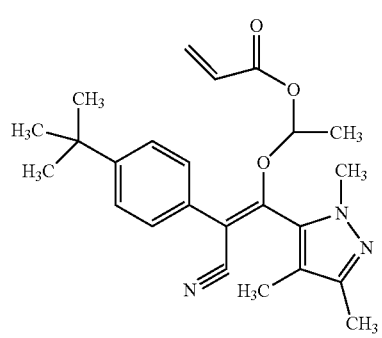
226
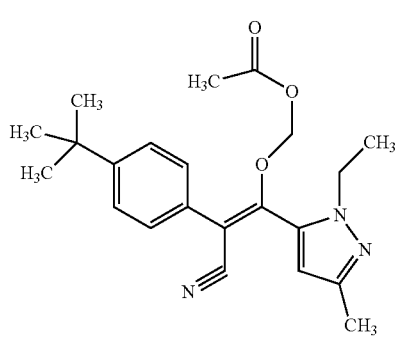
227
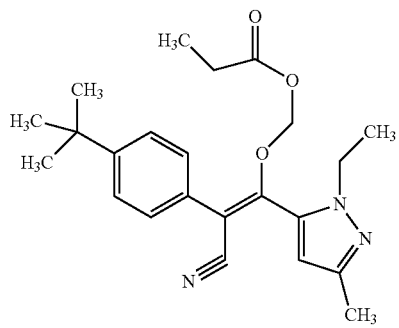
228
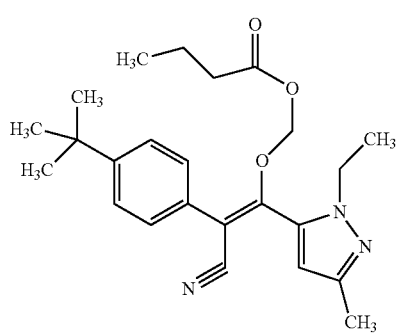
229
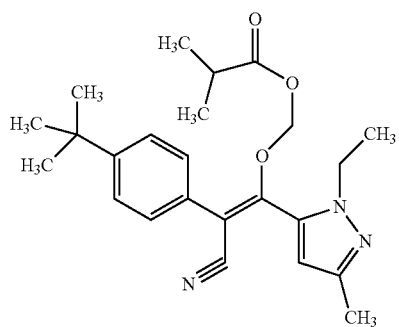
230
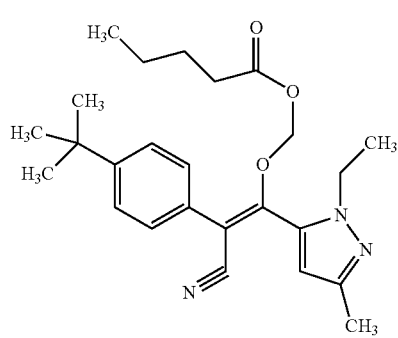
231

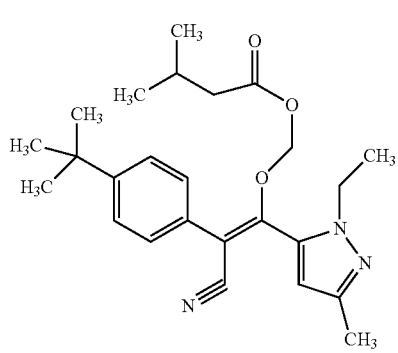
232
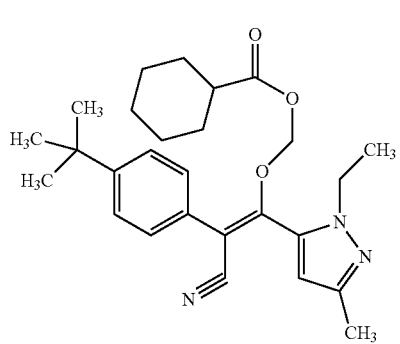
236
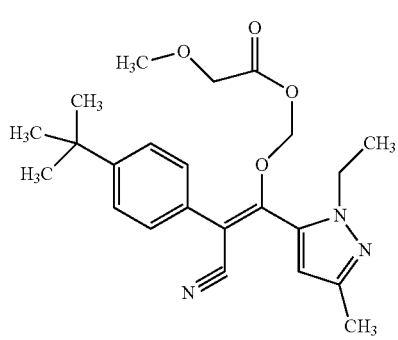
233
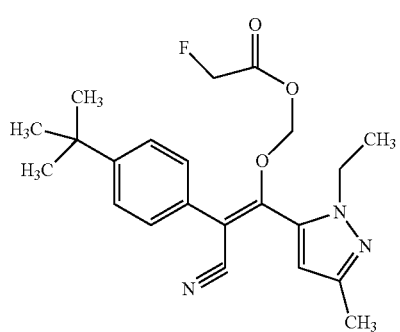
237
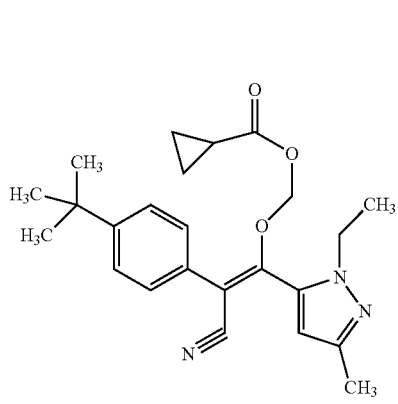
234
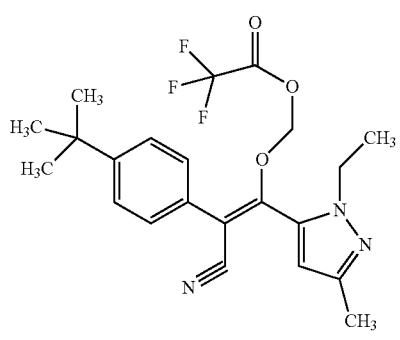
238
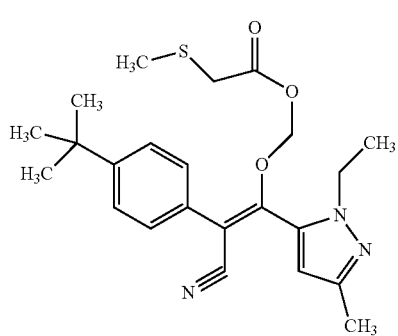
235
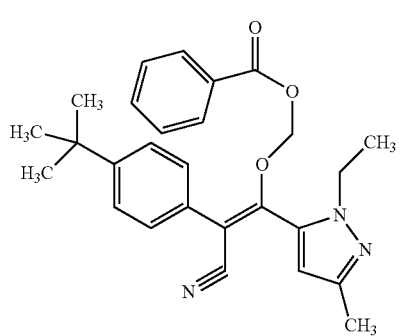
239

240
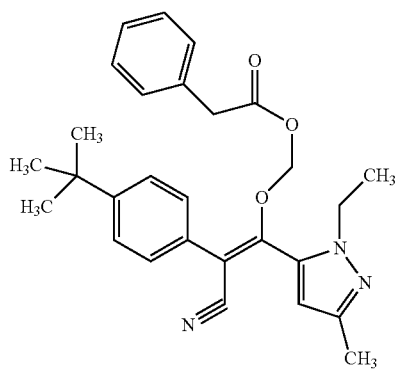
241
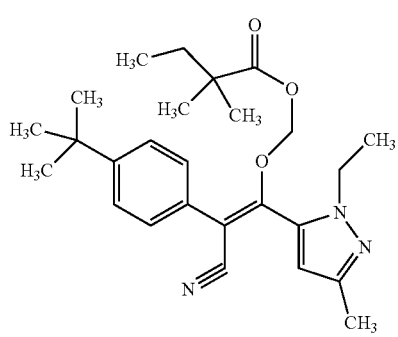
242
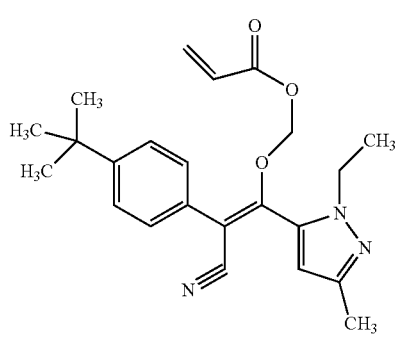
251
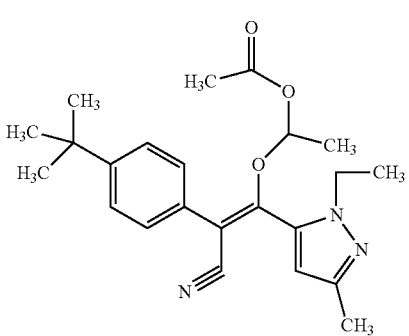
252
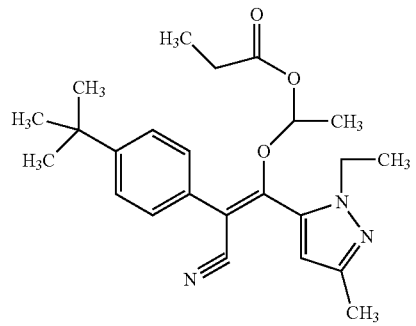
253
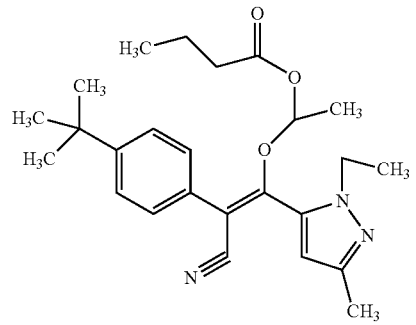
254
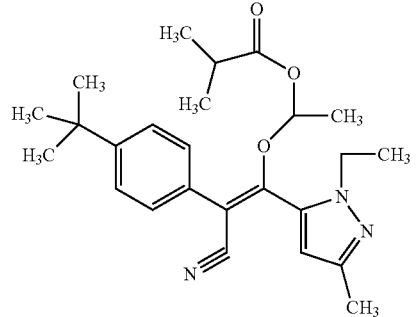
255
256
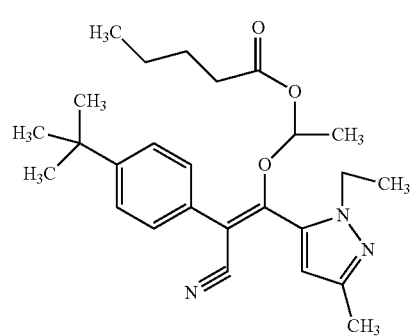

-continued
257
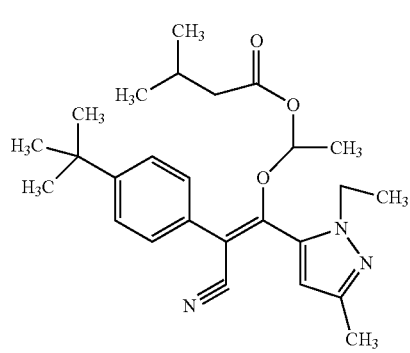
258
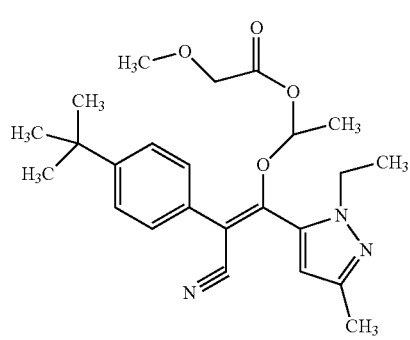
259
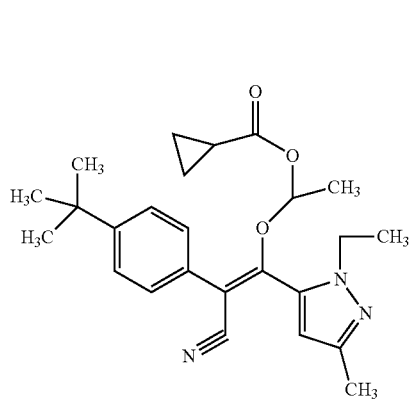
260
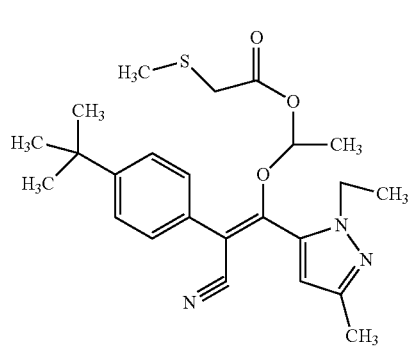
-continued
261
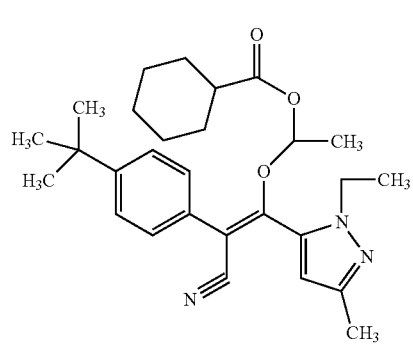
262
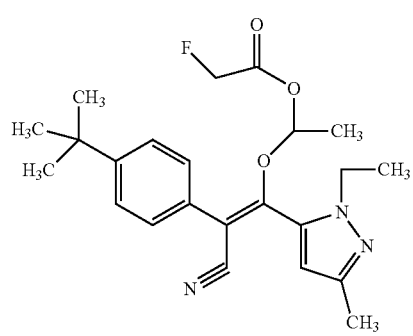
263
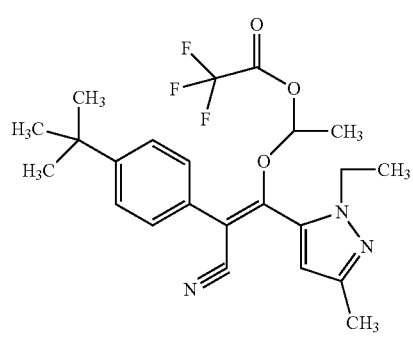
264
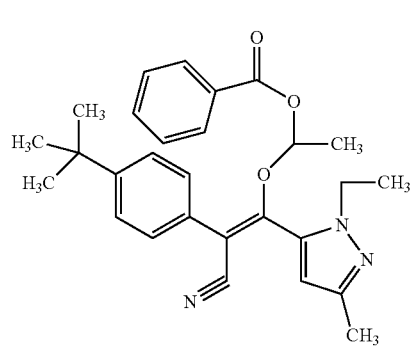

265
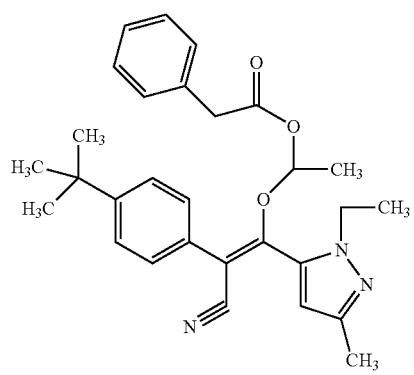
266
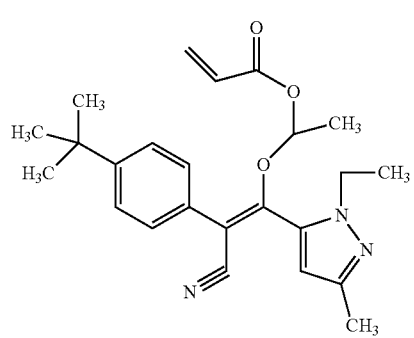
267
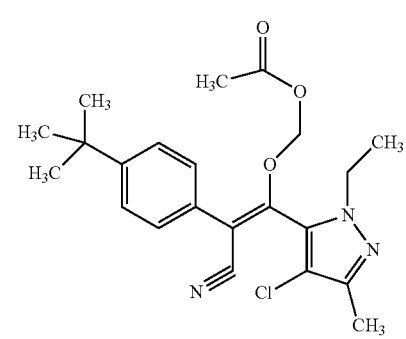
301
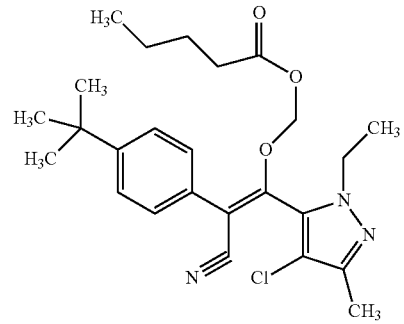
302
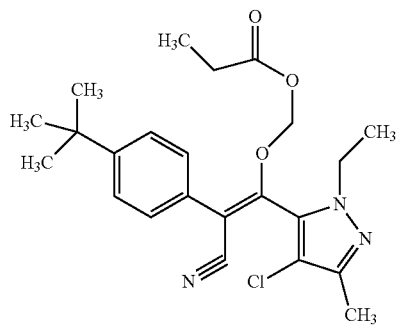
303
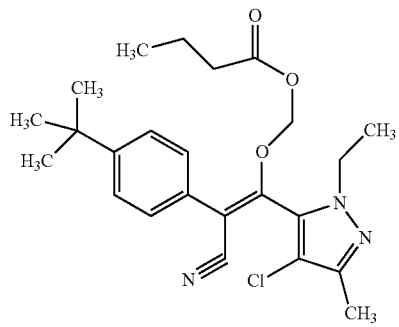
304
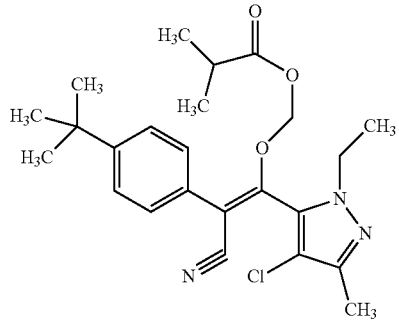
305
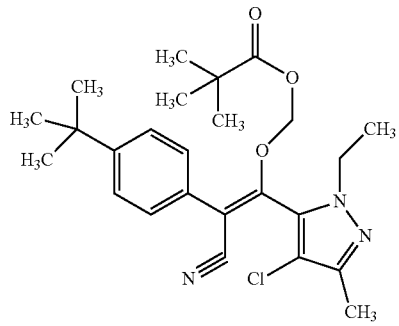
306

307 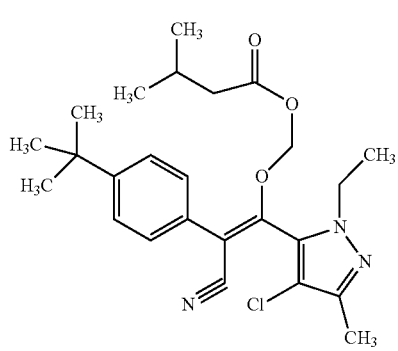
308 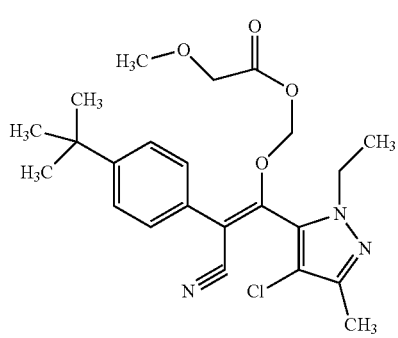
309 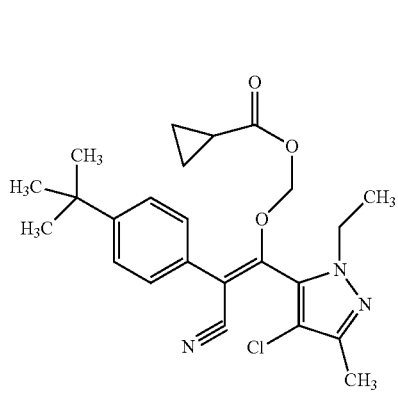
310 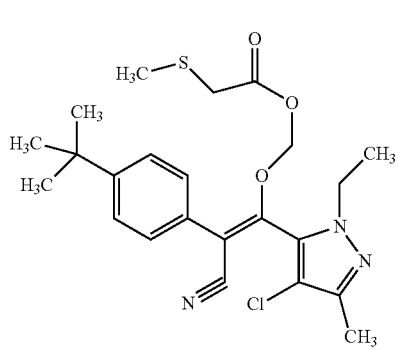
311 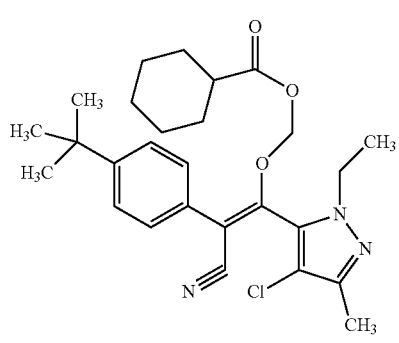
312 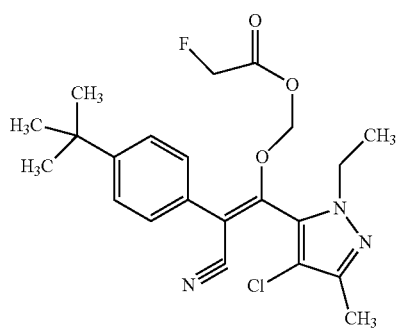
313 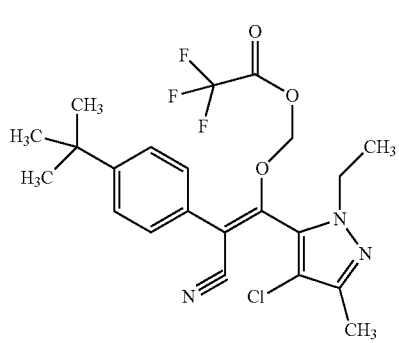
314 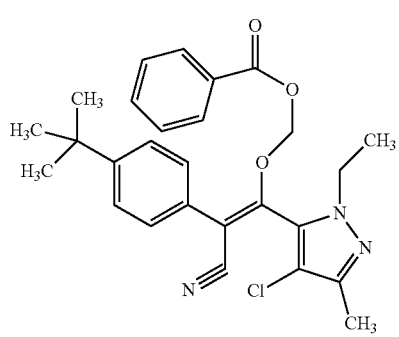

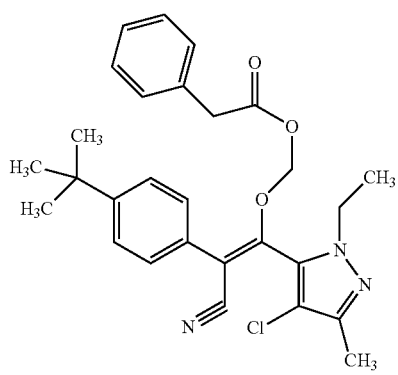
315
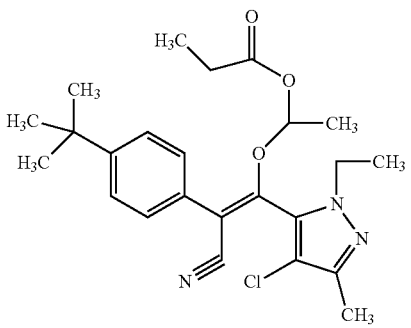
327
316
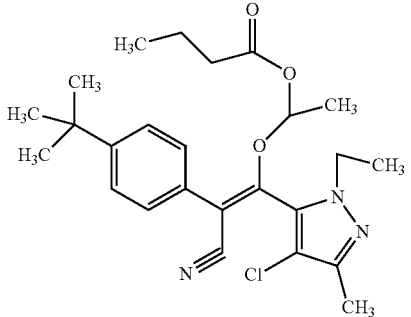
328
317
329
326
330
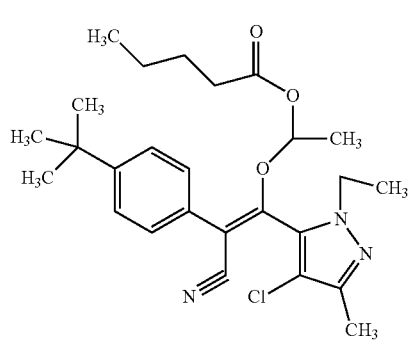
331

332
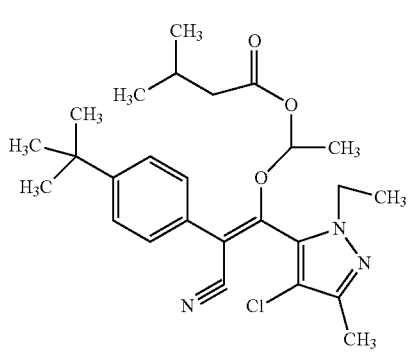
333
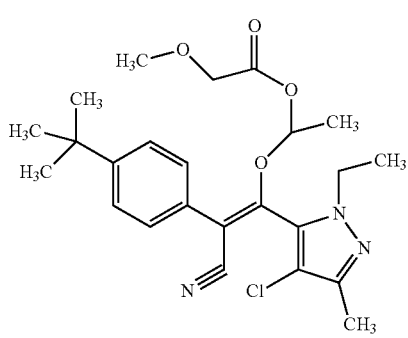
334
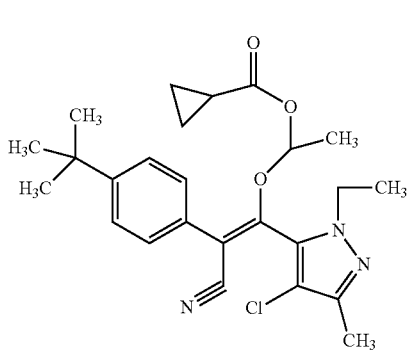
335
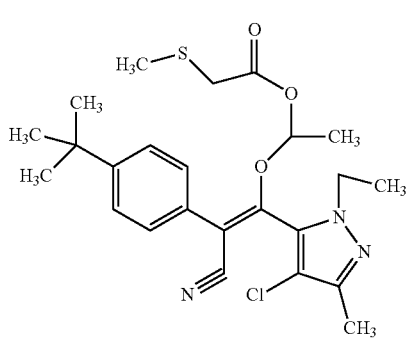
336
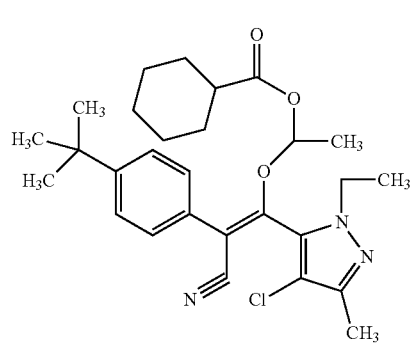
337
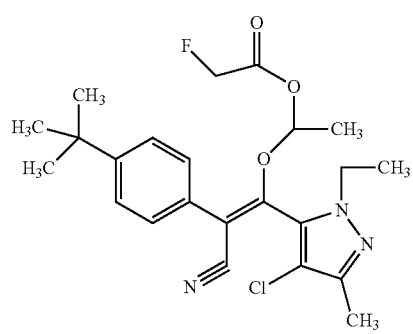
338
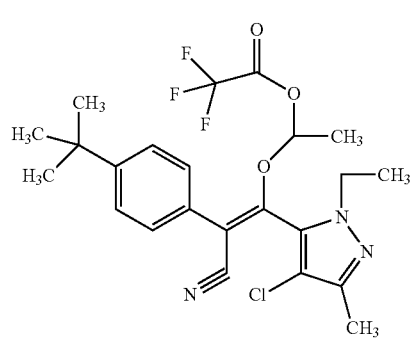
339
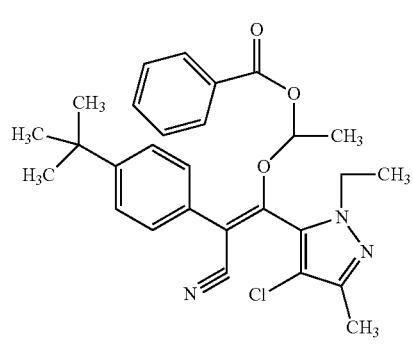

340

341

342

376

377

378

379

380

381

382 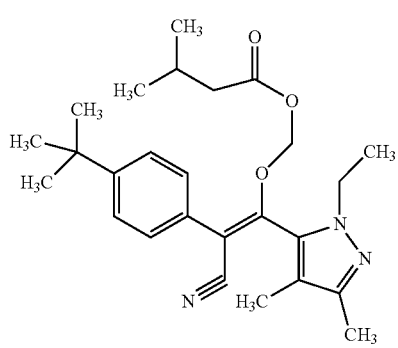
383 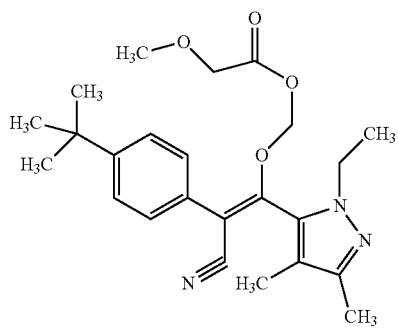
384 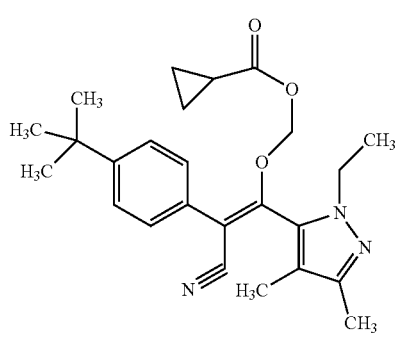
385 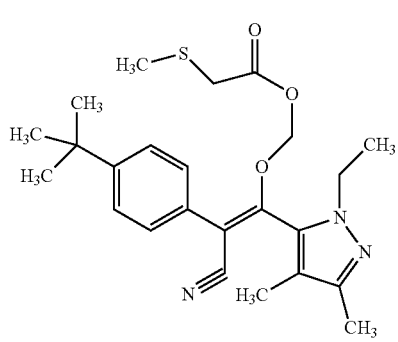
386 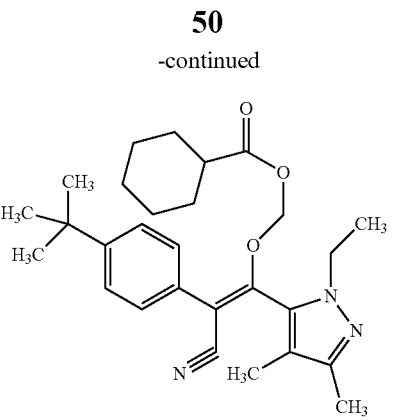
387 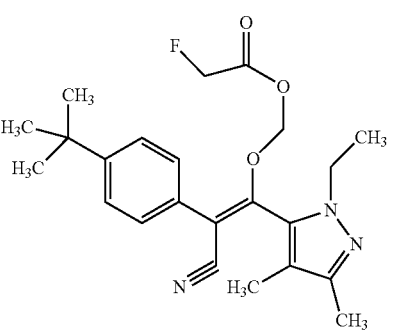
388 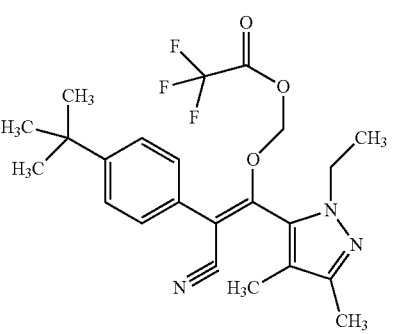
389 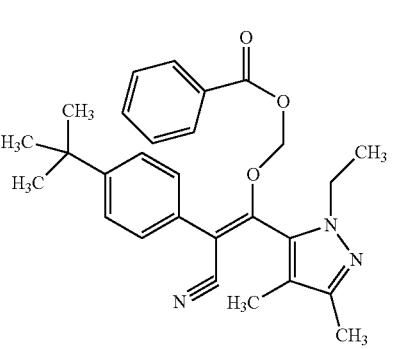

390
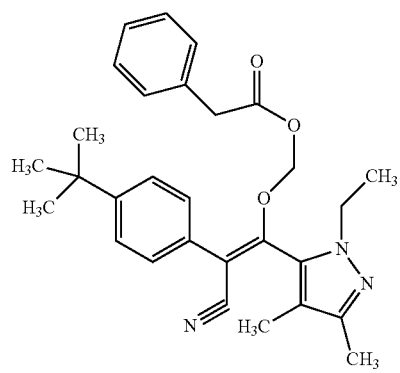
391
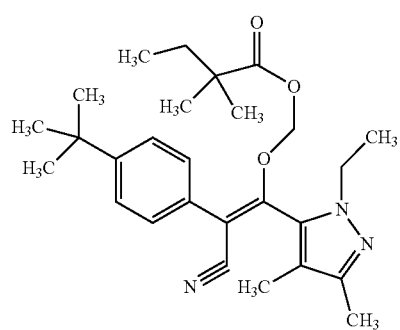
392
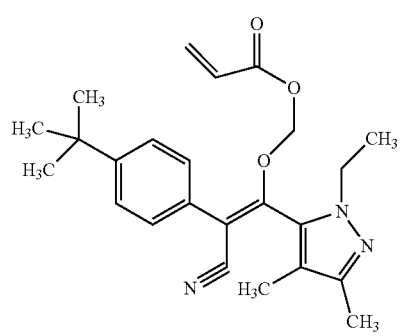
401
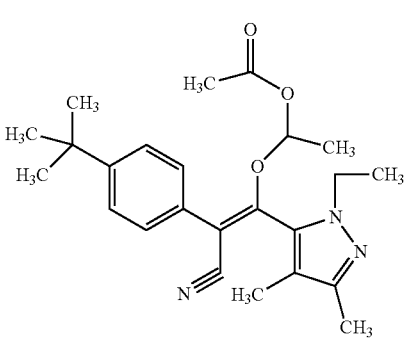
402
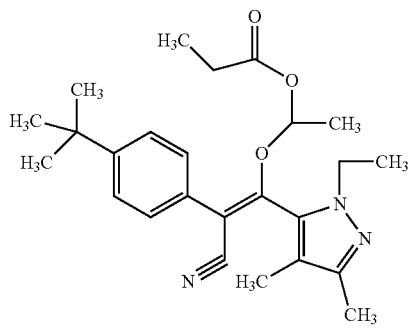
403
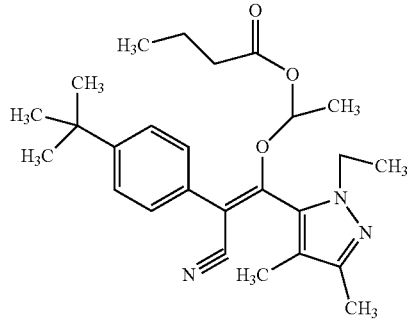
404
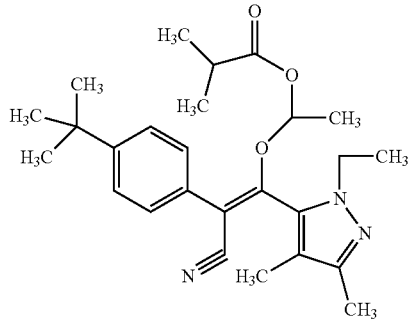
405
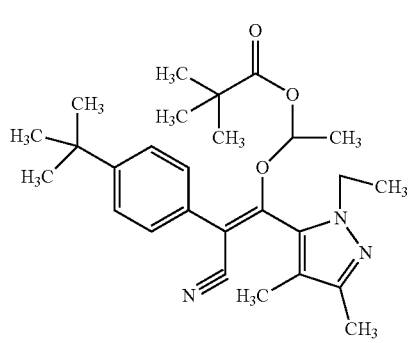
406
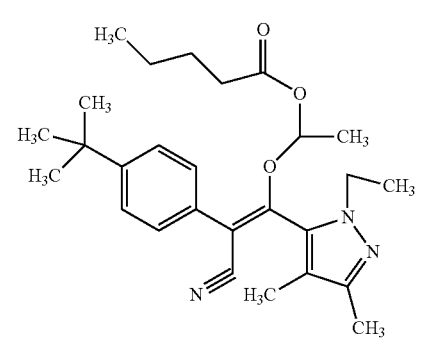

407 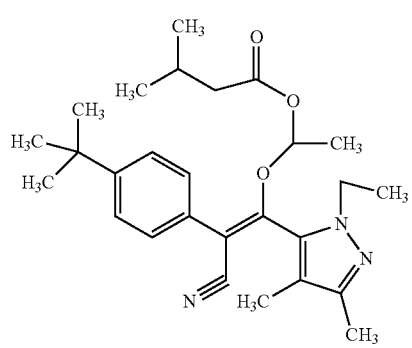
408 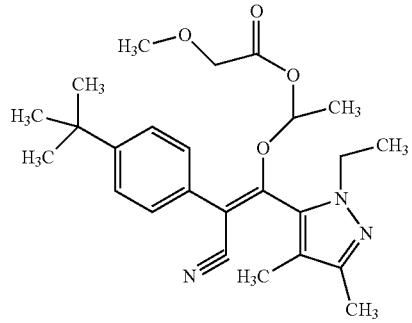
409 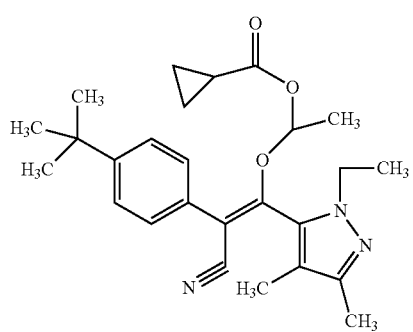
410 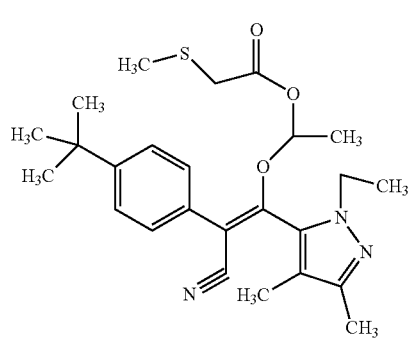
411 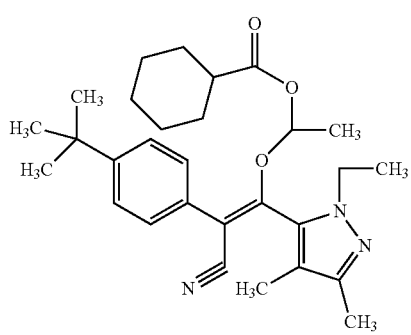
412 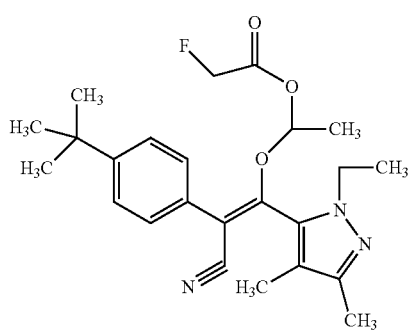
413 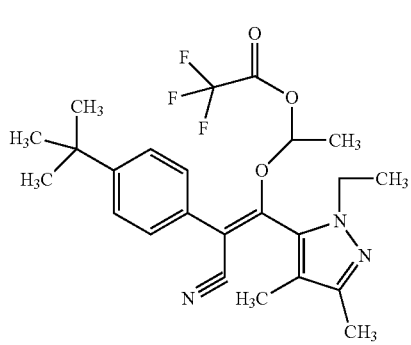
414 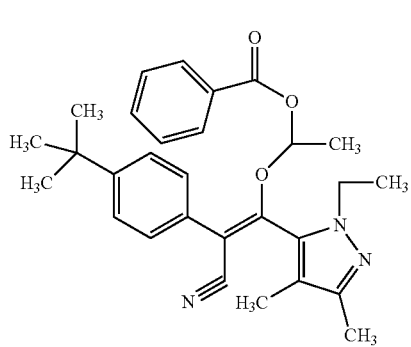

415 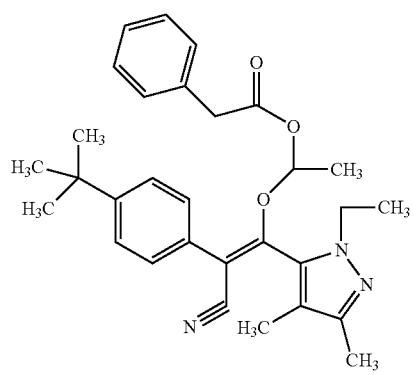
416 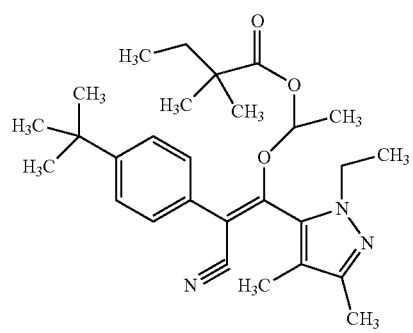
417 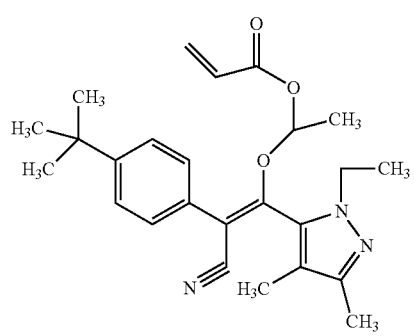
451 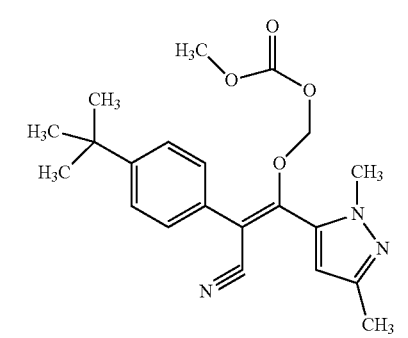
452 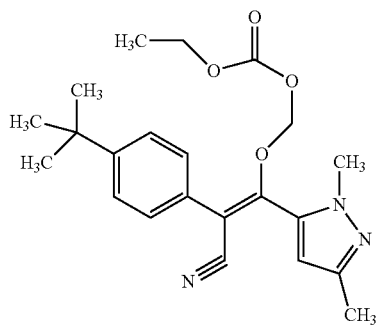
453 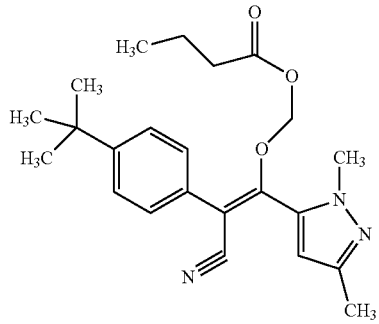
454 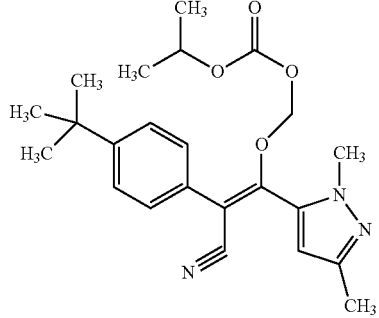
456 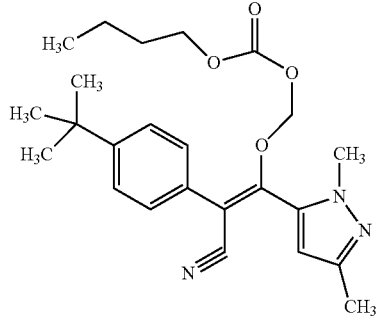
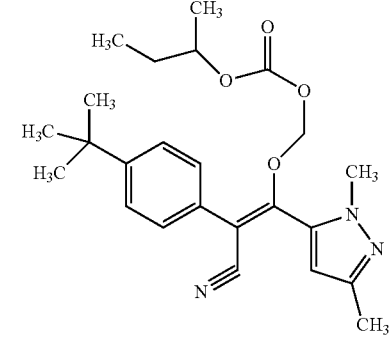

457
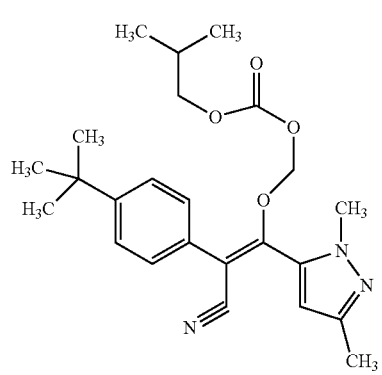
460
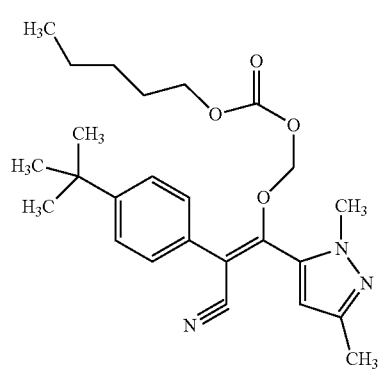
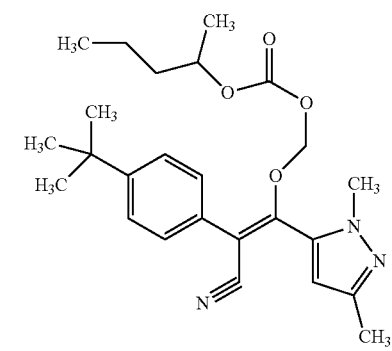
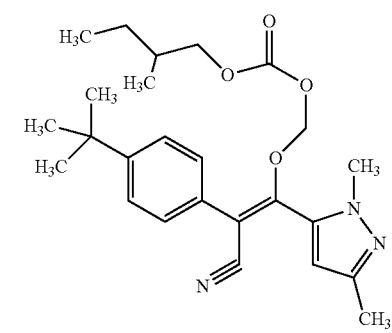
458
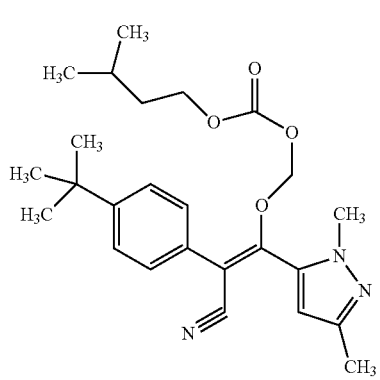
462
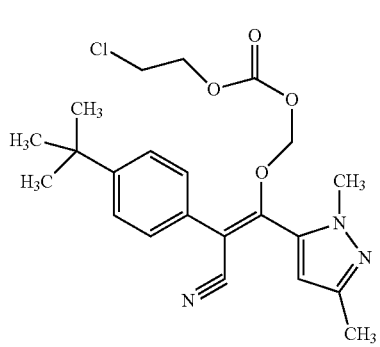
467
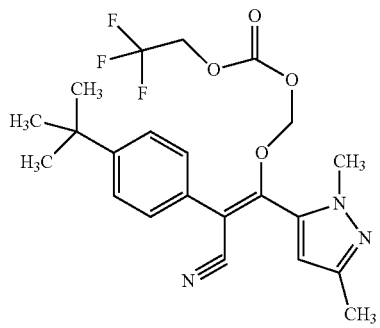
468
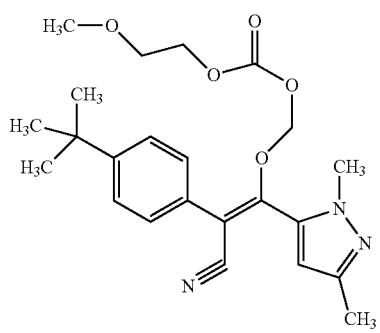

-continued
471
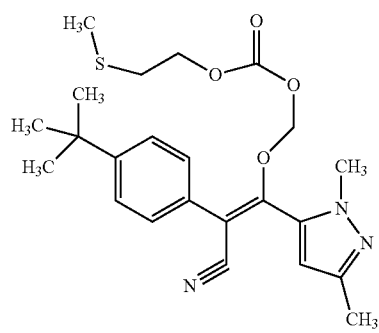
477
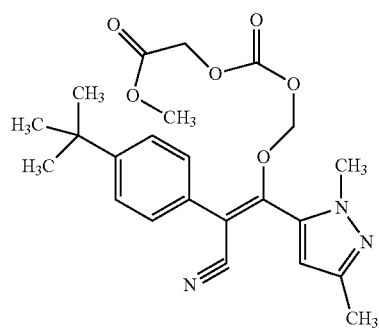
481
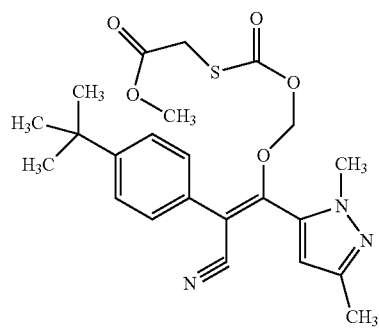
480
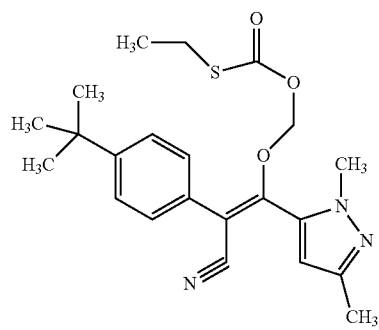
-continued
474
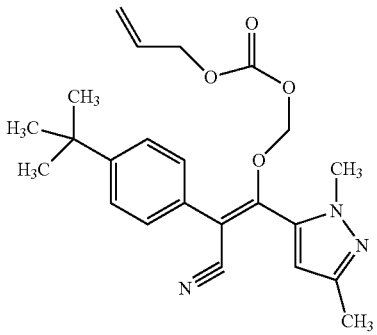
476
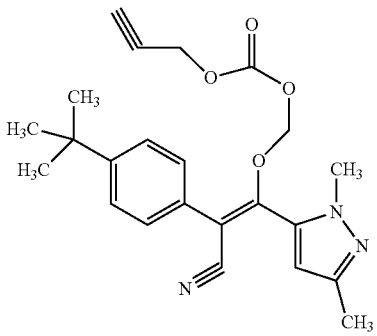
643
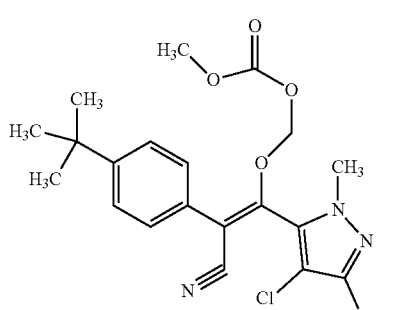
644
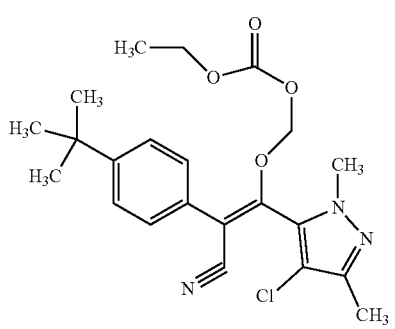

| | |
|---|---|
| 645 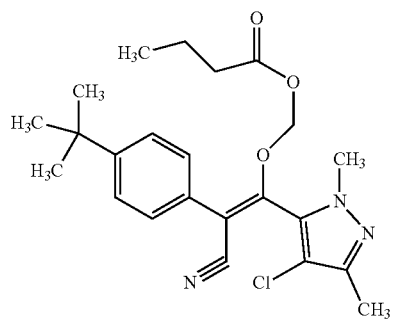 | 649 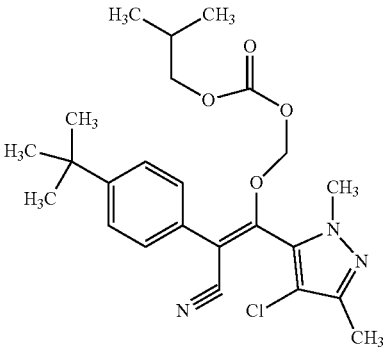 |
| 646 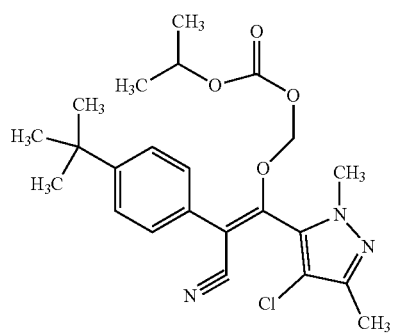 | 652 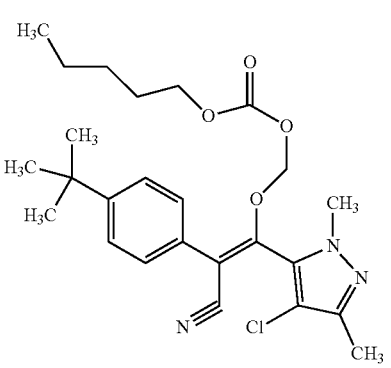 |
| 648 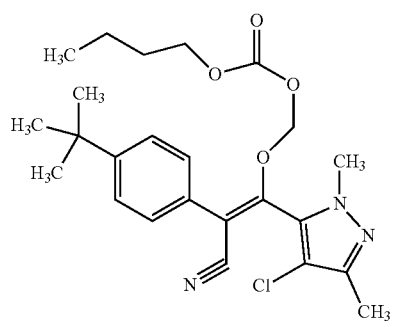 | 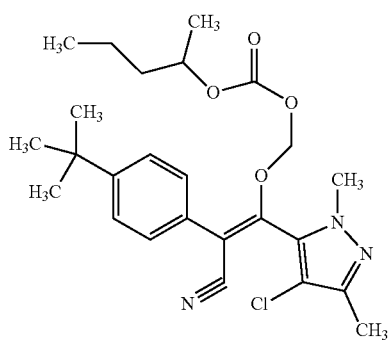 |
| 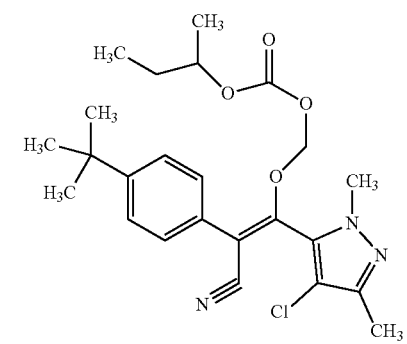 | 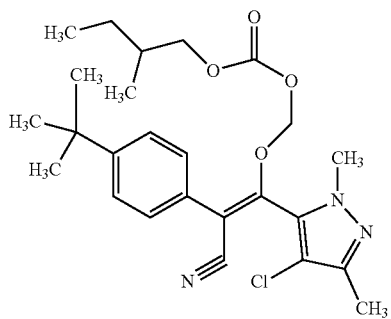 |

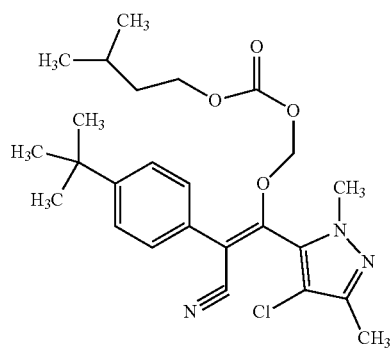
650
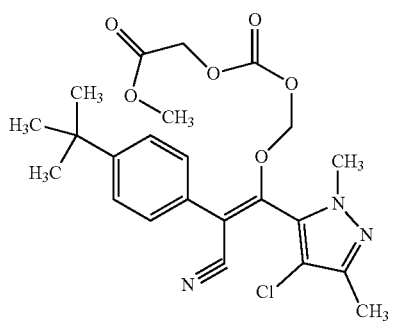
669
654
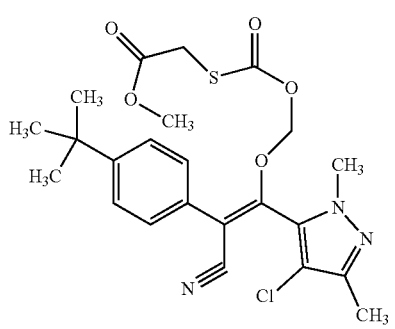
673
659
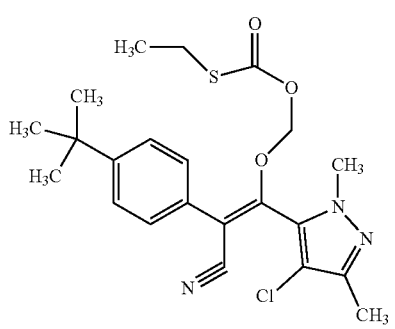
672
660
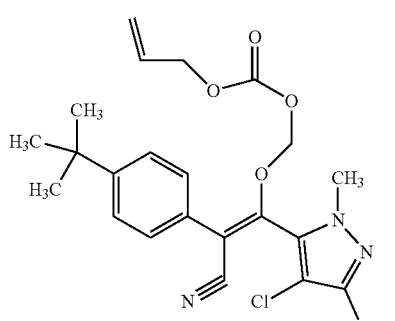
666
663
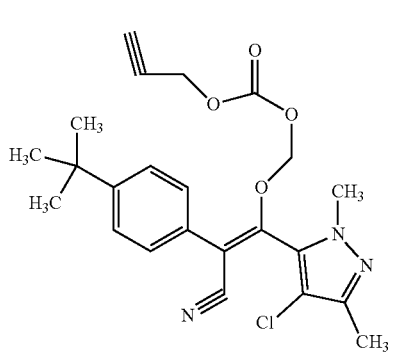
668

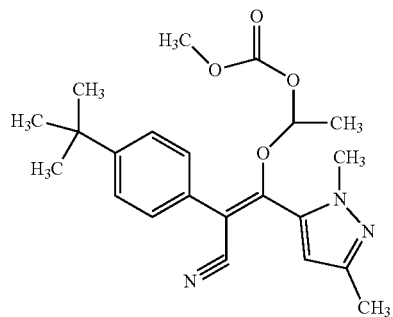
483
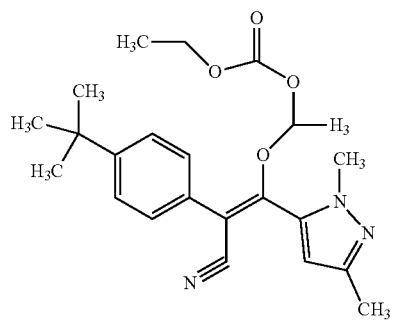
484
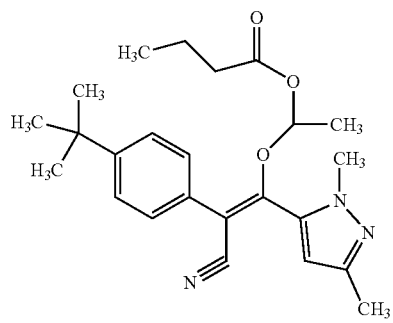
485
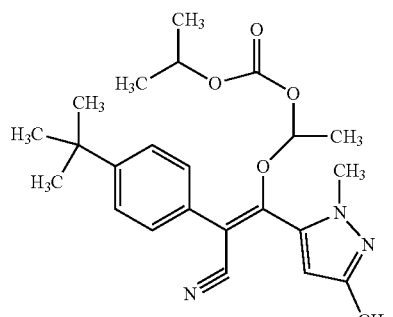
486
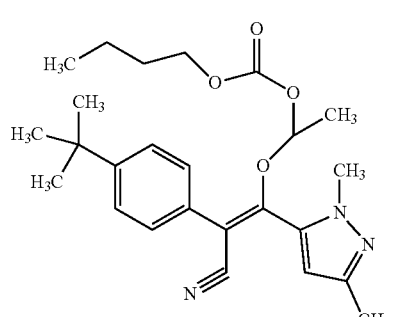
488
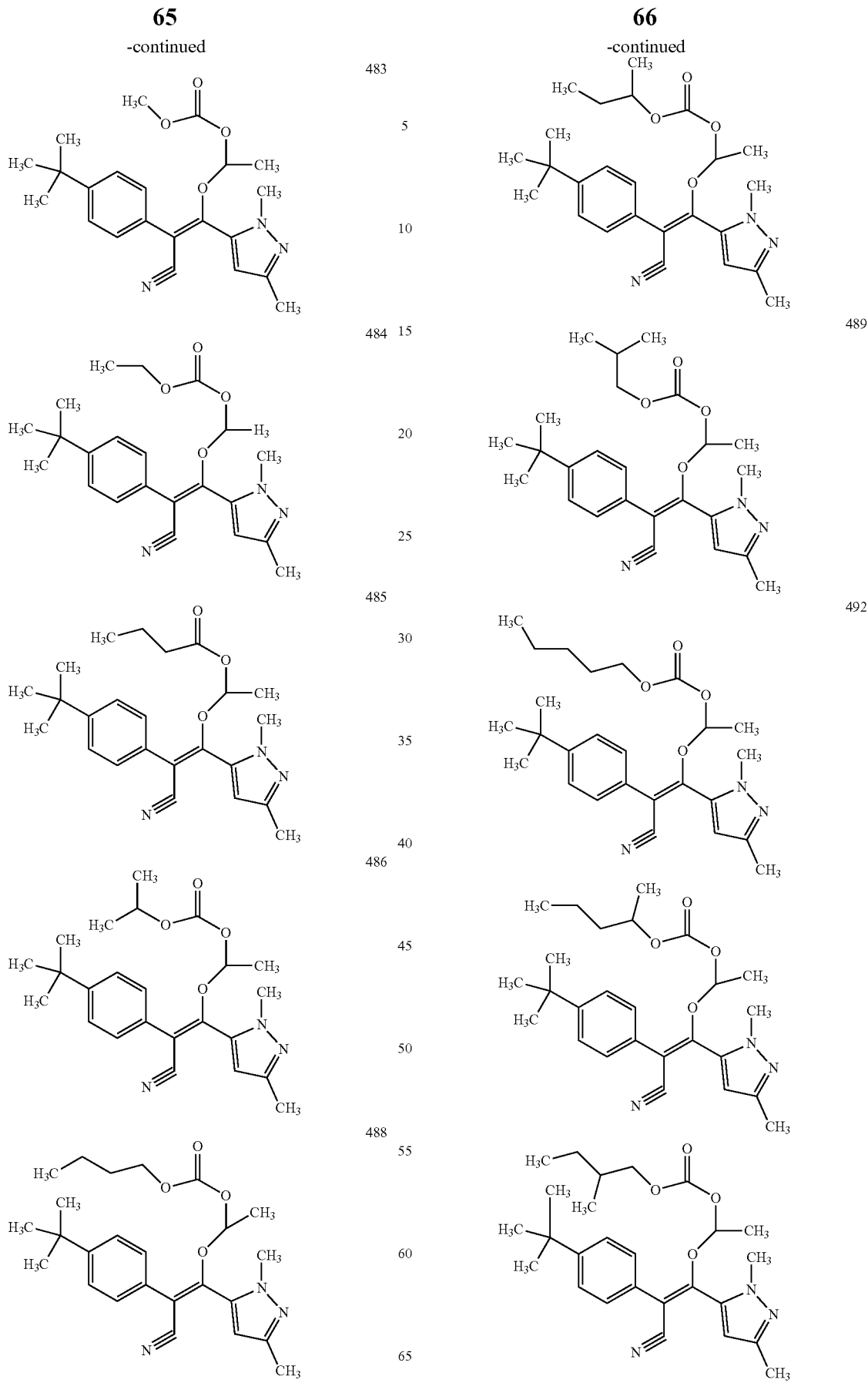

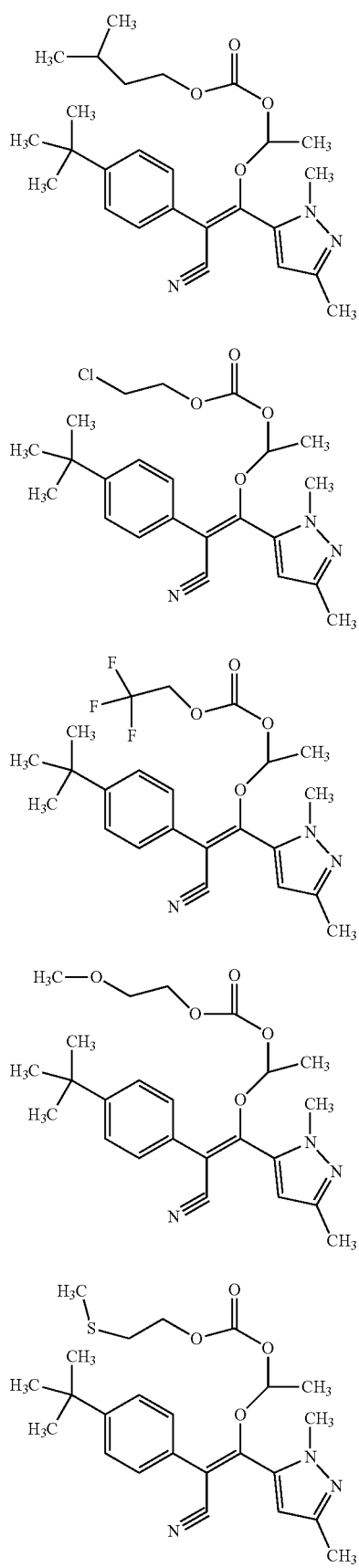
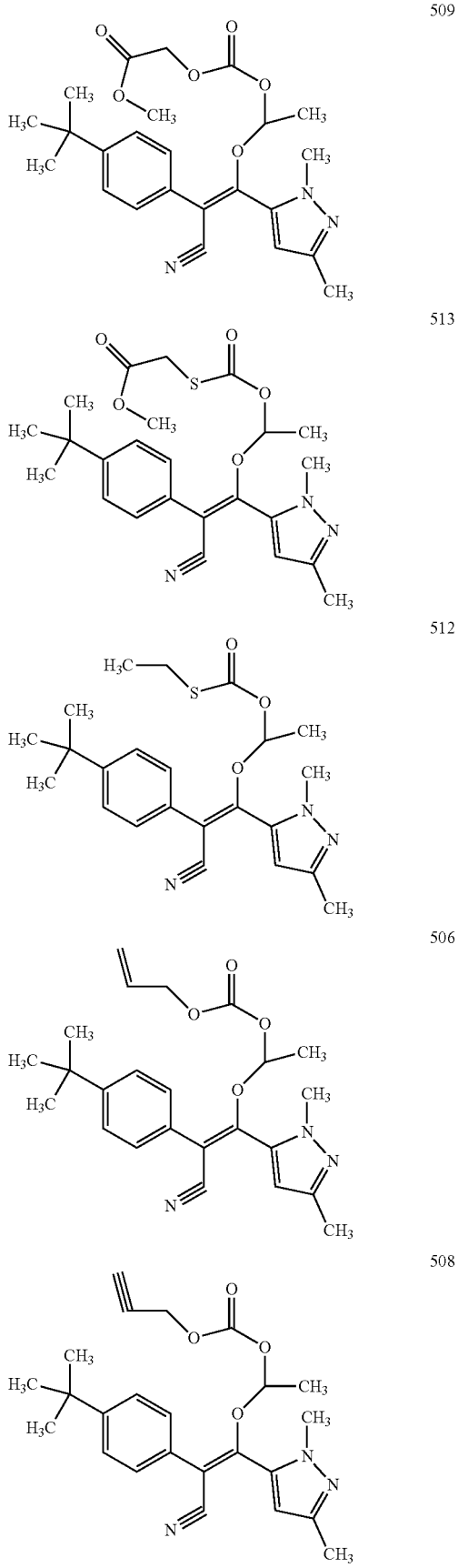 [SMILES: COC(=O)COC(=O)OCO/C(=C(/C#N)c1ccc(C(C)(C)C)cc1)c1c(Cl)c(C)nn1C ; COC(=O)CSC(=O)OCO/C(=C(/C#N)c1ccc(C(C)(C)C)cc1)c1c(Cl)c(C)nn1C ; CCSC(=O)OCO/C(=C(/C#N)c1ccc(C(C)(C)C)cc1)c1c(Cl)c(C)nn1C ; C=CCOC(=O)OCO/C(=C(/C#N)c1ccc(C(C)(C)C)cc1)c1c(Cl)c(C)nn1C ; C#CCOC(=O)OCO/C(=C(/C#N)c1ccc(C(C)(C)C)cc1)c1c(Cl)c(C)nn1C]

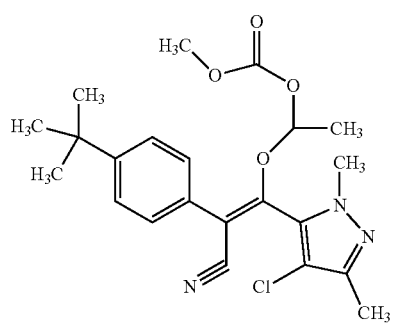
675
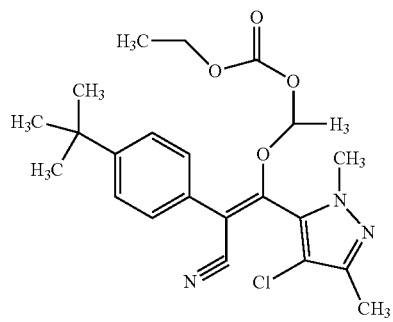
676
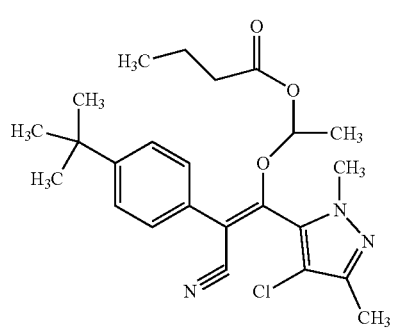
677
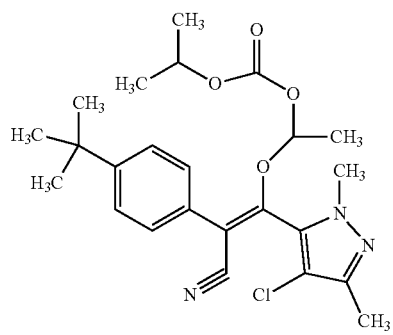
678
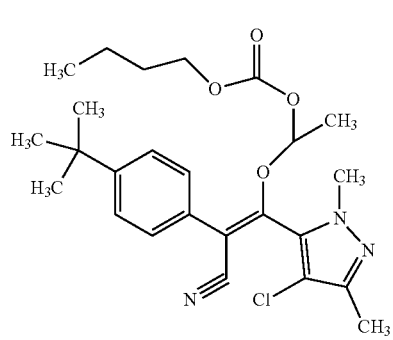
680
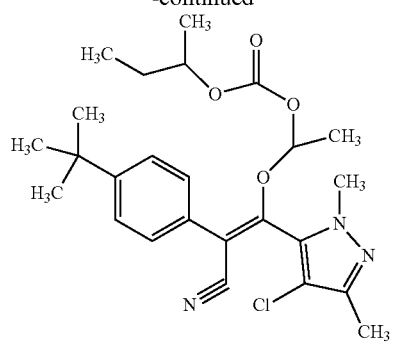
5
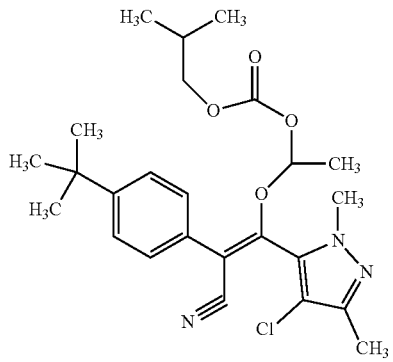
681
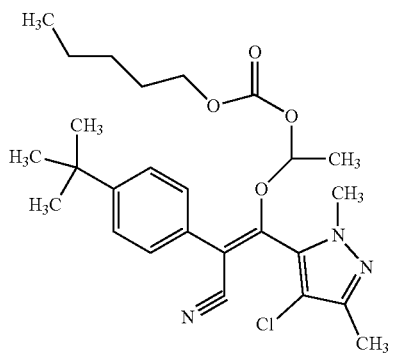
684
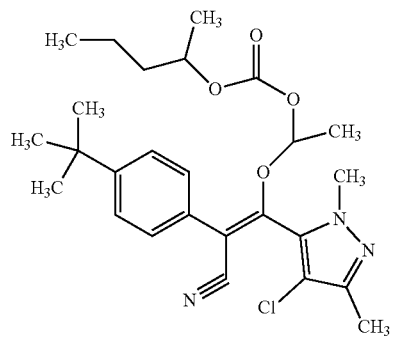

71
-continued
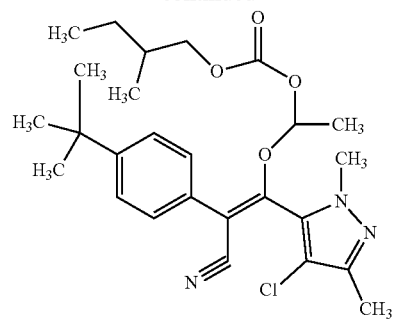
682
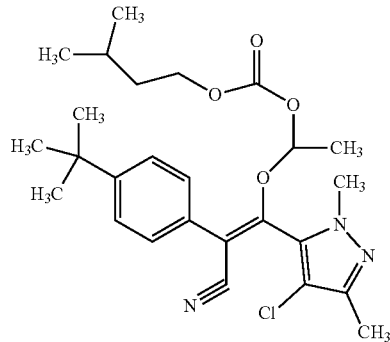
686
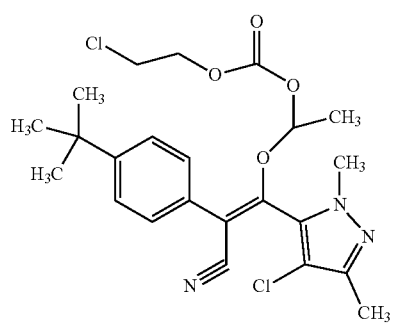
691
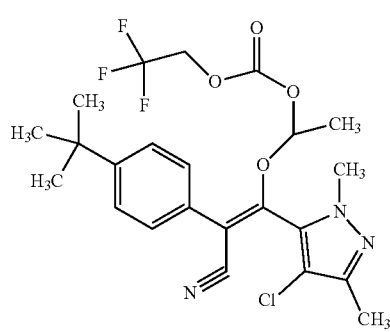
692
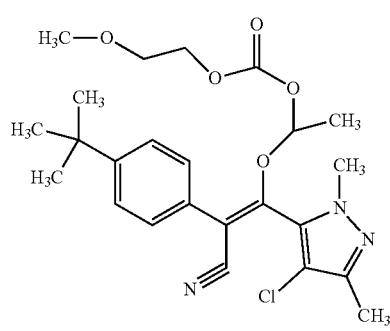
72
-continued
695
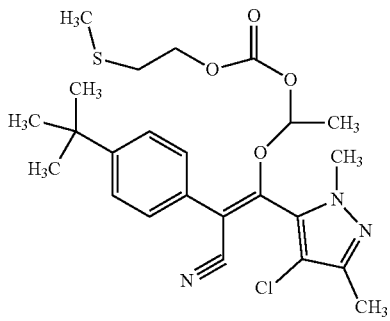
701
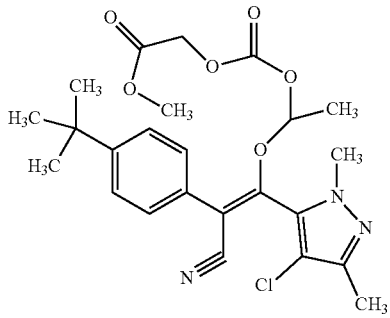
705
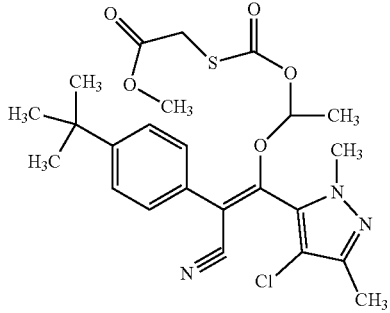
704
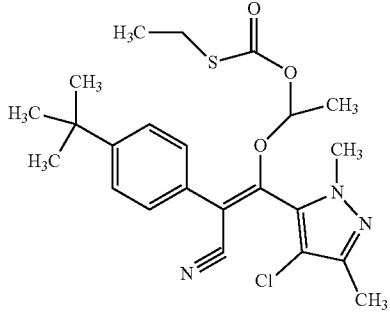
698
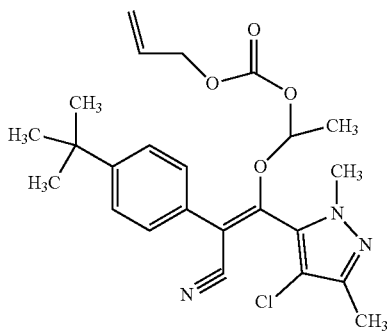

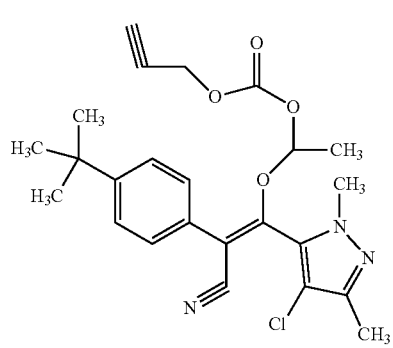
700
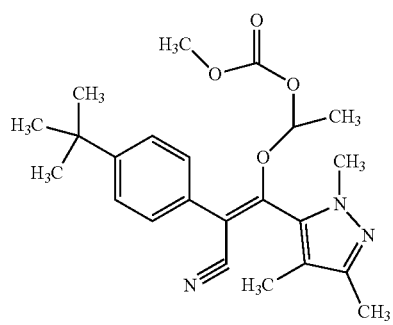
867
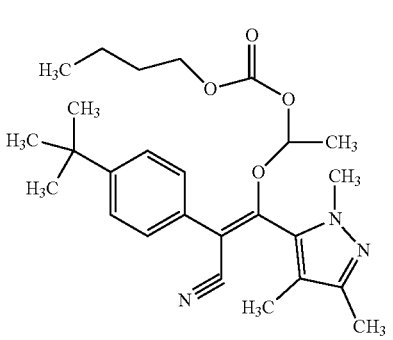
868
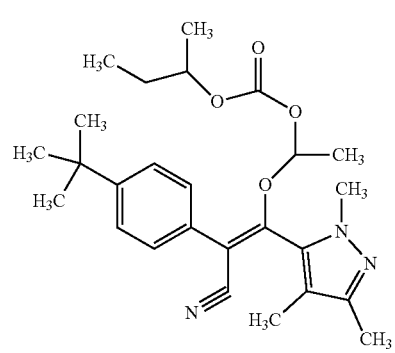
869
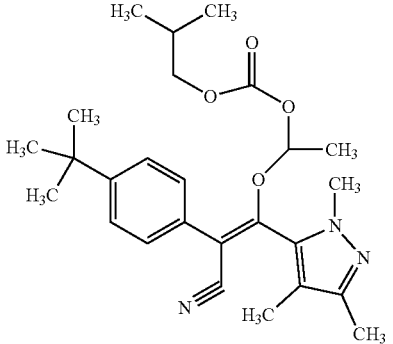
870
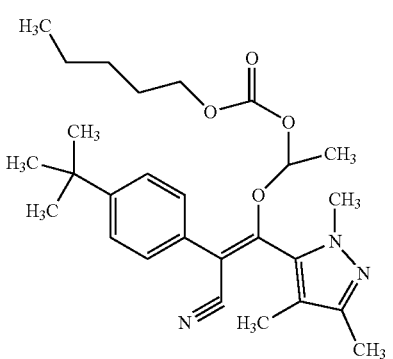

75
-continued
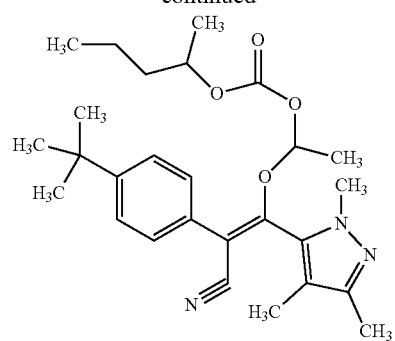
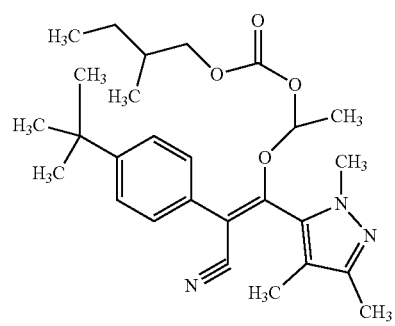
874
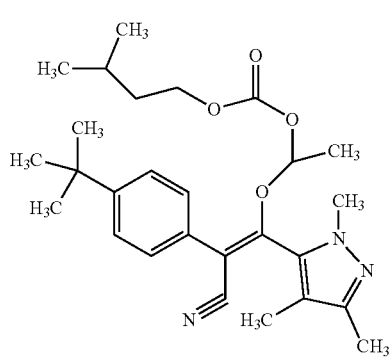
878
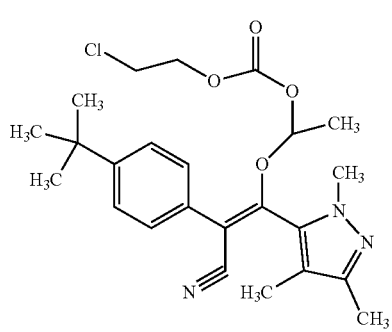
883
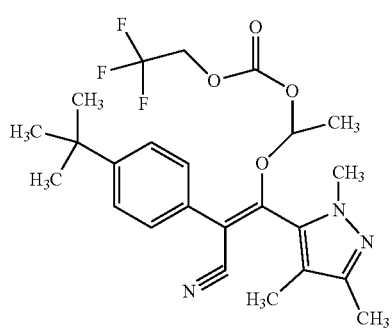
76
-continued
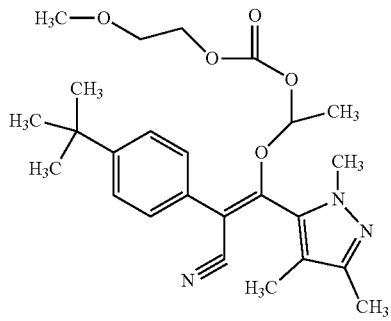
884
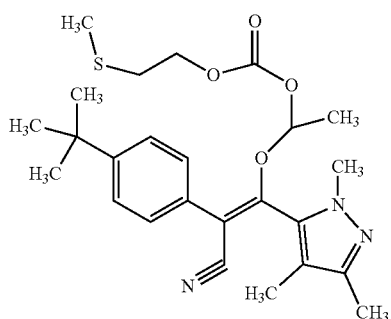
887
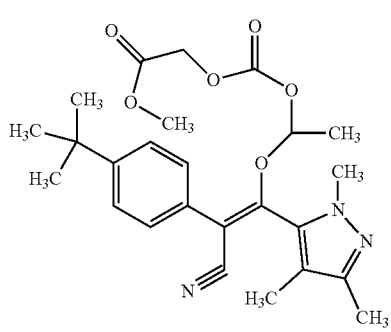
894
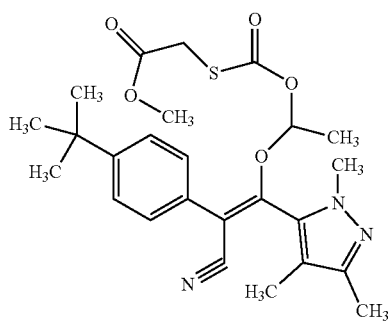
897
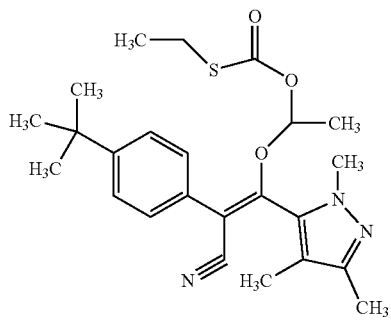
896

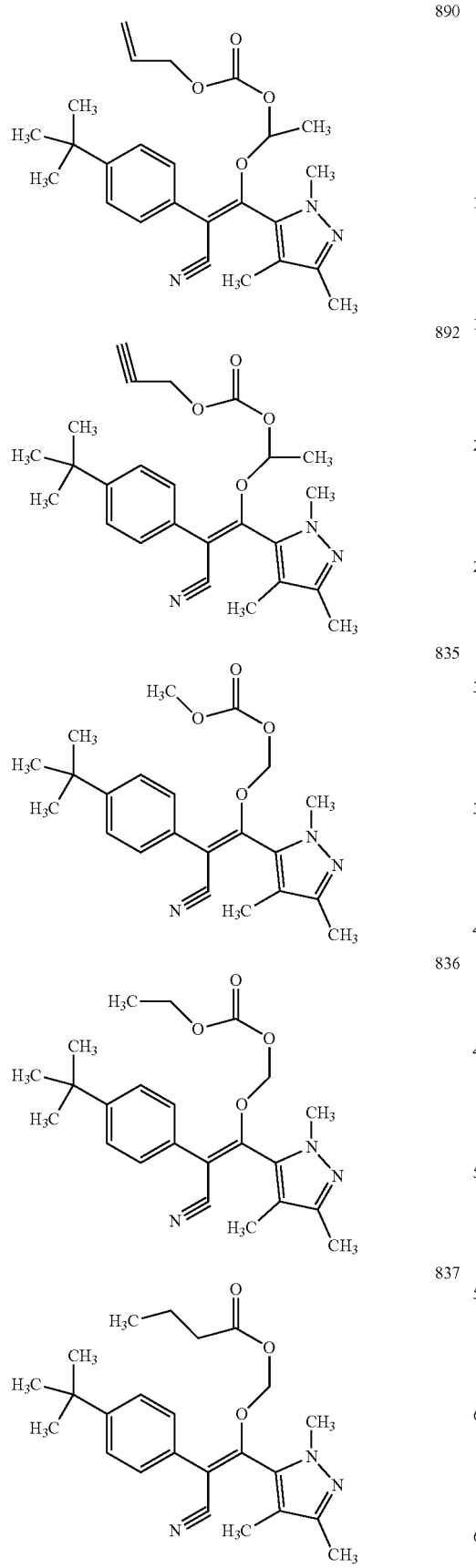
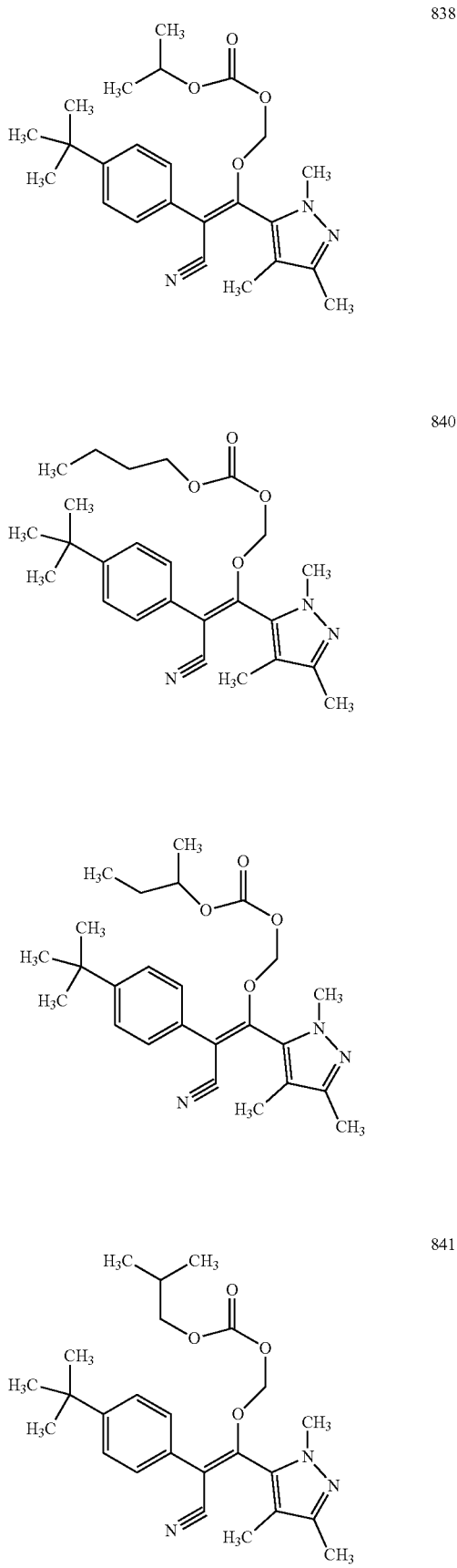

US 11,104,648 B2
79 -continued
844
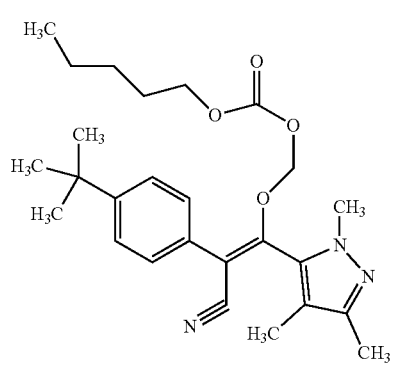
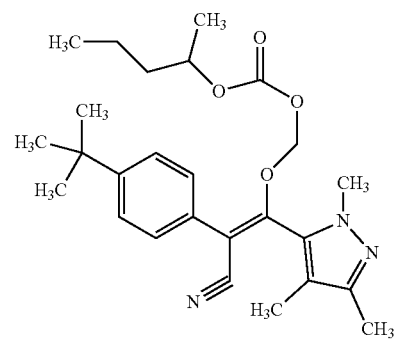
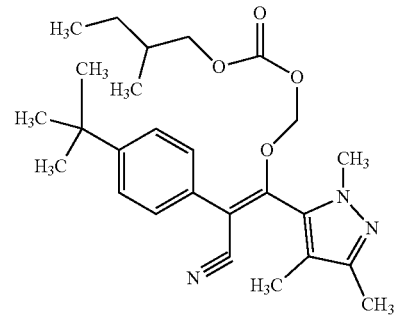
842
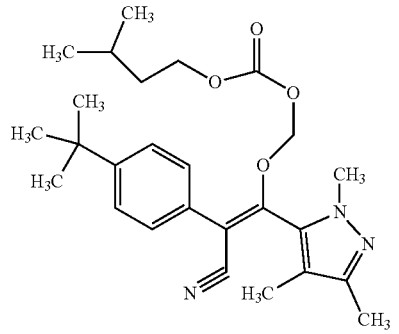
846
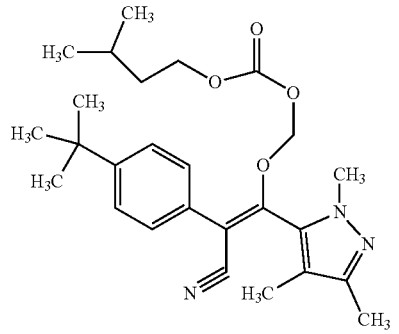
80 -continued
851
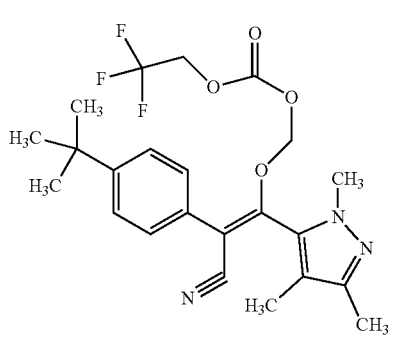
853
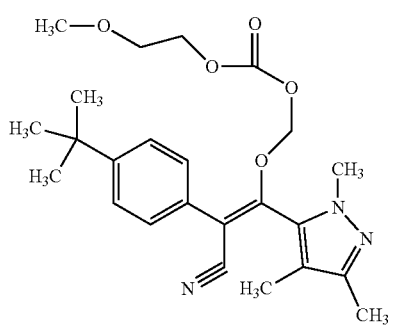
855
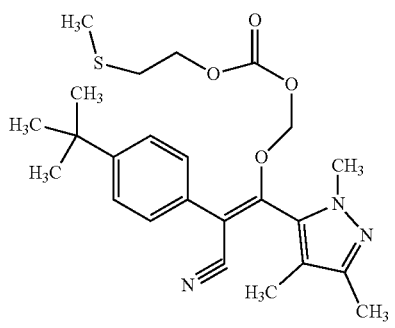
862
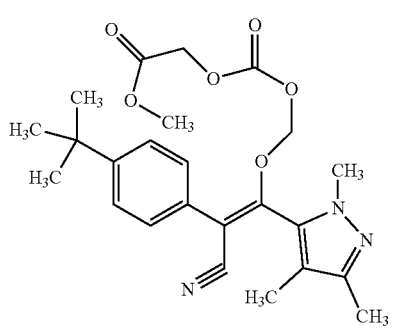
864
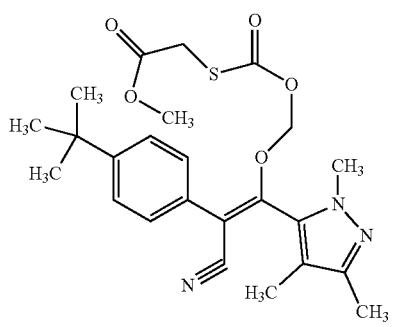

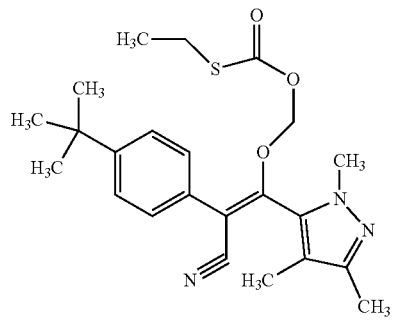
864
858
860
547
548
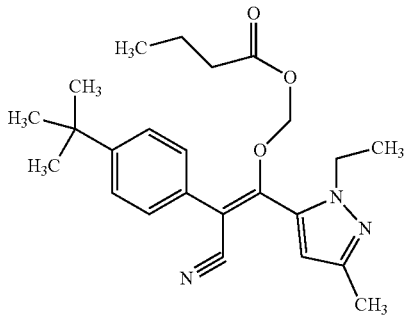
549
550
552
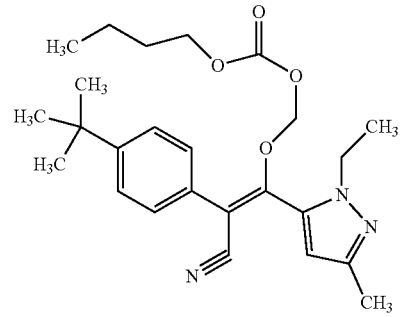
553
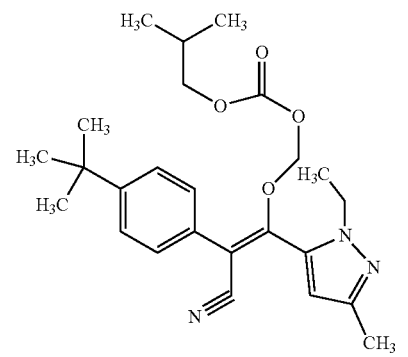

556
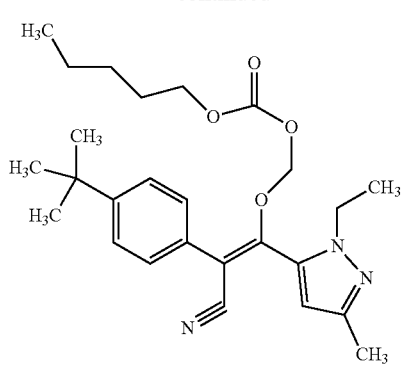
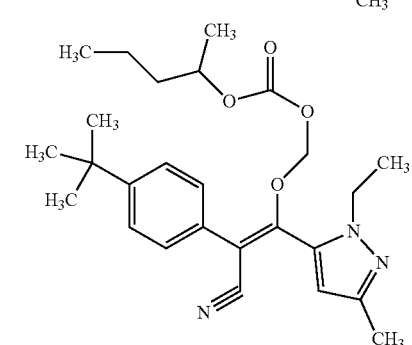
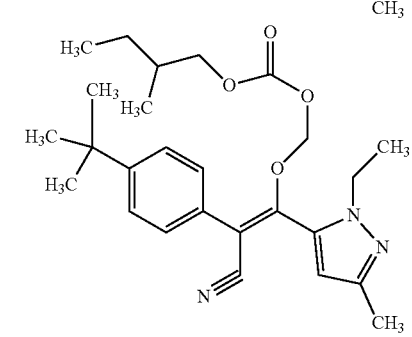
554
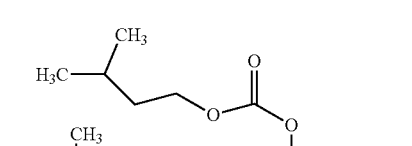
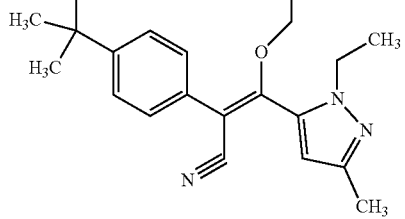
558
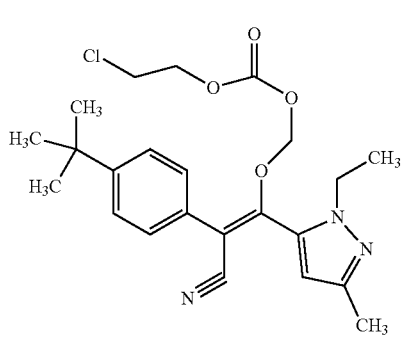
563
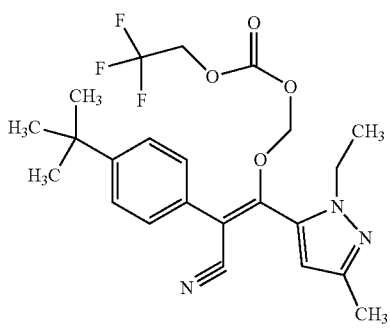
564
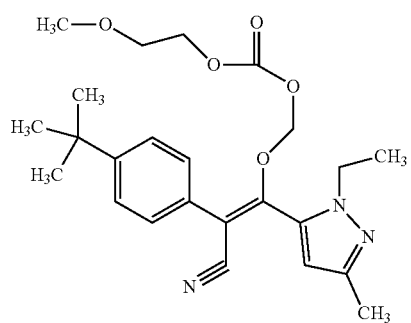
567
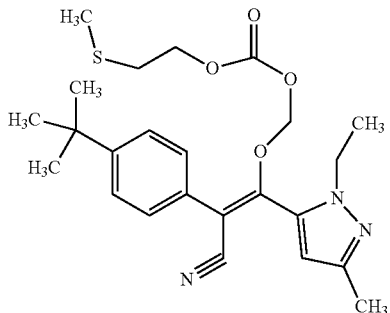
573
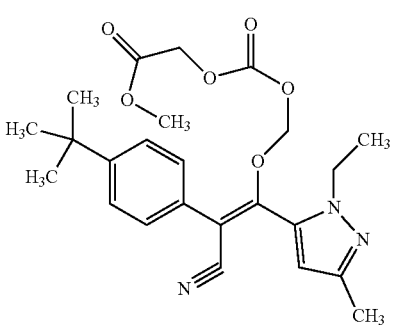
577
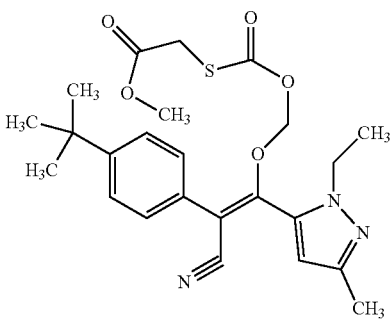

576
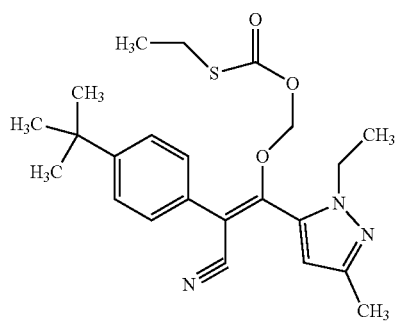
570
572
579
580
581
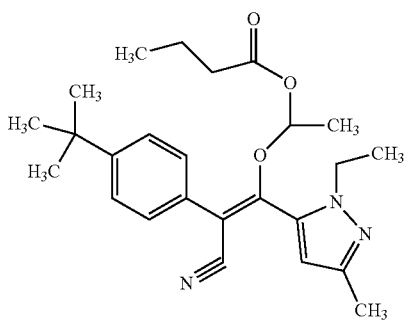
582
584
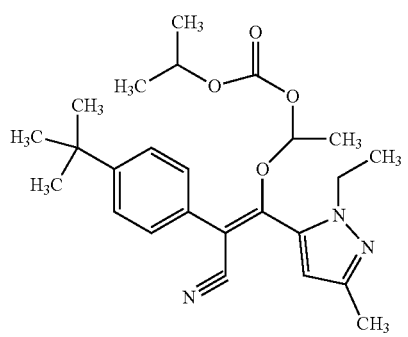
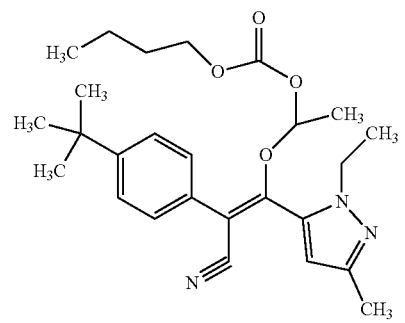
585
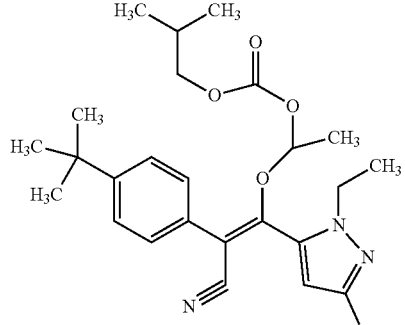

588
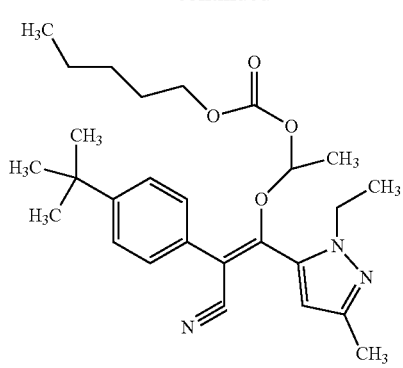
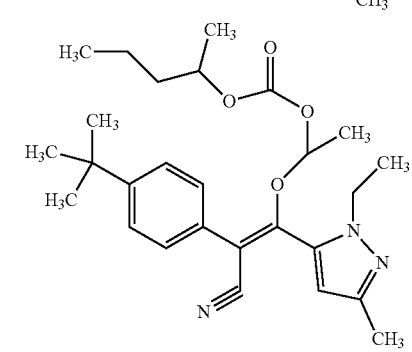
586
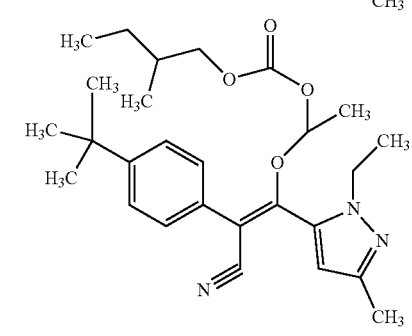
590
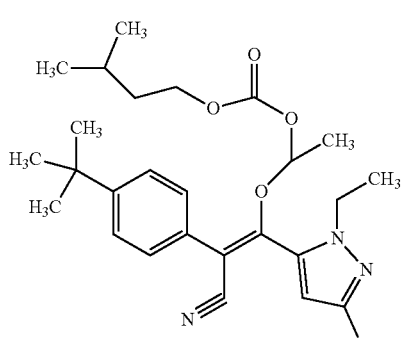
595
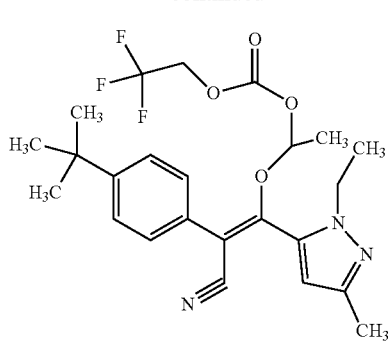
596
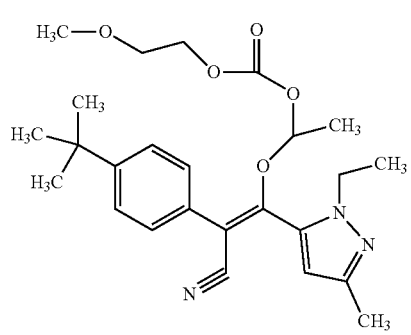
599
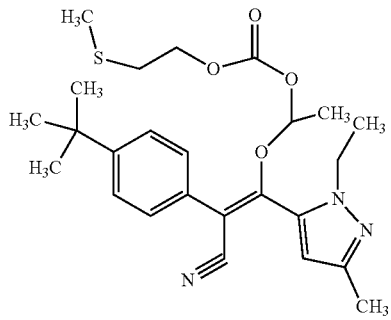
606
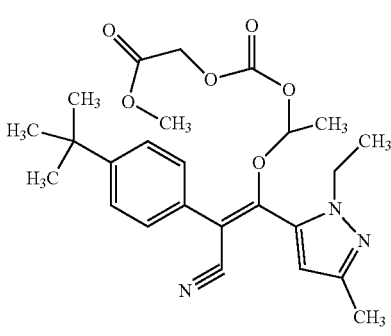
609
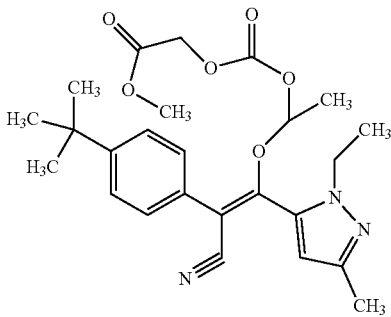

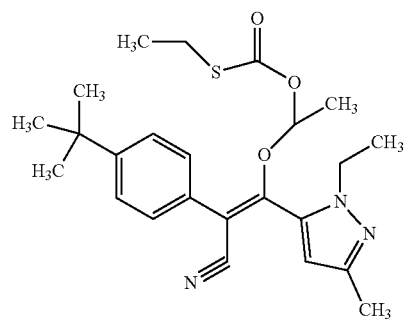
608
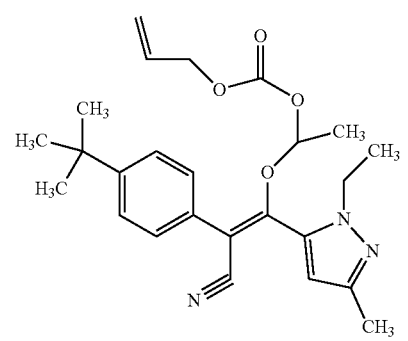
602
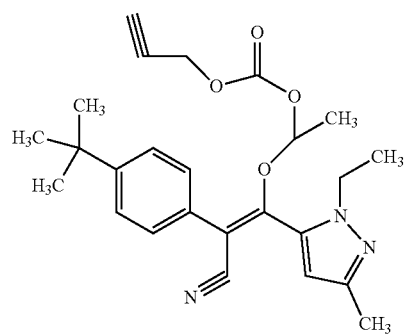
604
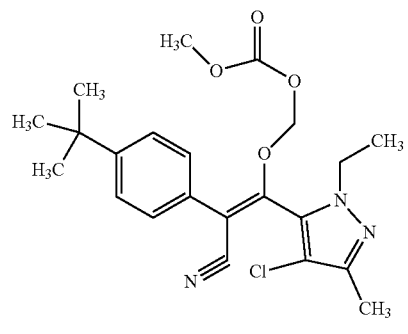
643
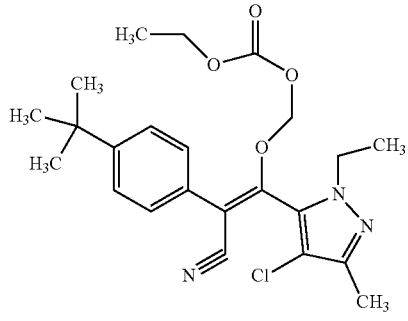
644
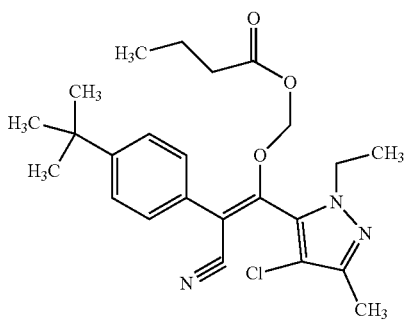
645
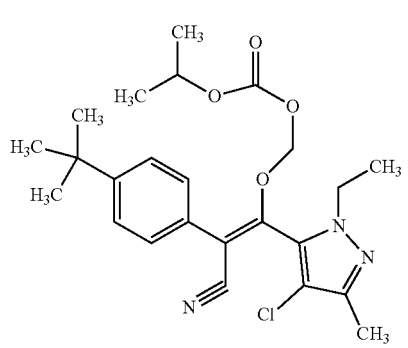
646
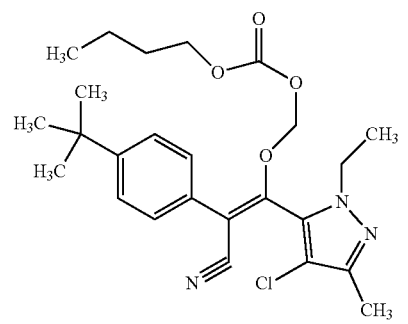
648
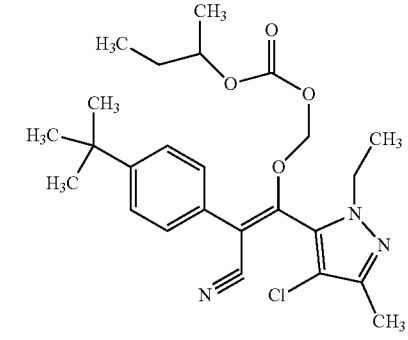

649
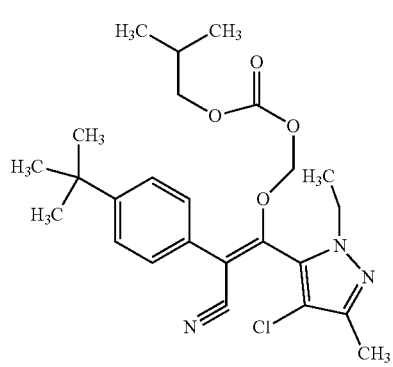
652
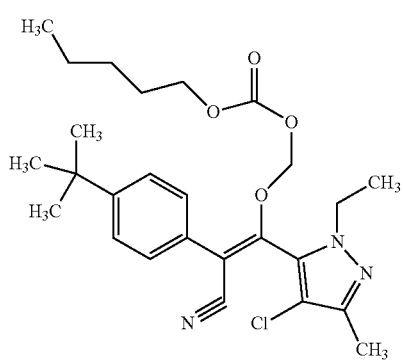
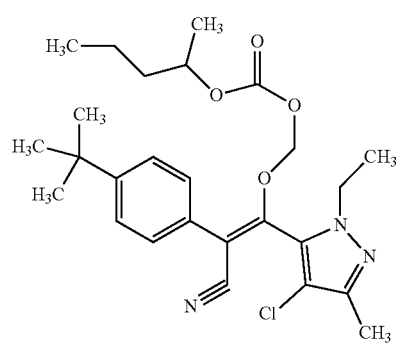
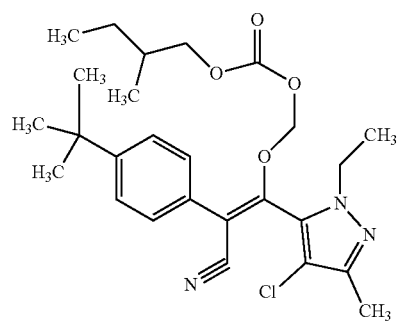
650
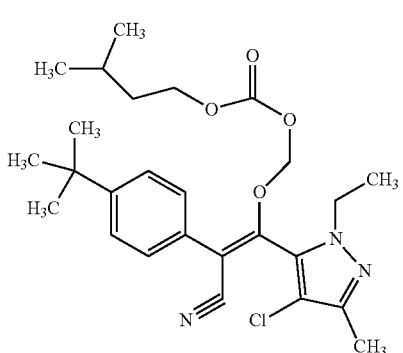
654
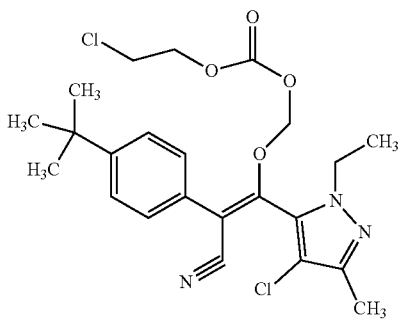
659
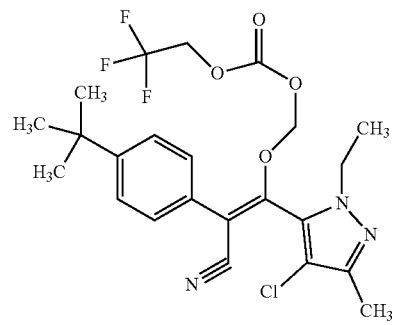
660
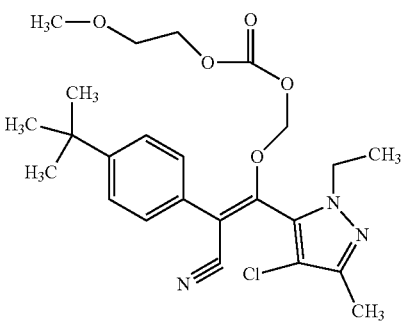
663
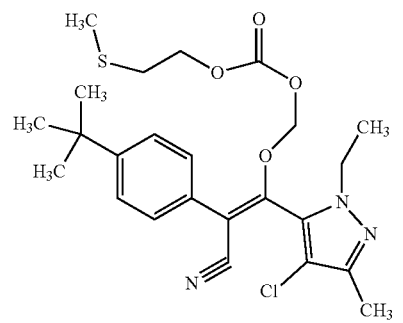

669
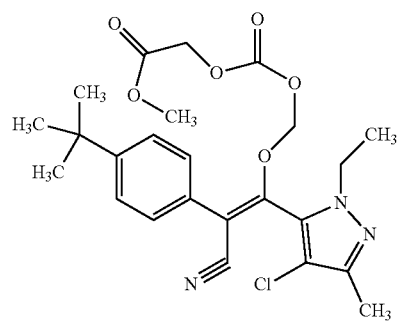
673
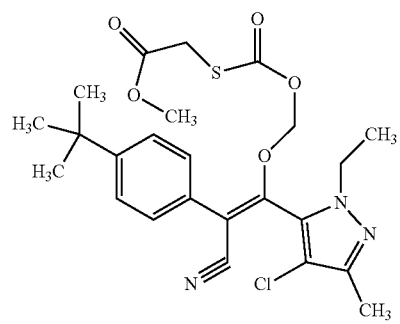
672
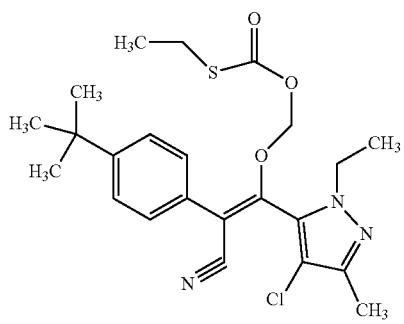
666
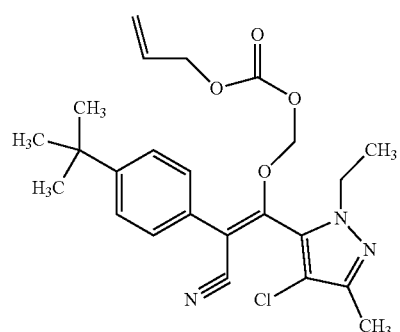
668
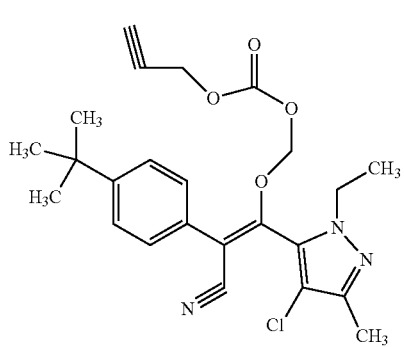
675
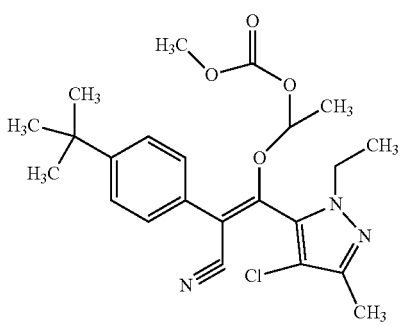
676
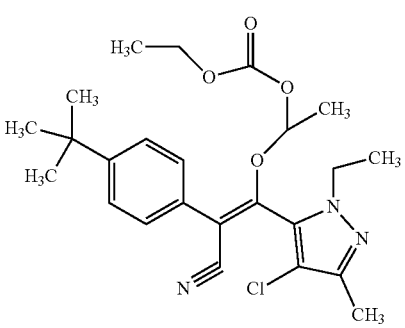
677
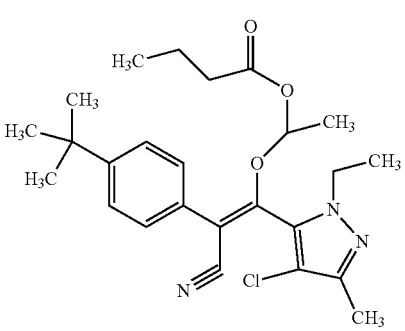
678
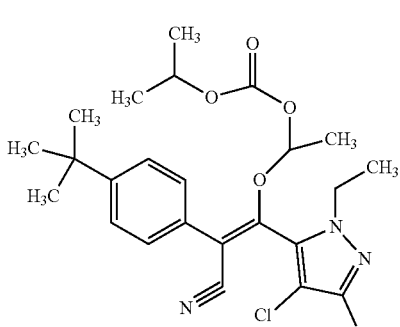
680
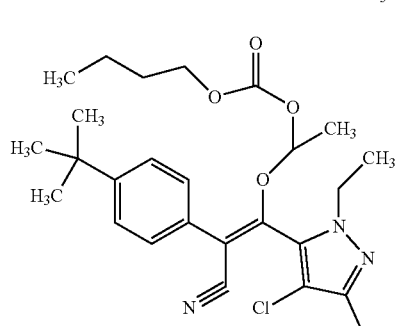

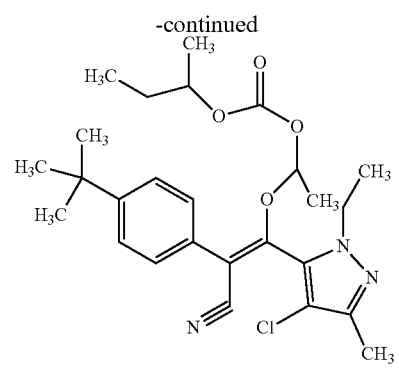
681
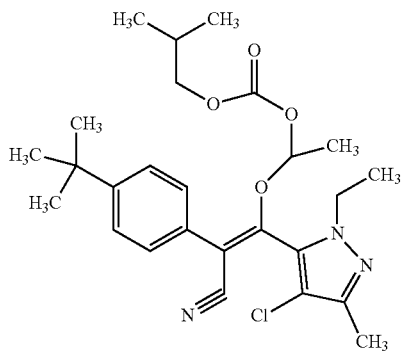
684
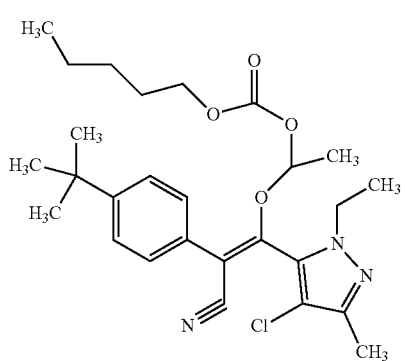
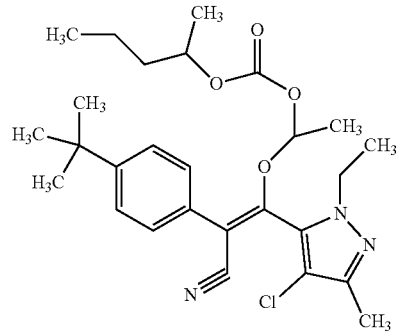
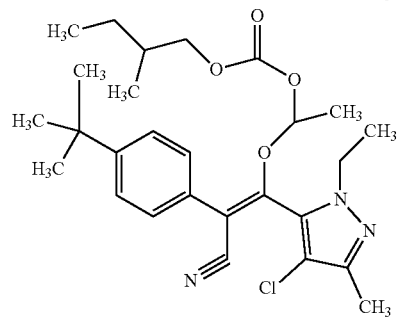
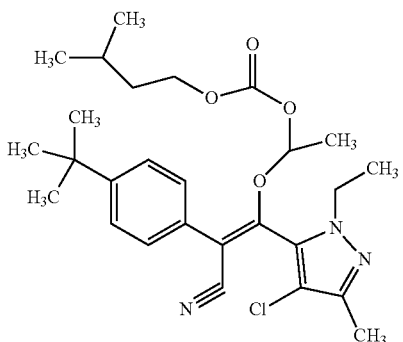
682
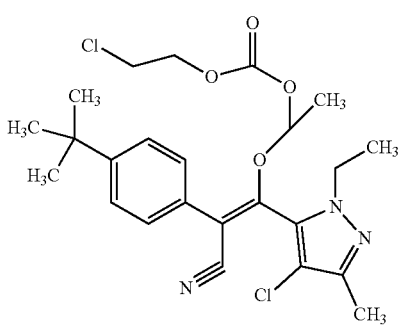
686
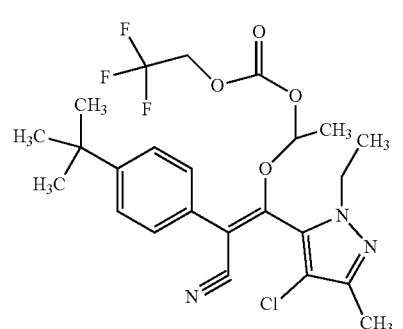
691
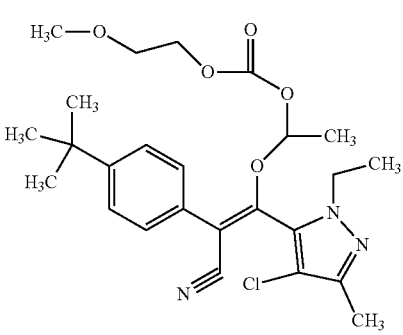
692
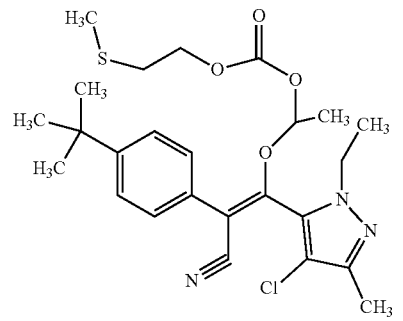
695

701
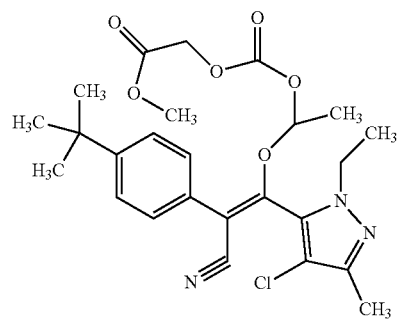
705
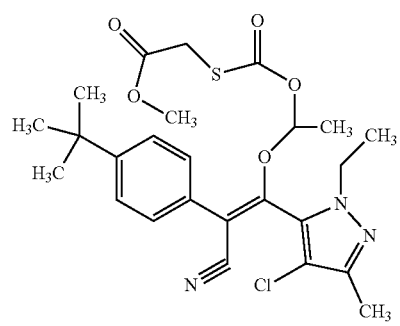
704
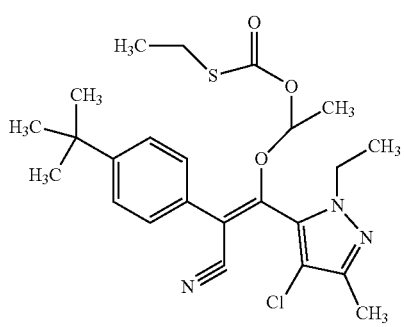
698
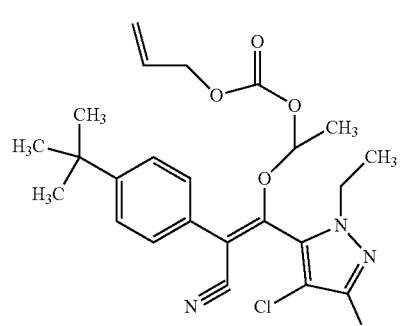
700
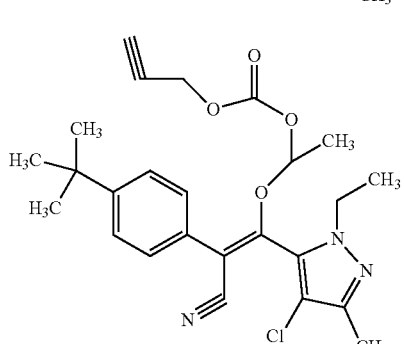
835
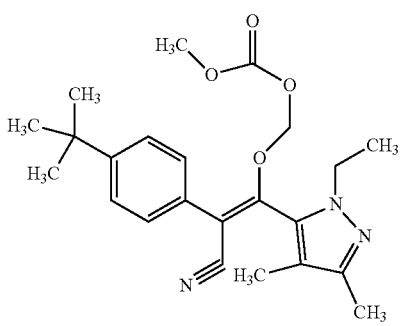
836
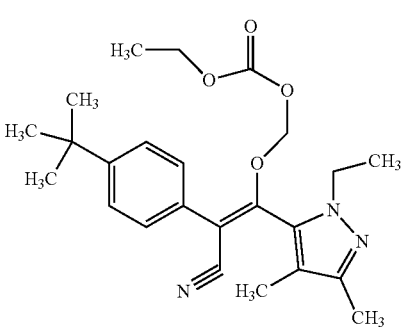
837
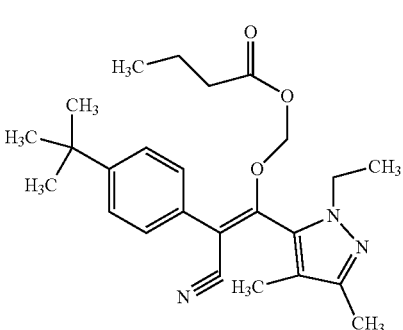
838
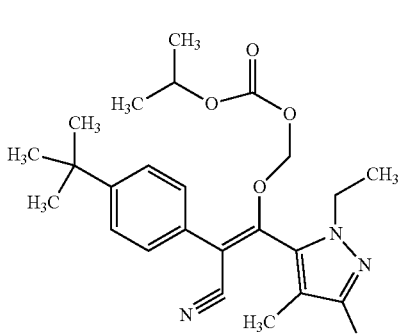
840
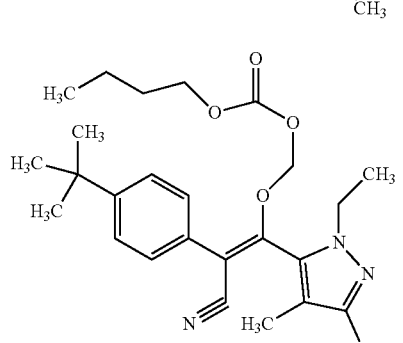

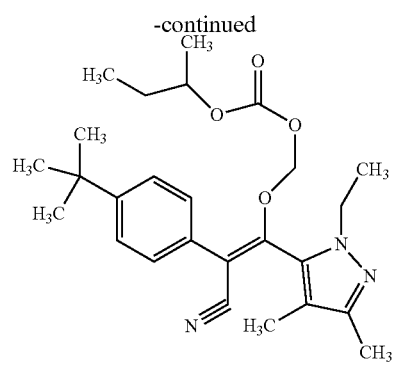
841
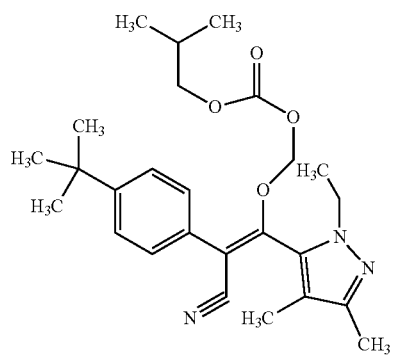
844
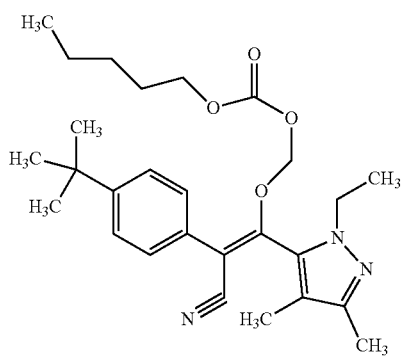
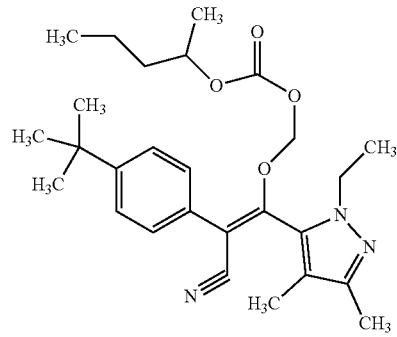
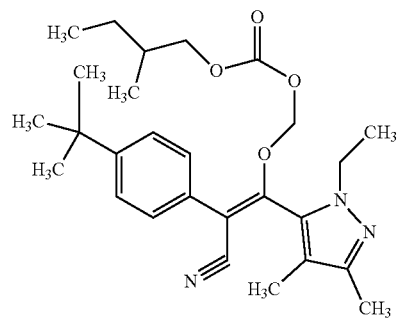
842
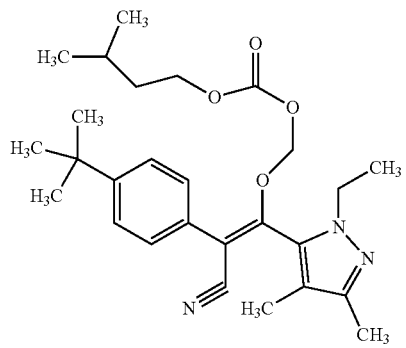
846
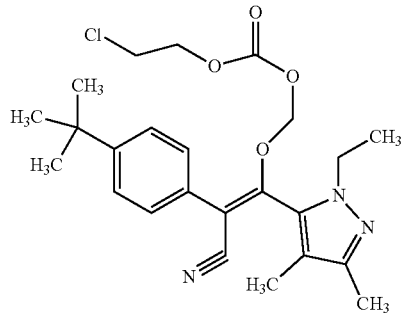
851
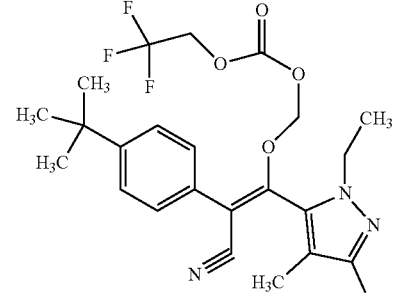
853
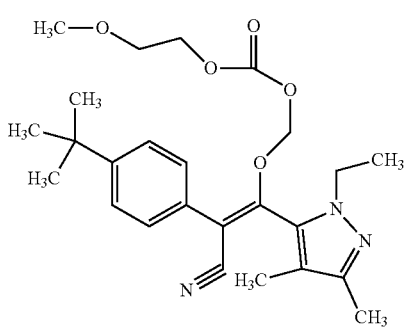
855
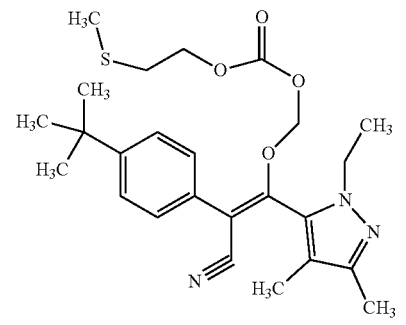

US 11,104,648 B2
| 101 | 102 |
|---|---|
| -continued | -continued |
862
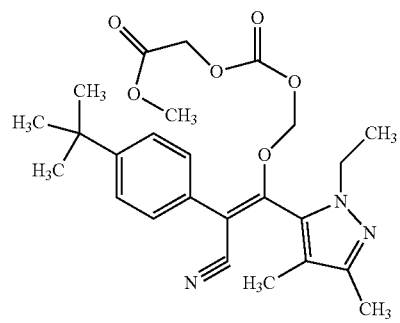
867
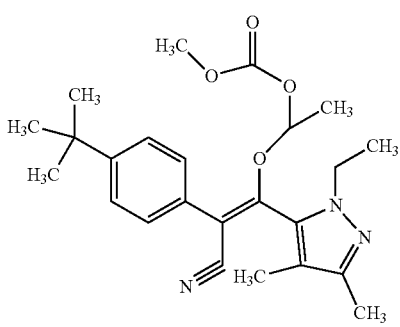
865
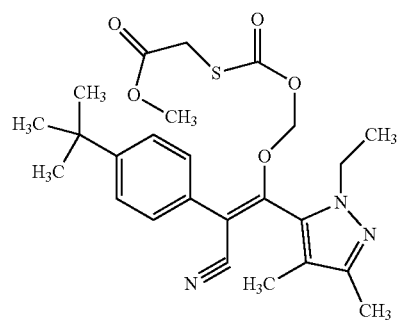
868
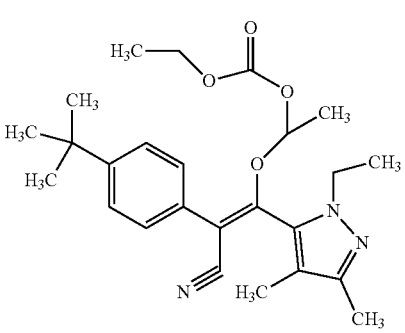
964
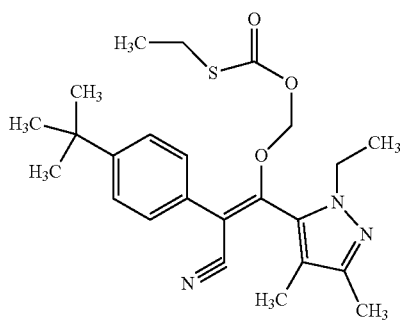
869
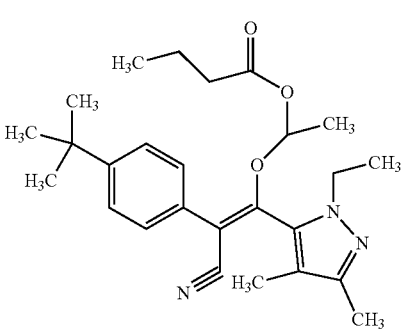
858
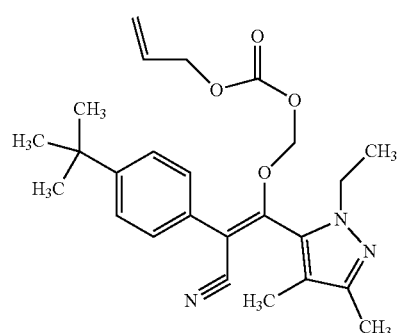
870
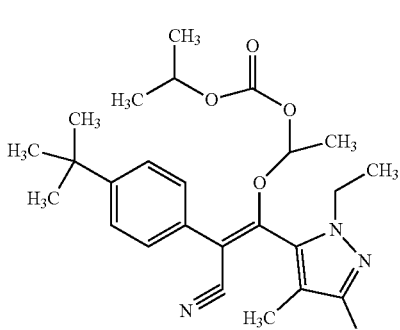
860
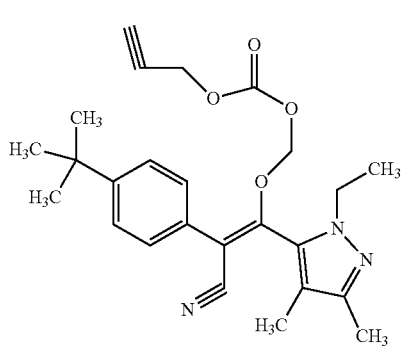
872
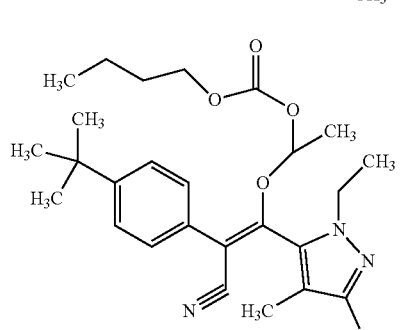

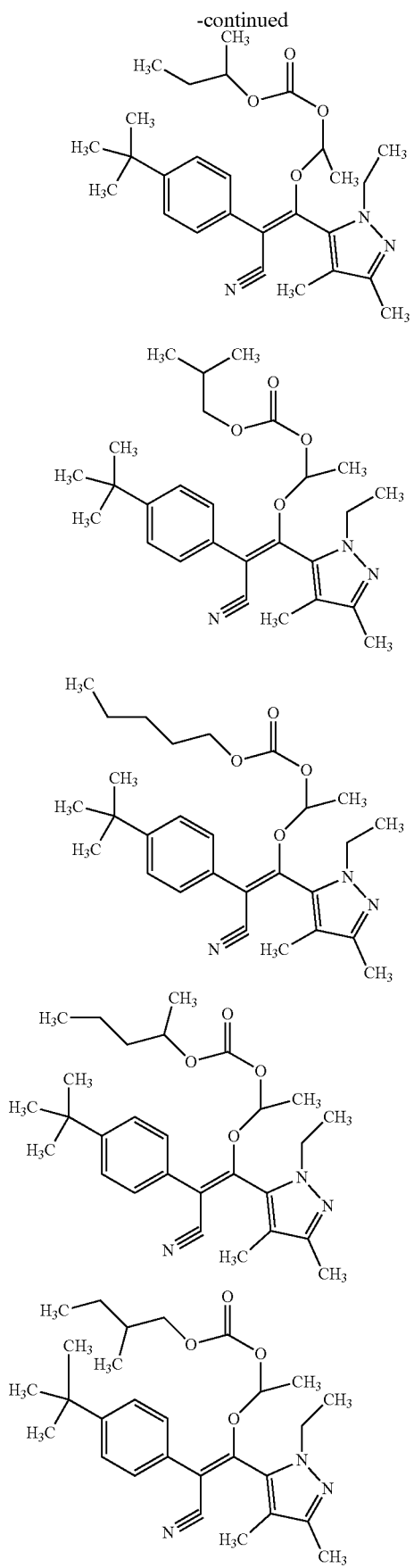
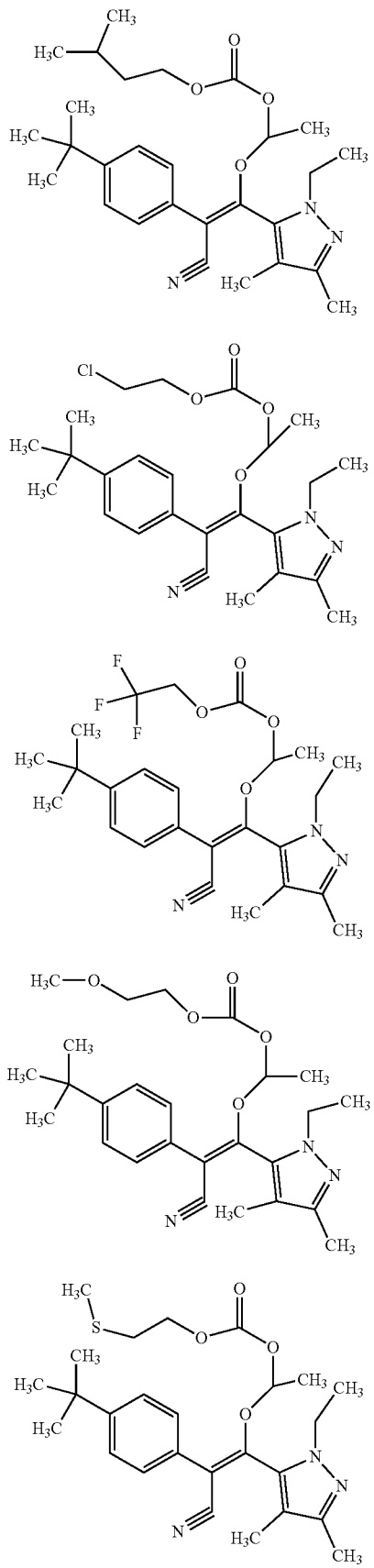

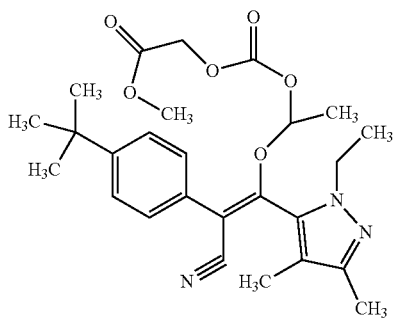

894

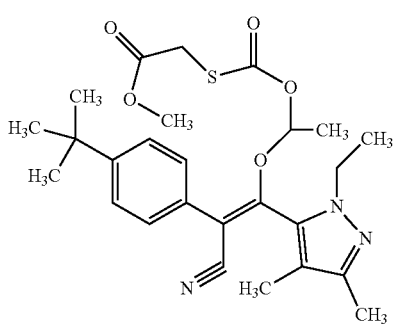

897

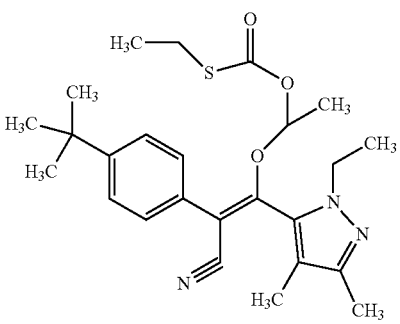

896

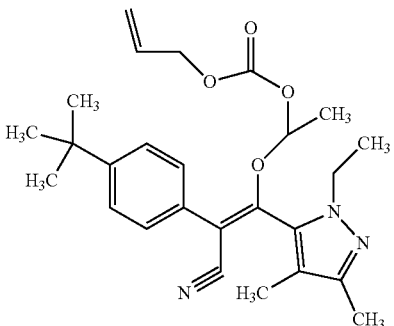

890

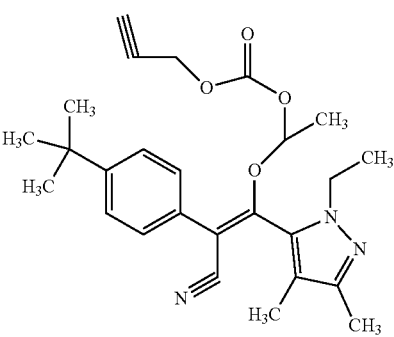

892

For pyrazole derivatives represented by the above numbers, preferably, the compound is an E-pyrazole derivative, that is, E-isomer.

The pyrazole derivatives represented by the formula stru-1 provided herein comprise at least one selected from the group consisting of an E-type pyrazole derivative and a Z-type pyrazole derivative. When the pyrazole derivative comprises an E-type pyrazole derivative and a Z-type pyrazole derivative, the E-type pyrazole derivative and the Z-type pyrazole derivative may be present in any ratio.

For pyrazole derivatives represented by the formula stru-1 provided herein when substituents R1, R2, R4, and R5 are hydrogen and Q is oxygen, as an example, when the pyrazole derivative represented by the formula stru-1 is an E-type compound, the pyrazole derivative represented by the formula stru-1 may be a compound shown in Table 1.

TABLE 1

| No. | R3 | R9 | R8 | R6 | R7 | L-R10 |
|---|---|---|---|---|---|---|
| 1. | $(CH_3)_3C$ | H | $CH_3$ | $CH_3$ | H | $CH_3$ |
| 2. | $(CH_3)_3C$ | H | $CH_3$ | $CH_3$ | H | $CH_3CH_2$ |
| 3. | $(CH_3)_3C$ | H | $CH_3$ | $CH_3$ | H | $CH_3CH_2CH_2$ |
| 4. | $(CH_3)_3C$ | H | $CH_3$ | $CH_3$ | H | $(CH_3)_2CH$ |
| 5. | $(CH_3)_3C$ | H | $CH_3$ | $CH_3$ | H | $(CH_3)_3C$ |
| 6. | $(CH_3)_3C$ | H | $CH_3$ | $CH_3$ | H | $CH_3CH_2CH_2CH_2$ |
| 7. | $(CH_3)_3C$ | H | $CH_3$ | $CH_3$ | H | $(CH_3)_2CHCH_2$ |
| 8. | $(CH_3)_3C$ | H | $CH_3$ | $CH_3$ | H | $CH_3OCH_2$ |
| 9. | $(CH_3)_3C$ | H | $CH_3$ | $CH_3$ | H | ▷ |
| 10. | $(CH_3)_3C$ | H | $CH_3$ | $CH_3$ | H | $CH_3SCH_2$ |
| 11. | $(CH_3)_3C$ | H | $CH_3$ | $CH_3$ | H | ⬡ |
| 12. | $(CH_3)_3C$ | H | $CH_3$ | $CH_3$ | H | $FCH_2$ |
| 13. | $(CH_3)_3C$ | H | $CH_3$ | $CH_3$ | H | $F_3C$ |

TABLE 1-continued

| No. | R3 | R9 | R8 | R6 | R7 | L-R10 |
|---|---|---|---|---|---|---|
| 14. | (CH$_3$)$_3$C | H | CH$_3$ | CH$_3$ | H | C$_6$H$_5$ |
| 15. | (CH$_3$)$_3$C | H | CH$_3$ | CH$_3$ | H | C$_6$H$_5$CH$_2$ |
| 16. | (CH$_3$)$_3$C | H | CH$_3$ | CH$_3$ | H | CH$_3$CH$_2$(CH$_3$)$_2$C |
| 17. | (CH$_3$)$_3$C | H | CH$_3$ | CH$_3$ | H | CH2=CH |
| 18. | (CH$_3$)$_3$C | H | CH$_3$ | CH$_3$ | H | CH$_3$CH$_2$OCH$_2$ |
| 19. | (CH$_3$)$_3$C | H | CH$_3$ | CH$_3$ | H | CH$_3$CH$_2$SCH$_2$ |
| 20. | (CH$_3$)$_3$C | H | CH$_3$ | CH$_3$ | H | 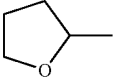 |
| 21. | (CH$_3$)$_3$C | H | CH$_3$ | CH$_3$ | H | 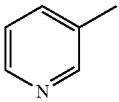 |
| 22. | (CH$_3$)$_3$C | H | CH$_3$ | CH$_3$ | H | CF$_3$CH$_2$SCH$_2$ |
| 23. | (CH$_3$)$_3$C | H | CH$_3$ | CH$_3$ | H | ClCH$_2$CH$_2$ |
| 24. | (CH$_3$)$_3$C | H | CH$_3$ | CH$_3$ | H | ClCH$_2$CH$_2$CH$_2$ |
| 25. | (CH$_3$)$_3$C | H | CH$_3$ | CH$_3$ | H | NCCH2 |
| 26. | (CH$_3$)$_3$C | CH$_3$ | CH$_3$ | CH$_3$ | H | CH$_3$ |
| 27. | (CH$_3$)$_3$C | CH$_3$ | CH$_3$ | CH$_3$ | H | CH$_3$CH$_2$ |
| 28. | (CH$_3$)$_3$C | CH$_3$ | CH$_3$ | CH$_3$ | H | CH$_3$CH$_2$CH$_2$ |
| 29. | (CH$_3$)$_3$C | CH$_3$ | CH$_3$ | CH$_3$ | H | (CH$_3$)$_2$CH |
| 30. | (CH$_3$)$_3$C | CH$_3$ | CH$_3$ | CH$_3$ | H | (CH$_3$)$_3$C |
| 31. | (CH$_3$)$_3$C | CH$_3$ | CH$_3$ | CH$_3$ | H | CH$_3$CH$_2$CH$_2$CH$_2$ |
| 32. | (CH$_3$)$_3$C | CH$_3$ | CH$_3$ | CH$_3$ | H | (CH$_3$)$_2$CHCH$_2$ |
| 33. | (CH$_3$)$_3$C | CH$_3$ | CH$_3$ | CH$_3$ | H | CH$_3$OCH$_2$ |
| 34. | (CH$_3$)$_3$C | CH$_3$ | CH$_3$ | CH$_3$ | H |  |
| 35. | (CH$_3$)$_3$C | CH$_3$ | CH$_3$ | CH$_3$ | H | CH$_3$SCH$_2$ |
| 36. | (CH$_3$)$_3$C | CH$_3$ | CH$_3$ | CH$_3$ | H |  |
| 37. | (CH$_3$)$_3$C | CH$_3$ | CH$_3$ | CH$_3$ | H | FCH$_2$ |
| 38. | (CH$_3$)$_3$C | CH$_3$ | CH$_3$ | CH$_3$ | H | F$_3$C |
| 39. | (CH$_3$)$_3$C | CH$_3$ | CH$_3$ | CH$_3$ | H | C$_6$H$_5$ |
| 40. | (CH$_3$)$_3$C | CH$_3$ | CH$_3$ | CH$_3$ | H | C$_6$H$_5$CH$_2$ |
| 41. | (CH$_3$)$_3$C | CH$_3$ | CH$_3$ | CH$_3$ | H | CH$_3$CH$_2$(CH$_3$)$_2$C |
| 42. | (CH$_3$)$_3$C | CH$_3$ | CH$_3$ | CH$_3$ | H | CH2=CH |
| 43. | (CH$_3$)$_3$C | CH$_3$ | CH$_3$ | CH$_3$ | H | CH$_3$CH$_2$OCH$_2$ |
| 44. | (CH$_3$)$_3$C | CH$_3$ | CH$_3$ | CH$_3$ | H | CH$_3$CH$_2$SCH$_2$ |
| 45. | (CH$_3$)$_3$C | CH$_3$ | CH$_3$ | CH$_3$ | H | 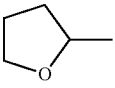 |
| 46. | (CH$_3$)$_3$C | CH$_3$ | CH$_3$ | CH$_3$ | H | 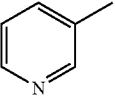 |
| 47. | (CH$_3$)$_3$C | CH$_3$ | CH$_3$ | CH$_3$ | H | CF$_3$CH$_2$SCH$_2$ |
| 48. | (CH$_3$)$_3$C | CH$_3$ | CH$_3$ | CH$_3$ | H | ClCH$_2$CH$_2$ |
| 49. | (CH$_3$)$_3$C | CH$_3$ | CH$_3$ | CH$_3$ | H | ClCH$_2$CH$_2$CH$_2$ |
| 50. | (CH$_3$)$_3$C | CH3 | CH$_3$ | CH$_3$ | H | NCCH2 |
| 51. | (CH$_3$)$_3$C | CH$_3$CH$_2$ | CH$_3$ | CH$_3$ | H | CH$_3$ |
| 52. | (CH$_3$)$_3$C | CH$_3$CH$_2$ | CH$_3$ | CH$_3$ | H | CH$_3$CH$_2$ |
| 53. | (CH$_3$)$_3$C | CH$_3$CH$_2$ | CH$_3$ | CH$_3$ | H | CH$_3$CH$_2$CH$_2$ |
| 54. | (CH$_3$)$_3$C | CH$_3$CH$_2$ | CH$_3$ | CH$_3$ | H | (CH$_3$)$_2$CH |
| 55. | (CH$_3$)$_3$C | CH$_3$CH$_2$ | CH$_3$ | CH$_3$ | H | (CH$_3$)$_3$C |
| 56. | (CH$_3$)$_3$C | CH$_3$CH$_2$ | CH$_3$ | CH$_3$ | H | CH$_3$CH$_2$CH$_2$CH$_2$ |
| 57. | (CH$_3$)$_3$C | CH$_3$CH$_2$ | CH$_3$ | CH$_3$ | H | (CH$_3$)$_2$CHCH$_2$ |
| 58. | (CH$_3$)$_3$C | CH$_3$CH$_2$ | CH$_3$ | CH$_3$ | H | CH$_3$OCH$_2$ |
| 59. | (CH$_3$)$_3$C | CH$_3$CH$_2$ | CH$_3$ | CH$_3$ | H |  |

TABLE 1-continued

| No. | R3 | R9 | R8 | R6 | R7 | L-R10 |
|---|---|---|---|---|---|---|
| 60. | (CH₃)₃C | CH₃CH₂ | CH₃ | CH₃ | H | CH₃SCH₂ |
| 61. | (CH₃)₃C | CH₃CH₂ | CH₃ | CH₃ | H |  |
| 62. | (CH₃)₃C | CH₃CH₂ | CH₃ | CH₃ | H | FCH₂ |
| 63. | (CH₃)₃C | CH₃CH₂ | CH₃ | CH₃ | H | F₃C |
| 64. | (CH₃)₃C | CH₃CH₂ | CH₃ | CH₃ | H | C₆H₅ |
| 65. | (CH₃)₃C | CH₃CH₂ | CH₃ | CH₃ | H | C₆H₅CH₂ |
| 66. | (CH₃)₃C | CH₃CH₂ | CH₃ | CH₃ | H | CH₃CH₂(CH₃)₂C |
| 67. | (CH₃)₃C | CH₃CH₂ | CH₃ | CH₃ | H | CH2=CH |
| 68. | (CH₃)₃C | CH₃CH₂ | CH₃ | CH₃ | H | CH₃CH₂OCH₂ |
| 69. | (CH₃)₃C | CH₃CH₂ | CH₃ | CH₃ | H | CH₃CH₂SCH₂ |
| 70. | (CH₃)₃C | CH₃CH₂ | CH₃ | CH₃ | H | 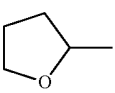 |
| 71. | (CH₃)₃C | CH₃CH₂ | CH₃ | CH₃ | H | 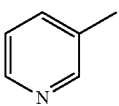 |
| 72. | (CH₃)₃C | CH₃CH₂ | CH₃ | CH₃ | H | CF₃CH₂SCH₂ |
| 73. | (CH₃)₃C | CH₃CH₂ | CH₃ | CH₃ | H | ClCH₂CH₂ |
| 74. | (CH₃)₃C | CH₃CH₂ | CH₃ | CH₃ | H | ClCH₂CH₂CH₂ |
| 75. | (CH₃)₃C | CH3CH2 | CH₃ | CH₃ | H | NCCH2 |
| 76. | (CH₃)₃C | H | CH₃ | CH₃ | Cl | CH₃ |
| 77. | (CH₃)₃C | H | CH₃ | CH₃ | Cl | CH₃CH₂ |
| 78. | (CH₃)₃C | H | CH₃ | CH₃ | Cl | CH₃CH₂CH₂ |
| 79. | (CH₃)₃C | H | CH₃ | CH₃ | Cl | (CH₃)₂CH |
| 80. | (CH₃)₃C | H | CH₃ | CH₃ | Cl | (CH₃)₃C |
| 81. | (CH₃)₃C | H | CH₃ | CH₃ | Cl | CH₃CH₂CH₂CH₂ |
| 82. | (CH₃)₃C | H | CH₃ | CH₃ | Cl | (CH₃)₂CHCH₂ |
| 83. | (CH₃)₃C | H | CH₃ | CH₃ | Cl | CH₃OCH₂ |
| 84. | (CH₃)₃C | H | CH₃ | CH₃ | Cl |  |
| 85. | (CH₃)₃C | H | CH₃ | CH₃ | Cl | CH₃SCH₂ |
| 86. | (CH₃)₃C | H | CH₃ | CH₃ | Cl |  |
| 87. | (CH₃)₃C | H | CH₃ | CH₃ | Cl | FCH₂ |
| 88. | (CH₃)₃C | H | CH₃ | CH₃ | Cl | F₃C |
| 89. | (CH₃)₃C | H | CH₃ | CH₃ | Cl | C₆H₅ |
| 90. | (CH₃)₃C | H | CH₃ | CH₃ | Cl | C₆H₅CH₂ |
| 91. | (CH₃)₃C | H | CH₃ | CH₃ | Cl | CH₃CH₂(CH₃)₂C |
| 92. | (CH₃)₃C | H | CH₃ | CH₃ | Cl | CH2=CH |
| 93. | (CH₃)₃C | H | CH₃ | CH₃ | Cl | CH₃CH₂OCH₂ |
| 94. | (CH₃)₃C | H | CH₃ | CH₃ | Cl | CH₃CH₂SCH₂ |
| 95. | (CH₃)₃C | H | CH₃ | CH₃ | Cl | 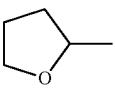 |
| 96. | (CH₃)₃C | H | CH₃ | CH₃ | Cl | 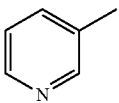 |
| 97. | (CH₃)₃C | H | CH₃ | CH₃ | Cl | CF₃CH₂SCH₂ |
| 98. | (CH₃)₃C | H | CH₃ | CH₃ | Cl | ClCH₂CH₂ |
| 99. | (CH₃)₃C | H | CH₃ | CH₃ | Cl | ClCH₂CH₂CH₂ |
| 100. | (CH₃)₃C | H | CH₃ | CH₃ | Cl | NCCH2 |
| 101. | (CH₃)₃C | CH₃ | CH₃ | CH₃ | Cl | CH₃ |
| 102. | (CH₃)₃C | CH₃ | CH₃ | CH₃ | Cl | CH₃CH₂ |
| 103. | (CH₃)₃C | CH₃ | CH₃ | CH₃ | Cl | CH₃CH₂CH₂ |

TABLE 1-continued

| No. | R3 | R9 | R8 | R6 | R7 | L-R10 |
|---|---|---|---|---|---|---|
| 104. | (CH₃)₃C | CH₃ | CH₃ | CH₃ | Cl | (CH₃)₂CH |
| 105. | (CH₃)₃C | CH₃ | CH₃ | CH₃ | Cl | (CH₃)₃C |
| 106. | (CH₃)₃C | CH₃ | CH₃ | CH₃ | Cl | CH₃CH₂CH₂CH₂ |
| 107. | (CH₃)₃C | CH₃ | CH₃ | CH₃ | Cl | (CH₃)₂CHCH₂ |
| 108. | (CH₃)₃C | CH₃ | CH₃ | CH₃ | Cl | CH₃OCH₂ |
| 109. | (CH₃)₃C | CH₃ | CH₃ | CH₃ | Cl |  |
| 110. | (CH₃)₃C | CH₃ | CH₃ | CH₃ | Cl | CH₃SCH₂ |
| 111. | (CH₃)₃C | CH₃ | CH₃ | CH₃ | Cl |  |
| 112. | (CH₃)₃C | CH₃ | CH₃ | CH₃ | Cl | FCH₂ |
| 113. | (CH₃)₃C | CH₃ | CH₃ | CH₃ | Cl | F₃C |
| 114. | (CH₃)₃C | CH₃ | CH₃ | CH₃ | Cl | C₆H₅ |
| 115. | (CH₃)₃C | CH₃ | CH₃ | CH₃ | Cl | C₆H₅CH₂ |
| 116. | (CH₃)₃C | CH₃ | CH₃ | CH₃ | Cl | CH₃CH₂(CH₃)₂C |
| 117. | (CH₃)₃C | CH₃ | CH₃ | CH₃ | Cl | CH2=CH |
| 118. | (CH₃)₃C | CH₃ | CH₃ | CH₃ | Cl | CH₃CH₂OCH₂ |
| 119. | (CH₃)₃C | CH₃ | CH₃ | CH₃ | Cl | CH₃CH₂SCH₂ |
| 120. | (CH₃)₃C | CH₃ | CH₃ | CH₃ | Cl | 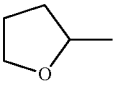 |
| 121. | (CH₃)₃C | CH₃ | CH₃ | CH₃ | Cl | 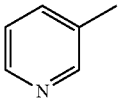 |
| 122. | (CH₃)₃C | CH₃ | CH₃ | CH₃ | Cl | CF₃CH₂SCH₂ |
| 123. | (CH₃)₃C | CH₃ | CH₃ | CH₃ | Cl | ClCH₂CH₂ |
| 124. | (CH₃)₃C | CH₃ | CH₃ | CH₃ | Cl | ClCH₂CH₂CH₂ |
| 125. | (CH₃)₃C | CH3 | CH₃ | CH₃ | Cl | NCCH2 |
| 126. | (CH₃)₃C | CH₃CH₂ | CH₃ | CH₃ | Cl | CH₃ |
| 127. | (CH₃)₃C | CH₃CH₂ | CH₃ | CH₃ | Cl | CH₃CH₂ |
| 128. | (CH₃)₃C | CH₃CH₂ | CH₃ | CH₃ | Cl | CH₃CH₂CH₂ |
| 129. | (CH₃)₃C | CH₃CH₂ | CH₃ | CH₃ | Cl | (CH₃)₂CH |
| 130. | (CH₃)₃C | CH₃CH₂ | CH₃ | CH₃ | Cl | (CH₃)₃C |
| 131. | (CH₃)₃C | CH₃CH₂ | CH₃ | CH₃ | Cl | CH₃CH₂CH₂CH₂ |
| 132. | (CH₃)₃C | CH₃CH₂ | CH₃ | CH₃ | Cl | (CH₃)₂CHCH₂ |
| 133. | (CH₃)₃C | CH₃CH₂ | CH₃ | CH₃ | Cl | CH₃OCH₂ |
| 134. | (CH₃)₃C | CH₃CH₂ | CH₃ | CH₃ | Cl |  |
| 135. | (CH₃)₃C | CH₃CH₂ | CH₃ | CH₃ | Cl | CH₃SCH₂ |
| 136. | (CH₃)₃C | CH₃CH₂ | CH₃ | CH₃ | Cl |  |
| 137. | (CH₃)₃C | CH₃CH₂ | CH₃ | CH₃ | Cl | FCH₂ |
| 138. | (CH₃)₃C | CH₃CH₂ | CH₃ | CH₃ | Cl | F₃C |
| 139. | (CH₃)₃C | CH₃CH₂ | CH₃ | CH₃ | Cl | C₆H₅ |
| 140. | (CH₃)₃C | CH₃CH₂ | CH₃ | CH₃ | Cl | C₆H₅CH₂ |
| 141. | (CH₃)₃C | CH₃CH₂ | CH₃ | CH₃ | Cl | CH₃CH₂(CH₃)₂C |
| 142. | (CH₃)₃C | CH₃CH₂ | CH₃ | CH₃ | Cl | CH2=CH |
| 143. | (CH₃)₃C | CH₃CH₂ | CH₃ | CH₃ | Cl | CH₃CH₂OCH₂ |
| 144. | (CH₃)₃C | CH₃CH₂ | CH₃ | CH₃ | Cl | CH₃CH₂SCH₂ |
| 145. | (CH₃)₃C | CH₃CH₂ | CH₃ | CH₃ | Cl | 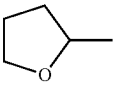 |

TABLE 1-continued

| No. | R3 | R9 | R8 | R6 | R7 | L-R10 |
|---|---|---|---|---|---|---|
| 146. | (CH₃)₃C | CH₃CH₂ | CH₃ | CH₃ | Cl | 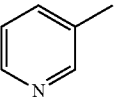 |
| 147. | (CH₃)₃C | CH₃CH₂ | CH₃ | CH₃ | Cl | CF₃CH₂SCH₂ |
| 148. | (CH₃)₃C | CH₃CH₂ | CH₃ | CH₃ | Cl | ClCH₂CH₂ |
| 149. | (CH₃)₃C | CH₃CH₂ | CH₃ | CH₃ | Cl | ClCH₂CH₂CH₂ |
| 150. | (CH₃)₃C | CH3CH2 | CH₃ | CH₃ | Cl | NCCH2 |
| 151. | (CH₃)₃C | H | CH₃ | CH₃ | CH₃ | CH₃ |
| 152. | (CH₃)₃C | H | CH₃ | CH₃ | CH₃ | CH₃CH₂ |
| 153. | (CH₃)₃C | H | CH₃ | CH₃ | CH₃ | CH₃CH₂CH₂ |
| 154. | (CH₃)₃C | H | CH₃ | CH₃ | CH₃ | (CH₃)₂CH |
| 155. | (CH₃)₃C | H | CH₃ | CH₃ | CH₃ | (CH₃)₃C |
| 156. | (CH₃)₃C | H | CH₃ | CH₃ | CH₃ | CH₃CH₂CH₂CH₂ |
| 157. | (CH₃)₃C | H | CH₃ | CH₃ | CH₃ | (CH₃)₂CHCH₂ |
| 158. | (CH₃)₃C | H | CH₃ | CH₃ | CH₃ | CH₃OCH₂ |
| 159. | (CH₃)₃C | H | CH₃ | CH₃ | CH₃ |  |
| 160. | (CH₃)₃C | H | CH₃ | CH₃ | CH₃ | CH₃SCH₂ |
| 161. | (CH₃)₃C | H | CH₃ | CH₃ | CH₃ |  |
| 162. | (CH₃)₃C | H | CH₃ | CH₃ | CH₃ | FCH₂ |
| 163. | (CH₃)₃C | H | CH₃ | CH₃ | CH₃ | F₃C |
| 164. | (CH₃)₃C | H | CH₃ | CH₃ | CH₃ | C₆H₅ |
| 165. | (CH₃)₃C | H | CH₃ | CH₃ | CH₃ | C₆H₅CH₂ |
| 166. | (CH₃)₃C | H | CH₃ | CH₃ | CH₃ | CH₃CH₂(CH₃)₂C |
| 167. | (CH₃)₃C | H | CH₃ | CH₃ | CH₃ | CH2=CH |
| 168. | (CH₃)₃C | H | CH₃ | CH₃ | CH₃ | CH₃CH₂OCH₂ |
| 169. | (CH₃)₃C | H | CH₃ | CH₃ | CH₃ | CH₃CH₂SCH₂ |
| 170. | (CH₃)₃C | H | CH₃ | CH₃ | CH₃ | 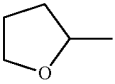 |
| 171. | (CH₃)₃C | H | CH₃ | CH₃ | CH₃ | 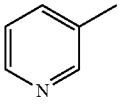 |
| 172. | (CH₃)₃C | H | CH₃ | CH₃ | CH₃ | CF₃CH₂SCH₂ |
| 173. | (CH₃)₃C | H | CH₃ | CH₃ | CH₃ | ClCH₂CH₂ |
| 174. | (CH₃)₃C | H | CH₃ | CH₃ | CH₃ | ClCH₂CH₂CH₂ |
| 175. | (CH₃)₃C | H | CH₃ | CH₃ | CH₃ | NCCH2 |
| 176. | (CH₃)₃C | CH₃ | CH₃ | CH₃ | CH₃ | CH₃ |
| 177. | (CH₃)₃C | CH₃ | CH₃ | CH₃ | CH₃ | CH₃CH₂ |
| 178. | (CH₃)₃C | CH₃ | CH₃ | CH₃ | CH₃ | CH₃CH₂CH₂ |
| 179. | (CH₃)₃C | CH₃ | CH₃ | CH₃ | CH₃ | (CH₃)₂CH |
| 180. | (CH₃)₃C | CH₃ | CH₃ | CH₃ | CH₃ | (CH₃)₃C |
| 181. | (CH₃)₃C | CH₃ | CH₃ | CH₃ | CH₃ | CH₃CH₂CH₂CH₂ |
| 182. | (CH₃)₃C | CH₃ | CH₃ | CH₃ | CH₃ | (CH₃)₂CHCH₂ |
| 183. | (CH₃)₃C | CH₃ | CH₃ | CH₃ | CH₃ | CH₃OCH₂ |
| 184. | (CH₃)₃C | CH₃ | CH₃ | CH₃ | CH₃ |  |
| 185. | (CH₃)₃C | CH₃ | CH₃ | CH₃ | CH₃ | CH₃SCH₂ |
| 186. | (CH₃)₃C | CH₃ | CH₃ | CH₃ | CH₃ |  |
| 187. | (CH₃)₃C | CH₃ | CH₃ | CH₃ | CH₃ | FCH₂ |
| 188. | (CH₃)₃C | CH₃ | CH₃ | CH₃ | CH₃ | F₃C |
| 189. | (CH₃)₃C | CH₃ | CH₃ | CH₃ | CH₃ | C₆H₅ |
| 190. | (CH₃)₃C | CH₃ | CH₃ | CH₃ | CH₃ | C₆H₅CH₂ |
| 191. | (CH₃)₃C | CH₃ | CH₃ | CH₃ | CH₃ | CH₃CH₂(CH₃)₂C |

TABLE 1-continued

| No. | R3 | R9 | R8 | R6 | R7 | L-R10 |
|---|---|---|---|---|---|---|
| 192. | (CH$_3$)$_3$C | CH$_3$ | CH$_3$ | CH$_3$ | CH$_3$ | CH2=CH |
| 193. | (CH$_3$)$_3$C | CH$_3$ | CH$_3$ | CH$_3$ | CH$_3$ | CH$_3$CH$_2$OCH$_2$ |
| 194. | (CH$_3$)$_3$C | CH$_3$ | CH$_3$ | CH$_3$ | CH$_3$ | CH$_3$CH$_2$SCH$_2$ |
| 195. | (CH$_3$)$_3$C | CH$_3$ | CH$_3$ | CH$_3$ | CH$_3$ | 2-methyltetrahydrofuran |
| 196. | (CH$_3$)$_3$C | CH$_3$ | CH$_3$ | CH$_3$ | CH$_3$ | 3-methylpyridine |
| 197. | (CH$_3$)$_3$C | CH$_3$ | CH$_3$ | CH$_3$ | CH$_3$ | CF$_3$CH$_2$SCH$_2$ |
| 198. | (CH$_3$)$_3$C | CH$_3$ | CH$_3$ | CH$_3$ | CH$_3$ | ClCH$_2$CH$_2$ |
| 199. | (CH$_3$)$_3$C | CH$_3$ | CH$_3$ | CH$_3$ | CH$_3$ | ClCH$_2$CH$_2$CH$_2$ |
| 200. | (CH$_3$)$_3$C | CH$_3$ | CH$_3$ | CH$_3$ | CH$_3$ | NCCH2 |
| 201. | (CH$_3$)$_3$C | CH$_3$CH$_2$ | CH$_3$ | CH$_3$ | CH$_3$ | CH$_3$ |
| 202. | (CH$_3$)$_3$C | CH$_3$CH$_2$ | CH$_3$ | CH$_3$ | CH$_3$ | CH$_3$CH$_2$ |
| 203. | (CH$_3$)$_3$C | CH$_3$CH$_2$ | CH$_3$ | CH$_3$ | CH$_3$ | CH$_3$CH$_2$CH$_2$ |
| 204. | (CH$_3$)$_3$C | CH$_3$CH$_2$ | CH$_3$ | CH$_3$ | CH$_3$ | (CH$_3$)$_2$CH |
| 205. | (CH$_3$)$_3$C | CH$_3$CH$_2$ | CH$_3$ | CH$_3$ | CH$_3$ | (CH$_3$)$_3$C |
| 206. | (CH$_3$)$_3$C | CH$_3$CH$_2$ | CH$_3$ | CH$_3$ | CH$_3$ | CH$_3$CH$_2$CH$_2$CH$_2$ |
| 207. | (CH$_3$)$_3$C | CH$_3$CH$_2$ | CH$_3$ | CH$_3$ | CH$_3$ | (CH$_3$)$_2$CHCH$_2$ |
| 208. | (CH$_3$)$_3$C | CH$_3$CH$_2$ | CH$_3$ | CH$_3$ | CH$_3$ | CH$_3$OCH$_2$ |
| 209. | (CH$_3$)$_3$C | CH$_3$CH$_2$ | CH$_3$ | CH$_3$ | CH$_3$ | cyclopropyl |
| 210. | (CH$_3$)$_3$C | CH$_3$CH$_2$ | CH$_3$ | CH$_3$ | CH$_3$ | CH$_3$SCH$_2$ |
| 211. | (CH$_3$)$_3$C | CH$_3$CH$_2$ | CH$_3$ | CH$_3$ | CH$_3$ | cyclohexyl |
| 212. | (CH$_3$)$_3$C | CH$_3$CH$_2$ | CH$_3$ | CH$_3$ | CH$_3$ | FCH$_2$ |
| 213. | (CH$_3$)$_3$C | CH$_3$CH$_2$ | CH$_3$ | CH$_3$ | CH$_3$ | F$_3$C |
| 214. | (CH$_3$)$_3$C | CH$_3$CH$_2$ | CH$_3$ | CH$_3$ | CH$_3$ | C$_6$H$_5$ |
| 215. | (CH$_3$)$_3$C | CH$_3$CH$_2$ | CH$_3$ | CH$_3$ | CH$_3$ | C$_6$H$_5$CH$_2$ |
| 216. | (CH$_3$)$_3$C | CH$_3$CH$_2$ | CH$_3$ | CH$_3$ | CH$_3$ | CH$_3$CH$_2$(CH$_3$)$_2$C |
| 217. | (CH$_3$)$_3$C | CH$_3$CH$_2$ | CH$_3$ | CH$_3$ | CH$_3$ | CH2=CH |
| 218. | (CH$_3$)$_3$C | CH$_3$CH$_2$ | CH$_3$ | CH$_3$ | CH$_3$ | CH$_3$CH$_2$OCH$_2$ |
| 219. | (CH$_3$)$_3$C | CH$_3$CH$_2$ | CH$_3$ | CH$_3$ | CH$_3$ | CH$_3$CH$_2$SCH$_2$ |
| 220. | (CH$_3$)$_3$C | CH$_3$CH$_2$ | CH$_3$ | CH$_3$ | CH$_3$ | 2-methyltetrahydrofuran |
| 221. | (CH$_3$)$_3$C | CH$_3$CH$_2$ | CH$_3$ | CH$_3$ | CH$_3$ | 3-methylpyridine |
| 222. | (CH$_3$)$_3$C | CH$_3$CH$_2$ | CH$_3$ | CH$_3$ | CH$_3$ | CF$_3$CH$_2$SCH$_2$ |
| 223. | (CH$_3$)$_3$C | CH$_3$CH$_2$ | CH$_3$ | CH$_3$ | CH$_3$ | ClCH$_2$CH$_2$ |
| 224. | (CH$_3$)$_3$C | CH$_3$CH$_2$ | CH$_3$ | CH$_3$ | CH$_3$ | ClCH$_2$CH$_2$CH$_2$ |
| 225. | (CH$_3$)$_3$C | CH3CH2 | CH$_3$ | CH$_3$ | CH$_3$ | NCCH2 |
| 226. | (CH$_3$)$_3$C | H | CH$_3$CH$_2$ | CH$_3$ | H | CH$_3$ |
| 227. | (CH$_3$)$_3$C | H | CH$_3$CH$_2$ | CH$_3$ | H | CH$_3$CH$_2$ |
| 228. | (CH$_3$)$_3$C | H | CH$_3$CH$_2$ | CH$_3$ | H | CH$_3$CH$_2$CH$_2$ |
| 229. | (CH$_3$)$_3$C | H | CH$_3$CH$_2$ | CH$_3$ | H | (CH$_3$)$_2$CH |
| 230. | (CH$_3$)$_3$C | H | CH$_3$CH$_2$ | CH$_3$ | H | (CH$_3$)$_3$C |
| 231. | (CH$_3$)$_3$C | H | CH$_3$CH$_2$ | CH$_3$ | H | CH$_3$CH$_2$CH$_2$CH$_2$ |
| 232. | (CH$_3$)$_3$C | H | CH$_3$CH$_2$ | CH$_3$ | H | (CH$_3$)$_2$CHCH$_2$ |
| 233. | (CH$_3$)$_3$C | H | CH$_3$CH$_2$ | CH$_3$ | H | CH$_3$OCH$_2$ |
| 234. | (CH$_3$)$_3$C | H | CH$_3$CH$_2$ | CH$_3$ | H | cyclopropyl |
| 235. | (CH$_3$)$_3$C | H | CH$_3$CH$_2$ | CH$_3$ | H | CH$_3$SCH$_2$ |

TABLE 1-continued

| No. | R3 | R9 | R8 | R6 | R7 | L-R10 |
|---|---|---|---|---|---|---|
| 236. | (CH₃)₃C | H | CH₃CH₂ | CH₃ | H |  |
| 237. | (CH₃)₃C | H | CH₃CH₂ | CH₃ | H | FCH₂ |
| 238. | (CH₃)₃C | H | CH₃CH₂ | CH₃ | H | F₃C |
| 239. | (CH₃)₃C | H | CH₃CH₂ | CH₃ | H | C₆H₅ |
| 240. | (CH₃)₃C | H | CH₃CH₂ | CH₃ | H | C₆H₅CH₂ |
| 241. | (CH₃)₃C | H | CH₃CH₂ | CH₃ | H | CH₃CH₂(CH₃)₂C |
| 242. | (CH₃)₃C | H | CH₃CH₂ | CH₃ | H | CH2=CH |
| 243. | (CH₃)₃C | H | CH₃CH₂ | CH₃ | H | CH₃CH₂OCH₂ |
| 244. | (CH₃)₃C | H | CH₃CH₂ | CH₃ | H | CH₃CH₂SCH₂ |
| 245. | (CH₃)₃C | H | CH₃CH₂ | CH₃ | H | 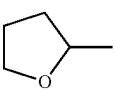 |
| 246. | (CH₃)₃C | H | CH₃CH₂ | CH₃ | H | 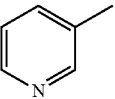 |
| 247. | (CH₃)₃C | H | CH₃CH₂ | CH₃ | H | CF₃CH₂SCH₂ |
| 248. | (CH₃)₃C | H | CH₃CH₂ | CH₃ | H | ClCH₂CH₂ |
| 249. | (CH₃)₃C | H | CH₃CH₂ | CH₃ | H | ClCH₂CH₂CH₂ |
| 250. | (CH₃)₃C | H | CH3CH2 | CH₃ | H | NCCH2 |
| 251. | (CH₃)₃C | CH₃ | CH₃CH₂ | CH₃ | H | CH₃ |
| 252. | (CH₃)₃C | CH₃ | CH₃CH₂ | CH₃ | H | CH₃CH₂ |
| 253. | (CH₃)₃C | CH₃ | CH₃CH₂ | CH₃ | H | CH₃CH₂CH₂ |
| 254. | (CH₃)₃C | CH₃ | CH₃CH₂ | CH₃ | H | (CH₃)₂CH |
| 255. | (CH₃)₃C | CH₃ | CH₃CH₂ | CH₃ | H | (CH₃)₃C |
| 256. | (CH₃)₃C | CH₃ | CH₃CH₂ | CH₃ | H | CH₃CH₂CH₂CH₂ |
| 257. | (CH₃)₃C | CH₃ | CH₃CH₂ | CH₃ | H | CH₃OCH₂ |
| 258. | (CH₃)₃C | CH₃ | CH₃CH₂ | CH₃ | H | CH₃OCH₂ |
| 259. | (CH₃)₃C | CH₃ | CH₃CH₂ | CH₃ | H |  |
| 260. | (CH₃)₃C | CH₃ | CH₃CH₂ | CH₃ | H | CH₃SCH₂ |
| 261. | (CH₃)₃C | CH₃ | CH₃CH₂ | CH₃ | H |  |
| 262. | (CH₃)₃C | CH₃ | CH₃CH₂ | CH₃ | H | FCH₂ |
| 263. | (CH₃)₃C | CH₃ | CH₃CH₂ | CH₃ | H | F₃C |
| 264. | (CH₃)₃C | CH₃ | CH₃CH₂ | CH₃ | H | C₆H₅ |
| 265. | (CH₃)₃C | CH₃ | CH₃CH₂ | CH₃ | H | C₆H₅CH₂ |
| 266. | (CH₃)₃C | CH₃ | CH₃CH₂ | CH₃ | H | CH₃CH₂(CH₃)₂C |
| 267. | (CH₃)₃C | CH₃ | CH₃CH₂ | CH₃ | H | CH2=CH |
| 268. | (CH₃)₃C | CH₃ | CH₃CH₂ | CH₃ | H | CH₃CH₂OCH₂ |
| 269. | (CH₃)₃C | CH₃ | CH₃CH₂ | CH₃ | H | CH₃CH₂SCH₂ |
| 270. | (CH₃)₃C | CH₃ | CH₃CH₂ | CH₃ | H | 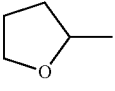 |
| 271. | (CH₃)₃C | CH₃ | CH₃CH₂ | CH₃ | H | 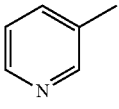 |
| 272. | (CH₃)₃C | CH₃ | CH₃CH₂ | CH₃ | H | CF₃CH₂SCH₂ |
| 273. | (CH₃)₃C | CH₃ | CH₃CH₂ | CH₃ | H | ClCH₂CH₂ |
| 274. | (CH₃)₃C | CH₃ | CH₃CH₂ | CH₃ | H | ClCH₂CH₂CH₂ |
| 275. | (CH₃)₃C | CH3 | CH3CH2 | CH₃ | H | NCCH2 |
| 276. | (CH₃)₃C | CH₃CH₂ | CH₃CH₂ | CH₃ | H | CH₃ |
| 277. | (CH₃)₃C | CH₃CH₂ | CH₃CH₂ | CH₃ | H | CH₃CH₂ |
| 278. | (CH₃)₃C | CH₃CH₂ | CH₃CH₂ | CH₃ | H | CH₃CH₂CH₂ |
| 279. | (CH₃)₃C | CH₃CH₂ | CH₃CH₂ | CH₃ | H | (CH₃)₂CH |
| 280. | (CH₃)₃C | CH₃CH₂ | CH₃CH₂ | CH₃ | H | (CH₃)₃C |

TABLE 1-continued

| No. | R3 | R9 | R8 | R6 | R7 | L-R10 |
|---|---|---|---|---|---|---|
| 281. | (CH$_3$)$_3$C | CH$_3$CH$_2$ | CH$_3$CH$_2$ | CH$_3$ | H | CH$_3$CH$_2$CH$_2$CH$_2$ |
| 282. | (CH$_3$)$_3$C | CH$_3$CH$_2$ | CH$_3$CH$_2$ | CH$_3$ | H | (CH$_3$)$_2$CHCH$_2$ |
| 283. | (CH$_3$)$_3$C | CH$_3$CH$_2$ | CH$_3$CH$_2$ | CH$_3$ | H | CH$_3$OCH$_2$ |
| 284. | (CH$_3$)$_3$C | CH$_3$CH$_2$ | CH$_3$CH$_2$ | CH$_3$ | H |  |
| 285. | (CH$_3$)$_3$C | CH$_3$CH$_2$ | CH$_3$CH$_2$ | CH$_3$ | H | CH$_3$SCH$_2$ |
| 286. | (CH$_3$)$_3$C | CH$_3$CH$_2$ | CH$_3$CH$_2$ | CH$_3$ | H |  |
| 287. | (CH$_3$)$_3$C | CH$_3$CH$_2$ | CH$_3$CH$_2$ | CH$_3$ | H | FCH$_2$ |
| 288. | (CH$_3$)$_3$C | CH$_3$CH$_2$ | CH$_3$CH$_2$ | CH$_3$ | H | F$_3$C |
| 289. | (CH$_3$)$_3$C | CH$_3$CH$_2$ | CH$_3$CH$_2$ | CH$_3$ | H | C$_6$H$_5$ |
| 290. | (CH$_3$)$_3$C | CH$_3$CH$_2$ | CH$_3$CH$_2$ | CH$_3$ | H | C$_6$H$_5$CH$_2$ |
| 291. | (CH$_3$)$_3$C | CH$_3$CH$_2$ | CH$_3$CH$_2$ | CH$_3$ | H | CH$_3$CH$_2$(CH$_3$)$_2$C |
| 292. | (CH$_3$)$_3$C | CH$_3$CH$_2$ | CH$_3$CH$_2$ | CH$_3$ | H | CH2=CH |
| 293. | (CH$_3$)$_3$C | CH$_3$CH$_2$ | CH$_3$CH$_2$ | CH$_3$ | H | CH$_3$CH$_2$OCH$_2$ |
| 294. | (CH$_3$)$_3$C | CH$_3$CH$_2$ | CH$_3$CH$_2$ | CH$_3$ | H | CH$_3$CH$_2$SCH$_2$ |
| 295. | (CH$_3$)$_3$C | CH$_3$CH$_2$ | CH$_3$CH$_2$ | CH$_3$ | H | 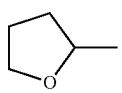 |
| 296. | (CH$_3$)$_3$C | CH$_3$CH$_2$ | CH$_3$CH$_2$ | CH$_3$ | H | 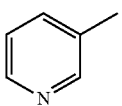 |
| 297. | (CH$_3$)$_3$C | CH$_3$CH$_2$ | CH$_3$CH$_2$ | CH$_3$ | H | CF$_3$CH$_2$SCH$_2$ |
| 298. | (CH$_3$)$_3$C | CH$_3$CH$_2$ | CH$_3$CH$_2$ | CH$_3$ | H | ClCH$_2$CH$_2$ |
| 299. | (CH$_3$)$_3$C | CH$_3$CH$_2$ | CH$_3$CH$_2$ | CH$_3$ | H | ClCH$_2$CH$_2$CH$_2$ |
| 300. | (CH$_3$)$_3$C | CH3CH2 | CH3CH2 | CH$_3$ | H | NCCH2 |
| 301. | (CH$_3$)$_3$C | H | CH$_3$CH$_2$ | CH$_3$ | Cl | CH$_3$ |
| 302. | (CH$_3$)$_3$C | H | CH$_3$CH$_2$ | CH$_3$ | Cl | CH$_3$CH$_2$ |
| 303. | (CH$_3$)$_3$C | H | CH$_3$CH$_2$ | CH$_3$ | Cl | CH$_3$CH$_2$CH$_2$ |
| 304. | (CH$_3$)$_3$C | H | CH$_3$CH$_2$ | CH$_3$ | Cl | (CH$_3$)$_2$CH |
| 305. | (CH$_3$)$_3$C | H | CH$_3$CH$_2$ | CH$_3$ | Cl | (CH$_3$)$_3$C |
| 306. | (CH$_3$)$_3$C | H | CH$_3$CH$_2$ | CH$_3$ | Cl | CH$_3$CH$_2$CH$_2$CH$_2$ |
| 307. | (CH$_3$)$_3$C | H | CH$_3$CH$_2$ | CH$_3$ | Cl | (CH$_3$)$_2$CHCH$_2$ |
| 308. | (CH$_3$)$_3$C | H | CH$_3$CH$_2$ | CH$_3$ | Cl | CH$_3$OCH$_2$ |
| 309. | (CH$_3$)$_3$C | H | CH$_3$CH$_2$ | CH$_3$ | Cl |  |
| 310. | (CH$_3$)$_3$C | H | CH$_3$CH$_2$ | CH$_3$ | Cl | CH$_3$SCH$_2$ |
| 311. | (CH$_3$)$_3$C | H | CH$_3$CH$_2$ | CH$_3$ | Cl |  |
| 312. | (CH$_3$)$_3$C | H | CH$_3$CH$_2$ | CH$_3$ | Cl | FCH$_2$ |
| 313. | (CH$_3$)$_3$C | H | CH$_3$CH$_2$ | CH$_3$ | Cl | F$_3$C |
| 314. | (CH$_3$)$_3$C | H | CH$_3$CH$_2$ | CH$_3$ | Cl | C$_6$H$_5$ |
| 315. | (CH$_3$)$_3$C | H | CH$_3$CH$_2$ | CH$_3$ | Cl | C$_6$H$_5$CH$_2$ |
| 316. | (CH$_3$)$_3$C | H | CH$_3$CH$_2$ | CH$_3$ | Cl | CH$_3$CH$_2$(CH$_3$)$_2$C |
| 317. | (CH$_3$)$_3$C | H | CH$_3$CH$_2$ | CH$_3$ | Cl | CH2=CH |
| 318. | (CH$_3$)$_3$C | H | CH$_3$CH$_2$ | CH$_3$ | Cl | CH$_3$CH$_2$OCH$_2$ |
| 319. | (CH$_3$)$_3$C | H | CH$_3$CH$_2$ | CH$_3$ | Cl | CH$_3$CH$_2$SCH$_2$ |
| 320. | (CH$_3$)$_3$C | H | CH$_3$CH$_2$ | CH$_3$ | Cl | 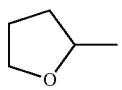 |
| 321. | (CH$_3$)$_3$C | H | CH$_3$CH$_2$ | CH$_3$ | Cl | 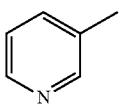 |

TABLE 1-continued

| No. | R3 | R9 | R8 | R6 | R7 | L-R10 |
|---|---|---|---|---|---|---|
| 322. | (CH$_3$)$_3$C | H | CH$_3$CH$_2$ | CH$_3$ | Cl | CF$_3$CH$_2$SCH$_2$ |
| 323. | (CH$_3$)$_3$C | H | CH$_3$CH$_2$ | CH$_3$ | Cl | ClCH$_2$CH$_2$ |
| 324. | (CH$_3$)$_3$C | H | CH$_3$CH$_2$ | CH$_3$ | Cl | ClCH$_2$CH$_2$CH$_2$ |
| 325. | (CH$_3$)$_3$C | H | CH3CH2 | CH$_3$ | Cl | NCCH2 |
| 326. | (CH$_3$)$_3$C | CH$_3$ | CH$_3$CH$_2$ | CH$_3$ | Cl | CH$_3$ |
| 327. | (CH$_3$)$_3$C | CH$_3$ | CH$_3$CH$_2$ | CH$_3$ | Cl | CH$_3$CH$_2$ |
| 328. | (CH$_3$)$_3$C | CH$_3$ | CH$_3$CH$_2$ | CH$_3$ | Cl | CH$_3$CH$_2$CH$_2$ |
| 329. | (CH$_3$)$_3$C | CH$_3$ | CH$_3$CH$_2$ | CH$_3$ | Cl | (CH$_3$)$_2$CH |
| 330. | (CH$_3$)$_3$C | CH$_3$ | CH$_3$CH$_2$ | CH$_3$ | Cl | (CH$_3$)$_3$C |
| 331. | (CH$_3$)$_3$C | CH$_3$ | CH$_3$CH$_2$ | CH$_3$ | Cl | CH$_3$CH$_2$CH$_2$CH$_2$ |
| 332. | (CH$_3$)$_3$C | CH$_3$ | CH$_3$CH$_2$ | CH$_3$ | Cl | (CH$_3$)$_2$CHCH$_2$ |
| 333. | (CH$_3$)$_3$C | CH$_3$ | CH$_3$CH$_2$ | CH$_3$ | Cl | CH$_3$OCH$_2$ |
| 334. | (CH$_3$)$_3$C | CH$_3$ | CH$_3$CH$_2$ | CH$_3$ | Cl |  |
| 335. | (CH$_3$)$_3$C | CH$_3$ | CH$_3$CH$_2$ | CH$_3$ | Cl | CH$_3$SCH$_2$ |
| 336. | (CH$_3$)$_3$C | CH$_3$ | CH$_3$CH$_2$ | CH$_3$ | Cl |  |
| 337. | (CH$_3$)$_3$C | CH$_3$ | CH$_3$CH$_2$ | CH$_3$ | Cl | FCH$_2$ |
| 338. | (CH$_3$)$_3$C | CH$_3$ | CH$_3$CH$_2$ | CH$_3$ | Cl | F$_3$C |
| 339. | (CH$_3$)$_3$C | CH$_3$ | CH$_3$CH$_2$ | CH$_3$ | Cl | C$_6$H$_5$ |
| 340. | (CH$_3$)$_3$C | CH$_3$ | CH$_3$CH$_2$ | CH$_3$ | Cl | C$_6$H$_5$CH$_2$ |
| 341. | (CH$_3$)$_3$C | CH$_3$ | CH$_3$CH$_2$ | CH$_3$ | Cl | CH$_3$CH$_2$(CH$_3$)$_2$C |
| 342. | (CH$_3$)$_3$C | CH$_3$ | CH$_3$CH$_2$ | CH$_3$ | Cl | CH2=CH |
| 343. | (CH$_3$)$_3$C | CH$_3$ | CH$_3$CH$_2$ | CH$_3$ | Cl | CH$_3$CH$_2$OCH$_2$ |
| 344. | (CH$_3$)$_3$C | CH$_3$ | CH$_3$CH$_2$ | CH$_3$ | Cl | CH$_3$CH$_2$SCH$_2$ |
| 345. | (CH$_3$)$_3$C | CH$_3$ | CH$_3$CH$_2$ | CH$_3$ | Cl | 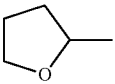 |
| 346. | (CH$_3$)$_3$C | CH$_3$ | CH$_3$CH$_2$ | CH$_3$ | Cl | 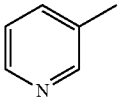 |
| 347. | (CH$_3$)$_3$C | CH$_3$ | CH$_3$CH$_2$ | CH$_3$ | Cl | CF$_3$CH$_2$SCH$_2$ |
| 348. | (CH$_3$)$_3$C | CH$_3$ | CH$_3$CH$_2$ | CH$_3$ | Cl | ClCH$_2$CH$_2$ |
| 349. | (CH$_3$)$_3$C | CH$_3$ | CH$_3$CH$_2$ | CH$_3$ | Cl | ClCH$_2$CH$_2$CH$_2$ |
| 350. | (CH$_3$)$_3$C | CH3 | CH3CH2 | CH$_3$ | Cl | NCCH2 |
| 351. | (CH$_3$)$_3$C | CH$_3$CH$_2$ | CH$_3$CH$_2$ | CH$_3$ | Cl | CH$_3$ |
| 352. | (CH$_3$)$_3$C | CH$_3$CH$_2$ | CH$_3$CH$_2$ | CH$_3$ | Cl | CH$_3$CH$_2$ |
| 353. | (CH$_3$)$_3$C | CH$_3$CH$_2$ | CH$_3$CH$_2$ | CH$_3$ | Cl | CH$_3$CH$_2$CH$_2$ |
| 354. | (CH$_3$)$_3$C | CH$_3$CH$_2$ | CH$_3$CH$_2$ | CH$_3$ | Cl | (CH$_3$)$_2$CH |
| 355. | (CH$_3$)$_3$C | CH$_3$CH$_2$ | CH$_3$CH$_2$ | CH$_3$ | Cl | (CH$_3$)$_3$C |
| 356. | (CH$_3$)$_3$C | CH$_3$CH$_2$ | CH$_3$CH$_2$ | CH$_3$ | Cl | CH$_3$CH$_2$CH$_2$CH$_2$ |
| 357. | (CH$_3$)$_3$C | CH$_3$CH$_2$ | CH$_3$CH$_2$ | CH$_3$ | Cl | (CH$_3$)$_2$CHCH$_2$ |
| 358. | (CH$_3$)$_3$C | CH$_3$CH$_2$ | CH$_3$CH$_2$ | CH$_3$ | Cl | CH$_3$OCH$_2$ |
| 359. | (CH$_3$)$_3$C | CH$_3$CH$_2$ | CH$_3$CH$_2$ | CH$_3$ | Cl |  |
| 360. | (CH$_3$)$_3$C | CH$_3$CH$_2$ | CH$_3$CH$_2$ | CH$_3$ | Cl | CH$_3$SCH$_2$ |
| 361. | (CH$_3$)$_3$C | CH$_3$CH$_2$ | CH$_3$CH$_2$ | CH$_3$ | Cl |  |
| 362. | (CH$_3$)$_3$C | CH$_3$CH$_2$ | CH$_3$CH$_2$ | CH$_3$ | Cl | FCH$_2$ |
| 363. | (CH$_3$)$_3$C | CH$_3$CH$_2$ | CH$_3$CH$_2$ | CH$_3$ | Cl | F$_3$C |
| 364. | (CH$_3$)$_3$C | CH$_3$CH$_2$ | CH$_3$CH$_2$ | CH$_3$ | Cl | C$_6$H$_5$ |
| 365. | (CH$_3$)$_3$C | CH$_3$CH$_2$ | CH$_3$CH$_2$ | CH$_3$ | Cl | C$_6$H$_5$CH$_2$ |
| 366. | (CH$_3$)$_3$C | CH$_3$CH$_2$ | CH$_3$CH$_2$ | CH$_3$ | Cl | CH$_3$CH$_2$(CH$_3$)$_2$C |
| 367. | (CH$_3$)$_3$C | CH$_3$CH$_2$ | CH$_3$CH$_2$ | CH$_3$ | Cl | CH2=CH |
| 368. | (CH$_3$)$_3$C | CH$_3$CH$_2$ | CH$_3$CH$_2$ | CH$_3$ | Cl | CH$_3$CH$_2$OCH$_2$ |
| 369. | (CH$_3$)$_3$C | CH$_3$CH$_2$ | CH$_3$CH$_2$ | CH$_3$ | Cl | CH$_3$CH$_2$SCH$_2$ |

TABLE 1-continued

| No. | R3 | R9 | R8 | R6 | R7 | L-R10 |
|---|---|---|---|---|---|---|
| 370. | (CH$_3$)$_3$C | CH$_3$CH$_2$ | CH$_3$CH$_2$ | CH$_3$ | Cl | 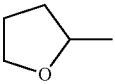 |
| 371. | (CH$_3$)$_3$C | CH$_3$CH$_2$ | CH$_3$CH$_2$ | CH$_3$ | Cl | 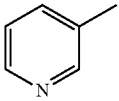 |
| 372. | (CH$_3$)$_3$C | CH$_3$CH$_2$ | CH$_3$CH$_2$ | CH$_3$ | Cl | CF$_3$CH$_2$SCH$_2$ |
| 373. | (CH$_3$)$_3$C | CH$_3$CH$_2$ | CH$_3$CH$_2$ | CH$_3$ | Cl | ClCH$_2$CH$_2$ |
| 374. | (CH$_3$)$_3$C | CH$_3$CH$_2$ | CH$_3$CH$_2$ | CH$_3$ | Cl | ClCH$_2$CH$_2$CH$_2$ |
| 375. | (CH$_3$)$_3$C | CH$_3$CH$_2$ | CH$_3$CH$_2$ | CH$_3$ | Cl | NCCH$_2$ |
| 376. | (CH$_3$)$_3$C | H | CH$_3$CH$_2$ | CH$_3$ | CH$_3$ | CH$_3$ |
| 377. | (CH$_3$)$_3$C | H | CH$_3$CH$_2$ | CH$_3$ | CH$_3$ | CH$_3$CH$_2$ |
| 378. | (CH$_3$)$_3$C | H | CH$_3$CH$_2$ | CH$_3$ | CH$_3$ | CH$_3$CH$_2$CH$_2$ |
| 379. | (CH$_3$)$_3$C | H | CH$_3$CH$_2$ | CH$_3$ | CH$_3$ | (CH$_3$)$_2$CH |
| 380. | (CH$_3$)$_3$C | H | CH$_3$CH$_2$ | CH$_3$ | CH$_3$ | (CH$_3$)$_3$C |
| 381. | (CH$_3$)$_3$C | H | CH$_3$CH$_2$ | CH$_3$ | CH$_3$ | CH$_3$CH$_2$CH$_2$CH$_2$ |
| 382. | (CH$_3$)$_3$C | H | CH$_3$CH$_2$ | CH$_3$ | CH$_3$ | (CH$_3$)$_2$CHCH$_2$ |
| 383. | (CH$_3$)$_3$C | H | CH$_3$CH$_2$ | CH$_3$ | CH$_3$ | CH$_3$OCH$_2$ |
| 384. | (CH$_3$)$_3$C | H | CH$_3$CH$_2$ | CH$_3$ | CH$_3$ |  |
| 385. | (CH$_3$)$_3$C | H | CH$_3$CH$_2$ | CH$_3$ | CH$_3$ | CH$_3$SCH$_2$ |
| 386. | (CH$_3$)$_3$C | H | CH$_3$CH$_2$ | CH$_3$ | CH$_3$ |  |
| 387. | (CH$_3$)$_3$C | H | CH$_3$CH$_2$ | CH$_3$ | CH$_3$ | FCH$_2$ |
| 388. | (CH$_3$)$_3$C | H | CH$_3$CH$_2$ | CH$_3$ | CH$_3$ | F$_3$C |
| 389. | (CH$_3$)$_3$C | H | CH$_3$CH$_2$ | CH$_3$ | CH$_3$ | C$_6$H$_5$ |
| 390. | (CH$_3$)$_3$C | H | CH$_3$CH$_2$ | CH$_3$ | CH$_3$ | C$_6$H$_5$CH$_2$ |
| 391. | (CH$_3$)$_3$C | H | CH$_3$CH$_2$ | CH$_3$ | CH$_3$ | CH$_3$CH$_2$(CH$_3$)$_2$C |
| 392. | (CH$_3$)$_3$C | H | CH$_3$CH$_2$ | CH$_3$ | CH$_3$ | CH2=CH |
| 393. | (CH$_3$)$_3$C | H | CH$_3$CH$_2$ | CH$_3$ | CH$_3$ | CH$_3$CH$_2$OCH$_2$ |
| 394. | (CH$_3$)$_3$C | H | CH$_3$CH$_2$ | CH$_3$ | CH$_3$ | CH$_3$CH$_2$SCH$_2$ |
| 395. | (CH$_3$)$_3$C | H | CH$_3$CH$_2$ | CH$_3$ | CH$_3$ | 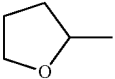 |
| 396. | (CH$_3$)$_3$C | H | CH$_3$CH$_2$ | CH$_3$ | CH$_3$ | 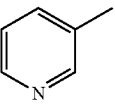 |
| 397. | (CH$_3$)$_3$C | H | CH$_3$CH$_2$ | CH$_3$ | CH$_3$ | CF$_3$CH$_2$SCH$_2$ |
| 398. | (CH$_3$)$_3$C | H | CH$_3$CH$_2$ | CH$_3$ | CH$_3$ | ClCH$_2$CH$_2$ |
| 399. | (CH$_3$)$_3$C | H | CH$_3$CH$_2$ | CH$_3$ | CH$_3$ | ClCH$_2$CH$_2$CH$_2$ |
| 400. | (CH$_3$)$_3$C | H | CH3CH2 | CH$_3$ | CH$_3$ | NCCH2 |
| 401. | (CH$_3$)$_3$C | CH$_3$ | CH$_3$CH$_2$ | CH$_3$ | CH$_3$ | CH$_3$ |
| 402. | (CH$_3$)$_3$C | CH$_3$ | CH$_3$CH$_2$ | CH$_3$ | CH$_3$ | CH$_3$CH$_2$ |
| 403. | (CH$_3$)$_3$C | CH$_3$ | CH$_3$CH$_2$ | CH$_3$ | CH$_3$ | CH$_3$CH$_2$CH$_2$ |
| 404. | (CH$_3$)$_3$C | CH$_3$ | CH$_3$CH$_2$ | CH$_3$ | CH$_3$ | (CH$_3$)$_2$CH |
| 405. | (CH$_3$)$_3$C | CH$_3$ | CH$_3$CH$_2$ | CH$_3$ | CH$_3$ | (CH$_3$)$_3$C |
| 406. | (CH$_3$)$_3$C | CH$_3$ | CH$_3$CH$_2$ | CH$_3$ | CH$_3$ | CH$_3$CH$_2$CH$_2$CH$_2$ |
| 407. | (CH$_3$)$_3$C | CH$_3$ | CH$_3$CH$_2$ | CH$_3$ | CH$_3$ | (CH$_3$)$_2$CHCH$_2$ |
| 408. | (CH$_3$)$_3$C | CH$_3$ | CH$_3$CH$_2$ | CH$_3$ | CH$_3$ | CH$_3$OCH$_2$ |
| 409. | (CH$_3$)$_3$C | CH$_3$ | CH$_3$CH$_2$ | CH$_3$ | CH$_3$ |  |
| 410. | (CH$_3$)$_3$C | CH$_3$ | CH$_3$CH$_2$ | CH$_3$ | CH$_3$ | CH$_3$SCH$_2$ |
| 411. | (CH$_3$)$_3$C | CH$_3$ | CH$_3$CH$_2$ | CH$_3$ | CH$_3$ |  |

TABLE 1-continued

| No. | R3 | R9 | R8 | R6 | R7 | L-R10 |
|---|---|---|---|---|---|---|
| 412. | (CH$_3$)$_3$C | CH$_3$ | CH$_3$CH$_2$ | CH$_3$ | CH$_3$ | FCH$_2$ |
| 413. | (CH$_3$)$_3$C | CH$_3$ | CH$_3$CH$_2$ | CH$_3$ | CH$_3$ | F$_3$C |
| 414. | (CH$_3$)$_3$C | CH$_3$ | CH$_3$CH$_2$ | CH$_3$ | CH$_3$ | C$_6$H$_5$ |
| 415. | (CH$_3$)$_3$C | CH$_3$ | CH$_3$CH$_2$ | CH$_3$ | CH$_3$ | C$_6$H$_5$CH$_2$ |
| 416. | (CH$_3$)$_3$C | CH$_3$ | CH$_3$CH$_2$ | CH$_3$ | CH$_3$ | CH$_3$CH$_2$(CH$_3$)$_2$C |
| 417. | (CH$_3$)$_3$C | CH$_3$ | CH$_3$CH$_2$ | CH$_3$ | CH$_3$ | CH2=CH |
| 418. | (CH$_3$)$_3$C | CH$_3$ | CH$_3$CH$_2$ | CH$_3$ | CH$_3$ | CH$_3$CH$_2$OCH$_2$ |
| 419. | (CH$_3$)$_3$C | CH$_3$ | CH$_3$CH$_2$ | CH$_3$ | CH$_3$ | CH$_3$CH$_2$SCH$_2$ |
| 420. | (CH$_3$)$_3$C | CH$_3$ | CH$_3$CH$_2$ | CH$_3$ | CH$_3$ | 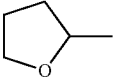 |
| 421. | (CH$_3$)$_3$C | CH$_3$ | CH$_3$CH$_2$ | CH$_3$ | CH$_3$ | 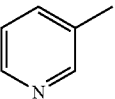 |
| 422. | (CH$_3$)$_3$C | CH$_3$ | CH$_3$CH$_2$ | CH$_3$ | CH$_3$ | CF$_3$CH$_2$SCH$_2$ |
| 423. | (CH$_3$)$_3$C | CH$_3$ | CH$_3$CH$_2$ | CH$_3$ | CH$_3$ | ClCH$_2$CH$_2$ |
| 424. | (CH$_3$)$_3$C | CH$_3$ | CH$_3$CH$_2$ | CH$_3$ | CH$_3$ | ClCH$_2$CH$_2$CH$_2$ |
| 425. | (CH$_3$)$_3$C | CH$_3$ | CH3CH2 | CH$_3$ | CH$_3$ | NCCH2 |
| 426. | (CH$_3$)$_3$C | CH$_3$CH$_2$ | CH$_3$CH$_2$ | CH$_3$ | CH$_3$ | CH$_3$ |
| 427. | (CH$_3$)$_3$C | CH$_3$CH$_2$ | CH$_3$CH$_2$ | CH$_3$ | CH$_3$ | CH$_3$CH$_2$ |
| 428. | (CH$_3$)$_3$C | CH$_3$CH$_2$ | CH$_3$CH$_2$ | CH$_3$ | CH$_3$ | CH$_3$CH$_2$CH$_2$ |
| 429. | (CH$_3$)$_3$C | CH$_3$CH$_2$ | CH$_3$CH$_2$ | CH$_3$ | CH$_3$ | (CH$_3$)$_2$CH |
| 430. | (CH$_3$)$_3$C | CH$_3$CH$_2$ | CH$_3$CH$_2$ | CH$_3$ | CH$_3$ | (CH$_3$)$_3$C |
| 431. | (CH$_3$)$_3$C | CH$_3$CH$_2$ | CH$_3$CH$_2$ | CH$_3$ | CH$_3$ | CH$_3$CH$_2$CH$_2$CH$_2$ |
| 432. | (CH$_3$)$_3$C | CH$_3$CH$_2$ | CH$_3$CH$_2$ | CH$_3$ | CH$_3$ | (CH$_3$)$_2$CHCH$_2$ |
| 433. | (CH$_3$)$_3$C | CH$_3$CH$_2$ | CH$_3$CH$_2$ | CH$_3$ | CH$_3$ | CH$_3$OCH$_2$ |
| 434. | (CH$_3$)$_3$C | CH$_3$CH$_2$ | CH$_3$CH$_2$ | CH$_3$ | CH$_3$ |  |
| 435. | (CH$_3$)$_3$C | CH$_3$CH$_2$ | CH$_3$CH$_2$ | CH$_3$ | CH$_3$ | CH$_3$SCH$_2$ |
| 436. | (CH$_3$)$_3$C | CH$_3$CH$_2$ | CH$_3$CH$_2$ | CH$_3$ | CH$_3$ |  |
| 437. | (CH$_3$)$_3$C | CH$_3$CH$_2$ | CH$_3$CH$_2$ | CH$_3$ | CH$_3$ | FCH$_2$ |
| 438. | (CH$_3$)$_3$C | CH$_3$CH$_2$ | CH$_3$CH$_2$ | CH$_3$ | CH$_3$ | F$_3$C |
| 439. | (CH$_3$)$_3$C | CH$_3$CH$_2$ | CH$_3$CH$_2$ | CH$_3$ | CH$_3$ | C$_6$H$_5$ |
| 440. | (CH$_3$)$_3$C | CH$_3$CH$_2$ | CH$_3$CH$_2$ | CH$_3$ | CH$_3$ | C$_6$H$_5$CH$_2$ |
| 441. | (CH$_3$)$_3$C | CH$_3$CH$_2$ | CH$_3$CH$_2$ | CH$_3$ | CH$_3$ | CH$_3$CH$_2$(CH$_3$)$_2$C |
| 442. | (CH$_3$)$_3$C | CH$_3$CH$_2$ | CH$_3$CH$_2$ | CH$_3$ | CH$_3$ | CH2=CH |
| 443. | (CH$_3$)$_3$C | CH$_3$CH$_2$ | CH$_3$CH$_2$ | CH$_3$ | CH$_3$ | CH$_3$CH$_2$OCH$_2$ |
| 444. | (CH$_3$)$_3$C | CH$_3$CH$_2$ | CH$_3$CH$_2$ | CH$_3$ | CH$_3$ | CH$_3$CH$_2$SCH$_2$ |
| 445. | (CH$_3$)$_3$C | CH$_3$CH$_2$ | CH$_3$CH$_2$ | CH$_3$ | CH$_3$ | 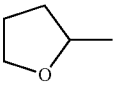 |
| 446. | (CH$_3$)$_3$C | CH$_3$CH$_2$ | CH$_3$CH$_2$ | CH$_3$ | CH$_3$ | 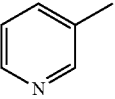 |
| 447. | (CH$_3$)$_3$C | CH$_3$CH$_2$ | CH$_3$CH$_2$ | CH$_3$ | CH$_3$ | CF$_3$CH$_2$SCH$_2$ |
| 448. | (CH$_3$)$_3$C | CH$_3$CH$_2$ | CH$_3$CH$_2$ | CH$_3$ | CH$_3$ | ClCH$_2$CH$_2$ |
| 449. | (CH$_3$)$_3$C | CH$_3$CH$_2$ | CH$_3$CH$_2$ | CH$_3$ | CH$_3$ | ClCH$_2$CH$_2$CH$_2$ |
| 450. | (CH$_3$)$_3$C | CH$_3$CH$_2$ | CH$_3$CH$_2$ | CH$_3$ | CH$_3$ | NCCH2 |
| 451. | (CH$_3$)$_3$C | H | CH$_3$ | CH$_3$ | H | OCH$_3$ |
| 452. | (CH$_3$)$_3$C | H | CH$_3$ | CH$_3$ | H | OCH$_2$CH$_3$ |
| 453. | (CH$_3$)$_3$C | H | CH$_3$ | CH$_3$ | H | O(CH$_2$)$_2$CH$_3$ |
| 454. | (CH$_3$)$_3$C | H | CH$_3$ | CH$_3$ | H | OCH(CH$_3$)$_2$ |
| 455. | (CH$_3$)$_3$C | H | CH$_3$ | CH$_3$ | H | O(CH$_3$)$_3$ |
| 456. | (CH$_3$)$_3$C | H | CH$_3$ | CH$_3$ | H | O(CH$_2$)$_3$CH$_3$ |
| 457. | (CH$_3$)$_3$C | H | CH$_3$ | CH$_3$ | H | OCH$_2$CH(CH$_3$)$_2$ |
| 458. | (CH$_3$)$_3$C | H | CH$_3$ | CH$_3$ | H | OCH$_2$CH$_2$CH(CH$_3$)$_2$ |
| 459. | (CH$_3$)$_3$C | H | CH$_3$ | CH$_3$ | H | OC(CH$_3$)$_2$CH$_2$CH$_3$ |
| 460. | (CH$_3$)$_3$C | H | CH$_3$ | CH$_3$ | H | O(CH$_2$)$_4$CH$_3$ |
| 461. | (CH$_3$)$_3$C | H | CH$_3$ | CH$_3$ | H | OCH$_2$Cl |

TABLE 1-continued

| No. | R3 | R9 | R8 | R6 | R7 | L-R10 |
|---|---|---|---|---|---|---|
| 462. | (CH$_3$)$_3$C | H | CH$_3$ | CH$_3$ | H | OCH$_2$CH$_2$Cl |
| 463. | (CH$_3$)$_3$C | H | CH$_3$ | CH$_3$ | H | OCH$_2$CH$_2$CH$_2$Cl |
| 464. | (CH$_3$)$_3$C | H | CH$_3$ | CH$_3$ | H | OCH$_2$CH$_2$Cl$_2$ |
| 465. | (CH$_3$)$_3$C | H | CH$_3$ | CH$_3$ | H | OCH$_2$CH$_2$F |
| 466. | (CH$_3$)$_3$C | H | CH$_3$ | CH$_3$ | H | OCH$_2$CHF$_2$ |
| 467. | (CH$_3$)$_3$C | H | CH$_3$ | CH$_3$ | H | OCH$_2$CF$_3$ |
| 468. | (CH$_3$)$_3$C | H | CH$_3$ | CH$_3$ | H | OCH$_2$CH$_2$OCH$_3$ |
| 469. | (CH$_3$)$_3$C | H | CH$_3$ | CH$_3$ | H | OCH$_2$CH$_2$OCH$_2$CH$_3$ |
| 470. | (CH$_3$)$_3$C | H | CH$_3$ | CH$_3$ | H | OCH$_2$OCH$_2$CH$_3$ |
| 471. | (CH$_3$)$_3$C | H | CH$_3$ | CH$_3$ | H | OCH$_2$CH$_2$SCH$_3$ |
| 472. | (CH$_3$)$_3$C | H | CH$_3$ | CH$_3$ | H | OCH$_2$C$_5$H$_6$ |
| 473. | (CH$_3$)$_3$C | H | CH$_3$ | CH$_3$ | H | OCH$_2$(4-ClC$_5$H$_6$) |
| 474. | (CH$_3$)$_3$C | H | CH$_3$ | CH$_3$ | H | OCH$_2$C═CH$_2$ |
| 475. | (CH$_3$)$_3$C | H | CH$_3$ | CH$_3$ | H | OCH$_2$(C═CH)CH$_3$ |
| 476. | (CH$_3$)$_3$C | H | CH$_3$ | CH$_3$ | H | OCH$_2$C≡CH |
| 477. | (CH$_3$)$_3$C | H | CH$_3$ | CH$_3$ | H | OCH$_2$COOCH$_3$ |
| 478. | (CH$_3$)$_3$C | H | CH$_3$ | CH$_3$ | H | OCH$_2$COOCH$_2$CH$_3$ |
| 479. | (CH$_3$)$_3$C | H | CH$_3$ | CH$_3$ | H | SCH$_3$ |
| 480. | (CH$_3$)$_3$C | H | CH$_3$ | CH$_3$ | H | SCH$_2$CH$_3$ |
| 481. | (CH$_3$)$_3$C | H | CH$_3$ | CH$_3$ | H | SCH2COOCH3 |
| 482. | (CH$_3$)$_3$C | H | CH$_3$ | CH$_3$ | H | SCH2(4-ClC5H6) |
| 483. | (CH$_3$)$_3$C | CH$_3$ | CH$_3$ | CH$_3$ | H | OCH$_3$ |
| 484. | (CH$_3$)$_3$C | CH$_3$ | CH$_3$ | CH$_3$ | H | OCH$_2$CH$_3$ |
| 485. | (CH$_3$)$_3$C | CH$_3$ | CH$_3$ | CH$_3$ | H | O(CH$_2$)$_2$CH$_3$ |
| 486. | (CH$_3$)$_3$C | CH$_3$ | CH$_3$ | CH$_3$ | H | OCH(CH$_3$)$_2$ |
| 487. | (CH$_3$)$_3$C | CH$_3$ | CH$_3$ | CH$_3$ | H | O(CH$_3$)$_3$ |
| 488. | (CH$_3$)$_3$C | CH$_3$ | CH$_3$ | CH$_3$ | H | O(CH$_2$)$_3$CH$_3$ |
| 489. | (CH$_3$)$_3$C | CH$_3$ | CH$_3$ | CH$_3$ | H | OCH$_2$CH(CH$_3$)$_2$ |
| 490. | (CH$_3$)$_3$C | CH$_3$ | CH$_3$ | CH$_3$ | H | OCH$_2$CH$_2$CH(CH$_3$)$_2$ |
| 491. | (CH$_3$)$_3$C | CH$_3$ | CH$_3$ | CH$_3$ | H | OC(CH$_3$)$_2$CH$_2$CH$_3$ |
| 492. | (CH$_3$)$_3$C | CH$_3$ | CH$_3$ | CH$_3$ | H | O(CH$_2$)$_4$CH$_3$ |
| 493. | (CH$_3$)$_3$C | CH$_3$ | CH$_3$ | CH$_3$ | H | OCH$_2$Cl |
| 494. | (CH$_3$)$_3$C | CH$_3$ | CH$_3$ | CH$_3$ | H | OCH$_2$CH$_2$Cl |
| 495. | (CH$_3$)$_3$C | CH$_3$ | CH$_3$ | CH$_3$ | H | OCH$_2$CH$_2$CH$_2$Cl |
| 496. | (CH$_3$)$_3$C | CH$_3$ | CH$_3$ | CH$_3$ | H | OCH$_2$CH$_2$Cl$_2$ |
| 497. | (CH$_3$)$_3$C | CH$_3$ | CH$_3$ | CH$_3$ | H | OCH$_2$CH$_2$F |
| 498. | (CH$_3$)$_3$C | CH$_3$ | CH$_3$ | CH$_3$ | H | OCH$_2$CHF$_2$ |
| 499. | (CH$_3$)$_3$C | CH$_3$ | CH$_3$ | CH$_3$ | H | OCH$_2$CF$_3$ |
| 500. | (CH$_3$)$_3$C | CH$_3$ | CH$_3$ | CH$_3$ | H | OCH$_2$CH$_2$OCH$_3$ |
| 501. | (CH$_3$)$_3$C | CH$_3$ | CH$_3$ | CH$_3$ | H | OCH$_2$CH$_2$OCH$_2$CH$_3$ |
| 502. | (CH$_3$)$_3$C | CH$_3$ | CH$_3$ | CH$_3$ | H | OCH$_2$OCH$_2$CH$_3$ |
| 503. | (CH$_3$)$_3$C | CH$_3$ | CH$_3$ | CH$_3$ | H | OCH$_2$CH$_2$SCH$_3$ |
| 504. | (CH$_3$)$_3$C | CH$_3$ | CH$_3$ | CH$_3$ | H | OCH$_2$C$_5$H$_6$ |
| 505. | (CH$_3$)$_3$C | CH$_3$ | CH$_3$ | CH$_3$ | H | OCH$_2$(4-ClC$_5$H$_6$) |
| 506. | (CH$_3$)$_3$C | CH$_3$ | CH$_3$ | CH$_3$ | H | OCH$_2$C═CH$_2$ |
| 507. | (CH$_3$)$_3$C | CH$_3$ | CH$_3$ | CH$_3$ | H | OCH$_2$(C═CH)CH$_3$ |
| 508. | (CH$_3$)$_3$C | CH$_3$ | CH$_3$ | CH$_3$ | H | OCH$_2$C≡CH |
| 509. | (CH$_3$)$_3$C | CH$_3$ | CH$_3$ | CH$_3$ | H | OCH$_2$COOCH$_3$ |
| 510. | (CH$_3$)$_3$C | CH$_3$ | CH$_3$ | CH$_3$ | H | OCH$_2$COOCH$_2$CH$_3$ |
| 511. | (CH$_3$)$_3$C | CH$_3$ | CH$_3$ | CH$_3$ | H | SCH$_3$ |
| 512. | (CH$_3$)$_3$C | CH$_3$ | CH$_3$ | CH$_3$ | H | SCH$_2$CH$_3$ |
| 513. | (CH$_3$)$_3$C | CH$_3$ | CH$_3$ | CH$_3$ | H | SCH2COOCH3 |
| 514. | (CH$_3$)$_3$C | CH$_3$ | CH$_3$ | CH$_3$ | H | SCH2(4-ClC5H6) |
| 515. | (CH$_3$)$_3$C | CH$_3$ | CH$_3$ | CH$_3$ | H | OCH$_3$ |
| 516. | (CH$_3$)$_3$C | CH$_3$CH$_2$ | CH$_3$ | CH$_3$ | H | OCH$_2$CH$_3$ |
| 517. | (CH$_3$)$_3$C | CH$_3$CH$_2$ | CH$_3$ | CH$_3$ | H | O(CH$_2$)$_2$CH$_3$ |
| 518. | (CH$_3$)$_3$C | CH$_3$CH$_2$ | CH$_3$ | CH$_3$ | H | OCH(CH$_3$)$_2$ |
| 519. | (CH$_3$)$_3$C | CH$_3$CH$_2$ | CH$_3$ | CH$_3$ | H | O(CH$_3$)$_3$ |
| 520. | (CH$_3$)$_3$C | CH$_3$CH$_2$ | CH$_3$ | CH$_3$ | H | O(CH$_2$)$_3$CH$_3$ |
| 521. | (CH$_3$)$_3$C | CH$_3$CH$_2$ | CH$_3$ | CH$_3$ | H | OCH$_2$CH(CH$_3$)$_2$ |
| 522. | (CH$_3$)$_3$C | CH$_3$CH$_2$ | CH$_3$ | CH$_3$ | H | OCH$_2$CH$_2$CH(CH$_3$)$_2$ |
| 523. | (CH$_3$)$_3$C | CH$_3$CH$_2$ | CH$_3$ | CH$_3$ | H | OC(CH$_3$)$_2$CH$_2$CH$_3$ |
| 524. | (CH$_3$)$_3$C | CH$_3$CH$_2$ | CH$_3$ | CH$_3$ | H | O(CH$_2$)$_4$CH$_3$ |
| 525. | (CH$_3$)$_3$C | CH$_3$CH$_2$ | CH$_3$ | CH$_3$ | H | OCH$_2$Cl |
| 526. | (CH$_3$)$_3$C | CH$_3$CH$_2$ | CH$_3$ | CH$_3$ | H | OCH$_2$CH$_2$Cl |
| 527. | (CH$_3$)$_3$C | CH$_3$CH$_2$ | CH$_3$ | CH$_3$ | H | OCH$_2$CH$_2$CH$_2$Cl |
| 528. | (CH$_3$)$_3$C | CH$_3$CH$_2$ | CH$_3$ | CH$_3$ | H | OCH$_2$CH$_2$Cl$_2$ |
| 529. | (CH$_3$)$_3$C | CH$_3$CH$_2$ | CH$_3$ | CH$_3$ | H | OCH$_2$CH$_2$F |
| 530. | (CH$_3$)$_3$C | CH$_3$CH$_2$ | CH$_3$ | CH$_3$ | H | OCH$_2$CHF$_2$ |
| 531. | (CH$_3$)$_3$C | CH$_3$CH$_2$ | CH$_3$ | CH$_3$ | H | OCH$_2$CF$_3$ |
| 532. | (CH$_3$)$_3$C | CH$_3$CH$_2$ | CH$_3$ | CH$_3$ | H | OCH$_2$CH$_2$OCH$_3$ |
| 533. | (CH$_3$)$_3$C | CH$_3$CH$_2$ | CH$_3$ | CH$_3$ | H | OCH$_2$CH$_2$OCH$_2$CH$_3$ |
| 534. | (CH$_3$)$_3$C | CH$_3$CH$_2$ | CH$_3$ | CH$_3$ | H | OCH$_2$OCH$_2$CH$_3$ |
| 535. | (CH$_3$)$_3$C | CH$_3$CH$_2$ | CH$_3$ | CH$_3$ | H | OCH$_2$CH$_2$SCH$_3$ |
| 536. | (CH$_3$)$_3$C | CH$_3$CH$_2$ | CH$_3$ | CH$_3$ | H | OCH$_2$C$_5$H$_6$ |
| 537. | (CH$_3$)$_3$C | CH$_3$CH$_2$ | CH$_3$ | CH$_3$ | H | OCH$_2$(4-ClC$_5$H$_6$) |
| 538. | (CH$_3$)$_3$C | CH$_3$CH$_2$ | CH$_3$ | CH$_3$ | H | OCH$_2$C═CH$_2$ |
| 539. | (CH$_3$)$_3$C | CH$_3$CH$_2$ | CH$_3$ | CH$_3$ | H | OCH$_2$(C═CH)CH$_3$ |

TABLE 1-continued

| No. | R3 | R9 | R8 | R6 | R7 | L-R10 |
|---|---|---|---|---|---|---|
| 540. | (CH$_3$)$_3$C | CH$_3$CH$_2$ | CH$_3$ | CH$_3$ | H | OCH$_2$C≡CH |
| 541. | (CH$_3$)$_3$C | CH$_3$CH$_2$ | CH$_3$ | CH$_3$ | H | OCH$_2$COOCH$_3$ |
| 542. | (CH$_3$)$_3$C | CH$_3$CH$_2$ | CH$_3$ | CH$_3$ | H | OCH$_2$COOCH$_2$CH$_3$ |
| 543. | (CH$_3$)$_3$C | CH$_3$CH$_2$ | CH$_3$ | CH$_3$ | H | SCH$_3$ |
| 544. | (CH$_3$)$_3$C | CH$_3$CH$_2$ | CH$_3$ | CH$_3$ | H | SCH$_2$CH$_3$ |
| 545. | (CH$_3$)$_3$C | CH$_3$CH$_2$ | CH$_3$ | CH$_3$ | H | SCH2COOCH3 |
| 546. | (CH$_3$)$_3$C | CH$_3$CH$_2$ | CH$_3$ | CH$_3$ | H | SCH2(4-ClC5H6) |
| 547. | (CH$_3$)$_3$C | H | CH$_3$CH$_2$ | CH$_3$ | H | OCH$_3$ |
| 548. | (CH$_3$)$_3$C | H | CH$_3$CH$_2$ | CH$_3$ | H | OCH$_2$CH$_3$ |
| 549. | (CH$_3$)$_3$C | H | CH$_3$CH$_2$ | CH$_3$ | H | O(CH$_2$)$_2$CH$_3$ |
| 550. | (CH$_3$)$_3$C | H | CH$_3$CH$_2$ | CH$_3$ | H | OCH(CH$_3$)$_2$ |
| 551. | (CH$_3$)$_3$C | H | CH$_3$CH$_2$ | CH$_3$ | H | O(CH$_3$)$_3$ |
| 552. | (CH$_3$)$_3$C | H | CH$_3$CH$_2$ | CH$_3$ | H | O(CH$_2$)$_3$CH$_3$ |
| 553. | (CH$_3$)$_3$C | H | CH$_3$CH$_2$ | CH$_3$ | H | OCH$_2$CH(CH$_3$)$_2$ |
| 554. | (CH$_3$)$_3$C | H | CH$_3$CH$_2$ | CH$_3$ | H | OCH$_2$CH$_2$CH(CH$_3$)$_2$ |
| 555. | (CH$_3$)$_3$C | H | CH$_3$CH$_2$ | CH$_3$ | H | OC(CH$_3$)$_2$CH$_2$CH$_3$ |
| 556. | (CH$_3$)$_3$C | H | CH$_3$CH$_2$ | CH$_3$ | H | O(CH$_2$)$_4$CH$_3$ |
| 557. | (CH$_3$)$_3$C | H | CH$_3$CH$_2$ | CH$_3$ | H | OCH$_2$Cl |
| 558. | (CH$_3$)$_3$C | H | CH$_3$CH$_2$ | CH$_3$ | H | OCH$_2$CH$_2$Cl |
| 559. | (CH$_3$)$_3$C | H | CH$_3$CH$_2$ | CH$_3$ | H | OCH$_2$CH$_2$CH$_2$CH$_2$Cl |
| 560. | (CH$_3$)$_3$C | H | CH$_3$CH$_2$ | CH$_3$ | H | OCH$_2$CH$_2$Cl$_2$ |
| 561. | (CH$_3$)$_3$C | H | CH$_3$CH$_2$ | CH$_3$ | H | OCH$_2$CH$_2$F |
| 562. | (CH$_3$)$_3$C | H | CH$_3$CH$_2$ | CH$_3$ | H | OCH$_2$CHF$_2$ |
| 563. | (CH$_3$)$_3$C | H | CH$_3$CH$_2$ | CH$_3$ | H | OCH$_2$CF$_3$ |
| 564. | (CH$_3$)$_3$C | H | CH$_3$CH$_2$ | CH$_3$ | H | OCH$_2$CH$_2$OCH$_3$ |
| 565. | (CH$_3$)$_3$C | H | CH$_3$CH$_2$ | CH$_3$ | H | OCH$_2$CH$_2$OCH$_2$CH$_3$ |
| 566. | (CH$_3$)$_3$C | H | CH$_3$CH$_2$ | CH$_3$ | H | OCH$_2$OCH$_2$CH$_3$ |
| 567. | (CH$_3$)$_3$C | H | CH$_3$CH$_2$ | CH$_3$ | H | OCH$_2$CH$_2$SCH$_3$ |
| 568. | (CH$_3$)$_3$C | H | CH$_3$CH$_2$ | CH$_3$ | H | OCH$_2$C$_5$H$_6$ |
| 569. | (CH$_3$)$_3$C | H | CH$_3$CH$_2$ | CH$_3$ | H | OCH$_2$(4-ClC$_5$H$_6$) |
| 570. | (CH$_3$)$_3$C | H | CH$_3$CH$_2$ | CH$_3$ | H | OCH$_2$C═CH$_2$ |
| 571. | (CH$_3$)$_3$C | H | CH$_3$CH$_2$ | CH$_3$ | H | OCH$_2$(C═CH)CH$_3$ |
| 572. | (CH$_3$)$_3$C | H | CH$_3$CH$_2$ | CH$_3$ | H | OCH$_2$C≡CH |
| 573. | (CH$_3$)$_3$C | H | CH$_3$CH$_2$ | CH$_3$ | H | OCH$_2$COOCH$_3$ |
| 574. | (CH$_3$)$_3$C | H | CH$_3$CH$_2$ | CH$_3$ | H | OCH$_2$COOCH$_2$CH$_3$ |
| 575. | (CH$_3$)$_3$C | H | CH$_3$CH$_2$ | CH$_3$ | H | SCH$_3$ |
| 576. | (CH$_3$)$_3$C | H | CH$_3$CH$_2$ | CH$_3$ | H | SCH$_2$CH$_3$ |
| 577. | (CH$_3$)$_3$C | H | CH$_3$CH$_2$ | CH$_3$ | H | SCH2COOCH3 |
| 578. | (CH$_3$)$_3$C | H | CH$_3$CH$_2$ | CH$_3$ | H | SCH2(4-ClC5H6) |
| 579. | (CH$_3$)$_3$C | CH$_3$ | CH$_3$CH$_2$ | CH$_3$ | H | OCH$_3$ |
| 580. | (CH$_3$)$_3$C | CH$_3$ | CH$_3$CH$_2$ | CH$_3$ | H | OCH$_2$CH$_3$ |
| 581. | (CH$_3$)$_3$C | CH$_3$ | CH$_3$CH$_2$ | CH$_3$ | H | O(CH$_2$)$_2$CH$_3$ |
| 582. | (CH$_3$)$_3$C | CH$_3$ | CH$_3$CH$_2$ | CH$_3$ | H | OCH(CH$_3$)$_2$ |
| 583. | (CH$_3$)$_3$C | CH$_3$ | CH$_3$CH$_2$ | CH$_3$ | H | O(CH$_3$)$_3$ |
| 584. | (CH$_3$)$_3$C | CH$_3$ | CH$_3$CH$_2$ | CH$_3$ | H | O(CH$_2$)$_3$CH$_3$ |
| 585. | (CH$_3$)$_3$C | CH$_3$ | CH$_3$CH$_2$ | CH$_3$ | H | OCH$_2$CH(CH$_3$)$_2$ |
| 586. | (CH$_3$)$_3$C | CH$_3$ | CH$_3$CH$_2$ | CH$_3$ | H | OCH$_2$CH$_2$CH(CH$_3$)$_2$ |
| 587. | (CH$_3$)$_3$C | CH$_3$ | CH$_3$CH$_2$ | CH$_3$ | H | OC(CH$_3$)$_2$CH$_2$CH$_3$ |
| 588. | (CH$_3$)$_3$C | CH$_3$ | CH$_3$CH$_2$ | CH$_3$ | H | O(CH$_2$)$_4$CH$_3$ |
| 589. | (CH$_3$)$_3$C | CH$_3$ | CH$_3$CH$_2$ | CH$_3$ | H | OCH$_2$Cl |
| 590. | (CH$_3$)$_3$C | CH$_3$ | CH$_3$CH$_2$ | CH$_3$ | H | OCH$_2$CH$_2$Cl |
| 591. | (CH$_3$)$_3$C | CH$_3$ | CH$_3$CH$_2$ | CH$_3$ | H | OCH$_2$CH$_2$CH$_2$CH$_2$Cl |
| 592. | (CH$_3$)$_3$C | CH$_3$ | CH$_3$CH$_2$ | CH$_3$ | H | OCH$_2$CH$_2$Cl$_2$ |
| 593. | (CH$_3$)$_3$C | CH$_3$ | CH$_3$CH$_2$ | CH$_3$ | H | OCH$_2$CH$_2$F |
| 594. | (CH$_3$)$_3$C | CH$_3$ | CH$_3$CH$_2$ | CH$_3$ | H | OCH$_2$CHF$_2$ |
| 595. | (CH$_3$)$_3$C | CH$_3$ | CH$_3$CH$_2$ | CH$_3$ | H | OCH$_2$CF$_3$ |
| 596. | (CH$_3$)$_3$C | CH$_3$ | CH$_3$CH$_2$ | CH$_3$ | H | OCH$_2$CH$_2$OCH$_3$ |
| 597. | (CH$_3$)$_3$C | CH$_3$ | CH$_3$CH$_2$ | CH$_3$ | H | OCH$_2$CH$_2$OCH$_2$CH$_3$ |
| 598. | (CH$_3$)$_3$C | CH$_3$ | CH$_3$CH$_2$ | CH$_3$ | H | OCH$_2$OCH$_2$CH$_3$ |
| 599. | (CH$_3$)$_3$C | CH$_3$ | CH$_3$CH$_2$ | CH$_3$ | H | OCH$_2$CH$_2$SCH$_3$ |
| 600. | (CH$_3$)$_3$C | CH$_3$ | CH$_3$CH$_2$ | CH$_3$ | H | OCH$_2$C$_5$H$_6$ |
| 601. | (CH$_3$)$_3$C | CH$_3$ | CH$_3$CH$_2$ | CH$_3$ | H | OCH$_2$(4-ClC$_5$H$_6$) |
| 602. | (CH$_3$)$_3$C | CH$_3$ | CH$_3$CH$_2$ | CH$_3$ | H | OCH$_2$C═CH$_2$ |
| 603. | (CH$_3$)$_3$C | CH$_3$ | CH$_3$CH$_2$ | CH$_3$ | H | OCH$_2$(C═CH)CH$_3$ |
| 604. | (CH$_3$)$_3$C | CH$_3$ | CH$_3$CH$_2$ | CH$_3$ | H | OCH$_2$C≡CH |
| 605. | (CH$_3$)$_3$C | CH$_3$ | CH$_3$CH$_2$ | CH$_3$ | H | OCH$_2$COOCH$_3$ |
| 606. | (CH$_3$)$_3$C | CH$_3$ | CH$_3$CH$_2$ | CH$_3$ | H | OCH$_2$COOCH$_2$CH$_3$ |
| 607. | (CH$_3$)$_3$C | CH$_3$ | CH$_3$CH$_2$ | CH$_3$ | H | SCH$_3$ |
| 608. | (CH$_3$)$_3$C | CH$_3$ | CH$_3$CH$_2$ | CH$_3$ | H | SCH$_2$CH$_3$ |
| 609. | (CH$_3$)$_3$C | CH$_3$ | CH$_3$CH$_2$ | CH$_3$ | H | SCH2COOCH3 |
| 610. | (CH$_3$)$_3$C | CH$_3$ | CH$_3$CH$_2$ | CH$_3$ | H | SCH2(4-ClC5H6) |
| 611. | (CH$_3$)$_3$C | CH$_3$ | CH$_3$CH$_2$ | CH$_3$ | H | OCH$_3$ |
| 612. | (CH$_3$)$_3$C | CH$_3$CH$_2$ | CH$_3$CH$_2$ | CH$_3$ | H | OCH$_2$CH$_3$ |
| 613. | (CH$_3$)$_3$C | CH$_3$CH$_2$ | CH$_3$CH$_2$ | CH$_3$ | H | O(CH$_2$)$_2$CH$_3$ |
| 614. | (CH$_3$)$_3$C | CH$_3$CH$_2$ | CH$_3$CH$_2$ | CH$_3$ | H | OCH(CH$_3$)$_2$ |
| 615. | (CH$_3$)$_3$C | CH$_3$CH$_2$ | CH$_3$CH$_2$ | CH$_3$ | H | O(CH$_3$)$_3$ |
| 616. | (CH$_3$)$_3$C | CH$_3$CH$_2$ | CH$_3$CH$_2$ | CH$_3$ | H | O(CH$_2$)$_3$CH$_3$ |
| 617. | (CH$_3$)$_3$C | CH$_3$CH$_2$ | CH$_3$CH$_2$ | CH$_3$ | H | OCH$_2$CH(CH$_3$)$_2$ |

TABLE 1-continued

| No. | R3 | R9 | R8 | R6 | R7 | L-R10 |
|---|---|---|---|---|---|---|
| 618. | (CH$_3$)$_3$C | CH$_3$CH$_2$ | CH$_3$CH$_2$ | CH$_3$ | H | OCH$_2$CH$_2$CH(CH$_3$)$_2$ |
| 619. | (CH$_3$)$_3$C | CH$_3$CH$_2$ | CH$_3$CH$_2$ | CH$_3$ | H | OC(CH$_3$)$_2$CH$_2$CH$_3$ |
| 620. | (CH$_3$)$_3$C | CH$_3$CH$_2$ | CH$_3$CH$_2$ | CH$_3$ | H | O(CH$_2$)$_4$CH$_3$ |
| 621. | (CH$_3$)$_3$C | CH$_3$CH$_2$ | CH$_3$CH$_2$ | CH$_3$ | H | OCH$_2$Cl |
| 622. | (CH$_3$)$_3$C | CH$_3$CH$_2$ | CH$_3$CH$_2$ | CH$_3$ | H | OCH$_2$CH$_2$Cl |
| 623. | (CH$_3$)$_3$C | CH$_3$CH$_2$ | CH$_3$CH$_2$ | CH$_3$ | H | OCH$_2$CH$_2$CH$_2$Cl |
| 624. | (CH$_3$)$_3$C | CH$_3$CH$_2$ | CH$_3$CH$_2$ | CH$_3$ | H | OCH$_2$CH$_2$Cl$_2$ |
| 625. | (CH$_3$)$_3$C | CH$_3$CH$_2$ | CH$_3$CH$_2$ | CH$_3$ | H | OCH$_2$CH$_2$F |
| 626. | (CH$_3$)$_3$C | CH$_3$CH$_2$ | CH$_3$CH$_2$ | CH$_3$ | H | OCH$_2$CHF$_2$ |
| 627. | (CH$_3$)$_3$C | CH$_3$CH$_2$ | CH$_3$CH$_2$ | CH$_3$ | H | OCH$_2$CF$_3$ |
| 628. | (CH$_3$)$_3$C | CH$_3$CH$_2$ | CH$_3$CH$_2$ | CH$_3$ | H | OCH$_2$CH$_2$OCH$_3$ |
| 629. | (CH$_3$)$_3$C | CH$_3$CH$_2$ | CH$_3$CH$_2$ | CH$_3$ | H | OCH$_2$CH$_2$OCH$_2$CH$_3$ |
| 630. | (CH$_3$)$_3$C | CH$_3$CH$_2$ | CH$_3$CH$_2$ | CH$_3$ | H | OCH$_2$OCH$_2$CH$_3$ |
| 631. | (CH$_3$)$_3$C | CH$_3$CH$_2$ | CH$_3$CH$_2$ | CH$_3$ | H | OCH$_2$CH$_2$SCH$_3$ |
| 632. | (CH$_3$)$_3$C | CH$_3$CH$_2$ | CH$_3$CH$_2$ | CH$_3$ | H | OCH$_2$C$_5$H$_6$ |
| 633. | (CH$_3$)$_3$C | CH$_3$CH$_2$ | CH$_3$CH$_2$ | CH$_3$ | H | OCH$_2$(4-ClC$_5$H$_6$) |
| 634. | (CH$_3$)$_3$C | CH$_3$CH$_2$ | CH$_3$CH$_2$ | CH$_3$ | H | OCH$_2$C=CH$_2$ |
| 635. | (CH$_3$)$_3$C | CH$_3$CH$_2$ | CH$_3$CH$_2$ | CH$_3$ | H | OCH$_2$(C=CH)CH$_3$ |
| 636. | (CH$_3$)$_3$C | CH$_3$CH$_2$ | CH$_3$CH$_2$ | CH$_3$ | H | OCH$_2$C≡CH |
| 637. | (CH$_3$)$_3$C | CH$_3$CH$_2$ | CH$_3$CH$_2$ | CH$_3$ | H | OCH$_2$COOCH$_3$ |
| 638. | (CH$_3$)$_3$C | CH$_3$CH$_2$ | CH$_3$CH$_2$ | CH$_3$ | H | OCH$_2$COOCH$_2$CH$_3$ |
| 639. | (CH$_3$)$_3$C | CH$_3$CH$_2$ | CH$_3$CH$_2$ | CH$_3$ | H | SCH$_3$ |
| 640. | (CH$_3$)$_3$C | CH$_3$CH$_2$ | CH$_3$CH$_2$ | CH$_3$ | H | SCH$_2$CH$_3$ |
| 641. | (CH$_3$)$_3$C | CH$_3$CH$_2$ | CH$_3$CH$_2$ | CH$_3$ | H | SCH2COOCH3 |
| 642. | (CH$_3$)$_3$C | CH$_3$CH$_2$ | CH$_3$CH$_2$ | CH$_3$ | H | SCH2(4-ClC5H6) |
| 643. | (CH$_3$)$_3$C | H | CH$_3$ | CH$_3$ | Cl | OCH$_3$ |
| 644. | (CH$_3$)$_3$C | H | CH$_3$ | CH$_3$ | Cl | OCH$_2$CH$_3$ |
| 645. | (CH$_3$)$_3$C | H | CH$_3$ | CH$_3$ | Cl | O(CH$_2$)$_2$CH$_3$ |
| 646. | (CH$_3$)$_3$C | H | CH$_3$ | CH$_3$ | Cl | OCH(CH$_3$)$_2$ |
| 647. | (CH$_3$)$_3$C | H | CH$_3$ | CH$_3$ | Cl | O(CH$_3$)$_3$ |
| 648. | (CH$_3$)$_3$C | H | CH$_3$ | CH$_3$ | Cl | O(CH$_2$)$_3$CH$_3$ |
| 649. | (CH$_3$)$_3$C | H | CH$_3$ | CH$_3$ | Cl | OCH$_2$CH(CH$_3$)$_2$ |
| 650. | (CH$_3$)$_3$C | H | CH$_3$ | CH$_3$ | Cl | OCH$_2$CH$_2$CH(CH$_3$)$_2$ |
| 651. | (CH$_3$)$_3$C | H | CH$_3$ | CH$_3$ | Cl | OC(CH$_3$)$_2$CH$_2$CH$_3$ |
| 652. | (CH$_3$)$_3$C | H | CH$_3$ | CH$_3$ | Cl | O(CH$_2$)$_4$CH$_3$ |
| 653. | (CH$_3$)$_3$C | H | CH$_3$ | CH$_3$ | Cl | OCH$_2$Cl |
| 654. | (CH$_3$)$_3$C | H | CH$_3$ | CH$_3$ | Cl | OCH$_2$CH$_2$Cl |
| 655. | (CH$_3$)$_3$C | H | CH$_3$ | CH$_3$ | Cl | OCH$_2$CH$_2$CH$_2$Cl |
| 656. | (CH$_3$)$_3$C | H | CH$_3$ | CH$_3$ | Cl | OCH$_2$CH$_2$Cl$_2$ |
| 657. | (CH$_3$)$_3$C | H | CH$_3$ | CH$_3$ | Cl | OCH$_2$CH$_2$F |
| 658. | (CH$_3$)$_3$C | H | CH$_3$ | CH$_3$ | Cl | OCH$_2$CHF$_2$ |
| 659. | (CH$_3$)$_3$C | H | CH$_3$ | CH$_3$ | Cl | OCH$_2$CF$_3$ |
| 660. | (CH$_3$)$_3$C | H | CH$_3$ | CH$_3$ | Cl | OCH$_2$CH$_2$OCH$_3$ |
| 661. | (CH$_3$)$_3$C | H | CH$_3$ | CH$_3$ | Cl | OCH$_2$CH$_2$OCH$_2$CH$_3$ |
| 662. | (CH$_3$)$_3$C | H | CH$_3$ | CH$_3$ | Cl | OCH$_2$OCH$_2$CH$_3$ |
| 663. | (CH$_3$)$_3$C | H | CH$_3$ | CH$_3$ | Cl | OCH$_2$CH$_2$SCH$_3$ |
| 664. | (CH$_3$)$_3$C | H | CH$_3$ | CH$_3$ | Cl | OCH$_2$C$_5$H$_6$ |
| 665. | (CH$_3$)$_3$C | H | CH$_3$ | CH$_3$ | Cl | OCH$_2$(4-ClC$_5$H$_6$) |
| 666. | (CH$_3$)$_3$C | H | CH$_3$ | CH$_3$ | Cl | OCH$_2$C=CH$_2$ |
| 667. | (CH$_3$)$_3$C | H | CH$_3$ | CH$_3$ | Cl | OCH$_2$(C=CH)CH$_3$ |
| 668. | (CH$_3$)$_3$C | H | CH$_3$ | CH$_3$ | Cl | OCH$_2$C≡CH |
| 669. | (CH$_3$)$_3$C | H | CH$_3$ | CH$_3$ | Cl | OCH$_2$COOCH$_3$ |
| 670. | (CH$_3$)$_3$C | H | CH$_3$ | CH$_3$ | Cl | OCH$_2$COOCH$_2$CH$_3$ |
| 671. | (CH$_3$)$_3$C | H | CH$_3$ | CH$_3$ | Cl | SCH$_3$ |
| 672. | (CH$_3$)$_3$C | H | CH$_3$ | CH$_3$ | Cl | SCH$_2$CH$_3$ |
| 673. | (CH$_3$)$_3$C | H | CH$_3$ | CH$_3$ | Cl | SCH2COOCH3 |
| 674. | (CH$_3$)$_3$C | H | CH$_3$ | CH$_3$ | Cl | SCH2(4-ClC5H6) |
| 675. | (CH$_3$)$_3$C | CH$_3$ | CH$_3$ | CH$_3$ | Cl | OCH$_3$ |
| 676. | (CH$_3$)$_3$C | CH$_3$ | CH$_3$ | CH$_3$ | Cl | OCH$_2$CH$_3$ |
| 677. | (CH$_3$)$_3$C | CH$_3$ | CH$_3$ | CH$_3$ | Cl | O(CH$_2$)$_2$CH$_3$ |
| 678. | (CH$_3$)$_3$C | CH$_3$ | CH$_3$ | CH$_3$ | Cl | OCH(CH$_3$)$_2$ |
| 679. | (CH$_3$)$_3$C | CH$_3$ | CH$_3$ | CH$_3$ | Cl | O(CH$_3$)$_3$ |
| 680. | (CH$_3$)$_3$C | CH$_3$ | CH$_3$ | CH$_3$ | Cl | O(CH$_2$)$_3$CH$_3$ |
| 681. | (CH$_3$)$_3$C | CH$_3$ | CH$_3$ | CH$_3$ | Cl | OCH$_2$CH(CH$_3$)$_2$ |
| 682. | (CH$_3$)$_3$C | CH$_3$ | CH$_3$ | CH$_3$ | Cl | OCH$_2$CH$_2$CH(CH$_3$)$_2$ |
| 683. | (CH$_3$)$_3$C | CH$_3$ | CH$_3$ | CH$_3$ | Cl | OC(CH$_3$)$_2$CH$_2$CH$_3$ |
| 684. | (CH$_3$)$_3$C | CH$_3$ | CH$_3$ | CH$_3$ | Cl | O(CH$_2$)$_4$CH$_3$ |
| 685. | (CH$_3$)$_3$C | CH$_3$ | CH$_3$ | CH$_3$ | Cl | OCH$_2$Cl |
| 686. | (CH$_3$)$_3$C | CH$_3$ | CH$_3$ | CH$_3$ | Cl | OCH$_2$CH$_2$Cl |
| 687. | (CH$_3$)$_3$C | CH$_3$ | CH$_3$ | CH$_3$ | Cl | OCH$_2$CH$_2$CH$_2$Cl |
| 688. | (CH$_3$)$_3$C | CH$_3$ | CH$_3$ | CH$_3$ | Cl | OCH$_2$CH$_2$Cl$_2$ |
| 689. | (CH$_3$)$_3$C | CH$_3$ | CH$_3$ | CH$_3$ | Cl | OCH$_2$CH$_2$F |
| 690. | (CH$_3$)$_3$C | CH$_3$ | CH$_3$ | CH$_3$ | Cl | OCH$_2$CHF$_2$ |
| 691. | (CH$_3$)$_3$C | CH$_3$ | CH$_3$ | CH$_3$ | Cl | OCH$_2$CF$_3$ |
| 692. | (CH$_3$)$_3$C | CH$_3$ | CH$_3$ | CH$_3$ | Cl | OCH$_2$CH$_2$OCH$_3$ |
| 693. | (CH$_3$)$_3$C | CH$_3$ | CH$_3$ | CH$_3$ | Cl | OCH$_2$CH$_2$OCH$_2$CH$_3$ |
| 694. | (CH$_3$)$_3$C | CH$_3$ | CH$_3$ | CH$_3$ | Cl | OCH$_2$OCH$_2$CH$_3$ |
| 695. | (CH$_3$)$_3$C | CH$_3$ | CH$_3$ | CH$_3$ | Cl | OCH$_2$CH$_2$SCH$_3$ |

TABLE 1-continued

| No. | R3 | R9 | R8 | R6 | R7 | L-R10 |
|---|---|---|---|---|---|---|
| 696. | $(CH_3)_3C$ | $CH_3$ | $CH_3$ | $CH_3$ | Cl | $OCH_2C_5H_6$ |
| 697. | $(CH_3)_3C$ | $CH_3$ | $CH_3$ | $CH_3$ | Cl | $OCH_2(4\text{-}ClC_5H_6)$ |
| 698. | $(CH_3)_3C$ | $CH_3$ | $CH_3$ | $CH_3$ | Cl | $OCH_2C=CH_2$ |
| 699. | $(CH_3)_3C$ | $CH_3$ | $CH_3$ | $CH_3$ | Cl | $OCH_2(C=CH)CH_3$ |
| 700. | $(CH_3)_3C$ | $CH_3$ | $CH_3$ | $CH_3$ | Cl | $OCH_2C\equiv CH$ |
| 701. | $(CH_3)_3C$ | $CH_3$ | $CH_3$ | $CH_3$ | Cl | $OCH_2COOCH_3$ |
| 702. | $(CH_3)_3C$ | $CH_3$ | $CH_3$ | $CH_3$ | Cl | $OCH_2COOCH_2CH_3$ |
| 703. | $(CH_3)_3C$ | $CH_3$ | $CH_3$ | $CH_3$ | Cl | $SCH_3$ |
| 704. | $(CH_3)_3C$ | $CH_3$ | $CH_3$ | $CH_3$ | Cl | $SCH_2CH_3$ |
| 705. | $(CH_3)_3C$ | $CH_3$ | $CH_3$ | $CH_3$ | Cl | SCH2COOCH3 |
| 706. | $(CH_3)_3C$ | $CH_3$ | $CH_3$ | $CH_3$ | Cl | SCH2(4-ClC5H6) |
| 707. | $(CH_3)_3C$ | $CH_3$ | $CH_3$ | $CH_3$ | Cl | $OCH_3$ |
| 708. | $(CH_3)_3C$ | $CH_3CH_2$ | $CH_3$ | $CH_3$ | Cl | $OCH_2CH_3$ |
| 709. | $(CH_3)_3C$ | $CH_3CH_2$ | $CH_3$ | $CH_3$ | Cl | $O(CH_2)_2CH_3$ |
| 710. | $(CH_3)_3C$ | $CH_3CH_2$ | $CH_3$ | $CH_3$ | Cl | $OCH(CH_3)_2$ |
| 711. | $(CH_3)_3C$ | $CH_3CH_2$ | $CH_3$ | $CH_3$ | Cl | $O(CH_3)_3$ |
| 712. | $(CH_3)_3C$ | $CH_3CH_2$ | $CH_3$ | $CH_3$ | Cl | $O(CH_2)_2CH_3$ |
| 713. | $(CH_3)_3C$ | $CH_3CH_2$ | $CH_3$ | $CH_3$ | Cl | $OCH_2CH(CH_3)_2$ |
| 714. | $(CH_3)_3C$ | $CH_3CH_2$ | $CH_3$ | $CH_3$ | Cl | $OCH_2CH_2CH(CH_3)_2$ |
| 715. | $(CH_3)_3C$ | $CH_3CH_2$ | $CH_3$ | $CH_3$ | Cl | $OC(CH_3)_2CH_2CH_3$ |
| 716. | $(CH_3)_3C$ | $CH_3CH_2$ | $CH_3$ | $CH_3$ | Cl | $O(CH_2)_4CH_3$ |
| 717. | $(CH_3)_3C$ | $CH_3CH_2$ | $CH_3$ | $CH_3$ | Cl | $OCH_2Cl$ |
| 718. | $(CH_3)_3C$ | $CH_3CH_2$ | $CH_3$ | $CH_3$ | Cl | $OCH_2CH_2Cl$ |
| 719. | $(CH_3)_3C$ | $CH_3CH_2$ | $CH_3$ | $CH_3$ | Cl | $OCH_2CH_2CH_2CH_2Cl$ |
| 720. | $(CH_3)_3C$ | $CH_3CH_2$ | $CH_3$ | $CH_3$ | Cl | $OCH_2CH_2Cl_2$ |
| 721. | $(CH_3)_3C$ | $CH_3CH_2$ | $CH_3$ | $CH_3$ | Cl | $OCH_2CH_2F$ |
| 722. | $(CH_3)_3C$ | $CH_3CH_2$ | $CH_3$ | $CH_3$ | Cl | $OCH_2CHF_2$ |
| 723. | $(CH_3)_3C$ | $CH_3CH_2$ | $CH_3$ | $CH_3$ | Cl | $OCH_2CF_3$ |
| 724. | $(CH_3)_3C$ | $CH_3CH_2$ | $CH_3$ | $CH_3$ | Cl | $OCH_2CH_2OCH_3$ |
| 725. | $(CH_3)_3C$ | $CH_3CH_2$ | $CH_3$ | $CH_3$ | Cl | $OCH_2CH_2OCH_2CH_3$ |
| 726. | $(CH_3)_3C$ | $CH_3CH_2$ | $CH_3$ | $CH_3$ | Cl | $OCH_2OCH_2CH_3$ |
| 727. | $(CH_3)_3C$ | $CH_3CH_2$ | $CH_3$ | $CH_3$ | Cl | $OCH_2CH_2SCH_3$ |
| 728. | $(CH_3)_3C$ | $CH_3CH_2$ | $CH_3$ | $CH_3$ | Cl | $OCH_2C_5H_6$ |
| 729. | $(CH_3)_3C$ | $CH_3CH_2$ | $CH_3$ | $CH_3$ | Cl | $OCH_2(4\text{-}ClC_5H_6)$ |
| 730. | $(CH_3)_3C$ | $CH_3CH_2$ | $CH_3$ | $CH_3$ | Cl | $OCH_2C=CH_2$ |
| 731. | $(CH_3)_3C$ | $CH_3CH_2$ | $CH_3$ | $CH_3$ | Cl | $OCH_2(C=CH)CH_3$ |
| 732. | $(CH_3)_3C$ | $CH_3CH_2$ | $CH_3$ | $CH_3$ | Cl | $OCH_2C\equiv CH$ |
| 733. | $(CH_3)_3C$ | $CH_3CH_{23}$ | $CH_3$ | $CH_3$ | Cl | $OCH_2COOCH_3$ |
| 734. | $(CH_3)_3C$ | $CH_3CH_2$ | $CH_3$ | $CH_3$ | Cl | $OCH_2COOCH_2CH_3$ |
| 735. | $(CH_3)_3C$ | $CH_3CH_2$ | $CH_3$ | $CH_3$ | Cl | $SCH_3$ |
| 736. | $(CH_3)_3C$ | $CH_3CH_2$ | $CH_3$ | $CH_3$ | Cl | $SCH_2CH_3$ |
| 737. | $(CH_3)_3C$ | $CH_3CH_2$ | $CH_3$ | $CH_3$ | Cl | SCH2COOCH3 |
| 738. | $(CH_3)_3C$ | $CH_3CH_2$ | $CH_3$ | $CH_3$ | Cl | SCH2(4-ClC5H6) |
| 739. | $(CH_3)_3C$ | H | $CH_3CH_2$ | $CH_3$ | Cl | $OCH_3$ |
| 740. | $(CH_3)_3C$ | H | $CH_3CH_2$ | $CH_3$ | Cl | $OCH_2CH_3$ |
| 741. | $(CH_3)_3C$ | H | $CH_3CH_2$ | $CH_3$ | Cl | $O(CH_2)_2CH_3$ |
| 742. | $(CH_3)_3C$ | H | $CH_3CH_2$ | $CH_3$ | Cl | $OCH(CH_3)_2$ |
| 743. | $(CH_3)_3C$ | H | $CH_3CH_2$ | $CH_3$ | Cl | $O(CH_3)_3$ |
| 744. | $(CH_3)_3C$ | H | $CH_3CH_2$ | $CH_3$ | Cl | $O(CH_2)_3CH_3$ |
| 745. | $(CH_3)_3C$ | H | $CH_3CH_2$ | $CH_3$ | Cl | $OCH_2CH(CH_3)_2$ |
| 746. | $(CH_3)_3C$ | H | $CH_3CH_2$ | $CH_3$ | Cl | $OCH_2CH_2CH(CH_3)_2$ |
| 747. | $(CH_3)_3C$ | H | $CH_3CH_2$ | $CH_3$ | Cl | $OC(CH_3)_2CH_2CH_3$ |
| 748. | $(CH_3)_3C$ | H | $CH_3CH_2$ | $CH_3$ | Cl | $O(CH_2)_4CH_3$ |
| 749. | $(CH_3)_3C$ | H | $CH_3CH_2$ | $CH_3$ | Cl | $OCH_2Cl$ |
| 750. | $(CH_3)_3C$ | H | $CH_3CH_2$ | $CH_3$ | Cl | $OCH_2CH_2Cl$ |
| 751. | $(CH_3)_3C$ | H | $CH_3CH_2$ | $CH_3$ | Cl | $OCH_2CH_2CH_2CH_2Cl$ |
| 752. | $(CH_3)_3C$ | H | $CH_3CH_2$ | $CH_3$ | Cl | $OCH_2CH_2Cl_2$ |
| 753. | $(CH_3)_3C$ | H | $CH_3CH_2$ | $CH_3$ | Cl | $OCH_2CH_2F$ |
| 754. | $(CH_3)_3C$ | H | $CH_3CH_2$ | $CH_3$ | Cl | $OCH_2CHF_2$ |
| 755. | $(CH_3)_3C$ | H | $CH_3CH_2$ | $CH_3$ | Cl | $OCH_2CF_3$ |
| 756. | $(CH_3)_3C$ | H | $CH_3CH_2$ | $CH_3$ | Cl | $OCH_2CH_2OCH_3$ |
| 757. | $(CH_3)_3C$ | H | $CH_3CH_2$ | $CH_3$ | Cl | $OCH_2CH_2OCH_2CH_3$ |
| 758. | $(CH_3)_3C$ | H | $CH_3CH_2$ | $CH_3$ | Cl | $OCH_2OCH_2CH_3$ |
| 759. | $(CH_3)_3C$ | H | $CH_3CH_2$ | $CH_3$ | Cl | $OCH_2CH_2SCH_3$ |
| 760. | $(CH_3)_3C$ | H | $CH_3CH_2$ | $CH_3$ | Cl | $OCH_2C_5H_6$ |
| 761. | $(CH_3)_3C$ | H | $CH_3CH_2$ | $CH_3$ | Cl | $OCH_2(4\text{-}ClC_5H_6)$ |
| 762. | $(CH_3)_3C$ | H | $CH_3CH_2$ | $CH_3$ | Cl | $OCH_2C=CH_2$ |
| 763. | $(CH_3)_3C$ | H | $CH_3CH_2$ | $CH_3$ | Cl | $OCH_2(C=CH)CH_3$ |
| 764. | $(CH_3)_3C$ | H | $CH_3CH_2$ | $CH_3$ | Cl | $OCH_2C\equiv CH$ |
| 765. | $(CH_3)_3C$ | H | $CH_3CH_2$ | $CH_3$ | Cl | $OCH_2COOCH_3$ |
| 766. | $(CH_3)_3C$ | H | $CH_3CH_2$ | $CH_3$ | Cl | $OCH_2COOCH_2CH_3$ |
| 767. | $(CH_3)_3C$ | H | $CH_3CH_2$ | $CH_3$ | Cl | $SCH_3$ |
| 768. | $(CH_3)_3C$ | H | $CH_3CH_2$ | $CH_3$ | Cl | $SCH_2CH_3$ |
| 769. | $(CH_3)_3C$ | H | $CH_3CH_2$ | $CH_3$ | Cl | SCH2COOCH3 |
| 770. | $(CH_3)_3C$ | H | $CH_3CH_2$ | $CH_3$ | Cl | SCH2(4-ClC5H6) |
| 771. | $(CH_3)_3C$ | $CH_3$ | $CH_3CH_2$ | $CH_3$ | Cl | $OCH_3$ |
| 772. | $(CH_3)_3C$ | $CH_3$ | $CH_3CH_2$ | $CH_3$ | Cl | $OCH_2CH_3$ |
| 773. | $(CH_3)_3C$ | $CH_3$ | $CH_3CH_2$ | $CH_3$ | Cl | $O(CH_2)_2CH_3$ |

TABLE 1-continued

| No. | R3 | R9 | R8 | R6 | R7 | L-R10 |
|---|---|---|---|---|---|---|
| 774. | (CH₃)₃C | CH₃ | CH₃CH₂ | CH₃ | Cl | OCH(CH₃)₂ |
| 775. | (CH₃)₃C | CH₃ | CH₃CH₂ | CH₃ | Cl | O(CH₃)₃ |
| 776. | (CH₃)₃C | CH₃ | CH₃CH₂ | CH₃ | Cl | O(CH₂)₃CH₃ |
| 777. | (CH₃)₃C | CH₃ | CH₃CH₂ | CH₃ | Cl | OCH₂CH(CH₃)₂ |
| 778. | (CH₃)₃C | CH₃ | CH₃CH₂ | CH₃ | Cl | OCH₂CH₂CH(CH₃)₂ |
| 779. | (CH₃)₃C | CH₃ | CH₃CH₂ | CH₃ | Cl | OC(CH₃)₂CH₂CH₃ |
| 780. | (CH₃)₃C | CH₃ | CH₃CH₂ | CH₃ | Cl | O(CH₂)₄CH₃ |
| 781. | (CH₃)₃C | CH₃ | CH₃CH₂ | CH₃ | Cl | OCH₂Cl |
| 782. | (CH₃)₃C | CH₃ | CH₃CH₂ | CH₃ | Cl | OCH₂CH₂Cl |
| 783. | (CH₃)₃C | CH₃ | CH₃CH₂ | CH₃ | Cl | OCH₂CH₂CH₂CH₂Cl |
| 784. | (CH₃)₃C | CH₃ | CH₃CH₂ | CH₃ | Cl | OCH₂CH₂Cl₂ |
| 785. | (CH₃)₃C | CH₃ | CH₃CH₂ | CH₃ | Cl | OCH₂CH₂F |
| 786. | (CH₃)₃C | CH₃ | CH₃CH₂ | CH₃ | Cl | OCH₂CHF₂ |
| 787. | (CH₃)₃C | CH₃ | CH₃CH₂ | CH₃ | Cl | OCH₂CF₃ |
| 788. | (CH₃)₃C | CH₃ | CH₃CH₂ | CH₃ | Cl | OCH₂CH₂OCH₃ |
| 789. | (CH₃)₃C | CH₃ | CH₃CH₂ | CH₃ | Cl | OCH₂CH₂OCH₂CH₃ |
| 790. | (CH₃)₃C | CH₃ | CH₃CH₂ | CH₃ | Cl | OCH₂OCH₂CH₃ |
| 791. | (CH₃)₃C | CH₃ | CH₃CH₂ | CH₃ | Cl | OCH₂CH₂SCH₃ |
| 792. | (CH₃)₃C | CH₃ | CH₃CH₂ | CH₃ | Cl | OCH₂C₅H₆ |
| 793. | (CH₃)₃C | CH₃ | CH₃CH₂ | CH₃ | Cl | OCH₂(4-ClC₅H₆) |
| 794. | (CH₃)₃C | CH₃ | CH₃CH₂ | CH₃ | Cl | OCH₂C=CH₂ |
| 795. | (CH₃)₃C | CH₃ | CH₃CH₂ | CH₃ | Cl | OCH₂(C=CH)CH₃ |
| 796. | (CH₃)₃C | CH₃ | CH₃CH₂ | CH₃ | Cl | OCH₂C≡CH |
| 797. | (CH₃)₃C | CH₃ | CH₃CH₂ | CH₃ | Cl | OCH₂COOCH₃ |
| 798. | (CH₃)₃C | CH₃ | CH₃CH₂ | CH₃ | Cl | OCH₂COOCH₂CH₃ |
| 799. | (CH₃)₃C | CH₃ | CH₃CH₂ | CH₃ | Cl | SCH₃ |
| 800. | (CH₃)₃C | CH₃ | CH₃CH₂ | CH₃ | Cl | SCH₂CH₃ |
| 801. | (CH₃)₃C | CH₃ | CH₃CH₂ | CH₃ | Cl | SCH2COOCH3 |
| 802. | (CH₃)₃C | CH₃ | CH₃CH₂ | CH₃ | Cl | SCH2(4-ClC5H6) |
| 803. | (CH₃)₃C | CH₃ | CH₃CH₂ | CH₃ | Cl | OCH₃ |
| 804. | (CH₃)₃C | CH₃CH₂ | CH₃CH₂ | CH₃ | Cl | OCH₂CH₃ |
| 805. | (CH₃)₃C | CH₃CH₂ | CH₃CH₂ | CH₃ | Cl | O(CH₂)₂CH₃ |
| 806. | (CH₃)₃C | CH₃CH₂ | CH₃CH₂ | CH₃ | Cl | OCH(CH₃)₂ |
| 807. | (CH₃)₃C | CH₃CH₂ | CH₃CH₂ | CH₃ | Cl | O(CH₃)₃ |
| 808. | (CH₃)₃C | CH₃CH₂ | CH₃CH₂ | CH₃ | Cl | O(CH₂)₂CH₃ |
| 809. | (CH₃)₃C | CH₃CH₂ | CH₃CH₂ | CH₃ | Cl | OCH₂CH(CH₃)₂ |
| 810. | (CH₃)₃C | CH₃CH₂ | CH₃CH₂ | CH₃ | Cl | OCH₂CH₂CH(CH₃)₂ |
| 811. | (CH₃)₃C | CH₃CH₂ | CH₃CH₂ | CH₃ | Cl | OC(CH₃)₂CH₂CH₃ |
| 812. | (CH₃)₃C | CH₃CH₂ | CH₃CH₂ | CH₃ | Cl | O(CH₂)₄CH₃ |
| 813. | (CH₃)₃C | CH₃CH₂ | CH₃CH₂ | CH₃ | Cl | OCH₂Cl |
| 814. | (CH₃)₃C | CH₃CH₂ | CH₃CH₂ | CH₃ | Cl | OCH₂CH₂Cl |
| 815. | (CH₃)₃C | CH₃CH₂ | CH₃CH₂ | CH₃ | Cl | OCH₂CH₂CH₂CH₂Cl |
| 816. | (CH₃)₃C | CH₃CH₂ | CH₃CH₂ | CH₃ | Cl | OCH₂CH₂Cl₂ |
| 817. | (CH₃)₃C | CH₃CH₂ | CH₃CH₂ | CH₃ | Cl | OCH₂CH₂F |
| 818. | (CH₃)₃C | CH₃CH₂ | CH₃CH₂ | CH₃ | Cl | OCH₂CHF₂ |
| 819. | (CH₃)₃C | CH₃CH₂ | CH₃CH₂ | CH₃ | Cl | OCH₂CF₃ |
| 820. | (CH₃)₃C | CH₃CH₂ | CH₃CH₂ | CH₃ | Cl | OCH₂CH₂OCH₃ |
| 821. | (CH₃)₃C | CH₃CH₂ | CH₃CH₂ | CH₃ | Cl | OCH₂CH₂OCH₂CH₃ |
| 822. | (CH₃)₃C | CH₃CH₂ | CH₃CH₂ | CH₃ | Cl | OCH₂OCH₂CH₃ |
| 823. | (CH₃)₃C | CH₃CH₂ | CH₃CH₂ | CH₃ | Cl | OCH₂CH₂SCH₃ |
| 824. | (CH₃)₃C | CH₃CH₂ | CH₃CH₂ | CH₃ | Cl | OCH₂C₅H₆ |
| 825. | (CH₃)₃C | CH₃CH₂ | CH₃CH₂ | CH₃ | Cl | OCH₂(4-ClC₅H₆) |
| 826. | (CH₃)₃C | CH₃CH₂ | CH₃CH₂ | CH₃ | Cl | OCH₂C=CH₂ |
| 827. | (CH₃)₃C | CH₃CH₂ | CH₃CH₂ | CH₃ | Cl | OCH₂(C=CH)CH₃ |
| 828. | (CH₃)₃C | CH₃CH₂ | CH₃CH₂ | CH₃ | Cl | OCH₂C≡CH |
| 829. | (CH₃)₃C | CH₃CH₂ | CH₃CH₂ | CH₃ | Cl | OCH₂COOCH₃ |
| 830. | (CH₃)₃C | CH₃CH₂ | CH₃CH₂ | CH₃ | Cl | OCH₂COOCH₂CH₃ |
| 831. | (CH₃)₃C | CH₃CH₂ | CH₃CH₂ | CH₃ | Cl | SCH₃ |
| 832. | (CH₃)₃C | CH₃CH₂ | CH₃CH₂ | CH₃ | Cl | SCH₂CH₃ |
| 833. | (CH₃)₃C | CH₃CH₂ | CH₃CH₂ | CH₃ | Cl | SCH2COOCH3 |
| 834. | (CH₃)₃C | CH₃CH₂ | CH₃CH₂ | CH₃ | Cl | SCH2(4-ClC5H6) |
| 835. | (CH₃)₃C | H | CH₃ | CH₃ | CH₃ | OCH₃ |
| 836. | (CH₃)₃C | H | CH₃ | CH₃ | CH₃ | OCH₂CH₃ |
| 837. | (CH₃)₃C | H | CH₃ | CH₃ | CH₃ | O(CH₂)₂CH₃ |
| 838. | (CH₃)₃C | H | CH₃ | CH₃ | CH₃ | OCH(CH₃)₂ |
| 839. | (CH₃)₃C | H | CH₃ | CH₃ | CH₃ | O(CH₃)₃ |
| 840. | (CH₃)₃C | H | CH₃ | CH₃ | CH₃ | O(CH₂)₃CH₃ |
| 841. | (CH₃)₃C | H | CH₃ | CH₃ | CH₃ | OCH₂CH(CH₃)₂ |
| 842. | (CH₃)₃C | H | CH₃ | CH₃ | CH₃ | OCH₂CH₂CH(CH₃)₂ |
| 843. | (CH₃)₃C | H | CH₃ | CH₃ | CH₃ | OC(CH₃)₂CH₂CH₃ |
| 844. | (CH₃)₃C | H | CH₃ | CH₃ | CH₃ | O(CH₂)₄CH₃ |
| 845. | (CH₃)₃C | H | CH₃ | CH₃ | CH₃ | OCH₂Cl |
| 846. | (CH₃)₃C | H | CH₃ | CH₃ | CH₃ | OCH₂CH₂Cl |
| 847. | (CH₃)₃C | H | CH₃ | CH₃ | CH₃ | OCH₂CH₂CH₂CH₂Cl |
| 848. | (CH₃)₃C | H | CH₃ | CH₃ | CH₃ | OCH₂CH₂Cl₂ |
| 849. | (CH₃)₃C | H | CH₃ | CH₃ | CH₃ | OCH₂CH₂F |
| 850. | (CH₃)₃C | H | CH₃ | CH₃ | CH₃ | OCH₂CHF₂ |
| 851. | (CH₃)₃C | H | CH₃ | CH₃ | CH₃ | OCH₂CF₃ |

TABLE 1-continued

| No. | R3 | R9 | R8 | R6 | R7 | L-R10 |
|---|---|---|---|---|---|---|
| 852. | (CH₃)₃C | H | CH₃ | CH₃ | CH₃ | OCH₂CH₂OCH₃ |
| 853. | (CH₃)₃C | H | CH₃ | CH₃ | CH₃ | OCH₂CH₂OCH₂CH₃ |
| 854. | (CH₃)₃C | H | CH₃ | CH₃ | CH₃ | OCH₂OCH₂CH₃ |
| 855. | (CH₃)₃C | H | CH₃ | CH₃ | CH₃ | OCH₂CH₂SCH₃ |
| 856. | (CH₃)₃C | H | CH₃ | CH₃ | CH₃ | OCH₂C₅H₆ |
| 857. | (CH₃)₃C | H | CH₃ | CH₃ | CH₃ | OCH₂(4-ClC₅H₆) |
| 858. | (CH₃)₃C | H | CH₃ | CH₃ | CH₃ | OCH₂C=CH₂ |
| 859. | (CH₃)₃C | H | CH₃ | CH₃ | CH₃ | OCH₂(C=CH)CH₃ |
| 860. | (CH₃)₃C | H | CH₃ | CH₃ | CH₃ | OCH₂C≡CH |
| 861. | (CH₃)₃C | H | CH₃ | CH₃ | CH₃ | OCH₂COOCH₃ |
| 862. | (CH₃)₃C | H | CH₃ | CH₃ | CH₃ | OCH₂COOCH₂CH₃ |
| 863. | (CH₃)₃C | H | CH₃ | CH₃ | CH₃ | SCH₃ |
| 864. | (CH₃)₃C | H | CH₃ | CH₃ | CH₃ | SCH₂CH₃ |
| 865. | (CH₃)₃C | H | CH₃ | CH₃ | CH₃ | SCH2COOCH3 |
| 866. | (CH₃)₃C | H | CH₃ | CH₃ | CH₃ | SCH2(4-ClC5H6) |
| 867. | (CH₃)₃C | CH₃ | CH₃ | CH₃ | CH₃ | OCH₃ |
| 868. | (CH₃)₃C | CH₃ | CH₃ | CH₃ | CH₃ | OCH₂CH₃ |
| 869. | (CH₃)₃C | CH₃ | CH₃ | CH₃ | CH₃ | O(CH₂)₂CH₃ |
| 870. | (CH₃)₃C | CH₃ | CH₃ | CH₃ | CH₃ | OCH(CH₃)₂ |
| 871. | (CH₃)₃C | CH₃ | CH₃ | CH₃ | CH₃ | O(CH₃)₃ |
| 872. | (CH₃)₃C | CH₃ | CH₃ | CH₃ | CH₃ | O(CH₂)₃CH₃ |
| 873. | (CH₃)₃C | CH₃ | CH₃ | CH₃ | CH₃ | OCH₂CH(CH₃)₂ |
| 874. | (CH₃)₃C | CH₃ | CH₃ | CH₃ | CH₃ | OCH₂CH₂CH(CH₃)₂ |
| 875. | (CH₃)₃C | CH₃ | CH₃ | CH₃ | CH₃ | OC(CH₃)₂CH₂CH₃ |
| 876. | (CH₃)₃C | CH₃ | CH₃ | CH₃ | CH₃ | O(CH₂)₄CH₃ |
| 877. | (CH₃)₃C | CH₃ | CH₃ | CH₃ | CH₃ | OCH₂Cl |
| 878. | (CH₃)₃C | CH₃ | CH₃ | CH₃ | CH₃ | OCH₂CH₂Cl |
| 879. | (CH₃)₃C | CH₃ | CH₃ | CH₃ | CH₃ | OCH₂CH₂CH₂CH₂Cl |
| 880. | (CH₃)₃C | CH₃ | CH₃ | CH₃ | CH₃ | OCH₂CH₂Cl₂ |
| 881. | (CH₃)₃C | CH₃ | CH₃ | CH₃ | CH₃ | OCH₂CH₂F |
| 882. | (CH₃)₃C | CH₃ | CH₃ | CH₃ | CH₃ | OCH₂CHF₂ |
| 883. | (CH₃)₃C | CH₃ | CH₃ | CH₃ | CH₃ | OCH₂CF₃ |
| 884. | (CH₃)₃C | CH₃ | CH₃ | CH₃ | CH₃ | OCH₂CH₂OCH₃ |
| 885. | (CH₃)₃C | CH₃ | CH₃ | CH₃ | CH₃ | OCH₂CH₂OCH₂CH₃ |
| 886. | (CH₃)₃C | CH₃ | CH₃ | CH₃ | CH₃ | OCH₂OCH₂CH₃ |
| 887. | (CH₃)₃C | CH₃ | CH₃ | CH₃ | CH₃ | OCH₂CH₂SCH₃ |
| 888. | (CH₃)₃C | CH₃ | CH₃ | CH₃ | CH₃ | OCH₂C₅H₆ |
| 889. | (CH₃)₃C | CH₃ | CH₃ | CH₃ | CH₃ | OCH₂(4-ClC₅H₆) |
| 890. | (CH₃)₃C | CH₃ | CH₃ | CH₃ | CH₃ | OCH₂C=CH₂ |
| 891. | (CH₃)₃C | CH₃ | CH₃ | CH₃ | CH₃ | OCH₂(C=CH)CH₃ |
| 892. | (CH₃)₃C | CH₃ | CH₃ | CH₃ | CH₃ | OCH₂C≡CH |
| 893. | (CH₃)₃C | CH₃ | CH₃ | CH₃ | CH₃ | OCH₂COOCH₃ |
| 894. | (CH₃)₃C | CH₃ | CH₃ | CH₃ | CH₃ | OCH₂COOCH₂CH₃ |
| 895. | (CH₃)₃C | CH₃ | CH₃ | CH₃ | CH₃ | SCH₃ |
| 896. | (CH₃)₃C | CH₃ | CH₃ | CH₃ | CH₃ | SCH₂CH₃ |
| 897. | (CH₃)₃C | CH₃ | CH₃ | CH₃ | CH₃ | SCH2COOCH3 |
| 898. | (CH₃)₃C | CH₃ | CH₃ | CH₃ | CH₃ | SCH2(4-ClC5H6) |
| 899. | (CH₃)₃C | CH₃ | CH₃ | CH₃ | CH₃ | OCH₃ |
| 900. | (CH₃)₃C | CH₃CH₂ | CH₃ | CH₃ | CH₃ | OCH₂CH₃ |
| 901. | (CH₃)₃C | CH₃CH₂ | CH₃ | CH₃ | CH₃ | O(CH₂)₂CH₃ |
| 902. | (CH₃)₃C | CH₃CH₂ | CH₃ | CH₃ | CH₃ | OCH(CH₃)₂ |
| 903. | (CH₃)₃C | CH₃CH₂ | CH₃ | CH₃ | CH₃ | O(CH₃)₃ |
| 904. | (CH₃)₃C | CH₃CH₂ | CH₃ | CH₃ | CH₃ | O(CH₂)₂CH₃ |
| 905. | (CH₃)₃C | CH₃CH₂ | CH₃ | CH₃ | CH₃ | OCH₂CH(CH₃)₂ |
| 906. | (CH₃)₃C | CH₃CH₂ | CH₃ | CH₃ | CH₃ | OCH₂CH₂CH(CH₃)₂ |
| 907. | (CH₃)₃C | CH₃CH₂ | CH₃ | CH₃ | CH₃ | OC(CH₃)₂CH₂CH₃ |
| 908. | (CH₃)₃C | CH₃CH₂ | CH₃ | CH₃ | CH₃ | O(CH₂)₄CH₃ |
| 909. | (CH₃)₃C | CH₃CH₂ | CH₃ | CH₃ | CH₃ | OCH₂Cl |
| 910. | (CH₃)₃C | CH₃CH₂ | CH₃ | CH₃ | CH₃ | OCH₂CH₂Cl |
| 911. | (CH₃)₃C | CH₃CH₂ | CH₃ | CH₃ | CH₃ | OCH₂CH₂CH₂CH₂Cl |
| 912. | (CH₃)₃C | CH₃CH₂ | CH₃ | CH₃ | CH₃ | OCH₂CH₂Cl₂ |
| 913. | (CH₃)₃C | CH₃CH₂ | CH₃ | CH₃ | CH₃ | OCH₂CH₂F |
| 914. | (CH₃)₃C | CH₃CH₂ | CH₃ | CH₃ | CH₃ | OCH₂CHF₂ |
| 915. | (CH₃)₃C | CH₃CH₂ | CH₃ | CH₃ | CH₃ | OCH₂CF₃ |
| 916. | (CH₃)₃C | CH₃CH₂ | CH₃ | CH₃ | CH₃ | OCH₂CH₂OCH₃ |
| 917. | (CH₃)₃C | CH₃CH₂ | CH₃ | CH₃ | CH₃ | OCH₂CH₂OCH₂CH₃ |
| 918. | (CH₃)₃C | CH₃CH₂ | CH₃ | CH₃ | CH₃ | OCH₂OCH₂CH₃ |
| 919. | (CH₃)₃C | CH₃CH₂ | CH₃ | CH₃ | CH₃ | OCH₂CH₂SCH₃ |
| 920. | (CH₃)₃C | CH₃CH₂ | CH₃ | CH₃ | CH₃ | OCH₂C₅H₆ |
| 921. | (CH₃)₃C | CH₃CH₂ | CH₃ | CH₃ | CH₃ | OCH₂(4-ClC₅H₆) |
| 922. | (CH₃)₃C | CH₃CH₂ | CH₃ | CH₃ | CH₃ | OCH₂C=CH₂ |
| 923. | (CH₃)₃C | CH₃CH₂ | CH₃ | CH₃ | CH₃ | OCH₂(C=CH)CH₃ |
| 924. | (CH₃)₃C | CH₃CH₂ | CH₃ | CH₃ | CH₃ | OCH₂C≡CH |
| 925. | (CH₃)₃C | CH₃CH₂ | CH₃ | CH₃ | CH₃ | OCH₂COOCH₃ |
| 926. | (CH₃)₃C | CH₃CH₂ | CH₃ | CH₃ | CH₃ | OCH₂COOCH₂CH₃ |
| 927. | (CH₃)₃C | CH₃CH₂ | CH₃ | CH₃ | CH₃ | SCH₃ |
| 928. | (CH₃)₃C | CH₃CH₂ | CH₃ | CH₃ | CH₃ | SCH₂CH₃ |
| 929. | (CH₃)₃C | CH₃CH₂ | CH₃ | CH₃ | CH₃ | SCH2COOCH3 |

TABLE 1-continued

| No. | R3 | R9 | R8 | R6 | R7 | L-R10 |
|---|---|---|---|---|---|---|
| 930. | (CH$_3$)$_3$C | CH$_3$CH$_2$ | CH$_3$ | CH$_3$ | CH$_3$ | SCH2(4-ClC5H6) |
| 931. | (CH$_3$)$_3$C | H | CH$_3$CH$_2$ | CH$_3$ | CH$_3$ | OCH$_3$ |
| 932. | (CH$_3$)$_3$C | H | CH$_3$CH$_2$ | CH$_3$ | CH$_3$ | OCH$_2$CH$_3$ |
| 933. | (CH$_3$)$_3$C | H | CH$_3$CH$_2$ | CH$_3$ | CH$_3$ | O(CH$_2$)$_2$CH$_3$ |
| 934. | (CH$_3$)$_3$C | H | CH$_3$CH$_2$ | CH$_3$ | CH$_3$ | OCH(CH$_3$)$_2$ |
| 935. | (CH$_3$)$_3$C | H | CH$_3$CH$_2$ | CH$_3$ | CH$_3$ | O(CH$_3$)$_3$ |
| 936. | (CH$_3$)$_3$C | H | CH$_3$CH$_2$ | CH$_3$ | CH$_3$ | O(CH$_2$)$_3$CH$_3$ |
| 937. | (CH$_3$)$_3$C | H | CH$_3$CH$_2$ | CH$_3$ | CH$_3$ | OCH$_2$CH(CH$_3$)$_2$ |
| 938. | (CH$_3$)$_3$C | H | CH$_3$CH$_2$ | CH$_3$ | CH$_3$ | OCH$_2$CH$_2$CH(CH$_3$)$_2$ |
| 939. | (CH$_3$)$_3$C | H | CH$_3$CH$_2$ | CH$_3$ | CH$_3$ | OC(CH$_3$)$_2$CH$_2$CH$_3$ |
| 940. | (CH$_3$)$_3$C | H | CH$_3$CH$_2$ | CH$_3$ | CH$_3$ | O(CH$_2$)$_4$CH$_3$ |
| 941. | (CH$_3$)$_3$C | H | CH$_3$CH$_2$ | CH$_3$ | CH$_3$ | OCH$_2$Cl |
| 942. | (CH$_3$)$_3$C | H | CH$_3$CH$_2$ | CH$_3$ | CH$_3$ | OCH$_2$CH$_2$Cl |
| 943. | (CH$_3$)$_3$C | H | CH$_3$CH$_2$ | CH$_3$ | CH$_3$ | OCH$_2$CH$_2$CH$_2$CH$_2$Cl |
| 944. | (CH$_3$)$_3$C | H | CH$_3$CH$_2$ | CH$_3$ | CH$_3$ | OCH$_2$CH$_2$Cl$_2$ |
| 945. | (CH$_3$)$_3$C | H | CH$_3$CH$_2$ | CH$_3$ | CH$_3$ | OCH$_2$CH$_2$F |
| 946. | (CH$_3$)$_3$C | H | CH$_3$CH$_2$ | CH$_3$ | CH$_3$ | OCH$_2$CHF$_2$ |
| 947. | (CH$_3$)$_3$C | H | CH$_3$CH$_2$ | CH$_3$ | CH$_3$ | OCH$_2$CF$_3$ |
| 948. | (CH$_3$)$_3$C | H | CH$_3$CH$_2$ | CH$_3$ | CH$_3$ | OCH$_2$CH$_2$OCH$_3$ |
| 949. | (CH$_3$)$_3$C | H | CH$_3$CH$_2$ | CH$_3$ | CH$_3$ | OCH$_2$CH$_2$OCH$_2$CH$_3$ |
| 950. | (CH$_3$)$_3$C | H | CH$_3$CH$_2$ | CH$_3$ | CH$_3$ | OCH$_2$OCH$_2$CH$_3$ |
| 951. | (CH$_3$)$_3$C | H | CH$_3$CH$_2$ | CH$_3$ | CH$_3$ | OCH$_2$CH$_2$SCH$_3$ |
| 952. | (CH$_3$)$_3$C | H | CH$_3$CH$_2$ | CH$_3$ | CH$_3$ | OCH$_2$C$_5$H$_6$ |
| 953. | (CH$_3$)$_3$C | H | CH$_3$CH$_2$ | CH$_3$ | CH$_3$ | OCH$_2$(4-ClC$_5$H$_6$) |
| 954. | (CH$_3$)$_3$C | H | CH$_3$CH$_2$ | CH$_3$ | CH$_3$ | OCH$_2$C=CH$_2$ |
| 955. | (CH$_3$)$_3$C | H | CH$_3$CH$_2$ | CH$_3$ | CH$_3$ | OCH$_2$(C=CH)CH$_3$ |
| 956. | (CH$_3$)$_3$C | H | CH$_3$CH$_2$ | CH$_3$ | CH$_3$ | OCH$_2$C≡CH |
| 957. | (CH$_3$)$_3$C | H | CH$_3$CH$_2$ | CH$_3$ | CH$_3$ | OCH$_2$COOCH$_3$ |
| 958. | (CH$_3$)$_3$C | H | CH$_3$CH$_2$ | CH$_3$ | CH$_3$ | OCH$_2$COOCH$_2$CH$_3$ |
| 959. | (CH$_3$)$_3$C | H | CH$_3$CH$_2$ | CH$_3$ | CH$_3$ | SCH$_3$ |
| 960. | (CH$_3$)$_3$C | H | CH$_3$CH$_2$ | CH$_3$ | CH$_3$ | SCH$_2$CH$_3$ |
| 961. | (CH$_3$)$_3$C | H | CH$_3$CH$_2$ | CH$_3$ | CH$_3$ | SCH2COOCH3 |
| 962. | (CH$_3$)$_3$C | H | CH$_3$CH$_2$ | CH$_3$ | CH$_3$ | SCH2(4-ClC5H6) |
| 963. | (CH$_3$)$_3$C | CH$_3$ | CH$_3$CH$_2$ | CH$_3$ | CH$_3$ | OCH$_3$ |
| 964. | (CH$_3$)$_3$C | CH$_3$ | CH$_3$CH$_2$ | CH$_3$ | CH$_3$ | OCH$_2$CH$_3$ |
| 965. | (CH$_3$)$_3$C | CH$_3$ | CH$_3$CH$_2$ | CH$_3$ | CH$_3$ | O(CH$_2$)$_2$CH$_3$ |
| 966. | (CH$_3$)$_3$C | CH$_3$ | CH$_3$CH$_2$ | CH$_3$ | CH$_3$ | OCH(CH$_3$)$_2$ |
| 967. | (CH$_3$)$_3$C | CH$_3$ | CH$_3$CH$_2$ | CH$_3$ | CH$_3$ | O(CH$_3$)$_3$ |
| 968. | (CH$_3$)$_3$C | CH$_3$ | CH$_3$CH$_2$ | CH$_3$ | CH$_3$ | O(CH$_2$)$_3$CH$_3$ |
| 969. | (CH$_3$)$_3$C | CH$_3$ | CH$_3$CH$_2$ | CH$_3$ | CH$_3$ | OCH$_2$CH(CH$_3$)$_2$ |
| 970. | (CH$_3$)$_3$C | CH$_3$ | CH$_3$CH$_2$ | CH$_3$ | CH$_3$ | OCH$_2$CH$_2$CH(CH$_3$)$_2$ |
| 971. | (CH$_3$)$_3$C | CH$_3$ | CH$_3$CH$_2$ | CH$_3$ | CH$_3$ | OC(CH$_3$)$_2$CH$_2$CH$_3$ |
| 972. | (CH$_3$)$_3$C | CH$_3$ | CH$_3$CH$_2$ | CH$_3$ | CH$_3$ | O(CH$_2$)$_4$CH$_3$ |
| 973. | (CH$_3$)$_3$C | CH$_3$ | CH$_3$CH$_2$ | CH$_3$ | CH$_3$ | OCH$_2$Cl |
| 974. | (CH$_3$)$_3$C | CH$_3$ | CH$_3$CH$_2$ | CH$_3$ | CH$_3$ | OCH$_2$CH$_2$Cl |
| 975. | (CH$_3$)$_3$C | CH$_3$ | CH$_3$CH$_2$ | CH$_3$ | CH$_3$ | OCH$_2$CH$_2$CH$_2$CH$_2$Cl |
| 976. | (CH$_3$)$_3$C | CH$_3$ | CH$_3$CH$_2$ | CH$_3$ | CH$_3$ | OCH$_2$CH$_2$Cl$_2$ |
| 977. | (CH$_3$)$_3$C | CH$_3$ | CH$_3$CH$_2$ | CH$_3$ | CH$_3$ | OCH$_2$CH$_2$F |
| 978. | (CH$_3$)$_3$C | CH$_3$ | CH$_3$CH$_2$ | CH$_3$ | CH$_3$ | OCH$_2$CHF$_2$ |
| 979. | (CH$_3$)$_3$C | CH$_3$ | CH$_3$CH$_2$ | CH$_3$ | CH$_3$ | OCH$_2$CF$_3$ |
| 980. | (CH$_3$)$_3$C | CH$_3$ | CH$_3$CH$_2$ | CH$_3$ | CH$_3$ | OCH$_2$CH$_2$OCH$_3$ |
| 981. | (CH$_3$)$_3$C | CH$_3$ | CH$_3$CH$_2$ | CH$_3$ | CH$_3$ | OCH$_2$CH$_2$OCH$_2$CH$_3$ |
| 982. | (CH$_3$)$_3$C | CH$_3$ | CH$_3$CH$_2$ | CH$_3$ | CH$_3$ | OCH$_2$OCH$_2$CH$_3$ |
| 983. | (CH$_3$)$_3$C | CH$_3$ | CH$_3$CH$_2$ | CH$_3$ | CH$_3$ | OCH$_2$CH$_2$SCH$_3$ |
| 984. | (CH$_3$)$_3$C | CH$_3$ | CH$_3$CH$_2$ | CH$_3$ | CH$_3$ | OCH$_2$C$_5$H$_6$ |
| 985. | (CH$_3$)$_3$C | CH$_3$ | CH$_3$CH$_2$ | CH$_3$ | CH$_3$ | OCH$_2$(4-ClC$_5$H$_6$) |
| 986. | (CH$_3$)$_3$C | CH$_3$ | CH$_3$CH$_2$ | CH$_3$ | CH$_3$ | OCH$_2$C=CH$_2$ |
| 987. | (CH$_3$)$_3$C | CH$_3$ | CH$_3$CH$_2$ | CH$_3$ | CH$_3$ | OCH$_2$(C=CH)CH$_3$ |
| 988. | (CH$_3$)$_3$C | CH$_3$ | CH$_3$CH$_2$ | CH$_3$ | CH$_3$ | OCH$_2$C≡CH |
| 989. | (CH$_3$)$_3$C | CH$_3$ | CH$_3$CH$_2$ | CH$_3$ | CH$_3$ | OCH$_2$COOCH$_3$ |
| 990. | (CH$_3$)$_3$C | CH$_3$ | CH$_3$CH$_2$ | CH$_3$ | CH$_3$ | OCH$_2$COOCH$_2$CH$_3$ |
| 991. | (CH$_3$)$_3$C | CH$_3$ | CH$_3$CH$_2$ | CH$_3$ | CH$_3$ | SCH$_3$ |
| 992. | (CH$_3$)$_3$C | CH$_3$ | CH$_3$CH$_2$ | CH$_3$ | CH$_3$ | SCH$_2$CH$_3$ |
| 993. | (CH$_3$)$_3$C | CH$_3$ | CH$_3$CH$_2$ | CH$_3$ | CH$_3$ | SCH2COOCH3 |
| 994. | (CH$_3$)$_3$C | CH$_3$ | CH$_3$CH$_2$ | CH$_3$ | CH$_3$ | SCH2(4-ClC5H6) |
| 995. | (CH$_3$)$_3$C | CH$_3$ | CH$_3$CH$_2$ | CH$_3$ | CH$_3$ | OCH$_3$ |
| 996. | (CH$_3$)$_3$C | CH$_3$CH$_2$ | CH$_3$CH$_2$ | CH$_3$ | CH$_3$ | OCH$_2$CH$_3$ |
| 997. | (CH$_3$)$_3$C | CH$_3$CH$_2$ | CH$_3$CH$_2$ | CH$_3$ | CH$_3$ | O(CH$_2$)$_2$CH$_3$ |
| 998. | (CH$_3$)$_3$C | CH$_3$CH$_2$ | CH$_3$CH$_2$ | CH$_3$ | CH$_3$ | OCH(CH$_3$)$_2$ |
| 999. | (CH$_3$)$_3$C | CH$_3$CH$_2$ | CH$_3$CH$_2$ | CH$_3$ | CH$_3$ | O(CH$_3$)$_3$ |
| 1000. | (CH$_3$)$_3$C | CH$_3$CH$_2$ | CH$_3$CH$_2$ | CH$_3$ | CH$_3$ | O(CH$_2$)$_3$CH$_3$ |
| 1001. | (CH$_3$)$_3$C | CH$_3$CH$_2$ | CH$_3$CH$_2$ | CH$_3$ | CH$_3$ | OCH$_2$CH(CH$_3$)$_2$ |
| 1002. | (CH$_3$)$_3$C | CH$_3$CH$_2$ | CH$_3$CH$_2$ | CH$_3$ | CH$_3$ | OCH$_2$CH$_2$CH(CH$_3$)$_2$ |
| 1003. | (CH$_3$)$_3$C | CH$_3$CH$_2$ | CH$_3$CH$_2$ | CH$_3$ | CH$_3$ | OC(CH$_3$)$_2$CH$_2$CH$_3$ |
| 1004. | (CH$_3$)$_3$C | CH$_3$CH$_2$ | CH$_3$CH$_2$ | CH$_3$ | CH$_3$ | O(CH$_2$)$_4$CH$_3$ |
| 1005. | (CH$_3$)$_3$C | CH$_3$CH$_2$ | CH$_3$CH$_2$ | CH$_3$ | CH$_3$ | OCH$_2$Cl |
| 1006. | (CH$_3$)$_3$C | CH$_3$CH$_2$ | CH$_3$CH$_2$ | CH$_3$ | CH$_3$ | OCH$_2$CH$_2$Cl |
| 1007. | (CH$_3$)$_3$C | CH$_3$CH$_2$ | CH$_3$CH$_2$ | CH$_3$ | CH$_3$ | OCH$_2$CH$_2$CH$_2$CH$_2$Cl |

TABLE 1-continued

| No. | R3 | R9 | R8 | R6 | R7 | L-R10 |
|---|---|---|---|---|---|---|
| 1008. | $(CH_3)_3C$ | $CH_3CH_2$ | $CH_3CH_2$ | $CH_3$ | $CH_3$ | $OCH_2CH_2Cl_2$ |
| 1009. | $(CH_3)_3C$ | $CH_3CH_2$ | $CH_3CH_2$ | $CH_3$ | $CH_3$ | $OCH_2CH_2F$ |
| 1010. | $(CH_3)_3C$ | $CH_3CH_2$ | $CH_3CH_2$ | $CH_3$ | $CH_3$ | $OCH_2CHF_2$ |
| 1011. | $(CH_3)_3C$ | $CH_3CH_2$ | $CH_3CH_2$ | $CH_3$ | $CH_3$ | $OCH_2CF_3$ |
| 1012. | $(CH_3)_3C$ | $CH_3CH_2$ | $CH_3CH_2$ | $CH_3$ | $CH_3$ | $OCH_2CH_2OCH_3$ |
| 1013. | $(CH_3)_3C$ | $CH_3CH_2$ | $CH_3CH_2$ | $CH_3$ | $CH_3$ | $OCH_2CH_2OCH_2CH_3$ |
| 1014. | $(CH_3)_3C$ | $CH_3CH_2$ | $CH_3CH_2$ | $CH_3$ | $CH_3$ | $OCH_2OCH_2CH_3$ |
| 1015. | $(CH_3)_3C$ | $CH_3CH_2$ | $CH_3CH_2$ | $CH_3$ | $CH_3$ | $OCH_2CH_2SCH_3$ |
| 1016. | $(CH_3)_3C$ | $CH_3CH_2$ | $CH_3CH_2$ | $CH_3$ | $CH_3$ | $OCH_2C_5H_6$ |
| 1017. | $(CH_3)_3C$ | $CH_3CH_2$ | $CH_3CH_2$ | $CH_3$ | $CH_3$ | $OCH_2(4\text{-}ClC_5H_6)$ |
| 1018. | $(CH_3)_3C$ | $CH_3CH_2$ | $CH_3CH_2$ | $CH_3$ | $CH_3$ | $OCH_2C{=}CH_2$ |
| 1019. | $(CH_3)_3C$ | $CH_3CH_2$ | $CH_3CH_2$ | $CH_3$ | $CH_3$ | $OCH_2(C{=}CH)CH_3$ |
| 1020. | $(CH_3)_3C$ | $CH_3CH_2$ | $CH_3CH_2$ | $CH_3$ | $CH_3$ | $OCH_2C{\equiv}CH$ |
| 1021. | $(CH_3)_3C$ | $CH_3CH_2$ | $CH_3CH_2$ | $CH_3$ | $CH_3$ | $OCH_2COOCH_3$ |
| 1022. | $(CH_3)_3C$ | $CH_3CH_2$ | $CH_3CH_2$ | $CH_3$ | $CH_3$ | $OCH_2COOCH_2CH_3$ |
| 1023. | $(CH_3)_3C$ | $CH_3CH_2$ | $CH_3CH_2$ | $CH_3$ | $CH_3$ | $SCH_3$ |
| 1024. | $(CH_3)_3C$ | $CH_3CH_2$ | $CH_3CH_2$ | $CH_3$ | $CH_3$ | $SCH_2CH_3$ |
| 1025. | $(CH_3)_3C$ | $CH_3CH_2$ | $CH_3CH_2$ | $CH_3$ | $CH_3$ | $SCH2COOCH3$ |
| 1026. | $(CH_3)_3C$ | $CH_3CH_2$ | $CH_3CH_2$ | $CH_3$ | $CH_3$ | $SCH2(4\text{-}ClC5H6)$ |
| 1027. | $(CH_3)_3C$ | $CH_3$ | $CH_3CH_2$ | $CH(CH_3)2$ | H | $OCH_2CH_3$ |
| 1028. | $(CH_3)_3C$ | $CH_3$ | $CH_3CH_2$ | $CH(CH_3)2$ | H | $OCH_3$ |
| 1029. | $(CH_3)_3C$ | $CH_3$ | $CH_3CH_2$ | $CH(CH_3)2$ | H | $O(CH_2)_3CH_3$ |
| 1030. | $(CH_3)_3C$ | $CH_3$ | $CH_3CH_2$ | $CH(CH_3)2$ | H | $OCH_2CH(CH_3)_2$ |
| 1031. | $(CH_3)_3C$ | $CH_3$ | $CH_3CH_2$ | $CH(CH_3)2$ | H | $OCH_2CH_2OCH_3$ |
| 1032. | $(CH_3)_3C$ | $CH_3$ | $CH_3CH_2$ | $CH(CH_3)2$ | H | $OCH_2CH_2CH(CH_3)_2$ |
| 1033. | $(CH_3)_3C$ | $CH_3$ | $CH_3CH_2$ | $CH(CH_3)2$ | H | $OCH_2C{=}CH_2$ |
| 1034. | $(CH_3)_3C$ | $CH_3$ | $CH_3CH_2$ | $CH(CH_3)2$ | H | $OCH_2C{\equiv}CH$ |
| 1035. | $(CH_3)_3C$ | $CH_3$ | $CH_3CH_2$ | $CH(CH_3)2$ | H | $CH_3$ |
| 1036. | $(CH_3)_3C$ | $CH_3$ | $CH_3$ | $CH_3$ | Br | $OCH_3$ |
| 1037. | $(CH_3)_3C$ | $CH_3$ | $CH_3$ | $CH_3$ | Br | $OCH_2CH_3$ |
| 1038. | $(CH_3)_3C$ | $CH_3$ | $CH_3$ | $CH_3$ | Br | $OCH_2CF_3$ |
| 1039. | $(CH_3)_3C$ | $CH_3$ | $CH_3$ | $CH_3$ | Br | $O(CH_2)_3CH_3$ |
| 1040. | $(CH_3)_3C$ | $CH_3$ | $CH_3$ | $CH_3$ | Br | $OCH_2CH(CH_3)_2$ |
| 1041. | $(CH_3)_3C$ | $CH_3$ | $CH_3$ | $CH_3$ | Br | $OCH_2CH(CH_3)_2$ |
| 1042. | $(CH_3)_3C$ | $CH_3$ | $CH_3$ | $CH_3$ | Br | $OCH_2C{=}CH_2$ |
| 1043. | $(CH_3)_3C$ | $CH_3$ | $CH_3$ | $CH_3$ | Br | $OCH_2CH_2OCH_3$ |
| 1044. | $(CH_3)_3C$ | $CH_3$ | $CH_3$ | $CH_3$ | Br | $CH_3$ |
| 1045. | $(CH_3)_3C$ | $CH_3$ | $CH_3$ | $CH_2CH_3$ | Cl | $OCH_3$ |
| 1046. | $(CH_3)_3C$ | $CH_3$ | $CH_3$ | $CH_2CH_3$ | Cl | $OCH_2CH_3$ |
| 1047. | $(CH_3)_3C$ | $CH_3$ | $CH_3$ | $CH_2CH_3$ | Cl | $OCH_2CF_3$ |
| 1048. | $(CH_3)_3C$ | $CH_3$ | $CH_3$ | $CH_2CH_3$ | Cl | $O(CH_2)_3CH_3$ |
| 1049. | $(CH_3)_3C$ | $CH_3$ | $CH_3$ | $CH_2CH_3$ | Cl | $O(CH_2)_3CH_3$ |
| 1050. | $(CH_3)_3C$ | $CH_3$ | $CH_3$ | $CH_2CH_3$ | Cl | $OCH_2CH(CH_3)_2$ |
| 1051. | $(CH_3)_3C$ | $CH_3$ | $CH_3$ | $CH_2CH_3$ | Cl | $OCH_2C{=}CH_2$ |
| 1052. | $(CH_3)_3C$ | $CH_3$ | $CH_3$ | $CH_2CH_3$ | Cl | $OCH_2CH_2OCH_3$ |
| 1053. | $(CH_3)_3C$ | $CH_3$ | $CH_3$ | $CH_2CH_3$ | Cl | $OCH_2C{\equiv}CH$ |
| 1054. | $(CH_3)_3C$ | $CH_3$ | $CH_3$ | $CH_2CH_3$ | Cl | $CH_3$ |
| 1055. | $(CH_3)_3C$ | $CH_3$ | $CH_2CH_3$ | $CH_3$ | Br | $OCH_3$ |
| 1056. | $(CH_3)_3C$ | $CH_3$ | $CH_2CH_3$ | $CH_3$ | Br | $OCH_2CH_3$ |
| 1057. | $(CH_3)_3C$ | $CH_3$ | $CH_2CH_3$ | $CH_3$ | Br | $OCH_2CF_3$ |
| 1058. | $(CH_3)_3C$ | $CH_3$ | $CH_2CH_3$ | $CH_3$ | Br | $O(CH_2)_3CH_3$ |
| 1059. | $(CH_3)_3C$ | $CH_3$ | $CH_2CH_3$ | $CH_3$ | Br | $O(CH_2)_3CH_3$ |
| 1060. | $(CH_3)_3C$ | $CH_3$ | $CH_3$ | $CH_2CH_3$ | Cl | $OCH_2CF_3$ |
| 1061. | $(CH_3)_3C$ | $CH_3$ | $CH_3$ | $CH_2CH_3$ | Cl | $O(CH_2)_3CH_3$ |
| 1062. | $(CH_3)_3C$ | $CH_3$ | $CH_3$ | $CH_2CH_3$ | Cl | $O(CH_2)_3CH_3$ |
| 1063. | $(CH_3)_3C$ | $CH_3$ | $CH_3$ | $CH_2CH_3$ | Cl | $OCH_2CH(CH_3)_2$ |
| 1064. | $(CH_3)_3C$ | $CH_3$ | $CH_3$ | $CH_2CH_3$ | Cl | $OCH_2C{=}CH_2$ |
| 1065. | $(CH_3)_3C$ | $CH_3$ | $CH_3$ | $CH_2CH_3$ | Cl | $OCH_2CH_2OCH_3$ |
| 1066. | $(CH_3)_3C$ | $CH_3$ | $CH_3$ | $CH_2CH_3$ | Cl | $OCH_2C{\equiv}CH$ |
| 1067. | $(CH_3)_3C$ | $CH_3$ | $CH_3$ | $CH_2CH_3$ | Cl | $CH_3$ |

For pyrazole derivatives represented by the formula stru-1 provided herein, when substituents R1, R2, R4, and R5 are hydrogen and Q is oxygen, as an example, when the pyrazole derivative represented by the formula stru-1 is a Z-type compound, the pyrazole derivative represented by the formula stru-1 may be a compound shown in Table 2.

TABLE 2

| No. | R3 | R9 | R8 | R6 | R7 | L-R10 |
|---|---|---|---|---|---|---|
| 1068. | $(CH_3)_3C$ | H | $CH_3$ | $CH_3$ | H | $CH_3$ |
| 1069. | $(CH_3)_3C$ | H | $CH_3$ | $CH_3$ | H | $CH_3CH_2$ |
| 1070. | $(CH_3)_3C$ | H | $CH_3$ | $CH_3$ | H | $CH_3CH_2CH_2$ |
| 1071. | $(CH_3)_3C$ | H | $CH_3$ | $CH_3$ | H | $(CH_3)_2CH$ |
| 1072. | $(CH_3)_3C$ | H | $CH_3$ | $CH_3$ | H | $(CH_3)_3C$ |
| 1073. | $(CH_3)_3C$ | H | $CH_3$ | $CH_3$ | H | $CH_3CH_2CH_2CH_2$ |

TABLE 2-continued

| No. | R3 | R9 | R8 | R6 | R7 | L-R10 |
|---|---|---|---|---|---|---|
| 1074. | (CH₃)₃C | H | CH₃ | CH₃ | H | (CH₃)₂CHCH₂ |
| 1075. | (CH₃)₃C | H | CH₃ | CH₃ | H | CH₃OCH₂ |
| 1076. | (CH₃)₃C | H | CH₃ | CH₃ | H |  |
| 1077. | (CH₃)₃C | H | CH₃ | CH₃ | H | CH₃SCH₂ |
| 1078. | (CH₃)₃C | H | CH₃ | CH₃ | H |  |
| 1079. | (CH₃)₃C | H | CH₃ | CH₃ | H | FCH₂ |
| 1080. | (CH₃)₃C | H | CH₃ | CH₃ | H | F₃C |
| 1081. | (CH₃)₃C | H | CH₃ | CH₃ | H | C₆H₅ |
| 1082. | (CH₃)₃C | H | CH₃ | CH₃ | H | C₆H₅CH₂ |
| 1083. | (CH₃)₃C | H | CH₃ | CH₃ | H | CH₃CH₂(CH₃)₂C |
| 1084. | (CH₃)₃C | H | CH₃ | CH₃ | H | CH2=CH |
| 1085. | (CH₃)₃C | H | CH₃ | CH₃ | H | CH₃CH₂OCH₂ |
| 1086. | (CH₃)₃C | H | CH₃ | CH₃ | H | CH₃CH₂SCH₂ |
| 1087. | (CH₃)₃C | H | CH₃ | CH₃ | H | 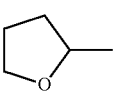 |
| 1088. | (CH₃)₃C | H | CH₃ | CH₃ | H | 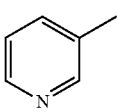 |
| 1089. | (CH₃)₃C | H | CH₃ | CH₃ | H | CF₃CH₂SCH₂ |
| 1090. | (CH₃)₃C | H | CH₃ | CH₃ | H | ClCH₂CH₂ |
| 1091. | (CH₃)₃C | H | CH₃ | CH₃ | H | ClCH₂CH₂CH₂ |
| 1092. | (CH₃)₃C | H | CH₃ | CH₃ | H | NCCH2 |
| 1093. | (CH₃)₃C | CH₃ | CH₃ | CH₃ | H | CH₃ |
| 1094. | (CH₃)₃C | CH₃ | CH₃ | CH₃ | H | CH₃CH₂ |
| 1095. | (CH₃)₃C | CH₃ | CH₃ | CH₃ | H | CH₃CH₂CH₂ |
| 1096. | (CH₃)₃C | CH₃ | CH₃ | CH₃ | H | (CH₃)₂CH |
| 1097. | (CH₃)₃C | CH₃ | CH₃ | CH₃ | H | (CH₃)₃C |
| 1098. | (CH₃)₃C | CH₃ | CH₃ | CH₃ | H | CH₃CH₂CH₂CH₂ |
| 1099. | (CH₃)₃C | CH₃ | CH₃ | CH₃ | H | (CH₃)₂CHCH₂ |
| 1100. | (CH₃)₃C | CH₃ | CH₃ | CH₃ | H | CH₃OCH₂ |
| 1101. | (CH₃)₃C | CH₃ | CH₃ | CH₃ | H |  |
| 1102. | (CH₃)₃C | CH₃ | CH₃ | CH₃ | H | CH₃SCH₂ |
| 1103. | (CH₃)₃C | CH₃ | CH₃ | CH₃ | H |  |
| 1104. | (CH₃)₃C | CH₃ | CH₃ | CH₃ | H | FCH₂ |
| 1105. | (CH₃)₃C | CH₃ | CH₃ | CH₃ | H | F₃C |
| 1106. | (CH₃)₃C | CH₃ | CH₃ | CH₃ | H | C₆H₅ |
| 1107. | (CH₃)₃C | CH₃ | CH₃ | CH₃ | H | C₆H₅CH₂ |
| 1108. | (CH₃)₃C | CH₃ | CH₃ | CH₃ | H | CH₃CH₂(CH₃)₂C |
| 1109. | (CH₃)₃C | CH₃ | CH₃ | CH₃ | H | CH2=CH |
| 1110. | (CH₃)₃C | CH₃ | CH₃ | CH₃ | H | CH₃CH₂OCH₂ |
| 1111. | (CH₃)₃C | CH₃ | CH₃ | CH₃ | H | CH₃CH₂SCH₂ |
| 1112. | (CH₃)₃C | CH₃ | CH₃ | CH₃ | H | 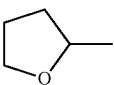 |
| 1113. | (CH₃)₃C | CH₃ | CH₃ | CH₃ | H | 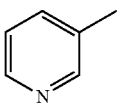 |

TABLE 2-continued

| No. | R3 | R9 | R8 | R6 | R7 | L-R10 |
|---|---|---|---|---|---|---|
| 1114. | (CH$_3$)$_3$C | CH$_3$ | CH$_3$ | CH$_3$ | H | CF$_3$CH$_2$SCH$_2$ |
| 1115. | (CH$_3$)$_3$C | CH$_3$ | CH$_3$ | CH$_3$ | H | ClCH$_2$CH$_2$ |
| 1116. | (CH$_3$)$_3$C | CH$_3$ | CH$_3$ | CH$_3$ | H | ClCH$_2$CH$_2$CH$_2$ |
| 1117. | (CH$_3$)$_3$C | CH3 | CH$_3$ | CH$_3$ | H | NCCH2 |
| 1118. | (CH$_3$)$_3$C | CH$_3$CH$_2$ | CH$_3$ | CH$_3$ | H | CH$_3$ |
| 1119. | (CH$_3$)$_3$C | CH$_3$CH$_2$ | CH$_3$ | CH$_3$ | H | CH$_3$CH$_2$ |
| 1120. | (CH$_3$)$_3$C | CH$_3$CH$_2$ | CH$_3$ | CH$_3$ | H | CH$_3$CH$_2$CH$_2$ |
| 1121. | (CH$_3$)$_3$C | CH$_3$CH$_2$ | CH$_3$ | CH$_3$ | H | (CH$_3$)$_2$CH |
| 1122. | (CH$_3$)$_3$C | CH$_3$CH$_2$ | CH$_3$ | CH$_3$ | H | (CH$_3$)$_3$C |
| 1123. | (CH$_3$)$_3$C | CH$_3$CH$_2$ | CH$_3$ | CH$_3$ | H | CH$_3$CH$_2$CH$_2$CH$_2$ |
| 1124. | (CH$_3$)$_3$C | CH$_3$CH$_2$ | CH$_3$ | CH$_3$ | H | (CH$_3$)$_2$CHCH$_2$ |
| 1125. | (CH$_3$)$_3$C | CH$_3$CH$_2$ | CH$_3$ | CH$_3$ | H | CH$_3$OCH$_2$ |
| 1126. | (CH$_3$)$_3$C | CH$_3$CH$_2$ | CH$_3$ | CH$_3$ | H |  |
| 1127. | (CH$_3$)$_3$C | CH$_3$CH$_2$ | CH$_3$ | CH$_3$ | H | CH$_3$SCH$_2$ |
| 1128. | (CH$_3$)$_3$C | CH$_3$CH$_2$ | CH$_3$ | CH$_3$ | H |  |
| 1129. | (CH$_3$)$_3$C | CH$_3$CH$_2$ | CH$_3$ | CH$_3$ | H | FCH$_2$ |
| 1130. | (CH$_3$)$_3$C | CH$_3$CH$_2$ | CH$_3$ | CH$_3$ | H | F$_3$C |
| 1131. | (CH$_3$)$_3$C | CH$_3$CH$_2$ | CH$_3$ | CH$_3$ | H | C$_6$H$_5$ |
| 1132. | (CH$_3$)$_3$C | CH$_3$CH$_2$ | CH$_3$ | CH$_3$ | H | C$_6$H$_5$CH$_2$ |
| 1133. | (CH$_3$)$_3$C | CH$_3$CH$_2$ | CH$_3$ | CH$_3$ | H | CH$_3$CH$_2$(CH$_3$)$_2$C |
| 1134. | (CH$_3$)$_3$C | CH$_3$CH$_2$ | CH$_3$ | CH$_3$ | H | CH2=CH |
| 1135. | (CH$_3$)$_3$C | CH$_3$CH$_2$ | CH$_3$ | CH$_3$ | H | CH$_3$CH$_2$OCH$_2$ |
| 1136. | (CH$_3$)$_3$C | CH$_3$CH$_2$ | CH$_3$ | CH$_3$ | H | CH$_3$CH$_2$SCH$_2$ |
| 1137. | (CH$_3$)$_3$C | CH$_3$CH$_2$ | CH$_3$ | CH$_3$ | H | 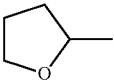 |
| 1138. | (CH$_3$)$_3$C | CH$_3$CH$_2$ | CH$_3$ | CH$_3$ | H | 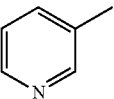 |
| 1139. | (CH$_3$)$_3$C | CH$_3$CH$_2$ | CH$_3$ | CH$_3$ | H | CF$_3$CH$_2$SCH$_2$ |
| 1140. | (CH$_3$)$_3$C | CH$_3$CH$_2$ | CH$_3$ | CH$_3$ | H | ClCH$_2$CH$_2$ |
| 1141. | (CH$_3$)$_3$C | CH$_3$CH$_2$ | CH$_3$ | CH$_3$ | H | ClCH$_2$CH$_2$CH$_2$ |
| 1142. | (CH$_3$)$_3$C | CH3CH2 | CH$_3$ | CH$_3$ | H | NCCH2 |
| 1143. | (CH$_3$)$_3$C | H | CH$_3$ | CH$_3$ | Cl | CH$_3$ |
| 1144. | (CH$_3$)$_3$C | H | CH$_3$ | CH$_3$ | Cl | CH$_3$CH$_2$ |
| 1145. | (CH$_3$)$_3$C | H | CH$_3$ | CH$_3$ | Cl | CH$_3$CH$_2$CH$_2$ |
| 1146. | (CH$_3$)$_3$C | H | CH$_3$ | CH$_3$ | Cl | (CH$_3$)$_2$CH |
| 1147. | (CH$_3$)$_3$C | H | CH$_3$ | CH$_3$ | Cl | (CH$_3$)$_3$C |
| 1148. | (CH$_3$)$_3$C | H | CH$_3$ | CH$_3$ | Cl | CH$_3$CH$_2$CH$_2$CH$_2$ |
| 1149. | (CH$_3$)$_3$C | H | CH$_3$ | CH$_3$ | Cl | (CH$_3$)$_2$CHCH$_2$ |
| 1150. | (CH$_3$)$_3$C | H | CH$_3$ | CH$_3$ | Cl | CH$_3$OCH$_2$ |
| 1151. | (CH$_3$)$_3$C | H | CH$_3$ | CH$_3$ | Cl |  |
| 1152. | (CH$_3$)$_3$C | H | CH$_3$ | CH$_3$ | Cl | CH$_3$SCH$_2$ |
| 1153. | (CH$_3$)$_3$C | H | CH$_3$ | CH$_3$ | Cl |  |
| 1154. | (CH$_3$)$_3$C | H | CH$_3$ | CH$_3$ | Cl | FCH$_2$ |
| 1155. | (CH$_3$)$_3$C | H | CH$_3$ | CH$_3$ | Cl | F$_3$C |
| 1156. | (CH$_3$)$_3$C | H | CH$_3$ | CH$_3$ | Cl | C$_6$H$_5$ |
| 1157. | (CH$_3$)$_3$C | H | CH$_3$ | CH$_3$ | Cl | C$_6$H$_5$CH$_2$ |
| 1158. | (CH$_3$)$_3$C | H | CH$_3$ | CH$_3$ | Cl | CH$_3$CH$_2$(CH$_3$)$_2$C |
| 1159. | (CH$_3$)$_3$C | H | CH$_3$ | CH$_3$ | Cl | CH2=CH |
| 1160. | (CH$_3$)$_3$C | H | CH$_3$ | CH$_3$ | Cl | CH$_3$CH$_2$OCH$_2$ |
| 1161. | (CH$_3$)$_3$C | H | CH$_3$ | CH$_3$ | Cl | CH$_3$CH$_2$SCH$_2$ |

TABLE 2-continued

| No. | R3 | R9 | R8 | R6 | R7 | L-R10 |
|---|---|---|---|---|---|---|
| 1162. | (CH₃)₃C | H | CH₃ | CH₃ | Cl | 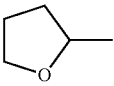 |
| 1163. | (CH₃)₃C | H | CH₃ | CH₃ | Cl | 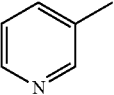 |
| 1164. | (CH₃)₃C | H | CH₃ | CH₃ | Cl | CF₃CH₂SCH₂ |
| 1165. | (CH₃)₃C | H | CH₃ | CH₃ | Cl | ClCH₂CH₂ |
| 1166. | (CH₃)₃C | H | CH₃ | CH₃ | Cl | ClCH₂CH₂CH₂ |
| 1167. | (CH₃)₃C | H | CH₃ | CH₃ | Cl | NCCH2 |
| 1168. | (CH₃)₃C | CH₃ | CH₃ | CH₃ | Cl | CH₃ |
| 1169. | (CH₃)₃C | CH₃ | CH₃ | CH₃ | Cl | CH₃CH₂ |
| 1170. | (CH₃)₃C | CH₃ | CH₃ | CH₃ | Cl | CH₃CH₂CH₂ |
| 1171. | (CH₃)₃C | CH₃ | CH₃ | CH₃ | Cl | (CH₃)₂CH |
| 1172. | (CH₃)₃C | CH₃ | CH₃ | CH₃ | Cl | (CH₃)₃C |
| 1173. | (CH₃)₃C | CH₃ | CH₃ | CH₃ | Cl | CH₃CH₂CH₂CH₂ |
| 1174. | (CH₃)₃C | CH₃ | CH₃ | CH₃ | Cl | (CH₃)₂CHCH₂ |
| 1175. | (CH₃)₃C | CH₃ | CH₃ | CH₃ | Cl | CH₃OCH₂ |
| 1176. | (CH₃)₃C | CH₃ | CH₃ | CH₃ | Cl |  |
| 1177. | (CH₃)₃C | CH₃ | CH₃ | CH₃ | Cl | CH₃SCH₂ |
| 1178. | (CH₃)₃C | CH₃ | CH₃ | CH₃ | Cl |  |
| 1179. | (CH₃)₃C | CH₃ | CH₃ | CH₃ | Cl | FCH₂ |
| 1180. | (CH₃)₃C | CH₃ | CH₃ | CH₃ | Cl | F₃C |
| 1181. | (CH₃)₃C | CH₃ | CH₃ | CH₃ | Cl | C₆H₅ |
| 1182. | (CH₃)₃C | CH₃ | CH₃ | CH₃ | Cl | C₆H₅CH₂ |
| 1183. | (CH₃)₃C | CH₃ | CH₃ | CH₃ | Cl | CH₃CH₂(CH₃)₂C |
| 1184. | (CH₃)₃C | CH₃ | CH₃ | CH₃ | Cl | CH2=CH |
| 1185. | (CH₃)₃C | CH₃ | CH₃ | CH₃ | Cl | CH₃CH₂OCH₂ |
| 1186. | (CH₃)₃C | CH₃ | CH₃ | CH₃ | Cl | CH₃CH₂SCH₂ |
| 1187. | (CH₃)₃C | CH₃ | CH₃ | CH₃ | Cl | 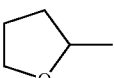 |
| 1188. | (CH₃)₃C | CH₃ | CH₃ | CH₃ | Cl | 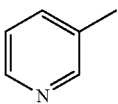 |
| 1189. | (CH₃)₃C | CH₃ | CH₃ | CH₃ | Cl | CF₃CH₂SCH₂ |
| 1190. | (CH₃)₃C | CH₃ | CH₃ | CH₃ | Cl | ClCH₂CH₂ |
| 1191. | (CH₃)₃C | CH₃ | CH₃ | CH₃ | Cl | ClCH₂CH₂CH₂ |
| 1192. | (CH₃)₃C | CH3 | CH₃ | CH₃ | Cl | NCCH2 |
| 1193. | (CH₃)₃C | CH₃CH₂ | CH₃ | CH₃ | Cl | CH₃ |
| 1194. | (CH₃)₃C | CH₃CH₂ | CH₃ | CH₃ | Cl | CH₃CH₂ |
| 1195. | (CH₃)₃C | CH₃CH₂ | CH₃ | CH₃ | Cl | CH₃CH₂CH₂ |
| 1196. | (CH₃)₃C | CH₃CH₂ | CH₃ | CH₃ | Cl | (CH₃)₂CH |
| 1197. | (CH₃)₃C | CH₃CH₂ | CH₃ | CH₃ | Cl | (CH₃)₃C |
| 1198. | (CH₃)₃C | CH₃CH₂ | CH₃ | CH₃ | Cl | CH₃CH₂CH₂CH₂ |
| 1199. | (CH₃)₃C | CH₃CH₂ | CH₃ | CH₃ | Cl | (CH₃)₂CHCH₂ |
| 1200. | (CH₃)₃C | CH₃CH₂ | CH₃ | CH₃ | Cl | CH₃OCH₂ |
| 1201. | (CH₃)₃C | CH₃CH₂ | CH₃ | CH₃ | Cl |  |
| 1202. | (CH₃)₃C | CH₃CH₂ | CH₃ | CH₃ | Cl | CH₃SCH₂ |
| 1203. | (CH₃)₃C | CH₃CH₂ | CH₃ | CH₃ | Cl |  |

TABLE 2-continued

| No. | R3 | R9 | R8 | R6 | R7 | L-R10 |
|---|---|---|---|---|---|---|
| 1204. | (CH$_3$)$_3$C | CH$_3$CH$_2$ | CH$_3$ | CH$_3$ | Cl | FCH$_2$ |
| 1205. | (CH$_3$)$_3$C | CH$_3$CH$_2$ | CH$_3$ | CH$_3$ | Cl | F$_3$C |
| 1206. | (CH$_3$)$_3$C | CH$_3$CH$_2$ | CH$_3$ | CH$_3$ | Cl | C$_6$H$_5$ |
| 1207. | (CH$_3$)$_3$C | CH$_3$CH$_2$ | CH$_3$ | CH$_3$ | Cl | C$_6$H$_5$CH$_2$ |
| 1208. | (CH$_3$)$_3$C | CH$_3$CH$_2$ | CH$_3$ | CH$_3$ | Cl | CH$_3$CH$_2$(CH$_3$)$_2$C |
| 1209. | (CH$_3$)$_3$C | CH$_3$CH$_2$ | CH$_3$ | CH$_3$ | Cl | CH2=CH |
| 1210. | (CH$_3$)$_3$C | CH$_3$CH$_2$ | CH$_3$ | CH$_3$ | Cl | CH$_3$CH$_2$OCH$_2$ |
| 1211. | (CH$_3$)$_3$C | CH$_3$CH$_2$ | CH$_3$ | CH$_3$ | Cl | CH$_3$CH$_2$SCH$_2$ |
| 1212. | (CH$_3$)$_3$C | CH$_3$CH$_2$ | CH$_3$ | CH$_3$ | Cl | 2-methyltetrahydrofuran |
| 1213. | (CH$_3$)$_3$C | CH$_3$CH$_2$ | CH$_3$ | CH$_3$ | Cl | 3-methylpyridine |
| 1214. | (CH$_3$)$_3$C | CH$_3$CH$_2$ | CH$_3$ | CH$_3$ | Cl | CF$_3$CH$_2$SCH$_2$ |
| 1215. | (CH$_3$)$_3$C | CH$_3$CH$_2$ | CH$_3$ | CH$_3$ | Cl | ClCH$_2$CH$_2$ |
| 1216. | (CH$_3$)$_3$C | CH$_3$CH$_2$ | CH$_3$ | CH$_3$ | Cl | ClCH$_2$CH$_2$CH$_2$ |
| 1217. | (CH$_3$)$_3$C | CH3CH2 | CH$_3$ | CH$_3$ | Cl | NCCH2 |
| 1218. | (CH$_3$)$_3$C | H | CH$_3$ | CH$_3$ | CH$_3$ | CH$_3$ |
| 1219. | (CH$_3$)$_3$C | H | CH$_3$ | CH$_3$ | CH$_3$ | CH$_3$CH$_2$ |
| 1220. | (CH$_3$)$_3$C | H | CH$_3$ | CH$_3$ | CH$_3$ | CH$_3$CH$_2$CH$_2$ |
| 1221. | (CH$_3$)$_3$C | H | CH$_3$ | CH$_3$ | CH$_3$ | (CH$_3$)$_2$CH |
| 1222. | (CH$_3$)$_3$C | H | CH$_3$ | CH$_3$ | CH$_3$ | (CH$_3$)$_3$C |
| 1223. | (CH$_3$)$_3$C | H | CH$_3$ | CH$_3$ | CH$_3$ | CH$_3$CH$_2$CH$_2$CH$_2$ |
| 1224. | (CH$_3$)$_3$C | H | CH$_3$ | CH$_3$ | CH$_3$ | (CH$_3$)$_2$CHCH$_2$ |
| 1225. | (CH$_3$)$_3$C | H | CH$_3$ | CH$_3$ | CH$_3$ | CH$_3$OCH$_2$ |
| 1226. | (CH$_3$)$_3$C | H | CH$_3$ | CH$_3$ | CH$_3$ | cyclopropyl |
| 1227. | (CH$_3$)$_3$C | H | CH$_3$ | CH$_3$ | CH$_3$ | CH$_3$SCH$_2$ |
| 1228. | (CH$_3$)$_3$C | H | CH$_3$ | CH$_3$ | CH$_3$ | cyclohexyl |
| 1229. | (CH$_3$)$_3$C | H | CH$_3$ | CH$_3$ | CH$_3$ | FCH$_2$ |
| 1230. | (CH$_3$)$_3$C | H | CH$_3$ | CH$_3$ | CH$_3$ | F$_3$C |
| 1231. | (CH$_3$)$_3$C | H | CH$_3$ | CH$_3$ | CH$_3$ | C$_6$H$_5$ |
| 1232. | (CH$_3$)$_3$C | H | CH$_3$ | CH$_3$ | CH$_3$ | C$_6$H$_5$CH$_2$ |
| 1233. | (CH$_3$)$_3$C | H | CH$_3$ | CH$_3$ | CH$_3$ | CH$_3$CH$_2$(CH$_3$)$_2$C |
| 1234. | (CH$_3$)$_3$C | H | CH$_3$ | CH$_3$ | CH$_3$ | CH2=CH |
| 1235. | (CH$_3$)$_3$C | H | CH$_3$ | CH$_3$ | CH$_3$ | CH$_3$CH$_2$OCH$_2$ |
| 1236. | (CH$_3$)$_3$C | H | CH$_3$ | CH$_3$ | CH$_3$ | CH$_3$CH$_2$SCH$_2$ |
| 1237. | (CH$_3$)$_3$C | H | CH$_3$ | CH$_3$ | CH$_3$ | 2-methyltetrahydrofuran |
| 1238. | (CH$_3$)$_3$C | H | CH$_3$ | CH$_3$ | CH$_3$ | 3-methylpyridine |
| 1239. | (CH$_3$)$_3$C | H | CH$_3$ | CH$_3$ | CH$_3$ | CF$_3$CH$_2$SCH$_2$ |
| 1240. | (CH$_3$)$_3$C | H | CH$_3$ | CH$_3$ | CH$_3$ | ClCH$_2$CH$_2$ |
| 1241. | (CH$_3$)$_3$C | H | CH$_3$ | CH$_3$ | CH$_3$ | ClCH$_2$CH$_2$CH$_2$ |
| 1242. | (CH$_3$)$_3$C | H | CH$_3$ | CH$_3$ | CH$_3$ | NCCH2 |
| 1243. | (CH$_3$)$_3$C | CH$_3$ | CH$_3$ | CH$_3$ | CH$_3$ | CH$_3$ |
| 1244. | (CH$_3$)$_3$C | CH$_3$ | CH$_3$ | CH$_3$ | CH$_3$ | CH$_3$CH$_2$ |
| 1245. | (CH$_3$)$_3$C | CH$_3$ | CH$_3$ | CH$_3$ | CH$_3$ | CH$_3$CH$_2$CH$_2$ |
| 1246. | (CH$_3$)$_3$C | CH$_3$ | CH$_3$ | CH$_3$ | CH$_3$ | (CH$_3$)$_2$CH |
| 1247. | (CH$_3$)$_3$C | CH$_3$ | CH$_3$ | CH$_3$ | CH$_3$ | (CH$_3$)$_3$C |
| 1248. | (CH$_3$)$_3$C | CH$_3$ | CH$_3$ | CH$_3$ | CH$_3$ | CH$_3$CH$_2$CH$_2$CH$_2$ |
| 1249. | (CH$_3$)$_3$C | CH$_3$ | CH$_3$ | CH$_3$ | CH$_3$ | (CH$_3$)$_2$CHCH$_2$ |
| 1250. | (CH$_3$)$_3$C | CH$_3$ | CH$_3$ | CH$_3$ | CH$_3$ | CH$_3$OCH$_2$ |

TABLE 2-continued

| No. | R3 | R9 | R8 | R6 | R7 | L-R10 |
|---|---|---|---|---|---|---|
| 1251. | (CH₃)₃C | CH₃ | CH₃ | CH₃ | CH₃ |  |
| 1252. | (CH₃)₃C | CH₃ | CH₃ | CH₃ | CH₃ | CH₃SCH₂ |
| 1253. | (CH₃)₃C | CH₃ | CH₃ | CH₃ | CH₃ |  |
| 1254. | (CH₃)₃C | CH₃ | CH₃ | CH₃ | CH₃ | FCH₂ |
| 1255. | (CH₃)₃C | CH₃ | CH₃ | CH₃ | CH₃ | F₃C |
| 1256. | (CH₃)₃C | CH₃ | CH₃ | CH₃ | CH₃ | C₆H₅ |
| 1257. | (CH₃)₃C | CH₃ | CH₃ | CH₃ | CH₃ | C₆H₅CH₂ |
| 1258. | (CH₃)₃C | CH₃ | CH₃ | CH₃ | CH₃ | CH₃CH₂(CH₃)₂C |
| 1259. | (CH₃)₃C | CH₃ | CH₃ | CH₃ | CH₃ | CH2=CH |
| 1260. | (CH₃)₃C | CH₃ | CH₃ | CH₃ | CH₃ | CH₃CH₂OCH₂ |
| 1261. | (CH₃)₃C | CH₃ | CH₃ | CH₃ | CH₃ | CH₃CH₂SCH₂ |
| 1262. | (CH₃)₃C | CH₃ | CH₃ | CH₃ | CH₃ | 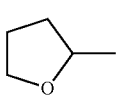 |
| 1263. | (CH₃)₃C | CH₃ | CH₃ | CH₃ | CH₃ | 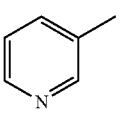 |
| 1264. | (CH₃)₃C | CH₃ | CH₃ | CH₃ | CH₃ | CF₃CH₂SCH₂ |
| 1265. | (CH₃)₃C | CH₃ | CH₃ | CH₃ | CH₃ | ClCH₂CH₂ |
| 1266. | (CH₃)₃C | CH₃ | CH₃ | CH₃ | CH₃ | ClCH₂CH₂CH₂ |
| 1267. | (CH₃)₃C | CH₃ | CH₃ | CH₃ | CH₃ | NCCH2 |
| 1268. | (CH₃)₃C | CH₃CH₂ | CH₃ | CH₃ | CH₃ | CH₃ |
| 1269. | (CH₃)₃C | CH₃CH₂ | CH₃ | CH₃ | CH₃ | CH₃CH₂ |
| 1270. | (CH₃)₃C | CH₃CH₂ | CH₃ | CH₃ | CH₃ | CH₃CH₂CH₂ |
| 1271. | (CH₃)₃C | CH₃CH₂ | CH₃ | CH₃ | CH₃ | (CH₃)₂CH |
| 1272. | (CH₃)₃C | CH₃CH₂ | CH₃ | CH₃ | CH₃ | (CH₃)₃C |
| 1273. | (CH₃)₃C | CH₃CH₂ | CH₃ | CH₃ | CH₃ | CH₃CH₂CH₂CH₂ |
| 1274. | (CH₃)₃C | CH₃CH₂ | CH₃ | CH₃ | CH₃ | (CH₃)₂CHCH₂ |
| 1275. | (CH₃)₃C | CH₃CH₂ | CH₃ | CH₃ | CH₃ | CH₃OCH₂ |
| 1276. | (CH₃)₃C | CH₃CH₂ | CH₃ | CH₃ | CH₃ |  |
| 1277. | (CH₃)₃C | CH₃CH₂ | CH₃ | CH₃ | CH₃ | CH₃SCH₂ |
| 1278. | (CH₃)₃C | CH₃CH₂ | CH₃ | CH₃ | CH₃ |  |
| 1279. | (CH₃)₃C | CH₃CH₂ | CH₃ | CH₃ | CH₃ | FCH₂ |
| 1280. | (CH₃)₃C | CH₃CH₂ | CH₃ | CH₃ | CH₃ | F₃C |
| 1281. | (CH₃)₃C | CH₃CH₂ | CH₃ | CH₃ | CH₃ | C₆H₅ |
| 1282. | (CH₃)₃C | CH₃CH₂ | CH₃ | CH₃ | CH₃ | C₆H₅CH₂ |
| 1283. | (CH₃)₃C | CH₃CH₂ | CH₃ | CH₃ | CH₃ | CH₃CH₂(CH₃)₂C |
| 1284. | (CH₃)₃C | CH₃CH₂ | CH₃ | CH₃ | CH₃ | CH2=CH |
| 1285. | (CH₃)₃C | CH₃CH₂ | CH₃ | CH₃ | CH₃ | CH₃CH₂OCH₂ |
| 1286. | (CH₃)₃C | CH₃CH₂ | CH₃ | CH₃ | CH₃ | CH₃CH₂SCH₂ |
| 1287. | (CH₃)₃C | CH₃CH₂ | CH₃ | CH₃ | CH₃ | 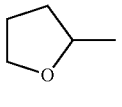 |
| 1288. | (CH₃)₃C | CH₃CH₂ | CH₃ | CH₃ | CH₃ | 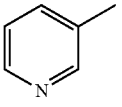 |
| 1289. | (CH₃)₃C | CH₃CH₂ | CH₃ | CH₃ | H | CF₃CH₂SCH₂ |
| 1290. | (CH₃)₃C | CH₃CH₂ | CH₃ | CH₃ | H | ClCH₂CH₂ |
| 1291. | (CH₃)₃C | CH₃CH₂ | CH₃ | CH₃ | H | ClCH₂CH₂CH₂ |
| 1292. | (CH₃)₃C | CH3CH2 | CH₃ | CH₃ | H | NCCH2 |

TABLE 2-continued

| No. | R3 | R9 | R8 | R6 | R7 | L-R10 |
|---|---|---|---|---|---|---|
| 1293. | (CH$_3$)$_3$C | H | CH$_3$CH$_2$ | CH$_3$ | H | CH$_3$ |
| 1294. | (CH$_3$)$_3$C | H | CH$_3$CH$_2$ | CH$_3$ | H | CH$_3$CH$_2$ |
| 1295. | (CH$_3$)$_3$C | H | CH$_3$CH$_2$ | CH$_3$ | H | CH$_3$CH$_2$CH$_2$ |
| 1296. | (CH$_3$)$_3$C | H | CH$_3$CH$_2$ | CH$_3$ | H | (CH$_3$)$_2$CH |
| 1297. | (CH$_3$)$_3$C | H | CH$_3$CH$_2$ | CH$_3$ | H | (CH$_3$)$_3$C |
| 1298. | (CH$_3$)$_3$C | H | CH$_3$CH$_2$ | CH$_3$ | H | CH$_3$CH$_2$CH$_2$CH$_2$ |
| 1299. | (CH$_3$)$_3$C | H | CH$_3$CH$_2$ | CH$_3$ | H | (CH$_3$)$_2$CHCH$_2$ |
| 1300. | (CH$_3$)$_3$C | H | CH$_3$CH$_2$ | CH$_3$ | H | CH$_3$OCH$_2$ |
| 1301. | (CH$_3$)$_3$C | H | CH$_3$CH$_2$ | CH$_3$ | H |  |
| 1302. | (CH$_3$)$_3$C | H | CH$_3$CH$_2$ | CH$_3$ | H | CH$_3$SCH$_2$ |
| 1303. | (CH$_3$)$_3$C | H | CH$_3$CH$_2$ | CH$_3$ | H |  |
| 1304. | (CH$_3$)$_3$C | H | CH$_3$CH$_2$ | CH$_3$ | H | FCH$_2$ |
| 1305. | (CH$_3$)$_3$C | H | CH$_3$CH$_2$ | CH$_3$ | H | F$_3$C |
| 1306. | (CH$_3$)$_3$C | H | CH$_3$CH$_2$ | CH$_3$ | H | C$_6$H$_5$ |
| 1307. | (CH$_3$)$_3$C | H | CH$_3$CH$_2$ | CH$_3$ | H | C$_6$H$_5$CH$_2$ |
| 1308. | (CH$_3$)$_3$C | H | CH$_3$CH$_2$ | CH$_3$ | H | CH$_3$CH$_2$(CH$_3$)$_2$C |
| 1309. | (CH$_3$)$_3$C | H | CH$_3$CH$_2$ | CH$_3$ | H | CH2=CH |
| 1310. | (CH$_3$)$_3$C | H | CH$_3$CH$_2$ | CH$_3$ | H | CH$_3$CH$_2$OCH$_2$ |
| 1311. | (CH$_3$)$_3$C | H | CH$_3$CH$_2$ | CH$_3$ | H | CH$_3$CH$_2$SCH$_2$ |
| 1312. | (CH$_3$)$_3$C | H | CH$_3$CH$_2$ | CH$_3$ | H | 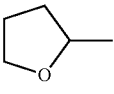 |
| 1313. | (CH$_3$)$_3$C | H | CH$_3$CH$_2$ | CH$_3$ | H | 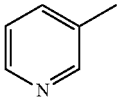 |
| 1314. | (CH$_3$)$_3$C | H | CH$_3$CH$_2$ | CH$_3$ | H | CF$_3$CH$_2$SCH$_2$ |
| 1315. | (CH$_3$)$_3$C | H | CH$_3$CH$_2$ | CH$_3$ | H | ClCH$_2$CH$_2$ |
| 1316. | (CH$_3$)$_3$C | H | CH$_3$CH$_2$ | CH$_3$ | H | ClCH$_2$CH$_2$CH$_2$ |
| 1317. | (CH$_3$)$_3$C | H | CH$_3$CH$_2$ | CH$_3$ | H | NCCH2 |
| 1318. | (CH$_3$)$_3$C | CH$_3$ | CH$_3$CH$_2$ | CH$_3$ | H | CH$_3$ |
| 1319. | (CH$_3$)$_3$C | CH$_3$ | CH$_3$CH$_2$ | CH$_3$ | H | CH$_3$CH$_2$ |
| 1320. | (CH$_3$)$_3$C | CH$_3$ | CH$_3$CH$_2$ | CH$_3$ | H | CH$_3$CH$_2$CH$_2$ |
| 1321. | (CH$_3$)$_3$C | CH$_3$ | CH$_3$CH$_2$ | CH$_3$ | H | (CH$_3$)$_2$CH |
| 1322. | (CH$_3$)$_3$C | CH$_3$ | CH$_3$CH$_2$ | CH$_3$ | H | (CH$_3$)$_3$C |
| 1323. | (CH$_3$)$_3$C | CH$_3$ | CH$_3$CH$_2$ | CH$_3$ | H | CH$_3$CH$_2$CH$_2$CH$_2$ |
| 1324. | (CH$_3$)$_3$C | CH$_3$ | CH$_3$CH$_2$ | CH$_3$ | H | (CH$_3$)$_2$CHCH$_2$ |
| 1325. | (CH$_3$)$_3$C | CH$_3$ | CH$_3$CH$_2$ | CH$_3$ | H | CH$_3$OCH$_2$ |
| 1326. | (CH$_3$)$_3$C | CH$_3$ | CH$_3$CH$_2$ | CH$_3$ | H |  |
| 1327. | (CH$_3$)$_3$C | CH$_3$ | CH$_3$CH$_2$ | CH$_3$ | H | CH$_3$SCH$_2$ |
| 1328. | (CH$_3$)$_3$C | CH$_3$ | CH$_3$CH$_2$ | CH$_3$ | H |  |
| 1329. | (CH$_3$)$_3$C | CH$_3$ | CH$_3$CH$_2$ | CH$_3$ | H | FCH$_2$ |
| 1330. | (CH$_3$)$_3$C | CH$_3$ | CH$_3$CH$_2$ | CH$_3$ | H | F$_3$C |
| 1331. | (CH$_3$)$_3$C | CH$_3$ | CH$_3$CH$_2$ | CH$_3$ | H | C$_6$H$_5$ |
| 1332. | (CH$_3$)$_3$C | CH$_3$ | CH$_3$CH$_2$ | CH$_3$ | H | C$_6$H$_5$CH$_2$ |
| 1333. | (CH$_3$)$_3$C | CH$_3$ | CH$_3$CH$_2$ | CH$_3$ | H | CH$_3$CH$_2$(CH$_3$)$_2$C |
| 1334. | (CH$_3$)$_3$C | CH$_3$ | CH$_3$CH$_2$ | CH$_3$ | H | CH2=CH |
| 1335. | (CH$_3$)$_3$C | CH$_3$ | CH$_3$CH$_2$ | CH$_3$ | H | CH$_3$CH$_2$OCH$_2$ |
| 1336. | (CH$_3$)$_3$C | CH$_3$ | CH$_3$CH$_2$ | CH$_3$ | H | CH$_3$CH$_2$SCH$_2$ |
| 1337. | (CH$_3$)$_3$C | CH$_3$ | CH$_3$CH$_2$ | CH$_3$ | H | 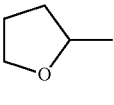 |

TABLE 2-continued

| No. | R3 | R9 | R8 | R6 | R7 | L-R10 |
|---|---|---|---|---|---|---|
| 1338. | (CH₃)₃C | CH₃ | CH₃CH₂ | CH₃ | H | 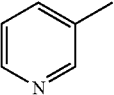 |
| 1339. | (CH₃)₃C | CH₃ | CH₃CH₂ | CH₃ | H | CF₃CH₂SCH₂ |
| 1340. | (CH₃)₃C | CH₃ | CH₃CH₂ | CH₃ | H | ClCH₂CH₂ |
| 1341. | (CH₃)₃C | CH₃ | CH₃CH₂ | CH₃ | H | ClCH₂CH₂CH₂ |
| 1342. | (CH₃)₃C | CH3 | CH₃CH₂ | CH₃ | H | NCCH2 |
| 1343. | (CH₃)₃C | CH₃CH₂ | CH₃CH₂ | CH₃ | H | CH₃ |
| 1344. | (CH₃)₃C | CH₃CH₂ | CH₃CH₂ | CH₃ | H | CH₃CH₂ |
| 1345. | (CH₃)₃C | CH₃CH₂ | CH₃CH₂ | CH₃ | H | CH₃CH₂CH₂ |
| 1346. | (CH₃)₃C | CH₃CH₂ | CH₃CH₂ | CH₃ | H | (CH₃)₂CH |
| 1347. | (CH₃)₃C | CH₃CH₂ | CH₃CH₂ | CH₃ | H | (CH₃)₃C |
| 1348. | (CH₃)₃C | CH₃CH₂ | CH₃CH₂ | CH₃ | H | CH₃CH₂CH₂CH₂ |
| 1349. | (CH₃)₃C | CH₃CH₂ | CH₃CH₂ | CH₃ | H | (CH₃)₂CHCH₂ |
| 1350. | (CH₃)₃C | CH₃CH₂ | CH₃CH₂ | CH₃ | H | CH₃OCH₂ |
| 1351. | (CH₃)₃C | CH₃CH₂ | CH₃CH₂ | CH₃ | H |  |
| 1352. | (CH₃)₃C | CH₃CH₂ | CH₃CH₂ | CH₃ | H | CH₃SCH₂ |
| 1353. | (CH₃)₃C | CH₃CH₂ | CH₃CH₂ | CH₃ | H |  |
| 1354. | (CH₃)₃C | CH₃CH₂ | CH₃CH₂ | CH₃ | H | FCH₂ |
| 1355. | (CH₃)₃C | CH₃CH₂ | CH₃CH₂ | CH₃ | H | F₃C |
| 1356. | (CH₃)₃C | CH₃CH₂ | CH₃CH₂ | CH₃ | H | C₆H₅ |
| 1357. | (CH₃)₃C | CH₃CH₂ | CH₃CH₂ | CH₃ | H | C₆H₅CH₂ |
| 1358. | (CH₃)₃C | CH₃CH₂ | CH₃CH₂ | CH₃ | H | CH₃CH₂(CH₃)₂C |
| 1359. | (CH₃)₃C | CH₃CH₂ | CH₃CH₂ | CH₃ | H | CH2=CH |
| 1360. | (CH₃)₃C | CH₃CH₂ | CH₃CH₂ | CH₃ | H | CH₃CH₂OCH₂ |
| 1361. | (CH₃)₃C | CH₃CH₂ | CH₃CH₂ | CH₃ | H | CH₃CH₂SCH₂ |
| 1362. | (CH₃)₃C | CH₃CH₂ | CH₃CH₂ | CH₃ | H | 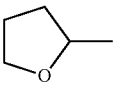 |
| 1363. | (CH₃)₃C | CH₃CH₂ | CH₃CH₂ | CH₃ | H | 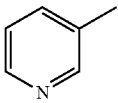 |
| 1364. | (CH₃)₃C | CH₃CH₂ | CH₃CH₂ | CH₃ | H | CF₃CH₂SCH₂ |
| 1365. | (CH₃)₃C | CH₃CH₂ | CH₃CH₂ | CH₃ | H | ClCH₂CH₂ |
| 1366. | (CH₃)₃C | CH₃CH₂ | CH₃CH₂ | CH₃ | H | ClCH₂CH₂CH₂ |
| 1367. | (CH₃)₃C | CH3CH2 | CH₃CH₂ | CH₃ | H | NCCH2 |
| 1368. | (CH₃)₃C | H | CH₃CH₂ | CH₃ | Cl | CH₃ |
| 1369. | (CH₃)₃C | H | CH₃CH₂ | CH₃ | Cl | CH₃CH₂ |
| 1370. | (CH₃)₃C | H | CH₃CH₂ | CH₃ | Cl | CH₃CH₂CH₂ |
| 1371. | (CH₃)₃C | H | CH₃CH₂ | CH₃ | Cl | (CH₃)₂CH |
| 1372. | (CH₃)₃C | H | CH₃CH₂ | CH₃ | Cl | (CH₃)₃C |
| 1373. | (CH₃)₃C | H | CH₃CH₂ | CH₃ | Cl | CH₃CH₂CH₂CH₂ |
| 1374. | (CH₃)₃C | H | CH₃CH₂ | CH₃ | Cl | (CH₃)₂CHCH₂ |
| 1375. | (CH₃)₃C | H | CH₃CH₂ | CH₃ | Cl | CH₃OCH₂ |
| 1376. | (CH₃)₃C | H | CH₃CH₂ | CH₃ | Cl |  |
| 1377. | (CH₃)₃C | H | CH₃CH₂ | CH₃ | Cl | CH₃SCH₂ |
| 1378. | (CH₃)₃C | H | CH₃CH₂ | CH₃ | Cl |  |
| 1379. | (CH₃)₃C | H | CH₃CH₂ | CH₃ | Cl | FCH₂ |
| 1380. | (CH₃)₃C | H | CH₃CH₂ | CH₃ | Cl | F₃C |
| 1381. | (CH₃)₃C | H | CH₃CH₂ | CH₃ | Cl | C₆H₅ |
| 1382. | (CH₃)₃C | H | CH₃CH₂ | CH₃ | Cl | C₆H₅CH₂ |
| 1383. | (CH₃)₃C | H | CH₃CH₂ | CH₃ | Cl | CH₃CH₂(CH₃)₂C |

TABLE 2-continued

| No. | R3 | R9 | R8 | R6 | R7 | L-R10 |
|---|---|---|---|---|---|---|
| 1384. | (CH3)3C | H | CH3CH2 | CH3 | Cl | CH2=CH |
| 1385. | (CH3)3C | H | CH3CH2 | CH3 | Cl | CH3CH2OCH2 |
| 1386. | (CH3)3C | H | CH3CH2 | CH3 | Cl | CH3CH2SCH2 |
| 1387. | (CH3)3C | H | CH3CH2 | CH3 | Cl | 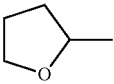 |
| 1388. | (CH3)3C | H | CH3CH2 | CH3 | Cl | 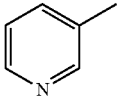 |
| 1389. | (CH3)3C | H | CH3CH2 | CH3 | Cl | CF3CH2SCH2 |
| 1390. | (CH3)3C | H | CH3CH2 | CH3 | Cl | ClCH2CH2 |
| 1391. | (CH3)3C | H | CH3CH2 | CH3 | Cl | ClCH2CH2CH2 |
| 1392. | (CH3)3C | H | CH3CH2 | CH3 | Cl | NCCH2 |
| 1393. | (CH3)3C | CH3 | CH3CH2 | CH3 | Cl | CH3 |
| 1394. | (CH3)3C | CH3 | CH3CH2 | CH3 | Cl | CH3CH2 |
| 1395. | (CH3)3C | CH3 | CH3CH2 | CH3 | Cl | CH3CH2CH2 |
| 1396. | (CH3)3C | CH3 | CH3CH2 | CH3 | Cl | (CH3)2CH |
| 1397. | (CH3)3C | CH3 | CH3CH2 | CH3 | Cl | (CH3)3C |
| 1398. | (CH3)3C | CH3 | CH3CH2 | CH3 | Cl | CH3CH2CH2CH2 |
| 1399. | (CH3)3C | CH3 | CH3CH2 | CH3 | Cl | (CH3)2CHCH2 |
| 1400. | (CH3)3C | CH3 | CH3CH2 | CH3 | Cl | CH3OCH2 |
| 1401. | (CH3)3C | CH3 | CH3CH2 | CH3 | Cl |  |
| 1402. | (CH3)3C | CH3 | CH3CH2 | CH3 | Cl | CH3SCH2 |
| 1403. | (CH3)3C | CH3 | CH3CH2 | CH3 | Cl |  |
| 1404. | (CH3)3C | CH3 | CH3CH2 | CH3 | Cl | FCH2 |
| 1405. | (CH3)3C | CH3 | CH3CH2 | CH3 | Cl | F3C |
| 1406. | (CH3)3C | CH3 | CH3CH2 | CH3 | Cl | C6H5 |
| 1407. | (CH3)3C | CH3 | CH3CH2 | CH3 | Cl | C6H5CH2 |
| 1408. | (CH3)3C | CH3 | CH3CH2 | CH3 | Cl | CH3CH2(CH3)2C |
| 1409. | (CH3)3C | CH3 | CH3CH2 | CH3 | Cl | CH2=CH |
| 1410. | (CH3)3C | CH3 | CH3CH2 | CH3 | Cl | CH3CH2OCH2 |
| 1411. | (CH3)3C | CH3 | CH3CH2 | CH3 | Cl | CH3CH2SCH2 |
| 1412. | (CH3)3C | CH3 | CH3CH2 | CH3 | Cl | 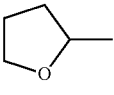 |
| 1413. | (CH3)3C | CH3 | CH3CH2 | CH3 | Cl | 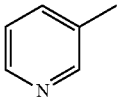 |
| 1414. | (CH3)3C | CH3 | CH3CH2 | CH3 | Cl | CF3CH2SCH2 |
| 1415. | (CH3)3C | CH3 | CH3CH2 | CH3 | Cl | ClCH2CH2 |
| 1416. | (CH3)3C | CH3 | CH3CH2 | CH3 | Cl | ClCH2CH2CH2 |
| 1417. | (CH3)3C | CH3 | CH3CH2 | CH3 | Cl | NCCH2 |
| 1418. | (CH3)3C | CH3CH2 | CH3CH2 | CH3 | Cl | CH3 |
| 1419. | (CH3)3C | CH3CH2 | CH3CH2 | CH3 | Cl | CH3CH2 |
| 1420. | (CH3)3C | CH3CH2 | CH3CH2 | CH3 | Cl | CH3CH2CH2 |
| 1421. | (CH3)3C | CH3CH2 | CH3CH2 | CH3 | Cl | (CH3)2CH |
| 1422. | (CH3)3C | CH3CH2 | CH3CH2 | CH3 | Cl | (CH3)3C |
| 1423. | (CH3)3C | CH3CH2 | CH3CH2 | CH3 | Cl | CH3CH2CH2CH2 |
| 1424. | (CH3)3C | CH3CH2 | CH3CH2 | CH3 | Cl | (CH3)2CHCH2 |
| 1425. | (CH3)3C | CH3CH2 | CH3CH2 | CH3 | Cl | CH3OCH2 |
| 1426. | (CH3)3C | CH3CH2 | CH3CH2 | CH3 | Cl |  |
| 1427. | (CH3)3C | CH3CH2 | CH3CH2 | CH3 | Cl | CH3SCH2 |

TABLE 2-continued

| No. | R3 | R9 | R8 | R6 | R7 | L-R10 |
|---|---|---|---|---|---|---|
| 1428. | (CH₃)₃C | CH₃CH₂ | CH₃CH₂ | CH₃ | Cl |  |
| 1429. | (CH₃)₃C | CH₃CH₂ | CH₃CH₂ | CH₃ | Cl | FCH₂ |
| 1430. | (CH₃)₃C | CH₃CH₂ | CH₃CH₂ | CH₃ | Cl | F₃C |
| 1431. | (CH₃)₃C | CH₃CH₂ | CH₃CH₂ | CH₃ | Cl | C₆H₅ |
| 1432. | (CH₃)₃C | CH₃CH₂ | CH₃CH₂ | CH₃ | Cl | C₆H₅CH₂ |
| 1433. | (CH₃)₃C | CH₃CH₂ | CH₃CH₂ | CH₃ | Cl | CH₃CH₂(CH₃)₂C |
| 1434. | (CH₃)₃C | CH₃CH₂ | CH₃CH₂ | CH₃ | Cl | CH2=CH |
| 1435. | (CH₃)₃C | CH₃CH₂ | CH₃CH₂ | CH₃ | Cl | CH₃CH₂OCH₂ |
| 1436. | (CH₃)₃C | CH₃CH₂ | CH₃CH₂ | CH₃ | Cl | CH₃CH₂SCH₂ |
| 1437. | (CH₃)₃C | CH₃CH₂ | CH₃CH₂ | CH₃ | Cl | 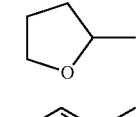 |
| 1438. | (CH₃)₃C | CH₃CH₂ | CH₃CH₂ | CH₃ | Cl | 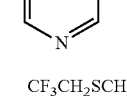 |
| 1439. | (CH₃)₃C | CH₃CH₂ | CH₃CH₂ | CH₃ | Cl | CF₃CH₂SCH₂ |
| 1440. | (CH₃)₃C | CH₃CH₂ | CH₃CH₂ | CH₃ | Cl | ClCH₂CH₂ |
| 1441. | (CH₃)₃C | CH₃CH₂ | CH₃CH₂ | CH₃ | Cl | ClCH₂CH₂CH₂ |
| 1442. | (CH₃)₃C | CH₃CH₂ | CH₃CH₂ | CH₃ | Cl | NCCH2 |
| 1443. | (CH₃)₃C | H | CH₃CH₂ | CH₃ | CH₃ | CH₃ |
| 1444. | (CH₃)₃C | H | CH₃CH₂ | CH₃ | CH₃ | CH₃CH₂ |
| 1445. | (CH₃)₃C | H | CH₃CH₂ | CH₃ | CH₃ | CH₃CH₂CH₂ |
| 1446. | (CH₃)₃C | H | CH₃CH₂ | CH₃ | CH₃ | (CH₃)₂CH |
| 1447. | (CH₃)₃C | H | CH₃CH₂ | CH₃ | CH₃ | (CH₃)₃C |
| 1448. | (CH₃)₃C | H | CH₃CH₂ | CH₃ | CH₃ | CH₃CH₂CH₂CH₂ |
| 1449. | (CH₃)₃C | H | CH₃CH₂ | CH₃ | CH₃ | (CH₃)₂CHCH₂ |
| 1450. | (CH₃)₃C | H | CH₃CH₂ | CH₃ | CH₃ | CH₃OCH₂ |
| 1451. | (CH₃)₃C | H | CH₃CH₂ | CH₃ | CH₃ |  |
| 1452. | (CH₃)₃C | H | CH₃CH₂ | CH₃ | CH₃ | CH₃SCH₂ |
| 1453. | (CH₃)₃C | H | CH₃CH₂ | CH₃ | CH₃ |  |
| 1454. | (CH₃)₃C | H | CH₃CH₂ | CH₃ | CH₃ | FCH₂ |
| 1455. | (CH₃)₃C | H | CH₃CH₂ | CH₃ | CH₃ | F₃C |
| 1456. | (CH₃)₃C | H | CH₃CH₂ | CH₃ | CH₃ | C₆H₅ |
| 1457. | (CH₃)₃C | H | CH₃CH₂ | CH₃ | CH₃ | C₆H₅CH₂ |
| 1458. | (CH₃)₃C | H | CH₃CH₂ | CH₃ | CH₃ | CH₃CH₂(CH₃)₂C |
| 1459. | (CH₃)₃C | H | CH₃CH₂ | CH₃ | CH₃ | CH2=CH |
| 1460. | (CH₃)₃C | H | CH₃CH₂ | CH₃ | CH₃ | CH₃CH₂OCH₂ |
| 1461. | (CH₃)₃C | H | CH₃CH₂ | CH₃ | CH₃ | CH₃CH₂SCH₂ |
| 1462. | (CH₃)₃C | H | CH₃CH₂ | CH₃ | CH₃ | 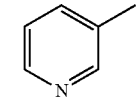 |
| 1463. | (CH₃)₃C | H | CH₃CH₂ | CH₃ | CH₃ | 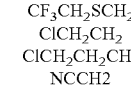 |
| 1464. | (CH₃)₃C | H | CH₃CH₂ | CH₃ | CH₃ | CF₃CH₂SCH₂ |
| 1465. | (CH₃)₃C | H | CH₃CH₂ | CH₃ | CH₃ | ClCH₂CH₂ |
| 1466. | (CH₃)₃C | H | CH₃CH₂ | CH₃ | CH₃ | ClCH₂CH₂CH₂ |
| 1467. | (CH₃)₃C | H | CH₃CH₂ | CH₃ | CH₃ | NCCH2 |
| 1468. | (CH₃)₃C | CH₃ | CH₃CH₂ | CH₃ | CH₃ | CH₃ |
| 1469. | (CH₃)₃C | CH₃ | CH₃CH₂ | CH₃ | CH₃ | CH₃CH₂ |
| 1470. | (CH₃)₃C | CH₃ | CH₃CH₂ | CH₃ | CH₃ | CH₃CH₂CH₂ |
| 1471. | (CH₃)₃C | CH₃ | CH₃CH₂ | CH₃ | CH₃ | (CH₃)₂CH |
| 1472. | (CH₃)₃C | CH₃ | CH₃CH₂ | CH₃ | CH₃ | (CH₃)₃C |

TABLE 2-continued

| No. | R3 | R9 | R8 | R6 | R7 | L-R10 |
|---|---|---|---|---|---|---|
| 1473. | (CH₃)₃C | CH₃ | CH₃CH₂ | CH₃ | CH₃ | CH₃CH₂CH₂CH₂ |
| 1474. | (CH₃)₃C | CH₃ | CH₃CH₂ | CH₃ | CH₃ | (CH₃)₂CHCH₂ |
| 1475. | (CH₃)₃C | CH₃ | CH₃CH₂ | CH₃ | CH₃ | CH₃OCH₂ |
| 1476. | (CH₃)₃C | CH₃ | CH₃CH₂ | CH₃ | CH₃ |  |
| 1477. | (CH₃)₃C | CH₃ | CH₃CH₂ | CH₃ | CH₃ | CH₃SCH₂ |
| 1478. | (CH₃)₃C | CH₃ | CH₃CH₂ | CH₃ | CH₃ |  |
| 1479. | (CH₃)₃C | CH₃ | CH₃CH₂ | CH₃ | CH₃ | FCH₂ |
| 1480. | (CH₃)₃C | CH₃ | CH₃CH₂ | CH₃ | CH₃ | F₃C |
| 1481. | (CH₃)₃C | CH₃ | CH₃CH₂ | CH₃ | CH₃ | C₆H₅ |
| 1482. | (CH₃)₃C | CH₃ | CH₃CH₂ | CH₃ | CH₃ | C₆H₅CH₂ |
| 1483. | (CH₃)₃C | CH₃ | CH₃CH₂ | CH₃ | CH₃ | CH₃CH₂(CH₃)₂C |
| 1484. | (CH₃)₃C | CH₃ | CH₃CH₂ | CH₃ | CH₃ | CH2=CH |
| 1485. | (CH₃)₃C | CH₃ | CH₃CH₂ | CH₃ | CH₃ | CH₃CH₂OCH₂ |
| 1486. | (CH₃)₃C | CH₃ | CH₃CH₂ | CH₃ | CH₃ | CH₃CH₂SCH₂ |
| 1487. | (CH₃)₃C | CH₃ | CH₃CH₂ | CH₃ | CH₃ | 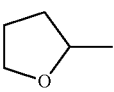 |
| 1488. | (CH₃)₃C | CH₃ | CH₃CH₂ | CH₃ | CH₃ | 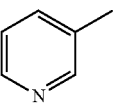 |
| 1489. | (CH₃)₃C | CH₃ | CH₃CH₂ | CH₃ | CH₃ | CF₃CH₂SCH₂ |
| 1490. | (CH₃)₃C | CH₃ | CH₃CH₂ | CH₃ | CH₃ | ClCH₂CH₂ |
| 1491. | (CH₃)₃C | CH₃ | CH₃CH₂ | CH₃ | CH₃ | ClCH₂CH₂CH₂ |
| 1492. | (CH₃)₃C | CH₃ | CH₃CH₂ | CH₃ | CH₃ | NCCH2 |
| 1493. | (CH₃)₃C | CH₃CH₂ | CH₃CH₂ | CH₃ | CH₃ | CH₃ |
| 1494. | (CH₃)₃C | CH₃CH₂ | CH₃CH₂ | CH₃ | CH₃ | CH₃CH₂ |
| 1495. | (CH₃)₃C | CH₃CH₂ | CH₃CH₂ | CH₃ | CH₃ | CH₃CH₂CH₂ |
| 1496. | (CH₃)₃C | CH₃CH₂ | CH₃CH₂ | CH₃ | CH₃ | (CH₃)₂CH |
| 1497. | (CH₃)₃C | CH₃CH₂ | CH₃CH₂ | CH₃ | CH₃ | (CH₃)₃C |
| 1498. | (CH₃)₃C | CH₃CH₂ | CH₃CH₂ | CH₃ | CH₃ | CH₃CH₂CH₂CH₂ |
| 1499. | (CH₃)₃C | CH₃CH₂ | CH₃CH₂ | CH₃ | CH₃ | (CH₃)₂CHCH₂ |
| 1500. | (CH₃)₃C | CH₃CH₂ | CH₃CH₂ | CH₃ | CH₃ | CH₃OCH₂ |
| 1501. | (CH₃)₃C | CH₃CH₂ | CH₃CH₂ | CH₃ | CH₃ |  |
| 1502. | (CH₃)₃C | CH₃CH₂ | CH₃CH₂ | CH₃ | CH₃ | CH₃SCH₂ |
| 1503. | (CH₃)₃C | CH₃CH₂ | CH₃CH₂ | CH₃ | CH₃ |  |
| 1504. | (CH₃)₃C | CH₃CH₂ | CH₃CH₂ | CH₃ | CH₃ | FCH₂ |
| 1505. | (CH₃)₃C | CH₃CH₂ | CH₃CH₂ | CH₃ | CH₃ | F₃C |
| 1506. | (CH₃)₃C | CH₃CH₂ | CH₃CH₂ | CH₃ | CH₃ | C₆H₅ |
| 1507. | (CH₃)₃C | CH₃CH₂ | CH₃CH₂ | CH₃ | CH₃ | C₆H₅CH₂ |
| 1508. | (CH₃)₃C | CH₃CH₂ | CH₃CH₂ | CH₃ | CH₃ | CH₃CH₂(CH₃)₂C |
| 1509. | (CH₃)₃C | CH₃CH₂ | CH₃CH₂ | CH₃ | CH₃ | CH2=CH |
| 1510. | (CH₃)₃C | CH₃CH₂ | CH₃CH₂ | CH₃ | CH₃ | CH₃CH₂OCH₂ |
| 1511. | (CH₃)₃C | CH₃CH₂ | CH₃CH₂ | CH₃ | CH₃ | CH₃CH₂SCH₂ |
| 1512. | (CH₃)₃C | CH₃CH₂ | CH₃CH₂ | CH₃ | CH₃ | 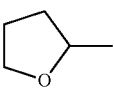 |
| 1513. | (CH₃)₃C | CH₃CH₂ | CH₃CH₂ | CH₃ | CH₃ | 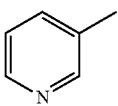 |

TABLE 2-continued

| No. | R3 | R9 | R8 | R6 | R7 | L-R10 |
|---|---|---|---|---|---|---|
| 1514. | (CH$_3$)$_3$C | CH$_3$CH$_2$ | CH$_3$CH$_2$ | CH$_3$ | CH$_3$ | CF$_3$CH$_2$SCH$_2$ |
| 1515. | (CH$_3$)$_3$C | CH$_3$CH$_2$ | CH$_3$CH$_2$ | CH$_3$ | CH$_3$ | ClCH$_2$CH$_2$ |
| 1516. | (CH$_3$)$_3$C | CH$_3$CH$_2$ | CH$_3$CH$_2$ | CH$_3$ | CH$_3$ | ClCH$_2$CH$_2$CH$_2$ |
| 1517. | (CH$_3$)$_3$C | CH$_3$CH$_2$ | CH$_3$CH$_2$ | CH$_3$ | CH$_3$ | NCCH2 |
| 1518. | | | | | | |
| 1519. | (CH$_3$)$_3$C | H | CH$_3$ | CH$_3$ | H | OCH$_3$ |
| 1520. | (CH$_3$)$_3$C | H | CH$_3$ | CH$_3$ | H | OCH$_2$CH$_3$ |
| 1521. | (CH$_3$)$_3$C | H | CH$_3$ | CH$_3$ | H | O(CH$_2$)$_2$CH$_3$ |
| 1522. | (CH$_3$)$_3$C | H | CH$_3$ | CH$_3$ | H | OCH(CH$_3$)$_2$ |
| 1523. | (CH$_3$)$_3$C | H | CH$_3$ | CH$_3$ | H | O(CH$_3$)$_3$ |
| 1524. | (CH$_3$)$_3$C | H | CH$_3$ | CH$_3$ | H | O(CH$_2$)$_2$CH$_3$ |
| 1525. | (CH$_3$)$_3$C | H | CH$_3$ | CH$_3$ | H | OCH$_2$CH(CH$_3$)$_2$ |
| 1526. | (CH$_3$)$_3$C | H | CH$_3$ | CH$_3$ | H | OCH$_2$CH$_2$CH(CH$_3$)$_2$ |
| 1527. | (CH$_3$)$_3$C | H | CH$_3$ | CH$_3$ | H | OC(CH$_3$)$_2$CH$_2$CH$_3$ |
| 1528. | (CH$_3$)$_3$C | H | CH$_3$ | CH$_3$ | H | O(CH$_2$)$_4$CH$_3$ |
| 1529. | (CH$_3$)$_3$C | H | CH$_3$ | CH$_3$ | H | OCH$_2$Cl |
| 1530. | (CH$_3$)$_3$C | H | CH$_3$ | CH$_3$ | H | OCH$_2$CH$_2$Cl |
| 1531. | (CH$_3$)$_3$C | H | CH$_3$ | CH$_3$ | H | OCH$_2$CH$_2$CH$_2$CH$_2$Cl |
| 1532. | (CH$_3$)$_3$C | H | CH$_3$ | CH$_3$ | H | OCH$_2$CH$_2$Cl$_2$ |
| 1533. | (CH$_3$)$_3$C | H | CH$_3$ | CH$_3$ | H | OCH$_2$CH$_2$F |
| 1534. | (CH$_3$)$_3$C | H | CH$_3$ | CH$_3$ | H | OCH$_2$CHF$_2$ |
| 1535. | (CH$_3$)$_3$C | H | CH$_3$ | CH$_3$ | H | OCH$_2$CF$_3$ |
| 1536. | (CH$_3$)$_3$C | H | CH$_3$ | CH$_3$ | H | OCH$_2$CH$_2$OCH$_3$ |
| 1537. | (CH$_3$)$_3$C | H | CH$_3$ | CH$_3$ | H | OCH$_2$CH$_2$OCH$_2$CH$_3$ |
| 1538. | (CH$_3$)$_3$C | H | CH$_3$ | CH$_3$ | H | OCH$_2$OCH$_2$CH$_3$ |
| 1539. | (CH$_3$)$_3$C | H | CH$_3$ | CH$_3$ | H | OCH$_2$CH$_2$SCH$_3$ |
| 1540. | (CH$_3$)$_3$C | H | CH$_3$ | CH$_3$ | H | OCH$_2$C$_5$H$_6$ |
| 1541. | (CH$_3$)$_3$C | H | CH$_3$ | CH$_3$ | H | OCH$_2$(4-ClC$_5$H$_6$) |
| 1542. | (CH$_3$)$_3$C | H | CH$_3$ | CH$_3$ | H | OCH$_2$C=CH$_2$ |
| 1543. | (CH$_3$)$_3$C | H | CH$_3$ | CH$_3$ | H | OCH$_2$(C=CH)CH$_3$ |
| 1544. | (CH$_3$)$_3$C | H | CH$_3$ | CH$_3$ | H | OCH$_2$C≡CH |
| 1545. | (CH$_3$)$_3$C | H | CH$_3$ | CH$_3$ | H | OCH$_2$COOCH$_3$ |
| 1546. | (CH$_3$)$_3$C | H | CH$_3$ | CH$_3$ | H | OCH$_2$COOCH$_2$CH$_3$ |
| 1547. | (CH$_3$)$_3$C | H | CH$_3$ | CH$_3$ | H | SCH$_3$ |
| 1548. | (CH$_3$)$_3$C | H | CH$_3$ | CH$_3$ | H | SCH$_2$CH$_3$ |
| 1549. | (CH$_3$)$_3$C | H | CH$_3$ | CH$_3$ | H | SCH2COOCH3 |
| 1550. | (CH$_3$)$_3$C | H | CH$_3$ | CH$_3$ | H | SCH2(4-ClC5H6) |
| 1551. | (CH$_3$)$_3$C | CH$_3$ | CH$_3$ | CH$_3$ | H | OCH$_3$ |
| 1552. | (CH$_3$)$_3$C | CH$_3$ | CH$_3$ | CH$_3$ | H | OCH$_2$CH$_3$ |
| 1553. | (CH$_3$)$_3$C | CH$_3$ | CH$_3$ | CH$_3$ | H | O(CH$_2$)$_2$CH$_3$ |
| 1554. | (CH$_3$)$_3$C | CH$_3$ | CH$_3$ | CH$_3$ | H | OCH(CH$_3$)$_2$ |
| 1555. | (CH$_3$)$_3$C | CH$_3$ | CH$_3$ | CH$_3$ | H | O(CH$_3$)$_3$ |
| 1556. | (CH$_3$)$_3$C | CH$_3$ | CH$_3$ | CH$_3$ | H | O(CH$_2$)$_2$CH$_3$ |
| 1557. | (CH$_3$)$_3$C | CH$_3$ | CH$_3$ | CH$_3$ | H | OCH$_2$CH(CH$_3$)$_2$ |
| 1558. | (CH$_3$)$_3$C | CH$_3$ | CH$_3$ | CH$_3$ | H | OCH$_2$CH$_2$CH(CH$_3$)$_2$ |
| 1559. | (CH$_3$)$_3$C | CH$_3$ | CH$_3$ | CH$_3$ | H | OC(CH$_3$)$_2$CH$_2$CH$_3$ |
| 1560. | (CH$_3$)$_3$C | CH$_3$ | CH$_3$ | CH$_3$ | H | O(CH$_2$)$_4$CH$_3$ |
| 1561. | (CH$_3$)$_3$C | CH$_3$ | CH$_3$ | CH$_3$ | H | OCH$_2$Cl |
| 1562. | (CH$_3$)$_3$C | CH$_3$ | CH$_3$ | CH$_3$ | H | OCH$_2$CH$_2$Cl |
| 1563. | (CH$_3$)$_3$C | CH$_3$ | CH$_3$ | CH$_3$ | H | OCH$_2$CH$_2$CH$_2$CH$_2$Cl |
| 1564. | (CH$_3$)$_3$C | CH$_3$ | CH$_3$ | CH$_3$ | H | OCH$_2$CH$_2$Cl$_2$ |
| 1565. | (CH$_3$)$_3$C | CH$_3$ | CH$_3$ | CH$_3$ | H | OCH$_2$CH$_2$F |
| 1566. | (CH$_3$)$_3$C | CH$_3$ | CH$_3$ | CH$_3$ | H | OCH$_2$CHF$_2$ |
| 1567. | (CH$_3$)$_3$C | CH$_3$ | CH$_3$ | CH$_3$ | H | OCH$_2$CF$_3$ |
| 1568. | (CH$_3$)$_3$C | CH$_3$ | CH$_3$ | CH$_3$ | H | OCH$_2$CH$_2$OCH$_3$ |
| 1569. | (CH$_3$)$_3$C | CH$_3$ | CH$_3$ | CH$_3$ | H | OCH$_2$CH$_2$OCH$_2$CH$_3$ |
| 1570. | (CH$_3$)$_3$C | CH$_3$ | CH$_3$ | CH$_3$ | H | OCH$_2$OCH$_2$CH$_3$ |
| 1571. | (CH$_3$)$_3$C | CH$_3$ | CH$_3$ | CH$_3$ | H | OCH$_2$CH$_2$SCH$_3$ |
| 1572. | (CH$_3$)$_3$C | CH$_3$ | CH$_3$ | CH$_3$ | H | OCH$_2$C$_5$H$_6$ |
| 1573. | (CH$_3$)$_3$C | CH$_3$ | CH$_3$ | CH$_3$ | H | OCH$_2$(4-ClC$_5$H$_6$) |
| 1574. | (CH$_3$)$_3$C | CH$_3$ | CH$_3$ | CH$_3$ | H | OCH$_2$C=CH$_2$ |
| 1575. | (CH$_3$)$_3$C | CH$_3$ | CH$_3$ | CH$_3$ | H | OCH$_2$(C=CH)CH$_3$ |
| 1576. | (CH$_3$)$_3$C | CH$_3$ | CH$_3$ | CH$_3$ | H | OCH$_2$C≡CH |
| 1577. | (CH$_3$)$_3$C | CH$_3$ | CH$_3$ | CH$_3$ | H | OCH$_2$COOCH$_3$ |
| 1578. | (CH$_3$)$_3$C | CH$_3$ | CH$_3$ | CH$_3$ | H | OCH$_2$COOCH$_2$CH$_3$ |
| 1579. | (CH$_3$)$_3$C | CH$_3$ | CH$_3$ | CH$_3$ | H | SCH$_3$ |
| 1580. | (CH$_3$)$_3$C | CH$_3$ | CH$_3$ | CH$_3$ | H | SCH$_2$CH$_3$ |
| 1581. | (CH$_3$)$_3$C | CH$_3$ | CH$_3$ | CH$_3$ | H | SCH2COOCH3 |
| 1582. | (CH$_3$)$_3$C | CH$_3$ | CH$_3$ | CH$_3$ | H | SCH2(4-ClC5H6) |
| 1583. | (CH$_3$)$_3$C | CH$_3$ | CH$_3$ | CH$_3$ | H | OCH$_3$ |
| 1584. | (CH$_3$)$_3$C | CH$_3$CH$_2$ | CH$_3$ | CH$_3$ | H | OCH$_2$CH$_3$ |
| 1585. | (CH$_3$)$_3$C | CH$_3$CH$_2$ | CH$_3$ | CH$_3$ | H | O(CH$_2$)$_2$CH$_3$ |
| 1586. | (CH$_3$)$_3$C | CH$_3$CH$_2$ | CH$_3$ | CH$_3$ | H | OCH(CH$_3$)$_2$ |
| 1587. | (CH$_3$)$_3$C | CH$_3$CH$_2$ | CH$_3$ | CH$_3$ | H | O(CH$_3$)$_3$ |
| 1588. | (CH$_3$)$_3$C | CH$_3$CH$_2$ | CH$_3$ | CH$_3$ | H | O(CH$_2$)$_2$CH$_3$ |
| 1589. | (CH$_3$)$_3$C | CH$_3$CH$_2$ | CH$_3$ | CH$_3$ | H | OCH$_2$CH(CH$_3$)$_2$ |
| 1590. | (CH$_3$)$_3$C | CH$_3$CH$_2$ | CH$_3$ | CH$_3$ | H | OCH$_2$CH$_2$CH(CH$_3$)$_2$ |
| 1591. | (CH$_3$)$_3$C | CH$_3$CH$_2$ | CH$_3$ | CH$_3$ | H | OC(CH$_3$)$_2$CH$_2$CH$_3$ |

TABLE 2-continued

| No. | R3 | R9 | R8 | R6 | R7 | L-R10 |
|---|---|---|---|---|---|---|
| 1592. | (CH$_3$)$_3$C | CH$_3$CH$_2$ | CH$_3$ | CH$_3$ | H | O(CH$_2$)$_4$CH$_3$ |
| 1593. | (CH$_3$)$_3$C | CH$_3$CH$_2$ | CH$_3$ | CH$_3$ | H | OCH$_2$Cl |
| 1594. | (CH$_3$)$_3$C | CH$_3$CH$_2$ | CH$_3$ | CH$_3$ | H | OCH$_2$CH$_2$Cl |
| 1595. | (CH$_3$)$_3$C | CH$_3$CH$_2$ | CH$_3$ | CH$_3$ | H | OCH$_2$CH$_2$CH$_2$CH$_2$Cl |
| 1596. | (CH$_3$)$_3$C | CH$_3$CH$_2$ | CH$_3$ | CH$_3$ | H | OCH$_2$CH$_2$Cl$_2$ |
| 1597. | (CH$_3$)$_3$C | CH$_3$CH$_2$ | CH$_3$ | CH$_3$ | H | OCH$_2$CH$_2$F |
| 1598. | (CH$_3$)$_3$C | CH$_3$CH$_2$ | CH$_3$ | CH$_3$ | H | OCH$_2$CHF$_2$ |
| 1599. | (CH$_3$)$_3$C | CH$_3$CH$_2$ | CH$_3$ | CH$_3$ | H | OCH$_2$CF$_3$ |
| 1600. | (CH$_3$)$_3$C | CH$_3$CH$_2$ | CH$_3$ | CH$_3$ | H | OCH$_2$CH$_2$OCH$_3$ |
| 1601. | (CH$_3$)$_3$C | CH$_3$CH$_2$ | CH$_3$ | CH$_3$ | H | OCH$_2$CH$_2$OCH$_2$CH$_3$ |
| 1602. | (CH$_3$)$_3$C | CH$_3$CH$_2$ | CH$_3$ | CH$_3$ | H | OCH$_2$OCH$_2$CH$_3$ |
| 1603. | (CH$_3$)$_3$C | CH$_3$CH$_2$ | CH$_3$ | CH$_3$ | H | OCH$_2$CH$_2$SCH$_3$ |
| 1604. | (CH$_3$)$_3$C | CH$_3$CH$_2$ | CH$_3$ | CH$_3$ | H | OCH$_2$C$_5$H$_6$ |
| 1605. | (CH$_3$)$_3$C | CH$_3$CH$_2$ | CH$_3$ | CH$_3$ | H | OCH$_2$(4-ClC$_5$H$_6$) |
| 1606. | (CH$_3$)$_3$C | CH$_3$CH$_2$ | CH$_3$ | CH$_3$ | H | OCH$_2$C=CH$_2$ |
| 1607. | (CH$_3$)$_3$C | CH$_3$CH$_2$ | CH$_3$ | CH$_3$ | H | OCH$_2$(C=CH)CH$_3$ |
| 1608. | (CH$_3$)$_3$C | CH$_3$CH$_2$ | CH$_3$ | CH$_3$ | H | OCH$_2$C≡CH |
| 1609. | (CH$_3$)$_3$C | CH$_3$CH$_2$ | CH$_3$ | CH$_3$ | H | OCH$_2$COOCH$_3$ |
| 1610. | (CH$_3$)$_3$C | CH$_3$CH$_2$ | CH$_3$ | CH$_3$ | H | OCH$_2$COOCH$_2$CH$_3$ |
| 1611. | (CH$_3$)$_3$C | CH$_3$CH$_2$ | CH$_3$ | CH$_3$ | H | SCH$_3$ |
| 1612. | (CH$_3$)$_3$C | CH$_3$CH$_2$ | CH$_3$ | CH$_3$ | H | SCH$_2$CH$_3$ |
| 1613. | (CH$_3$)$_3$C | CH$_3$CH$_2$ | CH$_3$ | CH$_3$ | H | SCH2COOCH3 |
| 1614. | (CH$_3$)$_3$C | CH$_3$CH$_2$ | CH$_3$ | CH$_3$ | H | SCH2(4-ClC5H6) |
| 1615. | (CH$_3$)$_3$C | H | CH$_3$CH$_2$ | CH$_3$ | H | OCH$_3$ |
| 1616. | (CH$_3$)$_3$C | H | CH$_3$CH$_2$ | CH$_3$ | H | OCH$_2$CH$_3$ |
| 1617. | (CH$_3$)$_3$C | H | CH$_3$CH$_2$ | CH$_3$ | H | O(CH$_2$)$_2$CH$_3$ |
| 1618. | (CH$_3$)$_3$C | H | CH$_3$CH$_2$ | CH$_3$ | H | OCH(CH$_3$)$_2$ |
| 1619. | (CH$_3$)$_3$C | H | CH$_3$CH$_2$ | CH$_3$ | H | O(CH$_3$)$_3$ |
| 1620. | (CH$_3$)$_3$C | H | CH$_3$CH$_2$ | CH$_3$ | H | O(CH$_2$)$_2$CH$_3$ |
| 1621. | (CH$_3$)$_3$C | H | CH$_3$CH$_2$ | CH$_3$ | H | OCH$_2$CH(CH$_3$)$_2$ |
| 1622. | (CH$_3$)$_3$C | H | CH$_3$CH$_2$ | CH$_3$ | H | OCH$_2$CH$_2$CH(CH$_3$)$_2$ |
| 1623. | (CH$_3$)$_3$C | H | CH$_3$CH$_2$ | CH$_3$ | H | OC(CH$_3$)$_2$CH$_2$CH$_3$ |
| 1624. | (CH$_3$)$_3$C | H | CH$_3$CH$_2$ | CH$_3$ | H | O(CH$_2$)$_4$CH$_3$ |
| 1625. | (CH$_3$)$_3$C | H | CH$_3$CH$_2$ | CH$_3$ | H | OCH$_2$Cl |
| 1626. | (CH$_3$)$_3$C | H | CH$_3$CH$_2$ | CH$_3$ | H | OCH$_2$CH$_2$Cl |
| 1627. | (CH$_3$)$_3$C | H | CH$_3$CH$_2$ | CH$_3$ | H | OCH$_2$CH$_2$CH$_2$CH$_2$Cl |
| 1628. | (CH$_3$)$_3$C | H | CH$_3$CH$_2$ | CH$_3$ | H | OCH$_2$CH$_2$Cl$_2$ |
| 1629. | (CH$_3$)$_3$C | H | CH$_3$CH$_2$ | CH$_3$ | H | OCH$_2$CH$_2$F |
| 1630. | (CH$_3$)$_3$C | H | CH$_3$CH$_2$ | CH$_3$ | H | OCH$_2$CHF$_2$ |
| 1631. | (CH$_3$)$_3$C | H | CH$_3$CH$_2$ | CH$_3$ | H | OCH$_2$CF$_3$ |
| 1632. | (CH$_3$)$_3$C | H | CH$_3$CH$_2$ | CH$_3$ | H | OCH$_2$CH$_2$OCH$_3$ |
| 1633. | (CH$_3$)$_3$C | H | CH$_3$CH$_2$ | CH$_3$ | H | OCH$_2$CH$_2$OCH$_2$CH$_3$ |
| 1634. | (CH$_3$)$_3$C | H | CH$_3$CH$_2$ | CH$_3$ | H | OCH$_2$OCH$_2$CH$_3$ |
| 1635. | (CH$_3$)$_3$C | H | CH$_3$CH$_2$ | CH$_3$ | H | OCH$_2$CH$_2$SCH$_3$ |
| 1636. | (CH$_3$)$_3$C | H | CH$_3$CH$_2$ | CH$_3$ | H | OCH$_2$C$_5$H$_6$ |
| 1637. | (CH$_3$)$_3$C | H | CH$_3$CH$_2$ | CH$_3$ | H | OCH$_2$(4-ClC$_5$H$_6$) |
| 1638. | (CH$_3$)$_3$C | H | CH$_3$CH$_2$ | CH$_3$ | H | OCH$_2$C=CH$_2$ |
| 1639. | (CH$_3$)$_3$C | H | CH$_3$CH$_2$ | CH$_3$ | H | OCH$_2$(C=CH)CH$_3$ |
| 1640. | (CH$_3$)$_3$C | H | CH$_3$CH$_2$ | CH$_3$ | H | OCH$_2$C≡CH |
| 1641. | (CH$_3$)$_3$C | H | CH$_3$CH$_2$ | CH$_3$ | H | OCH$_2$COOCH$_3$ |
| 1642. | (CH$_3$)$_3$C | H | CH$_3$CH$_2$ | CH$_3$ | H | OCH$_2$COOCH$_2$CH$_3$ |
| 1643. | (CH$_3$)$_3$C | H | CH$_3$CH$_2$ | CH$_3$ | H | SCH$_3$ |
| 1644. | (CH$_3$)$_3$C | H | CH$_3$CH$_2$ | CH$_3$ | H | SCH$_2$CH$_3$ |
| 1645. | (CH$_3$)$_3$C | H | CH$_3$CH$_2$ | CH$_3$ | H | SCH2COOCH3 |
| 1646. | (CH$_3$)$_3$C | H | CH$_3$CH$_2$ | CH$_3$ | H | SCH2(4-ClC5H6) |
| 1647. | (CH$_3$)$_3$C | CH$_3$ | CH$_3$CH$_2$ | CH$_3$ | H | OCH$_3$ |
| 1648. | (CH$_3$)$_3$C | CH$_3$ | CH$_3$CH$_2$ | CH$_3$ | H | OCH$_2$CH$_3$ |
| 1649. | (CH$_3$)$_3$C | CH$_3$ | CH$_3$CH$_2$ | CH$_3$ | H | O(CH$_2$)$_2$CH$_3$ |
| 1650. | (CH$_3$)$_3$C | CH$_3$ | CH$_3$CH$_2$ | CH$_3$ | H | OCH(CH$_3$)$_2$ |
| 1651. | (CH$_3$)$_3$C | CH$_3$ | CH$_3$CH$_2$ | CH$_3$ | H | O(CH$_3$)$_3$ |
| 1652. | (CH$_3$)$_3$C | CH$_3$ | CH$_3$CH$_2$ | CH$_3$ | H | O(CH$_2$)$_2$CH$_3$ |
| 1653. | (CH$_3$)$_3$C | CH$_3$ | CH$_3$CH$_2$ | CH$_3$ | H | OCH$_2$CH(CH$_3$)$_2$ |
| 1654. | (CH$_3$)$_3$C | CH$_3$ | CH$_3$CH$_2$ | CH$_3$ | H | OCH$_2$CH$_2$CH(CH$_3$)$_2$ |
| 1655. | (CH$_3$)$_3$C | CH$_3$ | CH$_3$CH$_2$ | CH$_3$ | H | OC(CH$_3$)$_2$CH$_2$CH$_3$ |
| 1656. | (CH$_3$)$_3$C | CH$_3$ | CH$_3$CH$_2$ | CH$_3$ | H | O(CH$_2$)$_4$CH$_3$ |
| 1657. | (CH$_3$)$_3$C | CH$_3$ | CH$_3$CH$_2$ | CH$_3$ | H | OCH$_2$Cl |
| 1658. | (CH$_3$)$_3$C | CH$_3$ | CH$_3$CH$_2$ | CH$_3$ | H | OCH$_2$CH$_2$Cl |
| 1659. | (CH$_3$)$_3$C | CH$_3$ | CH$_3$CH$_2$ | CH$_3$ | H | OCH$_2$CH$_2$CH$_2$CH$_2$Cl |
| 1660. | (CH$_3$)$_3$C | CH$_3$ | CH$_3$CH$_2$ | CH$_3$ | H | OCH$_2$CH$_2$Cl$_2$ |
| 1661. | (CH$_3$)$_3$C | CH$_3$ | CH$_3$CH$_2$ | CH$_3$ | H | OCH$_2$CH$_2$F |
| 1662. | (CH$_3$)$_3$C | CH$_3$ | CH$_3$CH$_2$ | CH$_3$ | H | OCH$_2$CHF$_2$ |
| 1663. | (CH$_3$)$_3$C | CH$_3$ | CH$_3$CH$_2$ | CH$_3$ | H | OCH$_2$CF$_3$ |
| 1664. | (CH$_3$)$_3$C | CH$_3$ | CH$_3$CH$_2$ | CH$_3$ | H | OCH$_2$CH$_2$OCH$_3$ |
| 1665. | (CH$_3$)$_3$C | CH$_3$ | CH$_3$CH$_2$ | CH$_3$ | H | OCH$_2$CH$_2$OCH$_2$CH$_3$ |
| 1666. | (CH$_3$)$_3$C | CH$_3$ | CH$_3$CH$_2$ | CH$_3$ | H | OCH$_2$OCH$_2$CH$_3$ |
| 1667. | (CH$_3$)$_3$C | CH$_3$ | CH$_3$CH$_2$ | CH$_3$ | H | OCH$_2$CH$_2$SCH$_3$ |
| 1668. | (CH$_3$)$_3$C | CH$_3$ | CH$_3$CH$_2$ | CH$_3$ | H | OCH$_2$C$_5$H$_6$ |
| 1669. | (CH$_3$)$_3$C | CH$_3$ | CH$_3$CH$_2$ | CH$_3$ | H | OCH$_2$(4-ClC$_5$H$_6$) |

TABLE 2-continued

| No. | R3 | R9 | R8 | R6 | R7 | L-R10 |
|---|---|---|---|---|---|---|
| 1670. | $(CH_3)_3C$ | $CH_3$ | $CH_3CH_2$ | $CH_3$ | H | $OCH_2C=CH_2$ |
| 1671. | $(CH_3)_3C$ | $CH_3$ | $CH_3CH_2$ | $CH_3$ | H | $OCH_2(C=CH)CH_3$ |
| 1672. | $(CH_3)_3C$ | $CH_3$ | $CH_3CH_2$ | $CH_3$ | H | $OCH_2C\equiv CH$ |
| 1673. | $(CH_3)_3C$ | $CH_3$ | $CH_3CH_2$ | $CH_3$ | H | $OCH_2COOCH_3$ |
| 1674. | $(CH_3)_3C$ | $CH_3$ | $CH_3CH_2$ | $CH_3$ | H | $OCH_2COOCH_2CH_3$ |
| 1675. | $(CH_3)_3C$ | $CH_3$ | $CH_3CH_2$ | $CH_3$ | H | $SCH_3$ |
| 1676. | $(CH_3)_3C$ | $CH_3$ | $CH_3CH_2$ | $CH_3$ | H | $SCH_2CH_3$ |
| 1677. | $(CH_3)_3C$ | $CH_3$ | $CH_3CH_2$ | $CH_3$ | H | SCH2COOCH3 |
| 1678. | $(CH_3)_3C$ | $CH_3$ | $CH_3CH_2$ | $CH_3$ | H | SCH2(4-ClC5H6) |
| 1679. | $(CH_3)_3C$ | $CH_3$ | $CH_3CH_2$ | $CH_3$ | H | $OCH_3$ |
| 1680. | $(CH_3)_3C$ | $CH_3CH_2$ | $CH_3CH_2$ | $CH_3$ | H | $OCH_2CH_3$ |
| 1681. | $(CH_3)_3C$ | $CH_3CH_2$ | $CH_3CH_2$ | $CH_3$ | H | $O(CH_2)_2CH_3$ |
| 1682. | $(CH_3)_3C$ | $CH_3CH_2$ | $CH_3CH_2$ | $CH_3$ | H | $OCH(CH_3)_2$ |
| 1683. | $(CH_3)_3C$ | $CH_3CH_2$ | $CH_3CH_2$ | $CH_3$ | H | $O(CH_3)_3$ |
| 1684. | $(CH_3)_3C$ | $CH_3CH_2$ | $CH_3CH_2$ | $CH_3$ | H | $O(CH_2)_2CH_3$ |
| 1685. | $(CH_3)_3C$ | $CH_3CH_2$ | $CH_3CH_2$ | $CH_3$ | H | $OCH_2CH(CH_3)_2$ |
| 1686. | $(CH_3)_3C$ | $CH_3CH_2$ | $CH_3CH_2$ | $CH_3$ | H | $OCH_2CH_2CH(CH_3)_2$ |
| 1687. | $(CH_3)_3C$ | $CH_3CH_2$ | $CH_3CH_2$ | $CH_3$ | H | $OC(CH_3)_2CH_2CH_3$ |
| 1688. | $(CH_3)_3C$ | $CH_3CH_2$ | $CH_3CH_2$ | $CH_3$ | H | $O(CH_2)_4CH_3$ |
| 1689. | $(CH_3)_3C$ | $CH_3CH_2$ | $CH_3CH_2$ | $CH_3$ | H | $OCH_2Cl$ |
| 1690. | $(CH_3)_3C$ | $CH_3CH_2$ | $CH_3CH_2$ | $CH_3$ | H | $OCH_2CH_2Cl$ |
| 1691. | $(CH_3)_3C$ | $CH_3CH_2$ | $CH_3CH_2$ | $CH_3$ | H | $OCH_2CH_2CH_2CH_2Cl$ |
| 1692. | $(CH_3)_3C$ | $CH_3CH_2$ | $CH_3CH_2$ | $CH_3$ | H | $OCH_2CH_2Cl_2$ |
| 1693. | $(CH_3)_3C$ | $CH_3CH_2$ | $CH_3CH_2$ | $CH_3$ | H | $OCH_2CH_2F$ |
| 1694. | $(CH_3)_3C$ | $CH_3CH_2$ | $CH_3CH_2$ | $CH_3$ | H | $OCH_2CHF_2$ |
| 1695. | $(CH_3)_3C$ | $CH_3CH_2$ | $CH_3CH_2$ | $CH_3$ | H | $OCH_2CF_3$ |
| 1696. | $(CH_3)_3C$ | $CH_3CH_2$ | $CH_3CH_2$ | $CH_3$ | H | $OCH_2CH_2OCH_3$ |
| 1697. | $(CH_3)_3C$ | $CH_3CH_2$ | $CH_3CH_2$ | $CH_3$ | H | $OCH_2CH_2OCH_2CH_3$ |
| 1698. | $(CH_3)_3C$ | $CH_3CH_2$ | $CH_3CH_2$ | $CH_3$ | H | $OCH_2OCH_2CH_3$ |
| 1699. | $(CH_3)_3C$ | $CH_3CH_2$ | $CH_3CH_2$ | $CH_3$ | H | $OCH_2CH_2SCH_3$ |
| 1700. | $(CH_3)_3C$ | $CH_3CH_2$ | $CH_3CH_2$ | $CH_3$ | H | $OCH_2C_5H_6$ |
| 1701. | $(CH_3)_3C$ | $CH_3CH_2$ | $CH_3CH_2$ | $CH_3$ | H | $OCH_2(4-ClC_5H_6)$ |
| 1702. | $(CH_3)_3C$ | $CH_3CH_2$ | $CH_3CH_2$ | $CH_3$ | H | $OCH_2C=CH_2$ |
| 1703. | $(CH_3)_3C$ | $CH_3CH_2$ | $CH_3CH_2$ | $CH_3$ | H | $OCH_2(C=CH)CH_3$ |
| 1704. | $(CH_3)_3C$ | $CH_3CH_2$ | $CH_3CH_2$ | $CH_3$ | H | $OCH_2C\equiv CH$ |
| 1705. | $(CH_3)_3C$ | $CH_3CH_2$ | $CH_3CH_2$ | $CH_3$ | H | $OCH_2COOCH_3$ |
| 1706. | $(CH_3)_3C$ | $CH_3CH_2$ | $CH_3CH_2$ | $CH_3$ | H | $OCH_2COOCH_2CH_3$ |
| 1707. | $(CH_3)_3C$ | $CH_3CH_2$ | $CH_3CH_2$ | $CH_3$ | H | $SCH_3$ |
| 1708. | $(CH_3)_3C$ | $CH_3CH_2$ | $CH_3CH_2$ | $CH_3$ | H | $SCH_2CH_3$ |
| 1709. | $(CH_3)_3C$ | $CH_3CH_2$ | $CH_3CH_2$ | $CH_3$ | H | SCH2COOCH3 |
| 1710. | $(CH_3)_3C$ | $CH_3CH_2$ | $CH_3CH_2$ | $CH_3$ | H | SCH2(4-ClC5H6) |
| 1711. | $(CH_3)_3C$ | H | $CH_3$ | $CH_3$ | Cl | $OCH_3$ |
| 1712. | $(CH_3)_3C$ | H | $CH_3$ | $CH_3$ | Cl | $OCH_2CH_3$ |
| 1713. | $(CH_3)_3C$ | H | $CH_3$ | $CH_3$ | Cl | $O(CH_2)_2CH_3$ |
| 1714. | $(CH_3)_3C$ | H | $CH_3$ | $CH_3$ | Cl | $OCH(CH_3)_2$ |
| 1715. | $(CH_3)_3C$ | H | $CH_3$ | $CH_3$ | Cl | $O(CH_3)_3$ |
| 1716. | $(CH_3)_3C$ | H | $CH_3$ | $CH_3$ | Cl | $O(CH_2)_2CH_3$ |
| 1717. | $(CH_3)_3C$ | H | $CH_3$ | $CH_3$ | Cl | $OCH_2CH(CH_3)_2$ |
| 1718. | $(CH_3)_3C$ | H | $CH_3$ | $CH_3$ | Cl | $OCH_2CH_2CH(CH_3)_2$ |
| 1719. | $(CH_3)_3C$ | H | $CH_3$ | $CH_3$ | Cl | $OC(CH_3)_2CH_2CH_3$ |
| 1720. | $(CH_3)_3C$ | H | $CH_3$ | $CH_3$ | Cl | $O(CH_2)_4CH_3$ |
| 1721. | $(CH_3)_3C$ | H | $CH_3$ | $CH_3$ | Cl | $OCH_2Cl$ |
| 1722. | $(CH_3)_3C$ | H | $CH_3$ | $CH_3$ | Cl | $OCH_2CH_2Cl$ |
| 1723. | $(CH_3)_3C$ | H | $CH_3$ | $CH_3$ | Cl | $OCH_2CH_2CH_2CH_2Cl$ |
| 1724. | $(CH_3)_3C$ | H | $CH_3$ | $CH_3$ | Cl | $OCH_2CH_2Cl_2$ |
| 1725. | $(CH_3)_3C$ | H | $CH_3$ | $CH_3$ | Cl | $OCH_2CH_2F$ |
| 1726. | $(CH_3)_3C$ | H | $CH_3$ | $CH_3$ | Cl | $OCH_2CHF_2$ |
| 1727. | $(CH_3)_3C$ | H | $CH_3$ | $CH_3$ | Cl | $OCH_2CF_3$ |
| 1728. | $(CH_3)_3C$ | H | $CH_3$ | $CH_3$ | Cl | $OCH_2CH_2OCH_3$ |
| 1729. | $(CH_3)_3C$ | H | $CH_3$ | $CH_3$ | Cl | $OCH_2CH_2OCH_2CH_3$ |
| 1730. | $(CH_3)_3C$ | H | $CH_3$ | $CH_3$ | Cl | $OCH_2OCH_2CH_3$ |
| 1731. | $(CH_3)_3C$ | H | $CH_3$ | $CH_3$ | Cl | $OCH_2CH_2SCH_3$ |
| 1732. | $(CH_3)_3C$ | H | $CH_3$ | $CH_3$ | Cl | $OCH_2C_5H_6$ |
| 1733. | $(CH_3)_3C$ | H | $CH_3$ | $CH_3$ | Cl | $OCH_2(4-ClC_5H_6)$ |
| 1734. | $(CH_3)_3C$ | H | $CH_3$ | $CH_3$ | Cl | $OCH_2C=CH_2$ |
| 1735. | $(CH_3)_3C$ | H | $CH_3$ | $CH_3$ | Cl | $OCH_2(C=CH)CH_3$ |
| 1736. | $(CH_3)_3C$ | H | $CH_3$ | $CH_3$ | Cl | $OCH_2C\equiv CH$ |
| 1737. | $(CH_3)_3C$ | H | $CH_3$ | $CH_3$ | Cl | $OCH_2COOCH_3$ |
| 1738. | $(CH_3)_3C$ | H | $CH_3$ | $CH_3$ | Cl | $OCH_2COOCH_2CH_3$ |
| 1739. | $(CH_3)_3C$ | H | $CH_3$ | $CH_3$ | Cl | $SCH_3$ |
| 1740. | $(CH_3)_3C$ | H | $CH_3$ | $CH_3$ | Cl | $SCH_2CH_3$ |
| 1741. | $(CH_3)_3C$ | H | $CH_3$ | $CH_3$ | Cl | SCH2COOCH3 |
| 1742. | $(CH_3)_3C$ | H | $CH_3$ | $CH_3$ | Cl | SCH2(4-ClC5H6) |
| 1743. | $(CH_3)_3C$ | $CH_3$ | $CH_3$ | $CH_3$ | Cl | $OCH_3$ |
| 1744. | $(CH_3)_3C$ | $CH_3$ | $CH_3$ | $CH_3$ | Cl | $OCH_2CH_3$ |
| 1745. | $(CH_3)_3C$ | $CH_3$ | $CH_3$ | $CH_3$ | Cl | $O(CH_2)_2CH_3$ |
| 1746. | $(CH_3)_3C$ | $CH_3$ | $CH_3$ | $CH_3$ | Cl | $OCH(CH_3)_2$ |
| 1747. | $(CH_3)_3C$ | $CH_3$ | $CH_3$ | $CH_3$ | Cl | $O(CH_3)_3$ |

TABLE 2-continued

| No. | R3 | R9 | R8 | R6 | R7 | L-R10 |
|---|---|---|---|---|---|---|
| 1748. | (CH$_3$)$_3$C | CH$_3$ | CH$_3$ | CH$_3$ | Cl | O(CH$_2$)$_2$CH$_3$ |
| 1749. | (CH$_3$)$_3$C | CH$_3$ | CH$_3$ | CH$_3$ | Cl | OCH$_2$CH(CH$_3$)$_2$ |
| 1750. | (CH$_3$)$_3$C | CH$_3$ | CH$_3$ | CH$_3$ | Cl | OCH$_2$CH$_2$CH(CH$_3$)$_2$ |
| 1751. | (CH$_3$)$_3$C | CH$_3$ | CH$_3$ | CH$_3$ | Cl | OC(CH$_3$)$_2$CH$_2$CH$_3$ |
| 1752. | (CH$_3$)$_3$C | CH$_3$ | CH$_3$ | CH$_3$ | Cl | O(CH$_2$)$_4$CH$_3$ |
| 1753. | (CH$_3$)$_3$C | CH$_3$ | CH$_3$ | CH$_3$ | Cl | OCH$_2$Cl |
| 1754. | (CH$_3$)$_3$C | CH$_3$ | CH$_3$ | CH$_3$ | Cl | OCH$_2$CH$_2$Cl |
| 1755. | (CH$_3$)$_3$C | CH$_3$ | CH$_3$ | CH$_3$ | Cl | OCH$_2$CH$_2$CH$_2$CH$_2$Cl |
| 1756. | (CH$_3$)$_3$C | CH$_3$ | CH$_3$ | CH$_3$ | Cl | OCH$_2$CH$_2$Cl$_2$ |
| 1757. | (CH$_3$)$_3$C | CH$_3$ | CH$_3$ | CH$_3$ | Cl | OCH$_2$CH$_2$F |
| 1758. | (CH$_3$)$_3$C | CH$_3$ | CH$_3$ | CH$_3$ | Cl | OCH$_2$CHF$_2$ |
| 1759. | (CH$_3$)$_3$C | CH$_3$ | CH$_3$ | CH$_3$ | Cl | OCH$_2$CF$_3$ |
| 1760. | (CH$_3$)$_3$C | CH$_3$ | CH$_3$ | CH$_3$ | Cl | OCH$_2$CH$_2$OCH$_3$ |
| 1761. | (CH$_3$)$_3$C | CH$_3$ | CH$_3$ | CH$_3$ | Cl | OCH$_2$CH$_2$OCH$_2$CH$_3$ |
| 1762. | (CH$_3$)$_3$C | CH$_3$ | CH$_3$ | CH$_3$ | Cl | OCH$_2$OCH$_2$CH$_3$ |
| 1763. | (CH$_3$)$_3$C | CH$_3$ | CH$_3$ | CH$_3$ | Cl | OCH$_2$CH$_2$SCH$_3$ |
| 1764. | (CH$_3$)$_3$C | CH$_3$ | CH$_3$ | CH$_3$ | Cl | OCH$_2$C$_5$H$_6$ |
| 1765. | (CH$_3$)$_3$C | CH$_3$ | CH$_3$ | CH$_3$ | Cl | OCH$_2$(4-ClC$_5$H$_6$) |
| 1766. | (CH$_3$)$_3$C | CH$_3$ | CH$_3$ | CH$_3$ | Cl | OCH$_2$C=CH$_2$ |
| 1767. | (CH$_3$)$_3$C | CH$_3$ | CH$_3$ | CH$_3$ | Cl | OCH$_2$(C=CH)CH$_3$ |
| 1768. | (CH$_3$)$_3$C | CH$_3$ | CH$_3$ | CH$_3$ | Cl | OCH$_2$C≡CH |
| 1769. | (CH$_3$)$_3$C | CH$_3$ | CH$_3$ | CH$_3$ | Cl | OCH$_2$COOCH$_3$ |
| 1770. | (CH$_3$)$_3$C | CH$_3$ | CH$_3$ | CH$_3$ | Cl | OCH$_2$COOCH$_2$CH$_3$ |
| 1771. | (CH$_3$)$_3$C | CH$_3$ | CH$_3$ | CH$_3$ | Cl | SCH$_3$ |
| 1772. | (CH$_3$)$_3$C | CH$_3$ | CH$_3$ | CH$_3$ | Cl | SCH$_2$CH$_3$ |
| 1773. | (CH$_3$)$_3$C | CH$_3$ | CH$_3$ | CH$_3$ | Cl | SCH2COOCH3 |
| 1774. | (CH$_3$)$_3$C | CH$_3$ | CH$_3$ | CH$_3$ | Cl | SCH2(4-ClC5H6) |
| 1775. | (CH$_3$)$_3$C | CH$_3$CH$_2$ | CH$_3$ | CH$_3$ | Cl | OCH$_3$ |
| 1776. | (CH$_3$)$_3$C | CH$_3$CH$_2$ | CH$_3$ | CH$_3$ | Cl | OCH$_2$CH$_3$ |
| 1777. | (CH$_3$)$_3$C | CH$_3$CH$_2$ | CH$_3$ | CH$_3$ | Cl | O(CH$_2$)$_2$CH$_3$ |
| 1778. | (CH$_3$)$_3$C | CH$_3$CH$_2$ | CH$_3$ | CH$_3$ | Cl | OCH(CH$_3$)$_2$ |
| 1779. | (CH$_3$)$_3$C | CH$_3$CH$_2$ | CH$_3$ | CH$_3$ | Cl | O(CH$_3$)$_3$ |
| 1780. | (CH$_3$)$_3$C | CH$_3$CH$_2$ | CH$_3$ | CH$_3$ | Cl | O(CH$_2$)$_2$CH$_3$ |
| 1781. | (CH$_3$)$_3$C | CH$_3$CH$_2$ | CH$_3$ | CH$_3$ | Cl | OCH$_2$CH(CH$_3$)$_2$ |
| 1782. | (CH$_3$)$_3$C | CH$_3$CH$_2$ | CH$_3$ | CH$_3$ | Cl | OCH$_2$CH$_2$CH(CH$_3$)$_2$ |
| 1783. | (CH$_3$)$_3$C | CH$_3$CH$_2$ | CH$_3$ | CH$_3$ | Cl | OC(CH$_3$)$_2$CH$_2$CH$_3$ |
| 1784. | (CH$_3$)$_3$C | CH$_3$CH$_2$ | CH$_3$ | CH$_3$ | Cl | O(CH$_2$)$_4$CH$_3$ |
| 1785. | (CH$_3$)$_3$C | CH$_3$CH$_2$ | CH$_3$ | CH$_3$ | Cl | OCH$_2$Cl |
| 1786. | (CH$_3$)$_3$C | CH$_3$CH$_2$ | CH$_3$ | CH$_3$ | Cl | OCH$_2$CH$_2$Cl |
| 1787. | (CH$_3$)$_3$C | CH$_3$CH$_2$ | CH$_3$ | CH$_3$ | Cl | OCH$_2$CH$_2$CH$_2$CH$_2$Cl |
| 1788. | (CH$_3$)$_3$C | CH$_3$CH$_2$ | CH$_3$ | CH$_3$ | Cl | OCH$_2$CH$_2$Cl$_2$ |
| 1789. | (CH$_3$)$_3$C | CH$_3$CH$_2$ | CH$_3$ | CH$_3$ | Cl | OCH$_2$CH$_2$F |
| 1790. | (CH$_3$)$_3$C | CH$_3$CH$_2$ | CH$_3$ | CH$_3$ | Cl | OCH$_2$CHF$_2$ |
| 1791. | (CH$_3$)$_3$C | CH$_3$CH$_2$ | CH$_3$ | CH$_3$ | Cl | OCH$_2$CF$_3$ |
| 1792. | (CH$_3$)$_3$C | CH$_3$CH$_2$ | CH$_3$ | CH$_3$ | Cl | OCH$_2$CH$_2$OCH$_3$ |
| 1793. | (CH$_3$)$_3$C | CH$_3$CH$_2$ | CH$_3$ | CH$_3$ | Cl | OCH$_2$CH$_2$OCH$_2$CH$_3$ |
| 1794. | (CH$_3$)$_3$C | CH$_3$CH$_2$ | CH$_3$ | CH$_3$ | Cl | OCH$_2$OCH$_2$CH$_3$ |
| 1795. | (CH$_3$)$_3$C | CH$_3$CH$_2$ | CH$_3$ | CH$_3$ | Cl | OCH$_2$CH$_2$SCH$_3$ |
| 1796. | (CH$_3$)$_3$C | CH$_3$CH$_2$ | CH$_3$ | CH$_3$ | Cl | OCH$_2$C$_5$H$_6$ |
| 1797. | (CH$_3$)$_3$C | CH$_3$CH$_2$ | CH$_3$ | CH$_3$ | Cl | OCH$_2$(4-ClC$_5$H$_6$) |
| 1798. | (CH$_3$)$_3$C | CH$_3$CH$_2$ | CH$_3$ | CH$_3$ | Cl | OCH$_2$C=CH$_2$ |
| 1799. | (CH$_3$)$_3$C | CH$_3$CH$_2$ | CH$_3$ | CH$_3$ | Cl | OCH$_2$(C=CH)CH$_3$ |
| 1800. | (CH$_3$)$_3$C | CH$_3$CH$_2$ | CH$_3$ | CH$_3$ | Cl | OCH$_2$C≡CH |
| 1801. | (CH$_3$)$_3$C | CH$_3$CH$_2$ | CH$_3$ | CH$_3$ | Cl | OCH$_2$COOCH$_3$ |
| 1802. | (CH$_3$)$_3$C | CH$_3$CH$_2$ | CH$_3$ | CH$_3$ | Cl | OCH$_2$COOCH$_2$CH$_3$ |
| 1803. | (CH$_3$)$_3$C | CH$_3$CH$_2$ | CH$_3$ | CH$_3$ | Cl | SCH$_3$ |
| 1804. | (CH$_3$)$_3$C | CH$_3$CH$_2$ | CH$_3$ | CH$_3$ | Cl | SCH$_2$CH$_3$ |
| 1805. | (CH$_3$)$_3$C | CH$_3$CH$_2$ | CH$_3$ | CH$_3$ | Cl | SCH2COOCH3 |
| 1806. | (CH$_3$)$_3$C | CH$_3$CH$_2$ | CH$_3$ | CH$_3$ | Cl | SCH2(4-ClC5H6) |
| 1807. | (CH$_3$)$_3$C | H | CH$_3$CH$_2$ | CH$_3$ | Cl | OCH$_3$ |
| 1808. | (CH$_3$)$_3$C | H | CH$_3$CH$_2$ | CH$_3$ | Cl | OCH$_2$CH$_3$ |
| 1809. | (CH$_3$)$_3$C | H | CH$_3$CH$_2$ | CH$_3$ | Cl | O(CH$_2$)$_2$CH$_3$ |
| 1810. | (CH$_3$)$_3$C | H | CH$_3$CH$_2$ | CH$_3$ | Cl | OCH(CH$_3$)$_2$ |
| 1811. | (CH$_3$)$_3$C | H | CH$_3$CH$_2$ | CH$_3$ | Cl | O(CH$_3$)$_3$ |
| 1812. | (CH$_3$)$_3$C | H | CH$_3$CH$_2$ | CH$_3$ | Cl | O(CH$_2$)$_2$CH$_3$ |
| 1813. | (CH$_3$)$_3$C | H | CH$_3$CH$_2$ | CH$_3$ | Cl | OCH$_2$CH(CH$_3$)$_2$ |
| 1814. | (CH$_3$)$_3$C | H | CH$_3$CH$_2$ | CH$_3$ | Cl | OCH$_2$CH$_2$CH(CH$_3$)$_2$ |
| 1815. | (CH$_3$)$_3$C | H | CH$_3$CH$_2$ | CH$_3$ | Cl | OC(CH$_3$)$_2$CH$_2$CH$_3$ |
| 1816. | (CH$_3$)$_3$C | H | CH$_3$CH$_2$ | CH$_3$ | Cl | O(CH$_2$)$_4$CH$_3$ |
| 1817. | (CH$_3$)$_3$C | H | CH$_3$CH$_2$ | CH$_3$ | Cl | OCH$_2$Cl |
| 1818. | (CH$_3$)$_3$C | H | CH$_3$CH$_2$ | CH$_3$ | Cl | OCH$_2$CH$_2$Cl |
| 1819. | (CH$_3$)$_3$C | H | CH$_3$CH$_2$ | CH$_3$ | Cl | OCH$_2$CH$_2$CH$_2$CH$_2$Cl |
| 1820. | (CH$_3$)$_3$C | H | CH$_3$CH$_2$ | CH$_3$ | Cl | OCH$_2$CH$_2$Cl$_2$ |
| 1821. | (CH$_3$)$_3$C | H | CH$_3$CH$_2$ | CH$_3$ | Cl | OCH$_2$CH$_2$F |
| 1822. | (CH$_3$)$_3$C | H | CH$_3$CH$_2$ | CH$_3$ | Cl | OCH$_2$CHF$_2$ |
| 1823. | (CH$_3$)$_3$C | H | CH$_3$CH$_2$ | CH$_3$ | Cl | OCH$_2$CF$_3$ |
| 1824. | (CH$_3$)$_3$C | H | CH$_3$CH$_2$ | CH$_3$ | Cl | OCH$_2$CH$_2$OCH$_3$ |
| 1825. | (CH$_3$)$_3$C | H | CH$_3$CH$_2$ | CH$_3$ | Cl | OCH$_2$CH$_2$OCH$_2$CH$_3$ |

TABLE 2-continued

| No. | R3 | R9 | R8 | R6 | R7 | L-R10 |
|---|---|---|---|---|---|---|
| 1826. | (CH$_3$)$_3$C | H | CH$_3$CH$_2$ | CH$_3$ | Cl | OCH$_2$OCH$_2$CH$_3$ |
| 1827. | (CH$_3$)$_3$C | H | CH$_3$CH$_2$ | CH$_3$ | Cl | OCH$_2$CH$_2$SCH$_3$ |
| 1828. | (CH$_3$)$_3$C | H | CH$_3$CH$_2$ | CH$_3$ | Cl | OCH$_2$C$_5$H$_6$ |
| 1829. | (CH$_3$)$_3$C | H | CH$_3$CH$_2$ | CH$_3$ | Cl | OCH$_2$(4-ClC$_5$H$_6$) |
| 1830. | (CH$_3$)$_3$C | H | CH$_3$CH$_2$ | CH$_3$ | Cl | OCH$_2$C=CH$_2$ |
| 1831. | (CH$_3$)$_3$C | H | CH$_3$CH$_2$ | CH$_3$ | Cl | OCH$_2$(C=CH)CH$_3$ |
| 1832. | (CH$_3$)$_3$C | H | CH$_3$CH$_2$ | CH$_3$ | Cl | OCH$_2$C≡CH |
| 1833. | (CH$_3$)$_3$C | H | CH$_3$CH$_2$ | CH$_3$ | Cl | OCH$_2$COOCH$_3$ |
| 1834. | (CH$_3$)$_3$C | H | CH$_3$CH$_2$ | CH$_3$ | Cl | OCH$_2$COOCH$_2$CH$_3$ |
| 1835. | (CH$_3$)$_3$C | H | CH$_3$CH$_2$ | CH$_3$ | Cl | SCH$_3$ |
| 1836. | (CH$_3$)$_3$C | H | CH$_3$CH$_2$ | CH$_3$ | Cl | SCH$_2$CH$_3$ |
| 1837. | (CH$_3$)$_3$C | H | CH$_3$CH$_2$ | CH$_3$ | Cl | SCH2COOCH3 |
| 1838. | (CH$_3$)$_3$C | H | CH$_3$CH$_2$ | CH$_3$ | Cl | SCH2(4-ClC5H6) |
| 1839. | (CH$_3$)$_3$C | CH$_3$ | CH$_3$CH$_2$ | CH$_3$ | Cl | OCH$_3$ |
| 1840. | (CH$_3$)$_3$C | CH$_3$ | CH$_3$CH$_2$ | CH$_3$ | Cl | OCH$_2$CH$_3$ |
| 1841. | (CH$_3$)$_3$C | CH$_3$ | CH$_3$CH$_2$ | CH$_3$ | Cl | O(CH$_2$)$_2$CH$_3$ |
| 1842. | (CH$_3$)$_3$C | CH$_3$ | CH$_3$CH$_2$ | CH$_3$ | Cl | OCH(CH$_3$)$_2$ |
| 1843. | (CH$_3$)$_3$C | CH$_3$ | CH$_3$CH$_2$ | CH$_3$ | Cl | O(CH$_3$)$_3$ |
| 1844. | (CH$_3$)$_3$C | CH$_3$ | CH$_3$CH$_2$ | CH$_3$ | Cl | O(CH$_2$)$_2$CH$_3$ |
| 1845. | (CH$_3$)$_3$C | CH$_3$ | CH$_3$CH$_2$ | CH$_3$ | Cl | OCH$_2$CH(CH$_3$)$_2$ |
| 1846. | (CH$_3$)$_3$C | CH$_3$ | CH$_3$CH$_2$ | CH$_3$ | Cl | OCH$_2$CH$_2$CH(CH$_3$)$_2$ |
| 1847. | (CH$_3$)$_3$C | CH$_3$ | CH$_3$CH$_2$ | CH$_3$ | Cl | OC(CH$_3$)$_2$CH$_2$CH$_3$ |
| 1848. | (CH$_3$)$_3$C | CH$_3$ | CH$_3$CH$_2$ | CH$_3$ | Cl | O(CH$_2$)$_4$CH$_3$ |
| 1849. | (CH$_3$)$_3$C | CH$_3$ | CH$_3$CH$_2$ | CH$_3$ | Cl | OCH$_2$Cl |
| 1850. | (CH$_3$)$_3$C | CH$_3$ | CH$_3$CH$_2$ | CH$_3$ | Cl | OCH$_2$CH$_2$Cl |
| 1851. | (CH$_3$)$_3$C | CH$_3$ | CH$_3$CH$_2$ | CH$_3$ | Cl | OCH$_2$CH$_2$CH$_2$CH$_2$Cl |
| 1852. | (CH$_3$)$_3$C | CH$_3$ | CH$_3$CH$_2$ | CH$_3$ | Cl | OCH$_2$CH$_2$Cl$_2$ |
| 1853. | (CH$_3$)$_3$C | CH$_3$ | CH$_3$CH$_2$ | CH$_3$ | Cl | OCH$_2$CH$_2$F |
| 1854. | (CH$_3$)$_3$C | CH$_3$ | CH$_3$CH$_2$ | CH$_3$ | Cl | OCH$_2$CHF$_2$ |
| 1855. | (CH$_3$)$_3$C | CH$_3$ | CH$_3$CH$_2$ | CH$_3$ | Cl | OCH$_2$CF$_3$ |
| 1856. | (CH$_3$)$_3$C | CH$_3$ | CH$_3$CH$_2$ | CH$_3$ | Cl | OCH$_2$CH$_2$OCH$_3$ |
| 1857. | (CH$_3$)$_3$C | CH$_3$ | CH$_3$CH$_2$ | CH$_3$ | Cl | OCH$_2$CH$_2$OCH$_2$CH$_3$ |
| 1858. | (CH$_3$)$_3$C | CH$_3$ | CH$_3$CH$_2$ | CH$_3$ | Cl | OCH$_2$OCH$_2$CH$_3$ |
| 1859. | (CH$_3$)$_3$C | CH$_3$ | CH$_3$CH$_2$ | CH$_3$ | Cl | OCH$_2$CH$_2$SCH$_3$ |
| 1860. | (CH$_3$)$_3$C | CH$_3$ | CH$_3$CH$_2$ | CH$_3$ | Cl | OCH$_2$C$_5$H$_6$ |
| 1861. | (CH$_3$)$_3$C | CH$_3$ | CH$_3$CH$_2$ | CH$_3$ | Cl | OCH$_2$(4-ClC$_5$H$_6$) |
| 1862. | (CH$_3$)$_3$C | CH$_3$ | CH$_3$CH$_2$ | CH$_3$ | Cl | OCH$_2$C=CH$_2$ |
| 1863. | (CH$_3$)$_3$C | CH$_3$ | CH$_3$CH$_2$ | CH$_3$ | Cl | OCH$_2$(C=CH)CH$_3$ |
| 1864. | (CH$_3$)$_3$C | CH$_3$ | CH$_3$CH$_2$ | CH$_3$ | Cl | OCH$_2$C≡CH |
| 1865. | (CH$_3$)$_3$C | CH$_3$ | CH$_3$CH$_2$ | CH$_3$ | Cl | OCH$_2$COOCH$_3$ |
| 1866. | (CH$_3$)$_3$C | CH$_3$ | CH$_3$CH$_2$ | CH$_3$ | Cl | OCH$_2$COOCH$_2$CH$_3$ |
| 1867. | (CH$_3$)$_3$C | CH$_3$ | CH$_3$CH$_2$ | CH$_3$ | Cl | SCH$_3$ |
| 1868. | (CH$_3$)$_3$C | CH$_3$ | CH$_3$CH$_2$ | CH$_3$ | Cl | SCH$_2$CH$_3$ |
| 1869. | (CH$_3$)$_3$C | CH$_3$ | CH$_3$CH$_2$ | CH$_3$ | Cl | SCH2COOCH3 |
| 1870. | (CH$_3$)$_3$C | CH$_3$ | CH$_3$CH$_2$ | CH$_3$ | Cl | SCH2(4-ClC5H6) |
| 1871. | (CH$_3$)$_3$C | CH$_3$ | CH$_3$CH$_2$ | CH$_3$ | Cl | OCH$_3$ |
| 1872. | (CH$_3$)$_3$C | CH$_3$CH$_2$ | CH$_3$CH$_2$ | CH$_3$ | Cl | OCH$_2$CH$_3$ |
| 1873. | (CH$_3$)$_3$C | CH$_3$CH$_2$ | CH$_3$CH$_2$ | CH$_3$ | Cl | O(CH$_2$)$_2$CH$_3$ |
| 1874. | (CH$_3$)$_3$C | CH$_3$CH$_2$ | CH$_3$CH$_2$ | CH$_3$ | Cl | OCH(CH$_3$)$_2$ |
| 1875. | (CH$_3$)$_3$C | CH$_3$CH$_2$ | CH$_3$CH$_2$ | CH$_3$ | Cl | O(CH$_3$)$_3$ |
| 1876. | (CH$_3$)$_3$C | CH$_3$CH$_2$ | CH$_3$CH$_2$ | CH$_3$ | Cl | O(CH$_2$)$_2$CH$_3$ |
| 1877. | (CH$_3$)$_3$C | CH$_3$CH$_2$ | CH$_3$CH$_2$ | CH$_3$ | Cl | OCH$_2$CH(CH$_3$)$_2$ |
| 1878. | (CH$_3$)$_3$C | CH$_3$CH$_2$ | CH$_3$CH$_2$ | CH$_3$ | Cl | OCH$_2$CH$_2$CH(CH$_3$)$_2$ |
| 1879. | (CH$_3$)$_3$C | CH$_3$CH$_2$ | CH$_3$CH$_2$ | CH$_3$ | Cl | OC(CH$_3$)$_2$CH$_2$CH$_3$ |
| 1880. | (CH$_3$)$_3$C | CH$_3$CH$_2$ | CH$_3$CH$_2$ | CH$_3$ | Cl | O(CH$_2$)$_4$CH$_3$ |
| 1881. | (CH$_3$)$_3$C | CH$_3$CH$_2$ | CH$_3$CH$_2$ | CH$_3$ | Cl | OCH$_2$Cl |
| 1882. | (CH$_3$)$_3$C | CH$_3$CH$_2$ | CH$_3$CH$_2$ | CH$_3$ | Cl | OCH$_2$CH$_2$Cl |
| 1883. | (CH$_3$)$_3$C | CH$_3$CH$_2$ | CH$_3$CH$_2$ | CH$_3$ | Cl | OCH$_2$CH$_2$CH$_2$CH$_2$Cl |
| 1884. | (CH$_3$)$_3$C | CH$_3$CH$_2$ | CH$_3$CH$_2$ | CH$_3$ | Cl | OCH$_2$CH$_2$Cl$_2$ |
| 1885. | (CH$_3$)$_3$C | CH$_3$CH$_2$ | CH$_3$CH$_2$ | CH$_3$ | Cl | OCH$_2$CH$_2$F |
| 1886. | (CH$_3$)$_3$C | CH$_3$CH$_2$ | CH$_3$CH$_2$ | CH$_3$ | Cl | OCH$_2$CHF$_2$ |
| 1887. | (CH$_3$)$_3$C | CH$_3$CH$_2$ | CH$_3$CH$_2$ | CH$_3$ | Cl | OCH$_2$CF$_3$ |
| 1888. | (CH$_3$)$_3$C | CH$_3$CH$_2$ | CH$_3$CH$_2$ | CH$_3$ | Cl | OCH$_2$CH$_2$OCH$_3$ |
| 1889. | (CH$_3$)$_3$C | CH$_3$CH$_2$ | CH$_3$CH$_2$ | CH$_3$ | Cl | OCH$_2$CH$_2$OCH$_2$CH$_3$ |
| 1890. | (CH$_3$)$_3$C | CH$_3$CH$_2$ | CH$_3$CH$_2$ | CH$_3$ | Cl | OCH$_2$OCH$_2$CH$_3$ |
| 1891. | (CH$_3$)$_3$C | CH$_3$CH$_2$ | CH$_3$CH$_2$ | CH$_3$ | Cl | OCH$_2$CH$_2$SCH$_3$ |
| 1892. | (CH$_3$)$_3$C | CH$_3$CH$_2$ | CH$_3$CH$_2$ | CH$_3$ | Cl | OCH$_2$C$_5$H$_6$ |
| 1893. | (CH$_3$)$_3$C | CH$_3$CH$_2$ | CH$_3$CH$_2$ | CH$_3$ | Cl | OCH$_2$(4-ClC$_5$H$_6$) |
| 1894. | (CH$_3$)$_3$C | CH$_3$CH$_2$ | CH$_3$CH$_2$ | CH$_3$ | Cl | OCH$_2$C=CH$_2$ |
| 1895. | (CH$_3$)$_3$C | CH$_3$CH$_2$ | CH$_3$CH$_2$ | CH$_3$ | Cl | OCH$_2$(C=CH)CH$_3$ |
| 1896. | (CH$_3$)$_3$C | CH$_3$CH$_2$ | CH$_3$CH$_2$ | CH$_3$ | Cl | OCH$_2$C≡CH |
| 1897. | (CH$_3$)$_3$C | CH$_3$CH$_2$ | CH$_3$CH$_2$ | CH$_3$ | Cl | OCH$_2$COOCH$_3$ |
| 1898. | (CH$_3$)$_3$C | CH$_3$CH$_2$ | CH$_3$CH$_2$ | CH$_3$ | Cl | OCH$_2$COOCH$_2$CH$_3$ |
| 1899. | (CH$_3$)$_3$C | CH$_3$CH$_2$ | CH$_3$CH$_2$ | CH$_3$ | Cl | SCH$_3$ |
| 1900. | (CH$_3$)$_3$C | CH$_3$CH$_2$ | CH$_3$CH$_2$ | CH$_3$ | Cl | SCH$_2$CH$_3$ |
| 1901. | (CH$_3$)$_3$C | CH$_3$CH$_2$ | CH$_3$CH$_2$ | CH$_3$ | Cl | SCH2COOCH3 |
| 1902. | (CH$_3$)$_3$C | CH$_3$CH$_2$ | CH$_3$CH$_2$ | CH$_3$ | Cl | SCH2(4-ClC5H6) |
| 1903. | (CH$_3$)$_3$C | H | CH$_3$ | CH$_3$ | CH$_3$ | OCH$_3$ |

TABLE 2-continued

| No. | R3 | R9 | R8 | R6 | R7 | L-R10 |
|---|---|---|---|---|---|---|
| 1904. | (CH$_3$)$_3$C | H | CH$_3$ | CH$_3$ | CH$_3$ | OCH$_2$CH$_3$ |
| 1905. | (CH$_3$)$_3$C | H | CH$_3$ | CH$_3$ | CH$_3$ | O(CH$_2$)$_2$CH$_3$ |
| 1906. | (CH$_3$)$_3$C | H | CH$_3$ | CH$_3$ | CH$_3$ | OCH(CH$_3$)$_2$ |
| 1907. | (CH$_3$)$_3$C | H | CH$_3$ | CH$_3$ | CH$_3$ | O(CH$_3$)$_3$ |
| 1908. | (CH$_3$)$_3$C | H | CH$_3$ | CH$_3$ | CH$_3$ | O(CH$_2$)$_2$CH$_3$ |
| 1909. | (CH$_3$)$_3$C | H | CH$_3$ | CH$_3$ | CH$_3$ | OCH$_2$CH(CH$_3$)$_2$ |
| 1910. | (CH$_3$)$_3$C | H | CH$_3$ | CH$_3$ | CH$_3$ | OCH$_2$CH$_2$CH(CH$_3$)$_2$ |
| 1911. | (CH$_3$)$_3$C | H | CH$_3$ | CH$_3$ | CH$_3$ | OC(CH$_3$)$_2$CH$_2$CH$_3$ |
| 1912. | (CH$_3$)$_3$C | H | CH$_3$ | CH$_3$ | CH$_3$ | O(CH$_2$)$_4$CH$_3$ |
| 1913. | (CH$_3$)$_3$C | H | CH$_3$ | CH$_3$ | CH$_3$ | OCH$_2$Cl |
| 1914. | (CH$_3$)$_3$C | H | CH$_3$ | CH$_3$ | CH$_3$ | OCH$_2$CH$_2$Cl |
| 1915. | (CH$_3$)$_3$C | H | CH$_3$ | CH$_3$ | CH$_3$ | OCH$_2$CH$_2$CH$_2$CH$_2$Cl |
| 1916. | (CH$_3$)$_3$C | H | CH$_3$ | CH$_3$ | CH$_3$ | OCH$_2$CH$_2$Cl$_2$ |
| 1917. | (CH$_3$)$_3$C | H | CH$_3$ | CH$_3$ | CH$_3$ | OCH$_2$CH$_2$F |
| 1918. | (CH$_3$)$_3$C | H | CH$_3$ | CH$_3$ | CH$_3$ | OCH$_2$CHF$_2$ |
| 1919. | (CH$_3$)$_3$C | H | CH$_3$ | CH$_3$ | CH$_3$ | OCH$_2$CF$_3$ |
| 1920. | (CH$_3$)$_3$C | H | CH$_3$ | CH$_3$ | CH$_3$ | OCH$_2$CH$_2$OCH$_3$ |
| 1921. | (CH$_3$)$_3$C | H | CH$_3$ | CH$_3$ | CH$_3$ | OCH$_2$CH$_2$OCH$_2$CH$_3$ |
| 1922. | (CH$_3$)$_3$C | H | CH$_3$ | CH$_3$ | CH$_3$ | OCH$_2$OCH$_2$CH$_3$ |
| 1923. | (CH$_3$)$_3$C | H | CH$_3$ | CH$_3$ | CH$_3$ | OCH$_2$CH$_2$SCH$_3$ |
| 1924. | (CH$_3$)$_3$C | H | CH$_3$ | CH$_3$ | CH$_3$ | OCH$_2$C$_5$H$_6$ |
| 1925. | (CH$_3$)$_3$C | H | CH$_3$ | CH$_3$ | CH$_3$ | OCH$_2$(4-ClC$_5$H$_6$) |
| 1926. | (CH$_3$)$_3$C | H | CH$_3$ | CH$_3$ | CH$_3$ | OCH$_2$C=CH$_2$ |
| 1927. | (CH$_3$)$_3$C | H | CH$_3$ | CH$_3$ | CH$_3$ | OCH$_2$(C=CH)CH$_3$ |
| 1928. | (CH$_3$)$_3$C | H | CH$_3$ | CH$_3$ | CH$_3$ | OCH$_2$C≡CH |
| 1929. | (CH$_3$)$_3$C | H | CH$_3$ | CH$_3$ | CH$_3$ | OCH$_2$COOCH$_3$ |
| 1930. | (CH$_3$)$_3$C | H | CH$_3$ | CH$_3$ | CH$_3$ | OCH$_2$COOCH$_2$CH$_3$ |
| 1931. | (CH$_3$)$_3$C | H | CH$_3$ | CH$_3$ | CH$_3$ | SCH$_3$ |
| 1932. | (CH$_3$)$_3$C | H | CH$_3$ | CH$_3$ | CH$_3$ | SCH$_2$CH$_3$ |
| 1933. | (CH$_3$)$_3$C | H | CH$_3$ | CH$_3$ | CH$_3$ | SCH2COOCH3 |
| 1934. | (CH$_3$)$_3$C | H | CH$_3$ | CH$_3$ | CH$_3$ | SCH2(4-ClC5H6) |
| 1935. | (CH$_3$)$_3$C | CH$_3$ | CH$_3$ | CH$_3$ | CH$_3$ | OCH$_3$ |
| 1936. | (CH$_3$)$_3$C | CH$_3$ | CH$_3$ | CH$_3$ | CH$_3$ | OCH$_2$CH$_3$ |
| 1937. | (CH$_3$)$_3$C | CH$_3$ | CH$_3$ | CH$_3$ | CH$_3$ | O(CH$_2$)$_2$CH$_3$ |
| 1938. | (CH$_3$)$_3$C | CH$_3$ | CH$_3$ | CH$_3$ | CH$_3$ | OCH(CH$_3$)$_2$ |
| 1939. | (CH$_3$)$_3$C | CH$_3$ | CH$_3$ | CH$_3$ | CH$_3$ | O(CH$_3$)$_3$ |
| 1940. | (CH$_3$)$_3$C | CH$_3$ | CH$_3$ | CH$_3$ | CH$_3$ | O(CH$_2$)$_2$CH$_3$ |
| 1941. | (CH$_3$)$_3$C | CH$_3$ | CH$_3$ | CH$_3$ | CH$_3$ | OCH$_2$CH(CH$_3$)$_2$ |
| 1942. | (CH$_3$)$_3$C | CH$_3$ | CH$_3$ | CH$_3$ | CH$_3$ | OCH$_2$CH$_2$CH(CH$_3$)$_2$ |
| 1943. | (CH$_3$)$_3$C | CH$_3$ | CH$_3$ | CH$_3$ | CH$_3$ | OC(CH$_3$)$_2$CH$_2$CH$_3$ |
| 1944. | (CH$_3$)$_3$C | CH$_3$ | CH$_3$ | CH$_3$ | CH$_3$ | O(CH$_2$)$_4$CH$_3$ |
| 1945. | (CH$_3$)$_3$C | CH$_3$ | CH$_3$ | CH$_3$ | CH$_3$ | OCH$_2$Cl |
| 1946. | (CH$_3$)$_3$C | CH$_3$ | CH$_3$ | CH$_3$ | CH$_3$ | OCH$_2$CH$_2$Cl |
| 1947. | (CH$_3$)$_3$C | CH$_3$ | CH$_3$ | CH$_3$ | CH$_3$ | OCH$_2$CH$_2$CH$_2$CH$_2$Cl |
| 1948. | (CH$_3$)$_3$C | CH$_3$ | CH$_3$ | CH$_3$ | CH$_3$ | OCH$_2$CH$_2$Cl$_2$ |
| 1949. | (CH$_3$)$_3$C | CH$_3$ | CH$_3$ | CH$_3$ | CH$_3$ | OCH$_2$CH$_2$F |
| 1950. | (CH$_3$)$_3$C | CH$_3$ | CH$_3$ | CH$_3$ | CH$_3$ | OCH$_2$CHF$_2$ |
| 1951. | (CH$_3$)$_3$C | CH$_3$ | CH$_3$ | CH$_3$ | CH$_3$ | OCH$_2$CF$_3$ |
| 1952. | (CH$_3$)$_3$C | CH$_3$ | CH$_3$ | CH$_3$ | CH$_3$ | OCH$_2$CH$_2$OCH$_3$ |
| 1953. | (CH$_3$)$_3$C | CH$_3$ | CH$_3$ | CH$_3$ | CH$_3$ | OCH$_2$CH$_2$OCH$_2$CH$_3$ |
| 1954. | (CH$_3$)$_3$C | CH$_3$ | CH$_3$ | CH$_3$ | CH$_3$ | OCH$_2$OCH$_2$CH$_3$ |
| 1955. | (CH$_3$)$_3$C | CH$_3$ | CH$_3$ | CH$_3$ | CH$_3$ | OCH$_2$CH$_2$SCH$_3$ |
| 1956. | (CH$_3$)$_3$C | CH$_3$ | CH$_3$ | CH$_3$ | CH$_3$ | OCH$_2$C$_5$H$_6$ |
| 1957. | (CH$_3$)$_3$C | CH$_3$ | CH$_3$ | CH$_3$ | CH$_3$ | OCH$_2$(4-ClC$_5$H$_6$) |
| 1958. | (CH$_3$)$_3$C | CH$_3$ | CH$_3$ | CH$_3$ | CH$_3$ | OCH$_2$C=CH$_2$ |
| 1959. | (CH$_3$)$_3$C | CH$_3$ | CH$_3$ | CH$_3$ | CH$_3$ | OCH$_2$(C=CH)CH$_3$ |
| 1960. | (CH$_3$)$_3$C | CH$_3$ | CH$_3$ | CH$_3$ | CH$_3$ | OCH$_2$C≡CH |
| 1961. | (CH$_3$)$_3$C | CH$_3$ | CH$_3$ | CH$_3$ | CH$_3$ | OCH$_2$COOCH$_3$ |
| 1962. | (CH$_3$)$_3$C | CH$_3$ | CH$_3$ | CH$_3$ | CH$_3$ | OCH$_2$COOCH$_2$CH$_3$ |
| 1963. | (CH$_3$)$_3$C | CH$_3$ | CH$_3$ | CH$_3$ | CH$_3$ | SCH$_3$ |
| 1964. | (CH$_3$)$_3$C | CH$_3$ | CH$_3$ | CH$_3$ | CH$_3$ | SCH$_2$CH$_3$ |
| 1965. | (CH$_3$)$_3$C | CH$_3$ | CH$_3$ | CH$_3$ | CH$_3$ | SCH2COOCH3 |
| 1966. | (CH$_3$)$_3$C | CH$_3$ | CH$_3$ | CH$_3$ | CH$_3$ | SCH2(4-ClC5H6) |
| 1967. | (CH$_3$)$_3$C | CH$_3$ | CH$_3$ | CH$_3$ | CH$_3$ | OCH$_3$ |
| 1968. | (CH$_3$)$_3$C | CH$_3$CH$_2$ | CH$_3$ | CH$_3$ | CH$_3$ | OCH$_2$CH$_3$ |
| 1969. | (CH$_3$)$_3$C | CH$_3$CH$_2$ | CH$_3$ | CH$_3$ | CH$_3$ | O(CH$_2$)$_2$CH$_3$ |
| 1970. | (CH$_3$)$_3$C | CH$_3$CH$_2$ | CH$_3$ | CH$_3$ | CH$_3$ | OCH(CH$_3$)$_2$ |
| 1971. | (CH$_3$)$_3$C | CH$_3$CH$_2$ | CH$_3$ | CH$_3$ | CH$_3$ | O(CH$_3$)$_3$ |
| 1972. | (CH$_3$)$_3$C | CH$_3$CH$_2$ | CH$_3$ | CH$_3$ | CH$_3$ | O(CH$_2$)$_2$CH$_3$ |
| 1973. | (CH$_3$)$_3$C | CH$_3$CH$_2$ | CH$_3$ | CH$_3$ | CH$_3$ | OCH$_2$CH(CH$_3$)$_2$ |
| 1974. | (CH$_3$)$_3$C | CH$_3$CH$_2$ | CH$_3$ | CH$_3$ | CH$_3$ | OCH$_2$CH$_2$CH(CH$_3$)$_2$ |
| 1975. | (CH$_3$)$_3$C | CH$_3$CH$_2$ | CH$_3$ | CH$_3$ | CH$_3$ | OC(CH$_3$)$_2$CH$_2$CH$_3$ |
| 1976. | (CH$_3$)$_3$C | CH$_3$CH$_2$ | CH$_3$ | CH$_3$ | CH$_3$ | O(CH$_2$)$_4$CH$_3$ |
| 1977. | (CH$_3$)$_3$C | CH$_3$CH$_2$ | CH$_3$ | CH$_3$ | CH$_3$ | OCH$_2$Cl |
| 1978. | (CH$_3$)$_3$C | CH$_3$CH$_2$ | CH$_3$ | CH$_3$ | CH$_3$ | OCH$_2$CH$_2$Cl |
| 1979. | (CH$_3$)$_3$C | CH$_3$CH$_2$ | CH$_3$ | CH$_3$ | CH$_3$ | OCH$_2$CH$_2$CH$_2$CH$_2$Cl |
| 1980. | (CH$_3$)$_3$C | CH$_3$CH$_2$ | CH$_3$ | CH$_3$ | CH$_3$ | OCH$_2$CH$_2$Cl$_2$ |
| 1981. | (CH$_3$)$_3$C | CH$_3$CH$_2$ | CH$_3$ | CH$_3$ | CH$_3$ | OCH$_2$CH$_2$F |

TABLE 2-continued

| No. | R3 | R9 | R8 | R6 | R7 | L-R10 |
|---|---|---|---|---|---|---|
| 1982. | (CH$_3$)$_3$C | CH$_3$CH$_2$ | CH$_3$ | CH$_3$ | CH$_3$ | OCH$_2$CHF$_2$ |
| 1983. | (CH$_3$)$_3$C | CH$_3$CH$_2$ | CH$_3$ | CH$_3$ | CH$_3$ | OCH$_2$CF$_3$ |
| 1984. | (CH$_3$)$_3$C | CH$_3$CH$_2$ | CH$_3$ | CH$_3$ | CH$_3$ | OCH$_2$CH$_2$OCH$_3$ |
| 1985. | (CH$_3$)$_3$C | CH$_3$CH$_2$ | CH$_3$ | CH$_3$ | CH$_3$ | OCH$_2$CH$_2$OCH$_2$CH$_3$ |
| 1986. | (CH$_3$)$_3$C | CH$_3$CH$_2$ | CH$_3$ | CH$_3$ | CH$_3$ | OCH$_2$OCH$_2$CH$_3$ |
| 1987. | (CH$_3$)$_3$C | CH$_3$CH$_2$ | CH$_3$ | CH$_3$ | CH$_3$ | OCH$_2$CH$_2$SCH$_3$ |
| 1988. | (CH$_3$)$_3$C | CH$_3$CH$_2$ | CH$_3$ | CH$_3$ | CH$_3$ | OCH$_2$C$_5$H$_6$ |
| 1989. | (CH$_3$)$_3$C | CH$_3$CH$_2$ | CH$_3$ | CH$_3$ | CH$_3$ | OCH$_2$(4-ClC$_5$H$_6$) |
| 1990. | (CH$_3$)$_3$C | CH$_3$CH$_2$ | CH$_3$ | CH$_3$ | CH$_3$ | OCH$_2$C=CH$_2$ |
| 1991. | (CH$_3$)$_3$C | CH$_3$CH$_2$ | CH$_3$ | CH$_3$ | CH$_3$ | OCH$_2$(C=CH)CH$_3$ |
| 1992. | (CH$_3$)$_3$C | CH$_3$CH$_2$ | CH$_3$ | CH$_3$ | CH$_3$ | OCH$_2$C≡CH |
| 1993. | (CH$_3$)$_3$C | CH$_3$CH$_2$ | CH$_3$ | CH$_3$ | CH$_3$ | OCH$_2$COOCH$_3$ |
| 1994. | (CH$_3$)$_3$C | CH$_3$CH$_2$ | CH$_3$ | CH$_3$ | CH$_3$ | OCH$_2$COOCH$_2$CH$_3$ |
| 1995. | (CH$_3$)$_3$C | CH$_3$CH$_2$ | CH$_3$ | CH$_3$ | CH$_3$ | SCH$_3$ |
| 1996. | (CH$_3$)$_3$C | CH$_3$CH$_2$ | CH$_3$ | CH$_3$ | CH$_3$ | SCH$_2$CH$_3$ |
| 1997. | (CH$_3$)$_3$C | CH$_3$CH$_2$ | CH$_3$ | CH$_3$ | CH$_3$ | SCH2COOCH3 |
| 1998. | (CH$_3$)$_3$C | CH$_3$CH$_2$ | CH$_3$ | CH$_3$ | CH$_3$ | SCH2(4-ClC5H6) |
| 1999. | (CH$_3$)$_3$C | H | CH$_3$CH$_2$ | CH$_3$ | CH$_3$ | OCH$_3$ |
| 2000. | (CH$_3$)$_3$C | H | CH$_3$CH$_2$ | CH$_3$ | CH$_3$ | OCH$_2$CH$_3$ |
| 2001. | (CH$_3$)$_3$C | H | CH$_3$CH$_2$ | CH$_3$ | CH$_3$ | O(CH$_2$)$_2$CH$_3$ |
| 2002. | (CH$_3$)$_3$C | H | CH$_3$CH$_2$ | CH$_3$ | CH$_3$ | OCH(CH$_3$)$_2$ |
| 2003. | (CH$_3$)$_3$C | H | CH$_3$CH$_2$ | CH$_3$ | CH$_3$ | O(CH$_3$)$_3$ |
| 2004. | (CH$_3$)$_3$C | H | CH$_3$CH$_2$ | CH$_3$ | CH$_3$ | O(CH$_2$)$_2$CH$_3$ |
| 2005. | (CH$_3$)$_3$C | H | CH$_3$CH$_2$ | CH$_3$ | CH$_3$ | OCH$_2$CH(CH$_3$)$_2$ |
| 2006. | (CH$_3$)$_3$C | H | CH$_3$CH$_2$ | CH$_3$ | CH$_3$ | OCH$_2$CH$_2$CH(CH$_3$)$_2$ |
| 2007. | (CH$_3$)$_3$C | H | CH$_3$CH$_2$ | CH$_3$ | CH$_3$ | OC(CH$_3$)$_2$CH$_2$CH$_3$ |
| 2008. | (CH$_3$)$_3$C | H | CH$_3$CH$_2$ | CH$_3$ | CH$_3$ | O(CH$_2$)$_4$CH$_3$ |
| 2009. | (CH$_3$)$_3$C | H | CH$_3$CH$_2$ | CH$_3$ | CH$_3$ | OCH$_2$Cl |
| 2010. | (CH$_3$)$_3$C | H | CH$_3$CH$_2$ | CH$_3$ | CH$_3$ | OCH$_2$CH$_2$Cl |
| 2011. | (CH$_3$)$_3$C | H | CH$_3$CH$_2$ | CH$_3$ | CH$_3$ | OCH$_2$CH$_2$CH$_2$CH$_2$Cl |
| 2012. | (CH$_3$)$_3$C | H | CH$_3$CH$_2$ | CH$_3$ | CH$_3$ | OCH$_2$CH$_2$Cl$_2$ |
| 2013. | (CH$_3$)$_3$C | H | CH$_3$CH$_2$ | CH$_3$ | CH$_3$ | OCH$_2$CH$_2$F |
| 2014. | (CH$_3$)$_3$C | H | CH$_3$CH$_2$ | CH$_3$ | CH$_3$ | OCH$_2$CHF$_2$ |
| 2015. | (CH$_3$)$_3$C | H | CH$_3$CH$_2$ | CH$_3$ | CH$_3$ | OCH$_2$CF$_3$ |
| 2016. | (CH$_3$)$_3$C | H | CH$_3$CH$_2$ | CH$_3$ | CH$_3$ | OCH$_2$CH$_2$OCH$_3$ |
| 2017. | (CH$_3$)$_3$C | H | CH$_3$CH$_2$ | CH$_3$ | CH$_3$ | OCH$_2$CH$_2$OCH$_2$CH$_3$ |
| 2018. | (CH$_3$)$_3$C | H | CH$_3$CH$_2$ | CH$_3$ | CH$_3$ | OCH$_2$OCH$_2$CH$_3$ |
| 2019. | (CH$_3$)$_3$C | H | CH$_3$CH$_2$ | CH$_3$ | CH$_3$ | OCH$_2$CH$_2$SCH$_3$ |
| 2020. | (CH$_3$)$_3$C | H | CH$_3$CH$_2$ | CH$_3$ | CH$_3$ | OCH$_2$C$_5$H$_6$ |
| 2021. | (CH$_3$)$_3$C | H | CH$_3$CH$_2$ | CH$_3$ | CH$_3$ | OCH$_2$(4-ClC$_5$H$_6$) |
| 2022. | (CH$_3$)$_3$C | H | CH$_3$CH$_2$ | CH$_3$ | CH$_3$ | OCH$_2$C=CH$_2$ |
| 2023. | (CH$_3$)$_3$C | H | CH$_3$CH$_2$ | CH$_3$ | CH$_3$ | OCH$_2$(C=CH)CH$_3$ |
| 2024. | (CH$_3$)$_3$C | H | CH$_3$CH$_2$ | CH$_3$ | CH$_3$ | OCH$_2$C≡CH |
| 2025. | (CH$_3$)$_3$C | H | CH$_3$CH$_2$ | CH$_3$ | CH$_3$ | OCH$_2$COOCH$_3$ |
| 2026. | (CH$_3$)$_3$C | H | CH$_3$CH$_2$ | CH$_3$ | CH$_3$ | OCH$_2$COOCH$_2$CH$_3$ |
| 2027. | (CH$_3$)$_3$C | H | CH$_3$CH$_2$ | CH$_3$ | CH$_3$ | SCH$_3$ |
| 2028. | (CH$_3$)$_3$C | H | CH$_3$CH$_2$ | CH$_3$ | CH$_3$ | SCH$_2$CH$_3$ |
| 2029. | (CH$_3$)$_3$C | H | CH$_3$CH$_2$ | CH$_3$ | CH$_3$ | SCH2COOCH3 |
| 2030. | (CH$_3$)$_3$C | H | CH$_3$CH$_2$ | CH$_3$ | CH$_3$ | SCH2(4-ClC5H6) |
| 2031. | (CH$_3$)$_3$C | CH$_3$ | CH$_3$CH$_2$ | CH$_3$ | CH$_3$ | OCH$_3$ |
| 2032. | (CH$_3$)$_3$C | CH$_3$ | CH$_3$CH$_2$ | CH$_3$ | CH$_3$ | OCH$_2$CH$_3$ |
| 2033. | (CH$_3$)$_3$C | CH$_3$ | CH$_3$CH$_2$ | CH$_3$ | CH$_3$ | O(CH$_2$)$_2$CH$_3$ |
| 2034. | (CH$_3$)$_3$C | CH$_3$ | CH$_3$CH$_2$ | CH$_3$ | CH$_3$ | OCH(CH$_3$)$_2$ |
| 2035. | (CH$_3$)$_3$C | CH$_3$ | CH$_3$CH$_2$ | CH$_3$ | CH$_3$ | O(CH$_3$)$_3$ |
| 2036. | (CH$_3$)$_3$C | CH$_3$ | CH$_3$CH$_2$ | CH$_3$ | CH$_3$ | O(CH$_2$)$_2$CH$_3$ |
| 2037. | (CH$_3$)$_3$C | CH$_3$ | CH$_3$CH$_2$ | CH$_3$ | CH$_3$ | OCH$_2$CH(CH$_3$)$_2$ |
| 2038. | (CH$_3$)$_3$C | CH$_3$ | CH$_3$CH$_2$ | CH$_3$ | CH$_3$ | OCH$_2$CH$_2$CH(CH$_3$)$_2$ |
| 2039. | (CH$_3$)$_3$C | CH$_3$ | CH$_3$CH$_2$ | CH$_3$ | CH$_3$ | OC(CH$_3$)$_2$CH$_2$CH$_3$ |
| 2040. | (CH$_3$)$_3$C | CH$_3$ | CH$_3$CH$_2$ | CH$_3$ | CH$_3$ | O(CH$_2$)$_4$CH$_3$ |
| 2041. | (CH$_3$)$_3$C | CH$_3$ | CH$_3$CH$_2$ | CH$_3$ | CH$_3$ | OCH$_2$Cl |
| 2042. | (CH$_3$)$_3$C | CH$_3$ | CH$_3$CH$_2$ | CH$_3$ | CH$_3$ | OCH$_2$CH$_2$Cl |
| 2043. | (CH$_3$)$_3$C | CH$_3$ | CH$_3$CH$_2$ | CH$_3$ | CH$_3$ | OCH$_2$CH$_2$CH$_2$CH$_2$Cl |
| 2044. | (CH$_3$)$_3$C | CH$_3$ | CH$_3$CH$_2$ | CH$_3$ | CH$_3$ | OCH$_2$CH$_2$Cl$_2$ |
| 2045. | (CH$_3$)$_3$C | CH$_3$ | CH$_3$CH$_2$ | CH$_3$ | CH$_3$ | OCH$_2$CH$_2$F |
| 2046. | (CH$_3$)$_3$C | CH$_3$ | CH$_3$CH$_2$ | CH$_3$ | CH$_3$ | OCH$_2$CHF$_2$ |
| 2047. | (CH$_3$)$_3$C | CH$_3$ | CH$_3$CH$_2$ | CH$_3$ | CH$_3$ | OCH$_2$CF$_3$ |
| 2048. | (CH$_3$)$_3$C | CH$_3$ | CH$_3$CH$_2$ | CH$_3$ | CH$_3$ | OCH$_2$CH$_2$OCH$_3$ |
| 2049. | (CH$_3$)$_3$C | CH$_3$ | CH$_3$CH$_2$ | CH$_3$ | CH$_3$ | OCH$_2$CH$_2$OCH$_2$CH$_3$ |
| 2050. | (CH$_3$)$_3$C | CH$_3$ | CH$_3$CH$_2$ | CH$_3$ | CH$_3$ | OCH$_2$OCH$_2$CH$_3$ |
| 2051. | (CH$_3$)$_3$C | CH$_3$ | CH$_3$CH$_2$ | CH$_3$ | CH$_3$ | OCH$_2$CH$_2$SCH$_3$ |
| 2052. | (CH$_3$)$_3$C | CH$_3$ | CH$_3$CH$_2$ | CH$_3$ | CH$_3$ | OCH$_2$C$_5$H$_6$ |
| 2053. | (CH$_3$)$_3$C | CH$_3$ | CH$_3$CH$_2$ | CH$_3$ | CH$_3$ | OCH$_2$(4-ClC$_5$H$_6$) |
| 2054. | (CH$_3$)$_3$C | CH$_3$ | CH$_3$CH$_2$ | CH$_3$ | CH$_3$ | OCH$_2$C=CH$_2$ |
| 2055. | (CH$_3$)$_3$C | CH$_3$ | CH$_3$CH$_2$ | CH$_3$ | CH$_3$ | OCH$_2$(C=CH)CH$_3$ |
| 2056. | (CH$_3$)$_3$C | CH$_3$ | CH$_3$CH$_2$ | CH$_3$ | CH$_3$ | OCH$_2$C≡CH |
| 2057. | (CH$_3$)$_3$C | CH$_3$ | CH$_3$CH$_2$ | CH$_3$ | CH$_3$ | OCH$_2$COOCH$_3$ |
| 2058. | (CH$_3$)$_3$C | CH$_3$ | CH$_3$CH$_2$ | CH$_3$ | CH$_3$ | OCH$_2$COOCH$_2$CH$_3$ |
| 2059. | (CH$_3$)$_3$C | CH$_3$ | CH$_3$CH$_2$ | CH$_3$ | CH$_3$ | SCH$_3$ |

TABLE 2-continued

| No. | R3 | R9 | R8 | R6 | R7 | L-R10 |
|---|---|---|---|---|---|---|
| 2060. | $(CH_3)_3C$ | $CH_3$ | $CH_3CH_2$ | $CH_3$ | $CH_3$ | $SCH_2CH_3$ |
| 2061. | $(CH_3)_3C$ | $CH_3$ | $CH_3CH_2$ | $CH_3$ | $CH_3$ | SCH2COOCH3 |
| 2062. | $(CH_3)_3C$ | $CH_3$ | $CH_3CH_2$ | $CH_3$ | $CH_3$ | SCH2(4-ClC5H6) |
| 2063. | $(CH_3)_3C$ | $CH_3$ | $CH_3CH_2$ | $CH_3$ | $CH_3$ | $OCH_3$ |
| 2064. | $(CH_3)_3C$ | $CH_3CH_2$ | $CH_3CH_2$ | $CH_3$ | $CH_3$ | $OCH_2CH_3$ |
| 2065. | $(CH_3)_3C$ | $CH_3CH_2$ | $CH_3CH_2$ | $CH_3$ | $CH_3$ | $O(CH_2)_2CH_3$ |
| 2066. | $(CH_3)_3C$ | $CH_3CH_2$ | $CH_3CH_2$ | $CH_3$ | $CH_3$ | $OCH(CH_3)_2$ |
| 2067. | $(CH_3)_3C$ | $CH_3CH_2$ | $CH_3CH_2$ | $CH_3$ | $CH_3$ | $O(CH_3)_3$ |
| 2068. | $(CH_3)_3C$ | $CH_3CH_2$ | $CH_3CH_2$ | $CH_3$ | $CH_3$ | $O(CH_2)_2CH_3$ |
| 2069. | $(CH_3)_3C$ | $CH_3CH_2$ | $CH_3CH_2$ | $CH_3$ | $CH_3$ | $OCH_2CH(CH_3)_2$ |
| 2070. | $(CH_3)_3C$ | $CH_3CH_2$ | $CH_3CH_2$ | $CH_3$ | $CH_3$ | $OCH_2CH_2CH(CH_3)_2$ |
| 2071. | $(CH_3)_3C$ | $CH_3CH_2$ | $CH_3CH_2$ | $CH_3$ | $CH_3$ | $OC(CH_3)_2CH_2CH_3$ |
| 2072. | $(CH_3)_3C$ | $CH_3CH_2$ | $CH_3CH_2$ | $CH_3$ | $CH_3$ | $O(CH_2)_4CH_3$ |
| 2073. | $(CH_3)_3C$ | $CH_3CH_2$ | $CH_3CH_2$ | $CH_3$ | $CH_3$ | $OCH_2Cl$ |
| 2074. | $(CH_3)_3C$ | $CH_3CH_2$ | $CH_3CH_2$ | $CH_3$ | $CH_3$ | $OCH_2CH_2Cl$ |
| 2075. | $(CH_3)_3C$ | $CH_3CH_2$ | $CH_3CH_2$ | $CH_3$ | $CH_3$ | $OCH_2CH_2CH_2CH_2Cl$ |
| 2076. | $(CH_3)_3C$ | $CH_3CH_2$ | $CH_3CH_2$ | $CH_3$ | $CH_3$ | $OCH_2CH_2Cl_2$ |
| 2077. | $(CH_3)_3C$ | $CH_3CH_2$ | $CH_3CH_2$ | $CH_3$ | $CH_3$ | $OCH_2CH_2F$ |
| 2078. | $(CH_3)_3C$ | $CH_3CH_2$ | $CH_3CH_2$ | $CH_3$ | $CH_3$ | $OCH_2CHF_2$ |
| 2079. | $(CH_3)_3C$ | $CH_3CH_2$ | $CH_3CH_2$ | $CH_3$ | $CH_3$ | $OCH_2CF_3$ |
| 2080. | $(CH_3)_3C$ | $CH_3CH_2$ | $CH_3CH_2$ | $CH_3$ | $CH_3$ | $OCH_2CH_2OCH_3$ |
| 2081. | $(CH_3)_3C$ | $CH_3CH_2$ | $CH_3CH_2$ | $CH_3$ | $CH_3$ | $OCH_2CH_2OCH_2CH_3$ |
| 2082. | $(CH_3)_3C$ | $CH_3CH_2$ | $CH_3CH_2$ | $CH_3$ | $CH_3$ | $OCH_2OCH_2CH_3$ |
| 2083. | $(CH_3)_3C$ | $CH_3CH_2$ | $CH_3CH_2$ | $CH_3$ | $CH_3$ | $OCH_2CH_2SCH_3$ |
| 2084. | $(CH_3)_3C$ | $CH_3CH_2$ | $CH_3CH_2$ | $CH_3$ | $CH_3$ | $OCH_2C_5H_6$ |
| 2085. | $(CH_3)_3C$ | $CH_3CH_2$ | $CH_3CH_2$ | $CH_3$ | $CH_3$ | $OCH_2(4-ClC_5H_6)$ |
| 2086. | $(CH_3)_3C$ | $CH_3CH_2$ | $CH_3CH_2$ | $CH_3$ | $CH_3$ | $OCH_2C=CH_2$ |
| 2087. | $(CH_3)_3C$ | $CH_3CH_2$ | $CH_3CH_2$ | $CH_3$ | $CH_3$ | $OCH_2(C=CH)CH_3$ |
| 2088. | $(CH_3)_3C$ | $CH_3CH_2$ | $CH_3CH_2$ | $CH_3$ | $CH_3$ | $OCH_2C\equiv CH$ |
| 2089. | $(CH_3)_3C$ | $CH_3CH_2$ | $CH_3CH_2$ | $CH_3$ | $CH_3$ | $OCH_2COOCH_3$ |
| 2090. | $(CH_3)_3C$ | $CH_3CH_2$ | $CH_3CH_2$ | $CH_3$ | $CH_3$ | $OCH_2COOCH_2CH_3$ |
| 2091. | $(CH_3)_3C$ | $CH_3CH_2$ | $CH_3CH_2$ | $CH_3$ | $CH_3$ | $SCH_3$ |
| 2092. | $(CH_3)_3C$ | $CH_3CH_2$ | $CH_3CH_2$ | $CH_3$ | $CH_3$ | $SCH_2CH_3$ |
| 2093. | $(CH_3)_3C$ | $CH_3CH_2$ | $CH_3CH_2$ | $CH_3$ | $CH_3$ | SCH2COOCH3 |
| 2094. | $(CH_3)_3C$ | $CH_3CH_2$ | $CH_3CH_2$ | $CH_3$ | $CH_3$ | SCH2(4-ClC5H6) |

Physical property data of part of compounds provided in the present invention are shown in Table 3 below

TABLE 3

| Compound No. | $^1$H NMR (600 MHZ, CDCl3/TMS) | MS (ESI) m/z: [M + 1] |
|---|---|---|
| 86 | 1.15-1.24 (m, 4H), 1.34 (s, 9H), 1.60-1.78 (m, 6H), 2.23-2.27 (m, 1H), 2.30 (s, 3H), 3.90 (s, 3H) 5.39 + 5.46 (s, 2H), 7.44-7.46 (d, 2H), 7.76-7.78 (d, 2H) | |
| 91 | 0.70-0.72 (t, 3H), 1.06 (s, 6H), 1.33 (s, 9H), 1.46-1.50 (q, 2H), 2.30 (s, 3H), 3.91 (s, 3H), 5.36 + 5.51 (s, 2H), 7.43-7.44 (d, 2H), 7.76-7.78 (d, 2H) | |
| 79 | 1.08-1.09 (d, 6H), 1.34 (s, 9H), 2.30 (s, 3H), 2.48-2.53 (m, 1H), 3.90 (s, 3H), 5.40 + 5.48 (s, 2H), 7.44-7.46 (d, 2H), 7.75-7.77 (d, 2H) | |
| 84 | 0.91-0.93 (m, 2H), 0.98-1.01 (m, 2H), 1.34 (s, 9H), 1.57-1.59 (m, 1H), 2.30 (s, 3H), 3.90 (s, 3H), 5.40 (s, 2H), 7.45-7.47 (d, 2H), 7.76-7.78 (d, 2H) | |
| 80 | 1.10 (s, 9H), 1.34 (s, 9H), 2.30 (s, 3H), 3.91 (s, 3H), 5.33 + 5.52 (s, 2H), 7.43-7.44 (d, 2H), 7.76-7.78 (d, 2H) | |
| 104 | 1.06-1.07 (d, 3H), 1.10-1.11 (d, 3H), 1.35 (s, 9H), 1.58-1.59 (d, 3H), 2.28 (s, 3H), 2.45-2.48 (m, 1H), 3.96 (s, 3H), 6.05-6.07 (m, 1H), 7.45-7.46 (d, 2H), 7.78-7.79 (d, 2H) | |
| 101 | 7.80-7.79(d, J = 6.63, 2H), 7.48-7.47 (d, J = 8.14, 2H), 6.06 (s, 1H), 3.93(s, 3H), 2.27(s, 3H), 2.00(s, 3H), 1.59-1.56(d, J = 19.54, 3H), 1.35(s, 9H) | |
| 116 | 0.73-0.75 (t, 3H), 1.07 (s, 3H), 1.08 (s, 3H), 1.34 (s, 9H), 1.46-1.50 (m, 2H), 1.58-1.59 (d, 3H), 2.38 (s, 3H, —CH3), 3.98 (s, 3H), 6.04-6.06 (m, 1H), 7.43-7.45 (d, 2H Hz), 7.79-7.80 (d, 2H) | |
| 105 | 1.12 (s, 9H), 1.34 (s, 9H), 1.57-1.58 (d, 3H), 2.28 (s, 3H), 3.98 (s, 3H), 6.03 (m, 1H), 7.43-7.45 (d, 2H), 7.76-7.78 (d, 2H) | |

TABLE 3-continued

| Compound No. | $^1$H NMR (600 MHZ, CDCl3/TMS) | MS (ESI) m/z: [M + 1] |
|---|---|---|
| 109 | 0.89-0.97 (m, 4H), 1.36 (s, 9H), 1.53-1.56 (m, 1H), 1.60-1.61 (d, 3H), 2.27 (s, 3H), 3.93 (s, 3H), 6.08 (m, 1H), 7.47-7.48 (d, 2H), 7.80-7.81 (d, 2H) | |
| 236 | 1.18-1.30 (m, 4H), 1.33 (s, 9H), 1.48-1.50 (t, 3H), 1.60-1.74 (m, 6H), 2.18-2.22 (m, 1H), 2.34 (s, 3H, —CH$_3$), 4.13-4.16 (q, 2H), 5.39 (s, 2H), 6.41 (s, 1H), 7.42-7.44 (d, 2H), 7.72-7.74 (d, 2H) | |
| 241 | 0.70-0.73 (t, 3H), 1.04 (s, 6H), 1.33 (s, 9H), 1.45-1.48 (q, 2H), 1.48-1.51 (t, 3H), 2.34 (s, 3H), 4.14-4.17 (q, 2H), 5.40 (s, 2H), 6.40 (s, 1H), 7.42-7.43 (d, 2H), 7.73-7.75 (d, 2H) | |
| 229 | 1.05-1.06 (d, 6H), 1.33 (s, 9H), 1.48-1.51 (t, 3H), 2.34 (s, 3H), 2.44-2.48 (m, 1H), 4.13-4.17 (q, 2H), 5.41 (s, 2H), 6.41 (s, 1H), 7.42-7.44 (d, 2H), 7.73-7.74 (d, 2H) | |
| 234 | 0.89-0.91 (m, 2H), 0.94-0.96 (m, 2H), 1.34 (s, 9H), 1.48-1.51 (t, 3H), 1.54-1.57 (m, 1H), 2.34 (s, 3H), 4.13-4.17 (q, 2H), 5.41 (s, 2H), 6.39 (s, 1H), 7.43-7.45 (d, 2H), 7.73-7.75 (d, 2H) | |
| 230 | 1.07 (s, 9H), 1.33 (s, 9H), 1.48-1.50 (t, 3H), 2.32 (s, 3H), 4.14-4.17 (q, 2H), 5.39 (s, 2H), 6.42 (s, 1H), 7.42-7.43 (d, 2H), 7.73-7.74 (d, 2H) | |
| 254 | 1.03-1.04 (d, 3H), 1.07-1.08 (d, 3H), 1.34 (s, 9H), 1.48-1.51 (t, 3H), 1.50-1.51 (d, 3H), 2.32 (s, 3H, —CH$_3$), 2.40-2.45 (m, 1H), 4.11-4.20 (m, 2H), 5.96-5.99 (q, 1H), 6.34 (s, 1H), 7.43-7.44 (d, 2H), 7.75-7.77 (d, 2H) | |
| 266 | 0.72-0.75 (t, 3H), 1.04 (s, 6H), 1.34 (s, 9H), 1.43-1.48 (m, 2H), 1.48-1.50 (t, 3H), 1.50-1.51 (d, 3H), 2.32 (s, 3H), 4.12-4.20 (m, 2H), 5.94-5.96 (q, 1H), 6.36 (s, 1H), 7.42-7.44 (d, 2H), 7.76-7.78 (d, 2H) | |
| 255 | 1.09 (s, 9H), 1.34 (s, 9H), 1.48-1.51 (t, 3H), 1.50-1.51 (d, 3H), 2.32 (s, 3H), 4.13-4.19 (m, 2H), 5.93-5.96 (q, 1H), 6.36 (s, 1H), 7.42-7.43 (d, 2H), 7.75-7.77 (d, 2H) | |
| 259 | 0.86-0.93 (m, 4H), 1.36 (s, 9H), 1.48-1.50 (t, 3H), 1.51-1.52 (d, 3H), 1.51-1.53 (m, 1H), 2.31 (s, 3H), 4.13-4.19 (m, 2H), 4.11-4.18 (m, 2H), 5.97-6.00 (m, 1H), 6.32 (s, 1H), 7.45-7.46 (d, 2H), 7.76-7.77 (d, 2H) | |
| 251 | 1.35 (s, 9H), 1.48-1.51 (t, 3H), 1.52-1.53 (d, 3H), 1.96 (s, 3H), 2.32 (s, 3H), 4.14-4.18 (m, 2H), 5.97-6.00 (q, 1H), 6.32 (s, 1H), 7.45-7.46 (d, 2H), 7.76-7.77 (d, 2H) | |
| 508 | 1.35 (s, 9H), 1.58-1.59 (d, 3H), 2.31 (s, 3H), 3.12-3.14 (br, 1H), 3.91 (s, 3H), 4.63-4.64 (br, 2H), 5.94-5.97 (q, 1H), 6.32 (s, 1H), 7.45-7.46 (d, 2H), 7.72-7.73 (d, 2H) | |
| 506 | 1.34 (s, 9H), 1.57-1.58 (d, 3H), 2.31 (s, 3H), 3.91 (s, 3H), 4.53-4.55 (br, 2H), 5.25-5.34 (m, 2H), 5.82-5.86 (m, 1H), 5.93-5.96 (q, 1H), 6.31 (s, 1H), 7.44-7.46 (d, 2H), 7.74-7.76 (d, 2H) | |
| 483 | 1.34 (s, 9H), 1.57-1.58 (d, 3H), 2.31 (s, 3H), 3.71 (s, 3H), 3.91 (s, 3H), 5.93-5.96 (q, 1H), 6.32 (s, 1H), 7.45-7.46 (d, 2H), 7.73-7.74 (d, 2H) | |
| 489 | 0.89-0.91 (d, 6H), 1.34 (s, 9H), 1.57-1.58 (d, 3H), 1.88-1.93 (m, 1H), 2.31 (s, 3H), 3.81-3.87 (m, 2H), 3.92 (s, 3H), 5.91-5.94 (q, 1H), 6.31 (s, 1H), 7.43-7.44 (d, 2H), 7.74-7.75 (d, 2H) | |
| 488 | 0.89-0.92 (t, 3H), 1.34 (s, 9H), 1.35-1.38 (m, 2H), 1.56-1.57 (d, 3H), 1.59-1.62 (m, 2H), 2.31 (s, 3H), 3.91 (s, 3H), 4.05-4.07 (m, 2H), 5.91-5.94 (q, 1H), 6.31 (s, 1H), 7.43-7.44 (d, 2H), 7.74-7.75 (d, 2H) | |
| 489 | 0.88-0.90 (m, 6H), 1.34 (s, 9H), 1.49-1.50 (m, 2H), 1.57-1.58 (d, 3H), 1.62-1.67 (m, 1H), 2.31 (s, 3H), 3.81-3.87 (m, 2H,), 3.92 (s, 3H), 4.07-4.11 (m, 2H), 5.92-5.94 (q, 1H), 6.31 (s, 1H), 7.43-7.44 (d, 2H), 7.74-7.75 (d, 2H) | |
| 499 | 1.34 (s, 9H), 1.61-1.62 (d, 3H), 2.31 (s, 3H), 3.90 (s, 3H), 4.38-4.42 (q, 2H), 5.93-5.96 (q, 1H), 6.32 (s, 1H), 7.45-7.46 (d, 2H), 7.72-7.73 (d, 2H) | |
| 484 | 1.23-1.24 (t, 3H), 1.34 (s, 9H), 1.56-1.57 (d, 3H), 2.31 (s, 3H), 3.91 (s, 3H), 4.09-4.13 (q, 2H), 5.92-5.94 (q, 1H), 6.32 (s, 1H), 7.44-7.45 (d, 2H), 7.73-7.74 (d, 2H) | |
| 675 | 7.80-7.79(d, 2H), 7.48-7.46 (d, 2H), 5.91 (s, 1H), 3.91(s, 3H), 3.72 (s, 3H), 2.28 (s, 3H), 1.61 (s, 3H), 1.35 (s, 9H). | |
| 676 | 7.80-7.79(d, 2H,), 7.47-7.46 (d, 2H), 5.91 (s, 1H), 4.14-4.10(q, 2H), 3.92(s, 3H), 2.28 (s, 3H), 1.61 (s, 3H), 1.35(s, 9H), 1.27-1.25(t, 3H). | |
| 680 | 7.80-7.79(d, 2H,), 7.47-7.46 (d, 2H), 5.93 (s, 1H), 4.08-4.05(q, 2H), 3.92(s, 3H), 2.28 (s, 3H), 1.72-1.66 (m, 2H), 1.45-1.39(10, 2H), 1.61 (s, 3H), 1.35 (s, 9H), 0.93-0.90 (t,s 3H). | |

TABLE 3-continued

| Compound No. | $^1$H NMR (600 MHZ, CDCl3/TMS) | MS (ESI) m/z: [M + 1] |
|---|---|---|
| 678 | 7.71-7.70(d, 2H,), 7.38-7.36 (d, 2H), 5.84 (s, 1H), 3.83(s, 3H), 3.75-3.74(dd, 6.73, 2H), 2.18(s, 3H), 1.85-1.80 (m, 1H), 1.55-1.48 (d, 2H), 1.25 (s, 9H), 0.82-0.81 (d, 6H). | |
| 682 | 7.80-7.79(d, 2H,), 7.47-7.46 (d, 2H), 5.93 (s, 1H), 4.10-4.08(t, 2H), 3.92(s, 3H), 2.28(s, 3H), 1.65-1.64(d, 3H), 1.51-1.50 m, 1H), 1.35 (s, 9H), 0.93-0.92 (dd, 2H), 0.91-0.89(dd, 6H). | |
| 698 | 7.71-7.69(d, 2H), 7.38-7.36 (d, 2H), 5.87 (s, 1H), 5.79-5.73(m, 1H), 5.25-5.17(m, 2H), 4.45-4.44(d, 2H), 3.82(s, 3H), 2.18(s, 3H), 1.55-1.49(d, 3H), 1.25 (s, 9H). | |
| 692 | 7.72-7.71(d, 2H,), 7.39-7.38 (d, 2H), 5.87 (s, 1H), 4.22-4.12(m, 2H), 3.84(s, 3H), 3.55-3.47(m, 2H), 3.27(s, 3H), 2.20(s, 3H) 1.56-1.55 (d, 3H), 1.27(s, 9H). | |
| 700 | 7.69-7.68(d, 2H,), 7.38-7.37 (d, 2H), 5.87 (s, 1H), 4.55(s, 2H), 3.99(s, 3H), 2.86-2.79(m, 1H), 2.18(s, 3H), 1.48(s, 3H), 1.26(s, 9H). | |
| 691 | 7.78-7.77(d, 2H,), 7.48-7.47 (d, 2H), 5.96 (s, 1H), 4.41-4.39(m, 2H), 3.90(s, 3H), 2.28(s, 3H), 1.55(s, 3H), 1.35(s, 9H). | |
| 602 | 1.34 (s, 9H), 1.49-1.51 (t, 3H), 1.56-1.57 (d, 3H), 2.32 (s, 3H), 4.12-4.16 (m, 2H), 4.54-4.55 (br, 2H), 5.25-5.34 (m, 2H), 5.82-5.87 (m, 1H), 5.88-5.90 (q, 1H,), 6.33 (s, 1H), 7.44-7.46 (d, 2H), 7.75-7.77 (d, 2H) | |
| 604 | 1.35 (s, 9H), 1.50-1.52 (t, 3H), 1.57-1.58 (d, 3H), 2.32 (s, 3H), 3.11-3.13 (br, 1H), 4.12-4.17 (m, 2H), 4.64-4.65 (br, 2H), 5.88-5.91 (q, 1H), 6.35 (s, 1H), 7.45-7.46 (d, 2H), 7.74-7.75 (d, 2H) | |
| 586 | 0.89-0.90 (d, 6H), 1.34 (s, 9H), 1.49-1.51 (t, 3H), 1.55-1.56 (d, 3H), 1.63-1.71 (m, 2H), 2.33 (s, 3H), 4.09-4.13 (br, 2H), 4.16-4.18 (m, 2H), 5.87-5.90 (q, 1H), 6.34 (s, 1H), 7.44-7.45 (d, 2H), 7.73-7.74 (d, 2H) | |
| 595 | 1.35 (s, 9H), 1.48-1.51 (t, 3H), 1.60-1.61 (d, 3H), 2.32 (s, 3H), 4.09-4.17 (m, 2H), 4.39-4.43 (q, 2H), 5.88-5.90 (q, 1H), 6.33 (s, 1H), 7.45-7.46 (d, 2H), 7.74-7.75 (d, 2H) | |
| 584 | 0.90-0.92 (t, 3H), 1.35 (s, 9H), 1.36-1.38 (m, 2H), 1.48-1.51 (t, 3H), 1.55-1.56 (d, 3H), 1.58-1.60 (m, 2H), 2.32 (s, 3H), 4.05-4.08 (m, 2H), 4.12-4.18 (m, 2H), 5.87-5.90 (q, 1H), 6.34 (s, 1H), 7.45-7.46 (d, 2H), 7.76-7.77 (d, 2H) | |
| 596 | 1.35 (s, 9H), 1.48-1.51 (t, 3H), 1.55-1.56 (d, 3H), 2.32 (s, 3H), 3.35 (s, 3H), 3.61-3.62 (t, 2H), 4.11-4.18 (m, 2H), 4.28-4.30 (t, 2H), 5.87-5.90 (q, 1H), 6.34 (s, 1H), 7.45-7.46 (d, 2H), 7.74-7.75 (d, 2H) | |
| 579 | 1.35 (s, 9H), 1.49-1.51 (t, 3H), 1.55-1.56 (d, 3H), 2.32 (s, 3H), 3.71 (s, 3H), 4.11-4.17 (m, 2H), 5.88-5.90 (q, 1H), 6.33 (s, 1H), 7.44-7.45 (d, 2H), 7.74-7.75 (d, 2H) | |
| 580 | 1.23-1.26 (t, 3H), 1.34 (s, 9H), 1.49-1.51 (t, 3H), 1.55-1.56 (d, 3H), 2.32 (s, 3H), 4.09-4.13 (q, 2H), 4.15-4.18 (m, 2H,), 5.87-5.90 (q, 1H), 6.34 (s, 1H), 7.44-7.46 (d, 2H), 7.75-7.77 (d, 2H) | |
| 585 | 0.90-0.91 (d, 6H), 3.34 (s, 9H), 1.49-3.51 (t, 3H), 1.56-1.57 (d, 3H), 1.89-1.93 (m, 1H), 2.32 (s, 3H), 3.81-3.87 (m, 2H), 4.10-4.18 (m, 2H), 5.87-5.89 (q, 1H), 6.34 (s, 1H), 7.43-7.45 (d, 2H), 7.75-7.77 (d, 2H) | |
| 1027 | 7.67-7.66(d, 2H,), 7.36-7.34 (d, 2H), 6.25(s, 1H), 5.77-5.74(q, 1H), 4.09-4.07(m, 2H), 4.05-4.00(m, 2H), 2.94-2,90(m, 1H), 1.47-1.46(d, 3H), 1.41-1.38(t, 3H), 1.25(s, 9H), 1.20-1.19(d, 6H), 1.17-1.16(t, 3H). | |
| 1028 | 7.76-7.74(d, 2H,), 7.46-7.44 (d, 2H), 6.35(s, 1H), 5.86-5.84(q, 1H), 4.14-4.10(m, 2H), 3.71(s, 3H), 3.04-2.99(m, 1H), 1.56-1.55(d, 3H), 1.50-1.48(t, 3H), 1.35(s, 9H), 1.30-1.29(d, 6H). | |
| 1029 | 7.76-7.75(d, 2H,), 7.45-7.44 (d, 2H), 6.35(s, 1H), 5.86-5.83(q, 1H), 4.20-4.10(m, 2H), 4.06-4.04(q, 2H), 3.04-2.99(m, 1H), 1.59(s, 4H), 1.56-1.55(4 3H), 1.50-1.48(t, 3H), 1.34(s, 9H), 1.30-1.28(d, 6H), 0.93-0.90(t, 3H). | |
| 1030 | 7.76-7.75(d, 2H,), 7.45-7.44 (d, 2H), 6.35(s, 1H), 5.86-5.83(q, 1H), 4.21-4.09(m, 2H), 3.84-3.82(q, 2H), 3.04-2.99(m, 1H), 1.93-1.89(m, 1H), 1.56-1.55(d, 3H), 1.50-1.48(t, 3H), 1.34(s, 9H), 1.29-1.28(d, 6H), 0.91-0.90(d, 6H). | |
| 1031 | 7.76- 7.74(d, 2H,), 7.45-7.44 (d, 2H), 6.35(s, 1H), 5.87-5.84(q, 1H), 4,19-4.13(m, 4H), 3.57-3.55(q, 2H), 3.36(s, 3H), 3.04-2.99(m, 1H), 1.56-1.55(d, 3H), 1.50-1.47(t, 3H), 1.34(s, 9H), 1.29-1.28(d, 6H). | |
| 1032 | 7.76-7.75(d, 2H), 7.45-7.44 (d, 2H), 6.35(s, 1H), 5.87-5.84(q, 1H), 4.20-4.11(m, 2H), 4.10-4.07(m, 2H), 3.04-2.99(m, 1H), 1.56-1.55(d, 3H), 1.5 l(m, 1H), 1.50-1.48(t, 3H), 1.34(s, 9H), 1.29-1.28(d, 6H), 0.90-0.89(d, J = 6.66, 6H). | |
| 1033 | 7.76-7.75(d, J 2H,), 7.45-7.44 (d, 2H), 6.35(s, 1H), 5.87-5.84(q, 1H), 5.26-5.17(m, 2H), 4.46-4.45(d, 2H), 4.10-4.03(m, 2H), 2.96-2.91(m, 1H), 1.49-1.48(d, 3H), 1.42-1.39(t, 3H), 1.26(s, 9H), 1.22-1.20(d, 6H). | |

TABLE 3-continued

| Compound No. | $^1$H NMR (600 MHZ, CDCl3/TMS) | MS (ESI) m/z: [M + 1] |
|---|---|---|
| 1034 | 7.75-7.74(d, 2H,), 7.46-7.44 (d, 2H), 6.36(s, 1H), 5.88-5.85(q, 1H), 4.64-4.63(dd, 2H), 4.17-4.12(m, 2H), 3.04-2.99-2.90(m, 1H), 2.52-2.53(t, 1H), 1.58-1.57(d, 3H), 1.50-1.48(t, 3H), 1.35(s,9H), 1.30-1.28(d, 6H). | |
| 1035 | 7.75-7.74(d, 2H,), 7.46-7.44 (d, 2H), 6.36(s, 1H), 5.88-5.85(q, 1H), 4.19-4.12(m, 2H), 3.03-2.99(m, 1H), 1.94(s, 3H), 1.52-1.51 (d, 3H), 1.50-1.48(t, 3H), 1.35(s, 9H), 1.29-1.28(d, 6H). | |
| 1036 | 7.81-7.80(d, 2H,), 7.48-7.47 (d, 2H), 5.95-5.93(q, 1H), 3.93(s, 3H), 3.71(s, 3H), 2.29(s, 3H), 1.66(d, 3H), 1.35(s, 9H). | |
| 1037 | 7.72-7.70(d, 2H), 7.38-7.37 (d, 2H), 5.85-5.83(q, 1H), 4.04-4.00(m, 2H), 3.84(s, 3H), 2.19(s, 3H), 1.57-1.56(d, 3H), 1.25(s, 9H), 1.18-1.15(t, 3H). | |
| 1038 | 7.79-7.78(d, 2H,), 7.49-7.47 (d, 2H), 5.96-5.94(q, 1H), 4.41-4.40(m, 2H), 3.91(s, 3H), 2.28(s, 3H), 1.71-170(d, 3H), 1.35(s, 9H). | |
| 1039 | 7.79-7.78(d, 2H,), 7.49-7.47 (d, 2H), 5.96-5.94(q, 1H), 4.41-4.40(m, 2H), 3.91(s, 3H), 2.28(s, 3H), 1.71-1.70(d, 3H), 1.35(s, 9H). | |
| 1040 | 7.83-7.80(d, 2H,), 7.48-7.46 (d, 2H), 5.94-5.92(q, 1H), 3.94(s, 3H), 3.85-3.83(m, 2H), 2.28(s, 3H), I.94-1.90(m, 1H), 1.67-1.66(d, 3H), 1.35(s, 9H), 0.92-0.91(t, 6H). | |
| 1041 | 7.81-7.80(d, 2H,), 7.47-7.46 (d, 2H), 5.94-5.92(q, 1H), 3.94(s, 3H), 2.28(s, 3H), 1.94-1.90(m, 1H), 1.66(d, 3H), 1.61-1.58 (m, 1H), 1.53-1.50(m, 2H), 1.35(s, 9H), 0.91-0.90(t, 6H). | |
| 1042 | 7.83-7.80(d, 2H,), 7.48-7.46 (d, 2H), 5.96-5.93(q, 1H), 5.89-5.82(m, 1H), 5.35-5.27(m, 2H), 4.54-4.53(d, 2H), 3.92(8, 3H), 2.28(s, 3H), 1.67-1.66(d, 3H), 1.35(s, 9H). | |
| 1043 | 7.81-7.79(d, 2H,), 7.48-7.46 (d, 2H), 5.96-5.93(q, 1H), 4.21-4.20(m, 2H), 3.93(s, 3H), 3.57-3.56(m, 2H), 3.36(s, 3H), 2.28(s, 3H), 1.66(d, 3H), 1.35(s, 9H). | |
| 1044 | 7.82-7.80(d, 2H,), 7.48-7.47 (d, 2H), 6.07-6.04(q, 1H), 3.94(s, 3H), 2.28(s, 3H), 1.99(s, 3H), 1.62-1.61(d, 3H), 1.35(s, 9H). | |
| 1045 | 7.80-7.79(d, 2H,), 7.48-7.46(d, 2H), 5.95(s, 1H), 3.92(s, 3H), 3.71(s, 3H), 2.69-2.66(q, 3H), 1.64-1.57(d, 3H), 1.35(s, 9H), 1.30-1.27(t, 3H). | |
| 1046 | 7.80-7.79(d, 2H,), 7.48-7.46(d, 2H), 5.94(s, 1H), 4.13-4.10(q, 2H), 3.92(s, 3H), 2.69-2.65(q, 3H), 1.63-1.57(d, 3H), 1.35(s, 9H), 1.30-1.27(t, 3H). | |
| 1047 | 7.78-7.77(d, 2H,), 7.48-7.47(d, 2H), 5.96(s, 1H), 4.39-4.38(m, 2H), 3.90(s, 3H), 2.69-2.65(q, 3H), 1.58(s, 3H), 1.35(s, 9H), 1.27-1.25(t, 3H) | |
| 1048 | 7.80-7.79(d, 2H,), 7.47-7.46(d, 2H), 5.94(s, 1H), 4.07-4.05(t, 2H), 3.93(s, 3H), 2.69-2.65(q, 3H), 1.67-1.66(m, 2H), 1.61-1.59(m, 3H), 1.35(s, 9H), 1.30-1.27(t, 3H), 1.26-1.23(m, 2H), 0.93-0.90(t, 3H). | |
| 1049 | 7.80-7.79(d, 2H,), 7.47-7.46(d, 2H), 5.94(s, 1H), 3.93(s, 3H), 3.84-3.83(d, 2H), 2.69-2.65(q, 3H), 1.94-1.90(m, 1H), 1.64-1.60(d, 3H), 1.35(s, 9H), 1.30-1.27(t, 3H), 0.92-0.91(d, 6H). | |
| 1050 | 7.80-7.79(d, 2H,), 7.47-7.46 (d, 2H), 5.94(s, 1H), 4.10-4.08(t, 2H), 3.93(s, 3H), 2.69-2.65(q, 3H), 1.64(m, 3H), 1.59-1.58(m, 2H), 1.53-1.49(q, 1H), 1.35(s, 9H), 1.30-1.27(t, 3H), 0.91-0.89(d, 6H). | |
| 1051 | 7.80-7.79(d, 2H,), 7.47-7.46(d, 2H), 5.96-5.95(m, 1H), 5.88-5.84 (m, 1H), 5.34-5.26(m, 2H), 4.54-4.53(4 J = 5.65, 2H), 3.91(s, 3H), 2.69-2.65 (q, 3H), 1.64(m, 3H), 1.35(s, 9H), 1.30-1.27(t, 3H). | |
| 1052 | 7.80-7.79(d, 2H,), 7.47-7.46(d, 2H), 5.95(s, 1H), 4.32-4.30(m, 2H), 3.92(s, 3H), 3.57-3.56(m, 2H), 3.36(s, 3H), 2.69-2.65(q, 3H), 1.67-1.62(m, 3H), 1.35(s, 9H), 1.30-1.27(t, 3H). | |
| 1053 | 7.79-7.78(d, 2H,), 7.48-7.46(d, 2H), 5.97(s, 1H), 4.14-4.08(m, 2H), 3.93(s, 3H), 2.68-2.65(m, 2H), 1,65-1.63(m, 3H), 1.35(s, 9H), 1.30-1.27(t, 3H). | |
| 1054 | 7.80-7.79(d, 2H,), 7.48-7.47(d, 2H), 6.06(s, 1H), 3.94(s, 3H), 2.69-2.65(q, 3H), 2.02-1.99(d, 3H), 1.58(m, 3H), 1.35(s, 9H), 1.26(s, 3H). | |
| 1055 | 7.82-7.80(d, 2H,), 7.48-7.47 (dd, 8.47, 2H), 5.91-5,88(q, 1H), 4.18-4.16(m, 2H), 3.71(s, 3H), 2.30(s, 3H), 1.64-1.63(d, 3H), 1.53-1.51(t, 3H), 1.35(s, 9H). | |
| 1056 | 7.82-7.81(d, 2H,), 7.48-7.46 (dd, 8.57, 2H), 5.90-5.88(q, 1H), 4.20-4.16(m, 2H), 4.13-4.11(qd, 2H), 2.30(s, 3H), 1.64-1.63(4 3H), 1.53-1.51 (t, 3H), 1.35(s, 9H), 1.27-1.25(t, 3H). | |
| 1057 | 7.80-7.79(d, 2H,), 7.49-7.47 (d, 2H), 5.92-5.89(q, J1H), 4.39-4.16 (m, 2H), 4.15-4.12(m, 2H), 2.30(s, 3H), 1.68-1.67(d, 3H), 1.53-1.50 (t, 3H), 1.35(s, 9H). | |
| 1058 | 7.82-7.81(d, 2H,), 7.48-7.46 (d, 2H), 5.90-5.87(q, 1H), 4.19-4.17(m, 2H), 4.07-4.04(m, 2H), 2.30(s, 3H), 1.64-1.63(d, 3H), 1.59-1.58(t, 2H), 1.53-1.51(t, 3H), 1.45-1.42(1, 2H), 1.35(s, 9H), 0.93-0.91(t, 3H). | |
| 1059 | 7.82-7.81(d, 2H,), 7.47-7.46 (d, 2H), 5.90-5.87(q, 1H), 4.14-4.10 (q, 2H), 3.85-3.83(m, 2H), 2.30(s, 3H), 1.95-1.91(m, 1H), 1.64-1.63(d, 3H), 1.35(s, 9H), 1.27-1.25(t, 3H), 0.93-0.92(d, 6H). | |

TABLE 3-continued

| Compound No. | ¹H NMR (600 MHZ, CDCl3/TMS) | MS (ESI) m/z: [M + 1] |
|---|---|---|
| 1060 | 7.78-7.77(d, 2H,), 7.48-7.47(d, 2H), 5.96(s, 1H), 4.39-4.38(m, 2H), 3.90(s, 3H), 2.69-2.65(q, 3H), 1.58(s, 3H), 1.35(s, 9H), 1.27-1.25(t, 3H). | |
| 1061 | 7.80-7.79(d, 2H,), 7.47-7.46(d, 2H), 5.94(s, 1H), 4.07-4.05(t, 2H), 3.93(s, 3H), 2.69-2.65(q, 3H), 1.67-1.66(m, 2H), 1.61-1.59 (m, 3H), 1.35(s, 9H), 1.30-1.27(t, 3H), 1.26-1.23(m, 2H), 0.93-0.90(t,3H). | |
| 1062 | 7.80-7.79(d, 2H,), 7.47-7.46(d, 2H), 5.94(s, 1H), 3.93(s, 3H), 3.84-3.83(d, 2H), 2.69-2.65(q, 3H), 1.94-1.90(m, 1H), 1.64-1.60(d, 3H), 1.35(s, 9H), 1.30-1.27(t, 3H), 0.92-0.91 (d, 6H). | |
| 1063 | 7.80-7.79(d, 2H,), 7.47-7.46(d, 2H), 5.94(s, 1H), 4.10-4.08 (t, 2H), 3.93(s, 3H), 2.69-2.65(q, 3H), 1.64(m, 3H), 1.59-1.58(m, 2H), 1.53-1.49(q, 1H), 1.35(s, 9H), 1.30-1.27(t, 3H), 0.91-0.89(d, 6H). | |
| 1064 | 7.80-7.79(d, 2H,), 7.47-7.46(d, 2H), 5.96-5.95(m, 1H), 5.88-5.84 (m, 1H), 5.34-5.26(m, 2H), 4.54-4.53(d, 2H), 3.91(s, 3H), 2.69-2.65(q, 3H), 1.64(m, 3H), 1.35(s, 9H), 1.30-1.27(t, 3H). | |
| 1065 | 7.80-7.79(d, 2R), 7.47-7.46(d, 2H), 5.95(s, 1H), 4.32-4.30(m, 2H), 3.92(s, 3H), 3.57-3.56(m, 2H), 3.36(s, 3H), 2.69-2.65 (q, 3H), 1.67-1.62 (m, 3H), 1.35(s, 9H), 1.30-1.270, 3H). | |
| 1066 | 7.79-7.78(d, 2H,), 7.48-7.46(d, 2H), 5.97(s, 1H), 4.14-4.08(m, 2H), 3.93(s, 3H), 2.68-2.65(m, 2H), 1.65-1.63(m, 3H), 1.35(s, 9H), 1.30-1.27(t, 3H). | |
| 1067 | 7.80-7.79(d, 2H,), 7.48-7.47(d, 2H), 6.06(s, 1H), 3.94 (s, 3H), 2.69-2.65 (q, 3H), 2.02-1.99(d, 3H), 1.58(m, 3H), 1.35(s, 9H), 1.26(s, 3H). | |
| 1318 | 0.99-1.02(t, 3H), 1.26 (s, 9H), 1.56-1.57 (d, 3H), 2.10 (s, 3H), 2.30 (s, 3H), 3.46-3.52 (m, 1H), 3.73-3.77 (m, 1H), 6.03-6.06 (q, 1H), 6.19 (s, 1H), 6.97-6.99 (4 2H), 7.25-7.27 (d, 2H) | |
| 159 | | 408 |
| 180 | | 438 |
| 320 | | 438 |
| 401 | | 410 |
| 547 | | 398 |
| 580 | | 426 |
| 740 | | 446 |
| 835 | | 398 |
| 873 | | 454 |
| 933 | | 440 |
| 969 | | 468 |
| 1308 | | 438 |
| 1742 | | 446 |

The present invention further provides the preparation method of a pyrazole derivative represented by the formula stru-1, the method comprising:

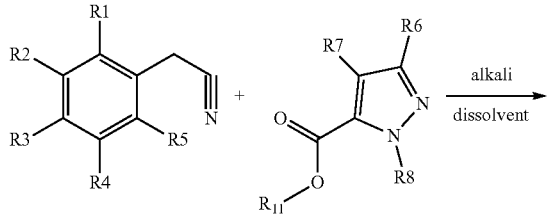

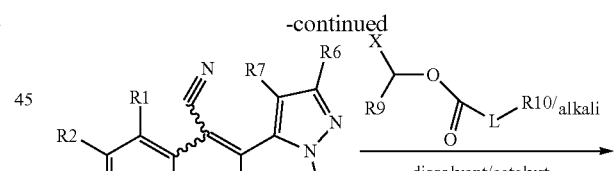

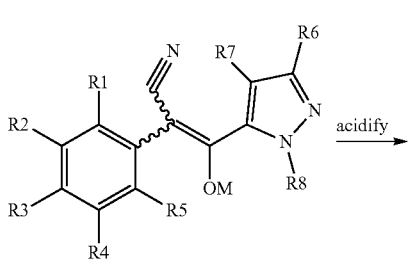

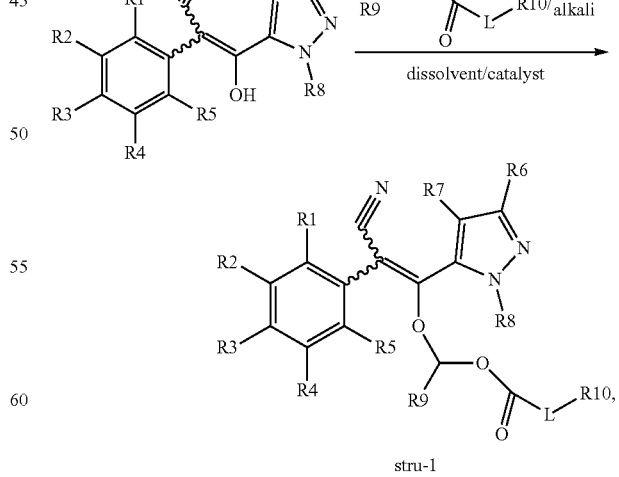

wherein X is selected from halogen.

In the preparation method provided herein, preferably, the base is at least one selected from an organic base and an inorganic base; further preferably, the base is at least one selected from sodium carbonate, potassium carbonate, sodium bicarbonate, potassium bicarbonate, sodium oxide, potassium hydroxide, sodium hydride, sodium alkoxide and potassium alkoxide.

In the preparation method provided herein, preferably, the acid is at least one selected from an organic acid and an inorganic acid; further preferably, the acid is at least one selected from hydrochloric acid, sulfuric acid and acetic acid.

In the preparation method provided herein, preferably, the solvent is at least one independently selected from a protic solvent and an aprotic solvent; further preferably, the solvent is at least one independently selected from acetone, methyl ethyl ketone, tetrahydrofuran, acetonitrile, N, N-dimethylformamide, toluene and chlorobenzene.

In the preparation method provided herein, the X is selected from a halogen; preferably, the X is selected from chlorine, bromine or iodine.

In the preparation method provided herein, the catalyst is at least one selected from potassium iodide, sodium iodide, and a phase transfer catalyst.

The present invention further provides an agricultural insecticide and an acaricide. The insecticide and acaricide contain a pyrazole derivative represented by the formula stru-1 with a mass percentage of 0.1~99%. The insecticide and acaricide may further contain a carrier and an auxiliary agent commonly used in the industry in addition to the pyrazole derivative represented by the formula stru-1.

The pyrazole derivative represented by the formula stru-1 provided in the present invention is suitable for pest prevention and control, particularly suitable for prevention and control of at least one of adult mites, nymphs, mite eggs, aphids and planthoppers on crops. The pyrazole derivatives are very suitable for the prevention and control of animal pests in vine plants, fruits, horticulture, agriculture, animal health, forests, storage products and the fields of materials and health.

Preferably, the pyrazole derivatives are used for the prevention and control of at least one species of Isopoda, Diplopoda, Chilopoda, Symphyla, Thysanura, Collembola, Orthoptera, Blattaria, Dermaptera, *Isoptera*, Phthiraptera, Thysanoptera, Heteroptera. Homoptera, Lepidoptera, Coleoptera, Hymenoptera, Diptera, Siphonaptera, Arachnida and plant parasitic nematodes.

The Isopoda, for example, *Oniscus asellus, Armadillidium vulgare, Porcellio scaber.*

The Diplopoda, for example, *Blaniulus guttulatus.*

The Chilopoda, for example, *Geophilus carpophagus, Sutigera* spp.

The Symphyla, for example, *Scutigerella immaculate.*

The Thysanura, for example, *Lepisma saccharina.*

The Collembola, for example, *Onychiurus armatus.*

The Orthoptera, for example, *Acheta domestcus, Gryllotalpa* spp., *Locusta migratoria, Melanoplus* spp., *Schistocer cagregaria.*

The Blattaria, for example, *Blatta orientahs, Periplanet aamericana, Leucophae amaderae, Blattella germanica.*

The Dermaptera, for example, *Forficula auricularia.*

The *Isoptera*, for example, *Reticulitermes* spp.

The Phthiraptera, for example, *Pediculus humanuscorporis, Haematopinus* spp., *Linognathus* spp., *richodectes* spp. and *Damalinia* spp.

The Thysanoptera, for example, *Hercinothrips femoralis, Thrips tabaci, Thrips palmi, Frankliniella occidentalis.*

The Heteroptera, for example, *Eurgaster* spp., *Dysdercus intermedius, Piesma quadrata, Cimexlectularius, Rhodnius prolixus, Triatoma* spp.

The Homoptera, for example, *Aleurodes brassicae, Bemisia tabaci, Trialeurodes vaporariorum, Aphis gossypii, Brevicoryne brassicae, Cryptomyzus ribis, Aphis jabae, Aphis pomi, Eriosoma lanigerum, Hyalopterus arundinis, Phylloxera vastatrix, Pemphigus* spp., *Macrosiphum avenae, Myzus* spp. *Phorodon humui, Rhopalosiphum padi, Empoasca* spp., *Euscelis bilobatus, Nephotettix cincticeps, Lecanium corni, Saissetia oleae, Laodelphax striatellus, Nilaparvatalugens, Aonidiella aurantii, Aspidiotus hederae, Pseudococcus* spp., *Psylla* spp.

The Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocrnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocap sapomonella, Pieris* spp., *Chilo* spp., *Pyrausta nubilalis, Ephestia kuehniella, Galleria mellonella, Tineola bisselliella, Tinea pellionella, Hofmannophilap seudospretella, Cacoecia podana, Choristoneura fumiferana, Clysia ambiguella, Homona magnanima, Tortrix viridana, Cnaphalocerus* spp., *Oulema oryzae.*

The Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hvpera postica, Dermestes* spp., *Togoderma* spp., *Anthrenus* spp., *Attagenus* spp., *Lyctus* spp., *Meligethes aeneus, Ptinus* spp., *Niptus bololeucus, Gibbium psylloides, Tribohum* spp., *Tenebrio molitor, Agriotes* spp., *Conoderus* spp., *Melolontha melolontha, Amphimallon solstitialis, Costelytra zealandica, Lissorhoptrus oryzophilus.*

The Hymenoptera, for example, *Diprion* spp., *Hoplocampa* spp., *Lasius* spp., *Monomorium pharaonis, Vespa* spp.

The Diptera, for example, *Aedes* spp., *Anopheles* spp., *Culex* spp., *Drosophila melanogaster, Musca* spp., *Fannia* spp., *Calliphora vicina. Lucilia* spp., *Chrsomyia* spp., *Cuterebra* spp., *Gastrophilus* spp., *Hyppobosca* spp., *Somoxys* spp., *Oestrus* spp., *Hypoderma* spp., *Tabanus* spp., *Bibio hortulanus, Oscinella frit, Phorbia* spp., *Pegomyia hyoscyumi, Ceratitis capitata, Dacus oleae, Tipula paludosa, Hylemyia* spp., *Lirionyza* spp.

The Siphonaptera, for example, *Xenopsylla cheopis, Ceratophyllus* spp.

The Arachnida, for example, *Scorpio maurus, Latrodectus mactans, Acarus siro, Argas* spp., *Ornithodoros* spp., *Dermanyssus gallinae, Erio phyesribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia pratiosa, Panonychus* spp., *Tetranychus* spp., *Hemitarsonemus* spp., *Brevipalpus* spp.

The plant parasitic nematodes, including, for example, *Pratylenchus* spp., *Radopholus similis, Ditvlenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

BRIEF DESCRIPTION OF THE DRAWINGS

The sole FIGURE is a single crystal diffraction pattern of Compound 251.

DETAILED DESCRIPTION OF THE EMBODIMENT

The present invention is further described in combination with particular embodiments, but the present invention is not limited to these particular embodiments. Those skilled in the art should be aware that the present invention encompasses all alternatives, modifications, and equivalents that may be included within the scope of the appended claims.

I. Preparation of Compounds

Example 1 Preparation of Intermediates (1) Synthesis of intermediate 1-ethyl-3-methyl-5-pyrazolecarboxylic acid ethyl ester

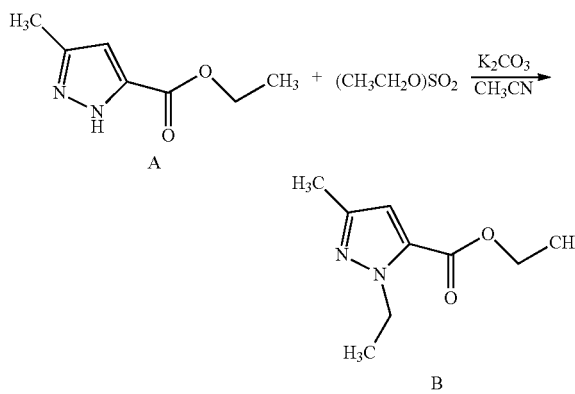

154.1 g (1 mol) of intermediate A was added to a 1000 ml flask, then 500 ml of acetonitrile and 138 g of potassium carbonate were added, and then 1 mol of diethyl sulfate was added, and the system was stirred and heated to reflux until the reaction was finished in about 3 hr by thin-layer chromatography method. The system was filtered and the mother liquor was evaporated to dryness by a rotary evaporator, and the residue was distilled under a reduced pressure to give 140 g of intermediate B, with a yield of 77.0%.

(2) Synthesis of intermediate 1-ethyl-3-methyl-4-chloro-5-pyrazolecarboxylic acid ethyl ester

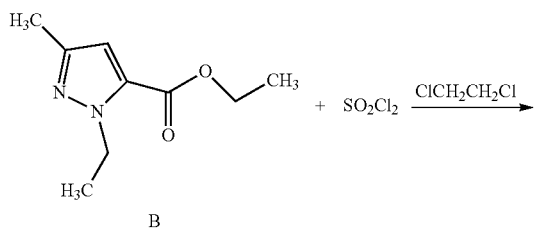

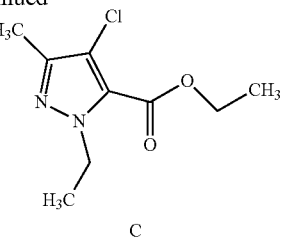

18.2 g (0.1 mol) of intermediate B was added to a 100 ml flask, and 50 ml of dichloroethane and 138 g of potassium carbonate were added, and then 0.11 mol of sulfonyl chloride was added. The system was stirred and heated to reflux until the reaction was finished in about 2.5 hr by thin-layer chromatography method. The mother liquor was evaporated to dryness and the residue was used in the next reaction without treatment.

(3) Synthesis of intermediate 1-ethyl-3-methyl-4-methyl-5-pyrazolecarboxylic acid ethyl ester

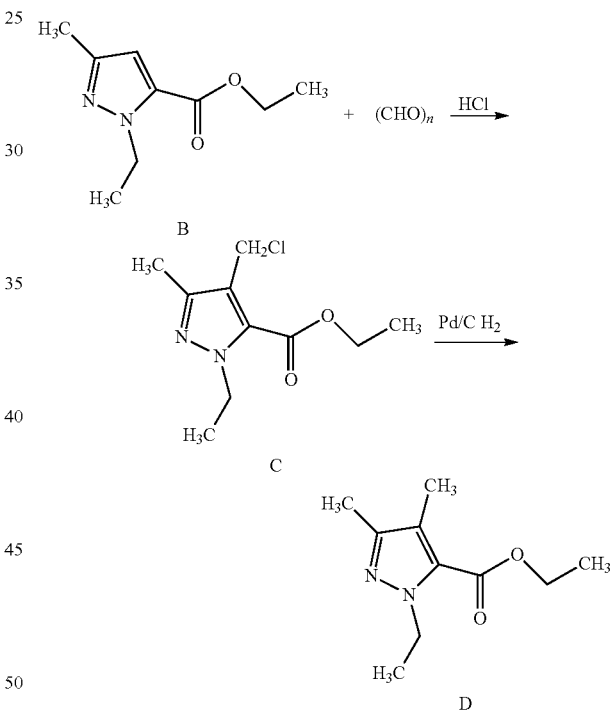

The intermediate D was prepared with reference to the method provided in JP2001342178A.

(4) Synthesis of intermediate 1-methyl-3-methyl-4-methyl-5-pyrazolecarboxylic acid ethyl ester

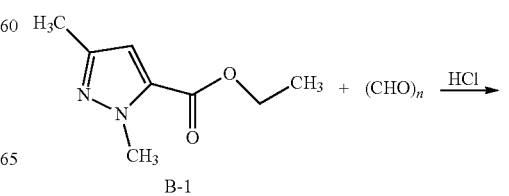

-continued

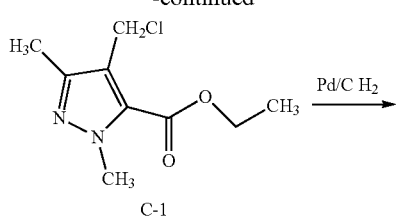
C-1

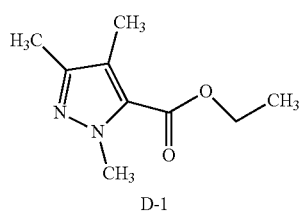
D-1

The intermediate D-1 was prepared with reference to the method provided in JP2001342178A.

(5) Synthesis of intermediate 1-methyl-3-methyl-4-chloro-5-pyrazolecarboxylic acid ethyl ester

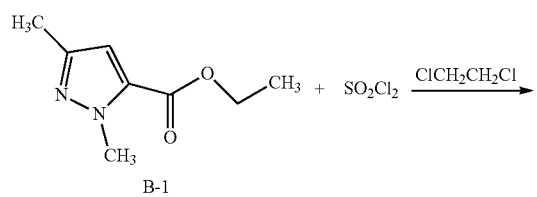

The intermediate C-1 is prepared according to the same method as preparation of interemdicate C.

(6) Preparation of Intermediate F

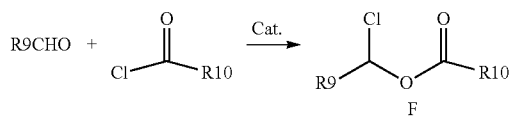

Conventional procedure; The substituted aldehyde and zinc chloride at the catalytic amount were uniformly stirred in a reactor, and the substituted acyl chloride was slowly added dropwise under a cooling state. After dropwise addition, the mixture was stirred continuously for 1-2 hr at a low temperature, and warmed up to continue reaction for 5 hr, and purified by distillation under a reduced pressure.

Preparation of Intermediate Chloromethyl Acetate:

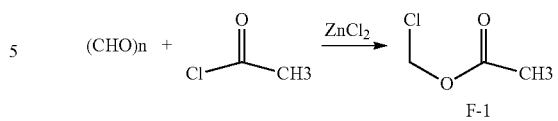
F-1

50 g (0.6 mol) of acetyl chloride was added dropwise to a mixture of 85 g paraformaldehyde and 1.75 g zinc chloride after cooled to 0° C. The dropwise addition was finished in about 2 hr, and then the reaction system was allowed to warm to room temperature for reaction for 1 hr, and then heated to 90° C. to continue reaction for 10 hr, cooled, filtered to remove solid, and then 45 g of intermediate F-1 was obtained by reduced pressure distillation.

(7) Preparation of Intermediate H

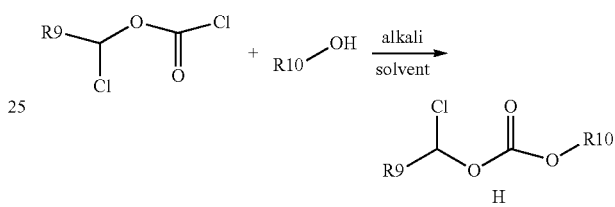

Conventional procedure: The chloro chloroformate was slowly added dropwise to the substituted alcohol and triethylamine solution under cooling state, after dropwise addition, the mixture was stirred continuously for 1-2 hr at a low temperature, and warmed up to continue reaction for 1 hr, filtered and the solvent was distilled off, and then purified by reduced pressure distillation to obtain the intermediate H.

Preparation of Intermediate H-1:

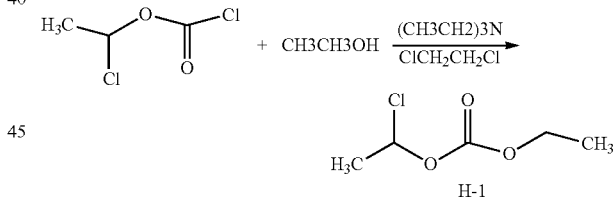
H-1

When cooled to 0° C., 71.5 g (0.5 mol) of 1-chloroethyl chloroformate was added dropwise to 40 g and 52.0 g of triethylamine in 250 ml of toluene solution. The dropwise addition was finished in about 2 hr, and then the reaction system was allowed to warm to room temperature for reaction for 1 hr, and then filtered to remove solid, to obtain 78.5 g of intermediate H-1 by reduced pressure distillation.

(8) Preparation of Intermediate TA-1

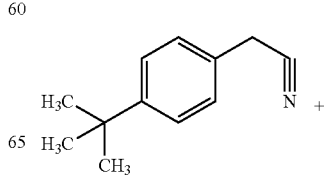

-continued

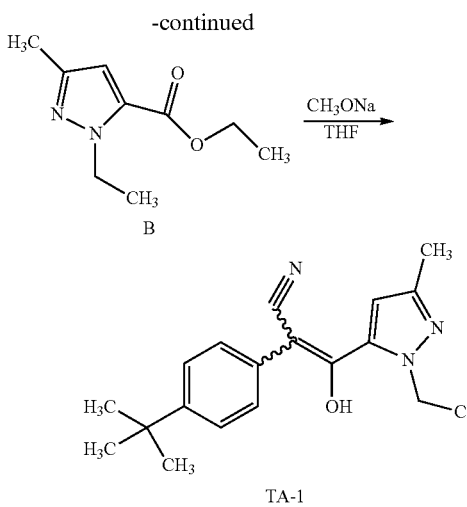

17.3 g of p-tert-butyl phenylacetonitrile was dissolved in 70 ml of anhydrous THF when the system was cooled to −5° C., equimolar amount of solid sodium methoxide was added, and then equimolar amount of intermediate B was added dropwise while stirring. When the dropwise addition was finished in 2 hr, the mixture was stirred continuously for 1.5 hr, and then warmed up to room temperature to continue stirring for 2 hr, after reaction, the THF was evaporated. The residue was dissolved in water and then neutralized with hydrochloric acid to about pH 4, extracted with ethyl acetate, dried over anhydrous sodium sulfate to evaporate ethyl acetate and obtain the intermediate TA-1, which was used in the next reaction without purification.

(9) Preparation of Intermediate TA-2

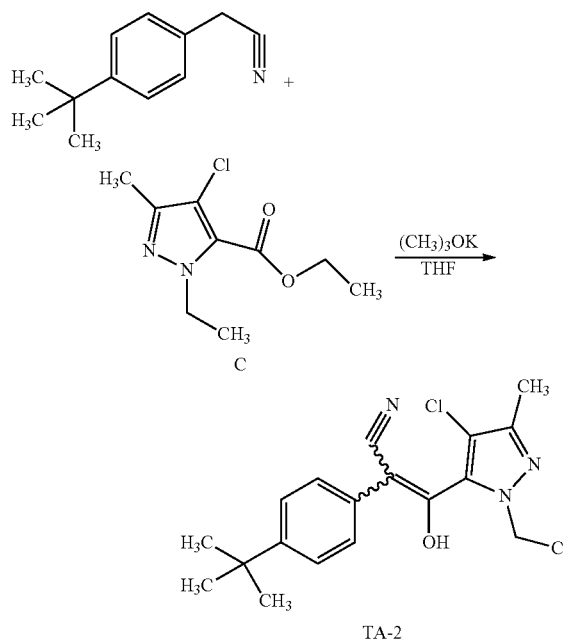

17.3 g of p-tert-butyl phenylacetonitrile was dissolved in 70 ml of anhydrous THF, when the system was cooled to −5° C., equimolar amount of solid potassium tert-butoxide was added, and then equimolar amount of intermediate C was added dropwise while stirring. When the dropwise addition was finished in 2.5 hr, the mixture was stirred continuously for 2.0 hr, and then warmed up to room temperature to continue stirring for 2 hr, after reaction, the THF was evaporated. The residue was dissolved in water and then neutralized with hydrochloric acid to about pH 4, extracted with ethyl acetate, dried over anhydrous sodium sulfate to evaporate ethyl acetate and obtain the intermediate TA-2, which was used in the next reaction without purification.

(10) Preparation of Intermediate TA-3

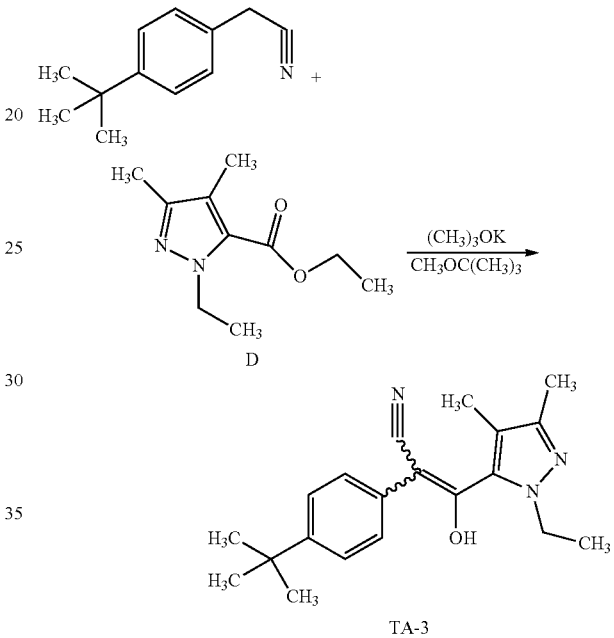

17.3 g of p-tert-butyl phenylacetonitrile was dissolved in 70 ml of methyl tert-butyl ether, when the system was cooled to −5° C., equimolar amount of solid potassium tert-butoxide was added, and then equimolar amount of intermediate D was added dropwise while stirring. When the dropwise addition was finished in 3.0 hr, the mixture was stirred continuously for 2.0 hr, and then warmed up to room temperature to continue stirring for 2 hr, after reaction, the methyl tert-butyl ether was evaporated. The residue was dissolved in water and then neutralized with hydrochloric acid to about pH 4, extracted with ethyl acetate, dried over anhydrous sodium sulfate to evaporate ethyl acetate and obtain the intermediate TA-3, which was used in the next reaction without purification.

(11) Preparation of Intermediate TA-4

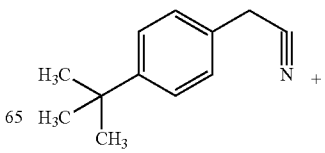

-continued

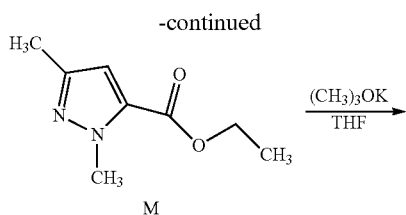

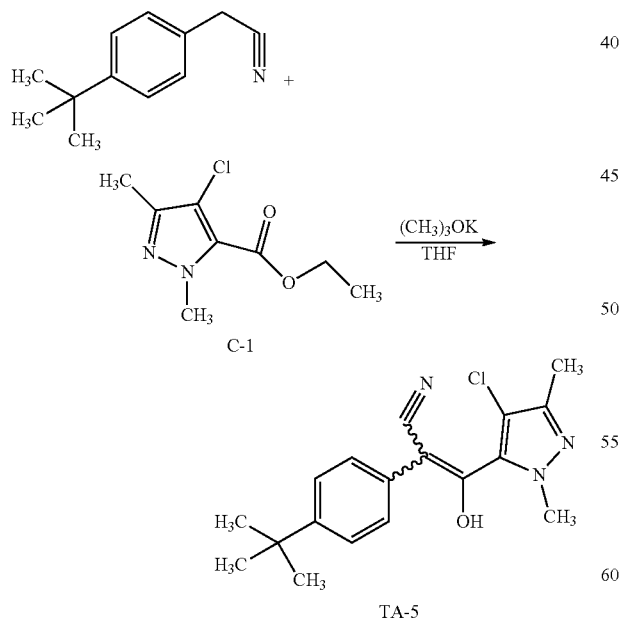

17.3 g of p-tert-butyl phenylacetonitrile was dissolved in 70 ml of anhydrous THF, when the system was cooled to −5° C., equimolar amount of solid sodium methoxide was added, and then equimolar amount of intermediate M was added dropwise while stirring. When the dropwise addition was finished in 2 hr, the mixture was stirred continuously for 1.5 hr, and then warmed up to room temperature to continue stirring for 2 hr, after reaction, the THF was evaporated. The residue was dissolved in water and then neutralized with hydrochloric acid to about pH 4, extracted with ethyl acetate, dried over anhydrous sodium sulfate to evaporate ethyl acetate and obtain the intermediate TA-1, which was used in the next reaction without purification.

Preparation of Intermediate TA-5

17.3 g of p-tert-butyl phenylacetonitrile was dissolved in 70 ml of anhydrous THF when the system was cooled to −5° C., equimolar amount of solid potassium tert-butoxide was added, and then equimolar amount of intermediate C was added dropwise while stirring. When the dropwise addition was finished in 2.5 hr, the mixture was stirred continuously for 2.0 hr, and then warmed up to room temperature to continue stirring for 2 hr, after reaction, the THF was evaporated. The residue was dissolved in water and then neutralized with hydrochloric acid to about pH 4, extracted with ethyl acetate, dried over anhydrous sodium sulfate to evaporate ethyl acetate and obtain the intermediate TA-5, which was used in the next reaction without purification.

Preparation of Intermediate TA-6

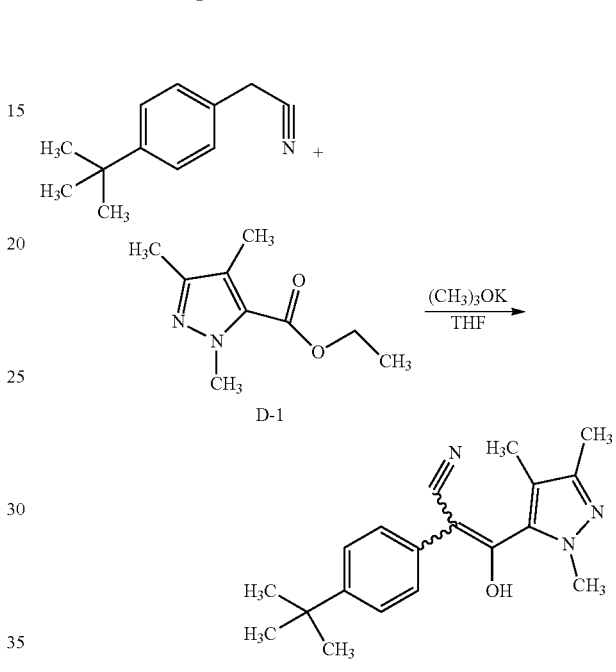

17.3 g of p-tert-butyl phenylacetonitrile was dissolved in 70 ml of THF, when the system was cooled to −5° C., equimolar amount of solid potassium tert-butoxide was added, and then equimolar amount of intermediate D-1 was added dropwise while stirring. When the dropwise addition was finished in 3.0 hr, the mixture was stirred continuously for 2.0 hr. and then warmed up to room temperature to continue stirring for 2 hr, after reaction, MTBE was evaporated. The residue was dissolved in water and then neutralized with hydrochloric acid to about pH 4, extracted with ethyl acetate, dried over anhydrous sodium sulfate to evaporate ethyl acetate and obtain the intermediate TA-3, which was used in the next reaction without purification.

Example 2 Preparation of Target Compounds (1) Preparation of Target Compound 226

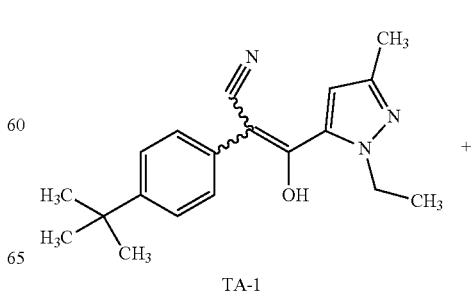

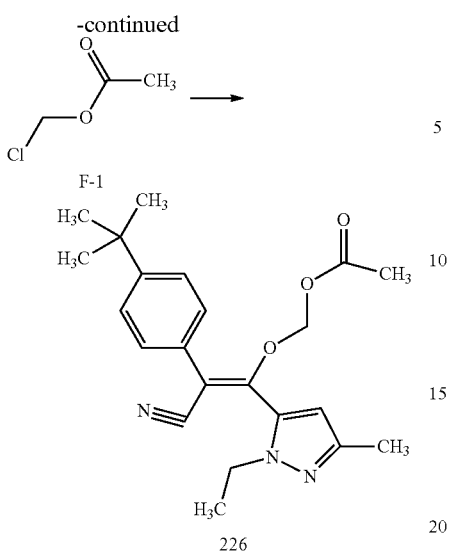

0.31 g (0.001 mol) of intermediate TA-1 and 0.12 g (0.0011 mol) of intermediate F-1, 0.15 sodium carbonate and a catalytic amount of sodium iodide were added to 25 ml of acetonitrile, heated to reflux for 7 hr, when the reaction was finished by thin-layer chromatography method, the system was cooled to room temperature to filter solid and evaporate acetonitrile. The residue was purified by column chromatography to obtain 0.32 g of product, with a yield of 84%.

(2) Preparation of Target Compound 251

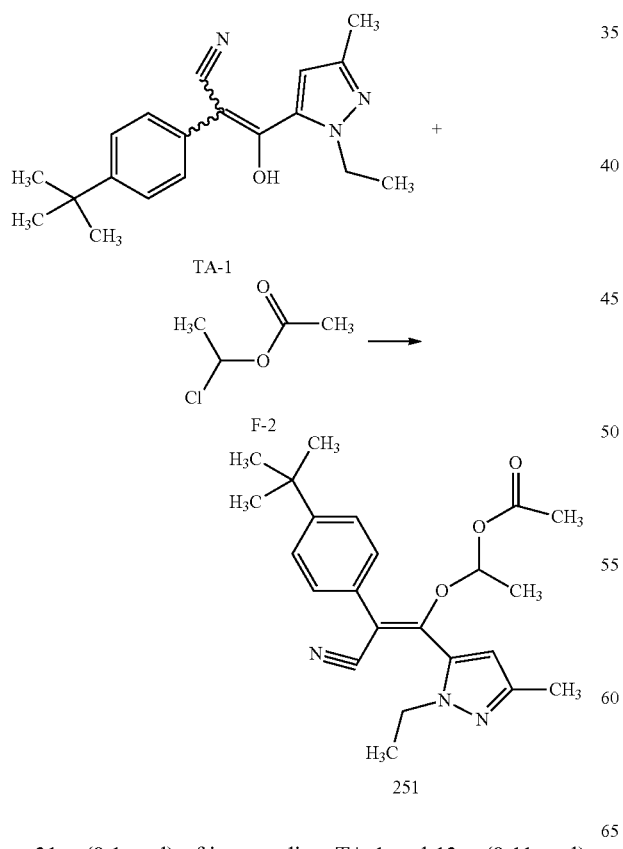

31 g (0.1 mol) of intermediate TA-1 and 13 g (0.11 mol) of intermediate F-2, 15 sodium carbonate and a catalytic amount of sodium iodide were added to 25 ml of acetonitrile, heated to reflux for 10 hr, when the reaction was finished by thin-layer chromatography method, the system was cooled to room temperature to filter solid and evaporate acetonitrile. The residue was purified by column chromatography to obtain 35.1 g of product, with a yield of 89%.

(3) Preparation of Target Compound 259

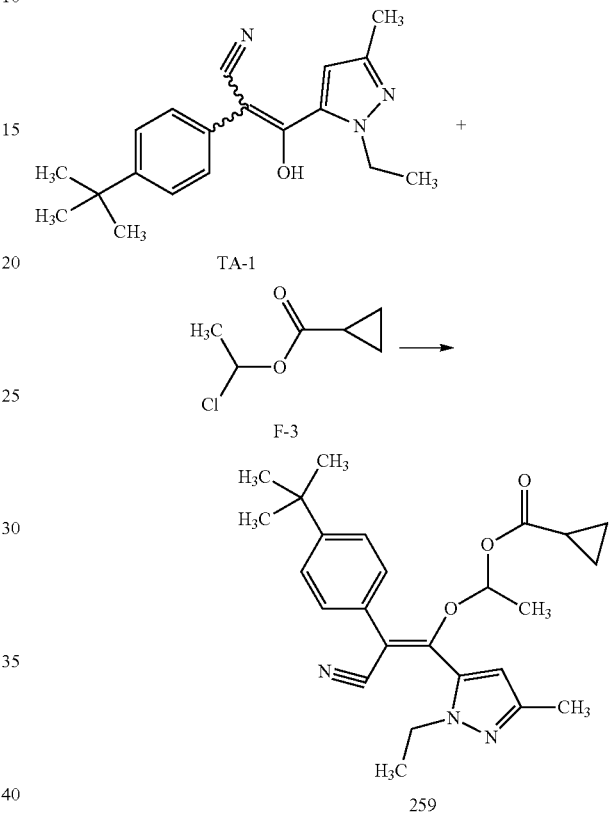

0.31 g (0.001 mol) of intermediate TA-1 and 0.13 g (0.0011 mol) of intermediate F-3, 0.15 sodium carbonate and a catalytic amount of sodium iodide were added to 25 ml of acetonitrile, heated to reflux for 12 hr, when the reaction was finished by thin-layer chromatography method, the system was cooled to room temperature to filter solid and evaporate acetonitrile. The residue was purified by column chromatography to obtain 0.28 g of product, with a yield of 66%.

(4) Preparation of Target Compound 326

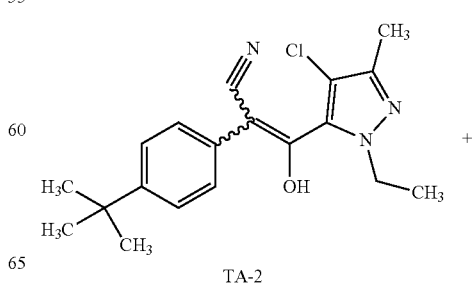

-continued

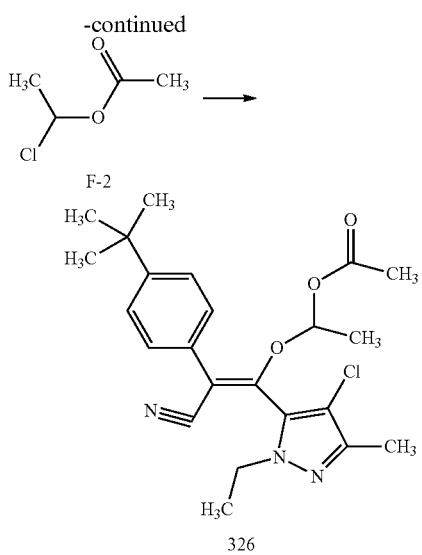
326

0.34 g (0.001 mol) of intermediate TA-2 and 0.13 g (0.0011 mol) of intermediate F-2, 0.15 sodium carbonate and a catalytic amount of sodium iodide were added to 25 N,N-Dimethylformamide, heated to 70° C. to react for 4 hr, when the reaction was finished by thin-layer chromatography method, the system was cooled to room temperature to filter solid and evaporate the solvent under a reduced pressure. The residue was purified by column chromatography to obtain 0.24 g of product, with a yield of 56%.

(5) Preparation of Target Compound 401

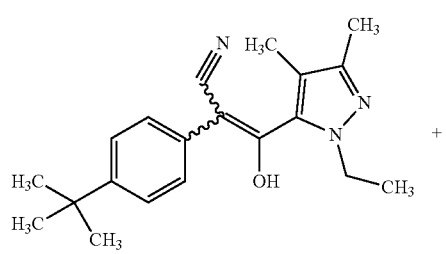

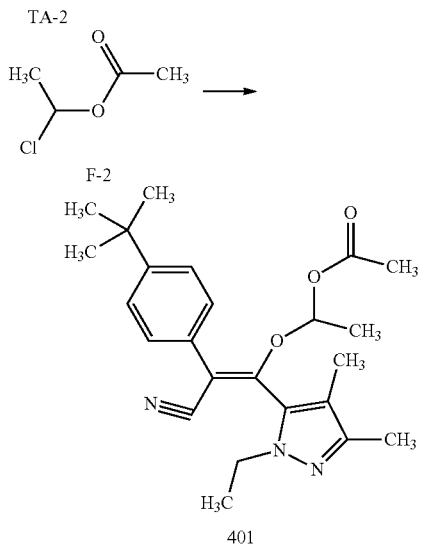
401

0.32 g (0.001 mol) of intermediate TA-2 and 0.13 g (0.0011 mol) of intermediate F-2, 0.15 sodium carbonate and a catalytic amount of sodium iodide were added to 25 ml of acetonitrile, heated to reflux for 11 hr, when the reaction was finished by thin-layer chromatography method, the system was cooled to room temperature to filter solid and evaporate the solvent under a reduced pressure. The residue was purified by column chromatography to obtain 0.29 g of product, with a yield of 71%.

(6) Preparation of Target Compound 105

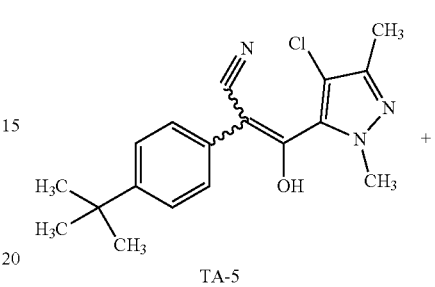
TA-5

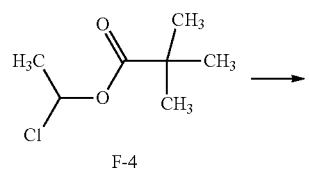
F-4

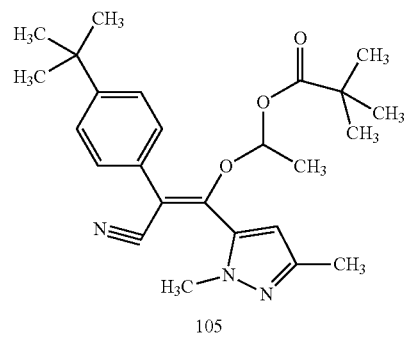
105

0.33 g (0.001 mol) of intermediate TA-5 and 0.18 g (0.0011 mol) of intermediate F-4, 0.15 sodium carbonate and a catalytic amount of sodium iodide were added to 25 ml of acetonitrile, heated to reflux for 11 hr, when the reaction was finished by thin-layer chromatography method, the system was cooled to room temperature to filter solid and evaporate acetonitrile. The residue was purified by column chromatography to obtain 0.25 g of product, with a yield of 55%.

(7) Preparation of Target Compound 4

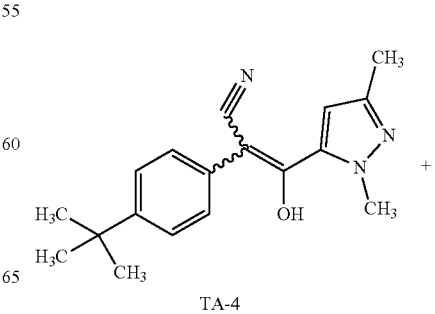
TA-4

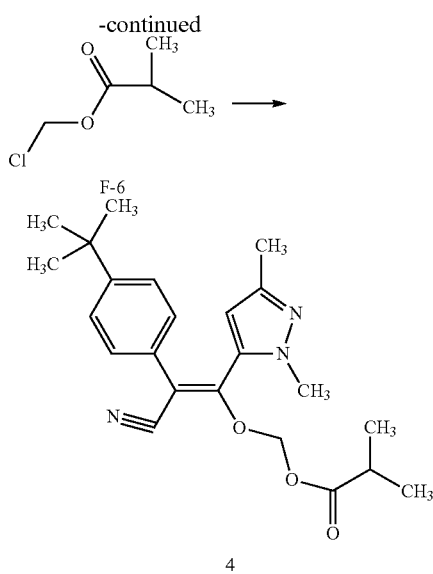

0.295 g (0.1 mol) of intermediate TA-4 and 0.15 g (0.11 mol) of intermediate F-6, 0.15 sodium carbonate and a catalytic amount of sodium iodide were added to 25 ml of acetonitrile, heated to reflux for 5 hr, when the reaction was finished by thin-layer chromatography method, the system was cooled to room temperature to filter solid and evaporate acetonitrile. The residue was purified by column chromatography to obtain 0.31 g of product, with a yield of 78%.

(8) Preparation of Target Compound 91

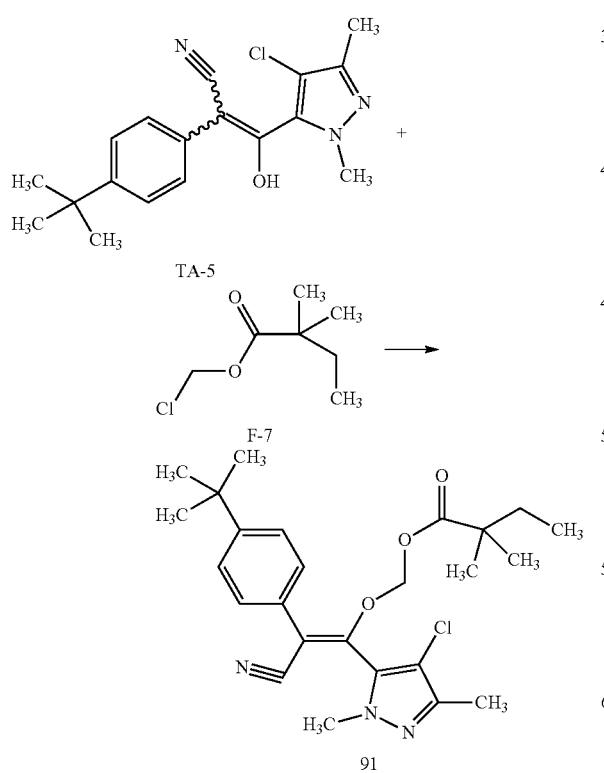

0.33 g (0.1 mol) of intermediate TA-5 and 0.18 g (0.11 mol) of intermediate F-4, 0.15 sodium carbonate and a catalytic amount of sodium iodide were added to 25 ml of acetonitrile, heated to reflux for 11 hr, when the reaction was finished by thin-layer chromatography method, the system was cooled to room temperature to filter solid and evaporate acetonitrile. The residue was purified by column chromatography to obtain 0.25 g of product, with a yield of 55%.

(9) Preparation of Target Compound 548

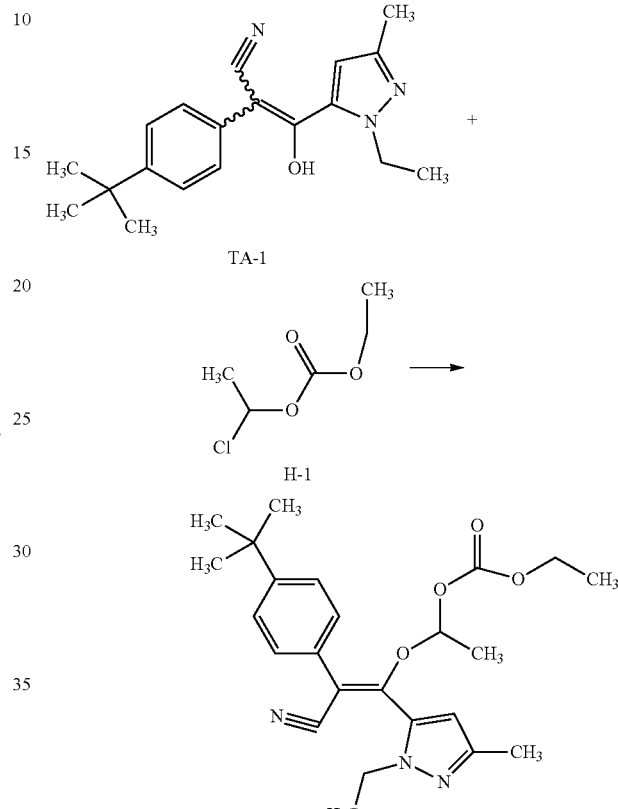

0.31 g (0.001 mol) of intermediate TA-1 and 0.16 g (0.0011 mol) of intermediate H-1, 0.15 sodium carbonate and a catalytic amount of sodium iodide were added to 25 ml of acetonitrile, heated to reflux for 6 hr, when the reaction was finished by thin-layer chromatography method, the system was cooled to room temperature to filter solid and evaporate acetonitrile. The residue was purified by column chromatography to obtain 0.33 g of product, with a yield of 78%.

(10) Preparation of Target Compound 739

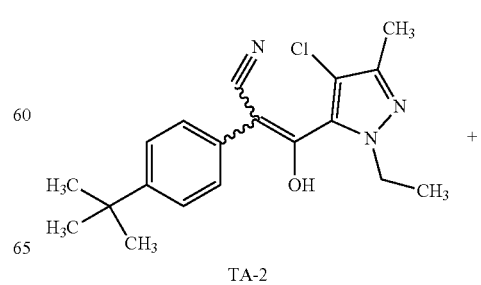

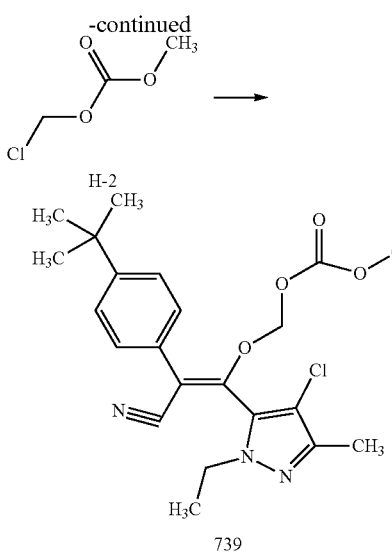

0.34 g (0.001 mol) of intermediate TA-2 and 0.13 g (0.0011 mol) of intermediate H-2, 0.15 potassium carbonate and a catalytic amount of sodium iodide were added to 25 N,N-Dimethylformamide, heated to 70° C. to react for 5 hr, when the reaction was finished by thin-layer chromatography method, the system was cooled to room temperature to filter solid and evaporate the solvent under a reduced pressure. The residue was purified by column chromatography to obtain 0.28 g of product, with a yield of 65%.

(11) Preparation of Target Compound 835

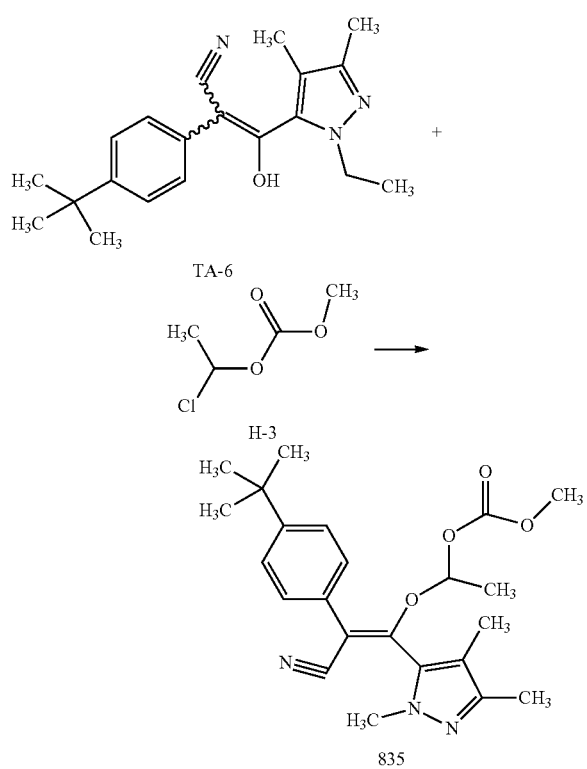

0.31 g (0.001 mol) of intermediate TA-6 and 0.13 g of intermediate H-3, 0.15 potassium carbonate and a catalytic amount of sodium iodide were added to 25 ml of THF, heated to reflux for 10 hr, when the reaction was finished by thin-layer chromatography method, the system was cooled to room temperature to filter solid and evaporate acetonitrile. The residue was purified by column chromatography to obtain 0.25 g of product, with a yield of 61%.

II. Preparation of Reagents

Reagents were prepared according to a mass ratio in the following embodiments.

Example 3. 30% Suspension

| | |
|---|---|
| Compound 251 | 30% |
| Ethylene glycol | 10% |
| Nonylphenol polyglycol ether | 6% |
| Sodium lignosulfonate | 10% |
| Carboxymethyl cellulose | 1% |
| 37% formaldehyde solution | 0.7% |
| 75% silicone oil emulsion | 0.8% |
| Water | added to 100% |

The compound 251 was fully mixed with other components, to obtain 30% suspension. The 30% suspension could be diluted with water to obtain diluent at any concentration.

Example 4. 30% Emulsion

| | |
|---|---|
| Compound 548 | 30% |
| Phosphorous acid | 10% |
| Ethoxylated triglyceride | 15% |
| Toluene | added to 100% |

Phosphorous acid was dissolved in toluene, then the compound 548 and ethoxylated triglyceride were added to obtain a transparent solution, i.e. 30% emulsion.

Example 5. 60% Wettable Powder

| | |
|---|---|
| Compound 91 | 60% |
| Sodium dodecylnaphthalene sulfonate | 2% |
| Sodium lignosulfonate | 9% |
| Diatomite | added to 100% |

The compound 91, sodium dodecylnaphthalene sulfonate, sodium lignosulfonate and diatomite were mixed together, and pulverized in a pulverizer until particles reached the standard, to obtain 60% wettable powder.

III. Biological Activity Assay

Example 6. Activity Assay of Eggs of *Tetranychus Cinnabarinus*

According to the solubility of the test compound, the crude drug was dissolved in N N-dimethylformamide, and then prepared into a test solution of the desired concentration with 1‰ Tween 80 aqueous solution. The content of N. N-dimethylformamide in the solution should not exceed 10%.

Spray method. The broad bean leaves with petioles were cut and inserted into a bottle with water. A certain number of female mites were placed, 24h later, adult mites were removed, and spray treatment was performed in 24 h. The experiment was repeated three times, and a blank control was set, and placed to an observation room (26±2° C., humidity 70%~80%, 16h light per day) for culture. When the blank control group was incubated, the results were investigated. The non-incubated ones were used as death for investigation.

According to the above method, the activity assay found that the ovicidal activity was equal to or higher than 90% at the concentration of 5 mg/L for the compounds 1-17, 26-72, 76-92, 101-117, 151-167, 176-192, 226-242, 251-267, 301-317, 326-342, 376-392, 401-417, 451-454, 456, 457, 458, 460, 467, 468, 471, 474, 476, 477, 480, 481, 483-486, 488, 489, 490, 492, 494, 499, 500, 503, 506, 508, 509, 512, 513, 574-548, 549, 550, 552, 553, 554, 556, 558, 563, 564, 567, 570, 572, 573, 576, 577, 579-582, 584, 585, 586, 588, 590, 595, 596, 599, 606, 602, 604, 606, 608, 609, 643-646, 648, 649, 650, 652, 654, 659, 660, 663, 666, 668, 669, 972, 673, 675-678, 680, 681, 682, 684, 691, 692, 695, 698, 700, 701, 704, 705, 739-742, 744, 745, 746, 748, 750, 755, 757, 759, 762, 764, 765, 768, 769, 771-774, 776, 777, 778, 780, 782, 787, 788, 791, 794, 796, 797, 801, 835-838, 840, 841, 842, 844, 846, 851, 853, 855, 858, 860, 862, 864, 865, 867-870, 872, 873, 874, 876, 878, 883, 884, 887, 890, 892, 894, 896, 897, 931-934, 936, 937, 938, 940, 942, 947, 948, 951, 956, 958, 961, 960, 963-966, 968, 969, 970, 972, 974, 978, 980, 986, 988, 983, 989, 992, 993, 1158, 1172, 1293, 1318, 1323, 1468; while the ovicidal activity of compounds 8-1, 8-2, 8-3, 8-4 disclosed in PCT patent application WO 01/68589 was less than 30% at a concentration of 5 mg/L.

According to the above method, the activity assay found that the ovicidal activity was equal to or higher than 90% at the concentration of 2 mg/L for the compounds 230, 234, 226, 227, 251, 252, 254, 255, 259, 301, 302, 305, 309, 326, 327, 401, 402, 409, 405, 547, 548, 549, 550, 553, 570, 579, 580, 585, 602, 771, 772, 780, 931, 932, 933, 940, 937, 963, 964 and 969; while the ovicidal activity of compounds 8-1, 8-2, 8-3, 8-4 disclosed in PCT patent application WO01/68589 was 0% at a concentration of 2 mg/L.

According to the above method, parallel determination of ovicidal activity was performed for the compounds 226, 227, 230, 234, 251, 252, 254, 255, 301, 302, 547, 585, 771, 772, 931, 932 and 937 of the present invention and the compounds 8-1, 8-2, 8-3, 8-4 disclosed in PCT patent application WO01/68589. The results were shown in Table 4.

TABLE 4

| Compound | Concentration (mg/L) | Death rate (%) |
|---|---|---|
| 226 | 2 | 100 |
| 227 | 2 | 97 |
| 230 | 2 | 100 |
| 234 | 2 | 100 |
| 241 | 2 | 100 |
| 251 | 2 | 100 |
| 252 | 2 | 100 |
| 254 | 2 | 99 |
| 255 | 2 | 96 |
| 301 | 2 | 95 |
| 302 | 2 | 97 |
| 547 | 2 | 100 |
| 585 | 2 | 100 |
| 675 | 2 | 100 |
| 771 | 2 | 100 |
| 772 | 2 | 100 |
| 931 | 2 | 98 |
| 932 | 2 | 97 |
| 937 | 2 | 100 |

TABLE 4-continued

| Compound | Concentration (mg/L) | Death rate (%) |
|---|---|---|
| 8-1 | 2 | 0 |
| 8-2 | 2 | 0 |
| 8-3 | 2 | 0 |
| 8-4 | 2 | 0 |

Example 7 Activity Assay of Adult *Tetranychus cinnabarnnus*

According to the solubility of the test compound, the crude drug was dissolved in N, N-dimethlformamide, and then prepared into a test solution of the desired concentration with 1‰ Tween 80 aqueous solution. The content of N,N-dimethylformamide in the solution should not exceed 10%.

Two euphylla bean seedlings were taken, after inoculated with adult *Tetranychus cinnabarinus* and the base number was investigated, whole plants were sprayed with a hand-held sprayer. The experiment was repeated three times for each treatment, after treatment, placed in a standard observation room after treatment, to investigate the survival number of mites in 48 hand calculate the death rate.

According to the above method, the activity assay found that the adult mite-killing activity was equal to or higher than 90% at the concentration of 2.5 mg/L for the compounds 1-17, 26-72, 76-92 101-117, 151-167, 176-192, 226-242, 251-267, 301-317, 326-342, 376-392, 401-417, 451-454, 456, 457, 458, 460, 467, 468, 471, 474, 476, 477, 480, 481, 483-486, 488, 489, 490, 492, 494, 499, 500, 503, 506, 508, 509, 512, 513, 574-548, 549, 550, 552, 553, 554, 556, 558, 563, 564, 567, 570, 572, 573, 576, 577, 579-582, 584, 585, 586, 588, 590, 595, 596, 599, 606, 602, 604, 606, 608, 609, 643-646, 648, 649, 650, 652, 654, 659, 660, 663, 666, 668, 669, 972, 673, 675-678, 680, 681, 682, 684, 691, 692, 695, 698, 700, 701, 704, 705, 739-742, 744, 745, 746, 748, 750, 755, 757, 759, 762, 764, 765, 768, 769, 771-774, 776, 777, 778, 780, 782, 787, 788, 791, 794, 796, 797, 801, 835-838, 840, 841, 842, 844, 846, 851, 853, 855, 858, 860, 862, 864, 865, 867-870, 872, 873, 874, 876, 878, 883, 884, 887, 890, 892, 894, 896, 897, 931-934, 936, 937, 938, 940, 942, 947, 948, 951, 956, 958, 961, 960, 963-966, 968, 969, 970, 972, 974, 978, 980, 986, 988, 983, 989, 992, 993, 1158, 1172, 1293, 1318, 1323, 1468; while the adult mite-killing activity of compounds 8-1, 8-2, 8-3, 8-4 disclosed in PCT patent application WO 01/68589 was less than 80% at a concentration of 2.5 mg/L.

According to the above method, the activity assay found that the adult mite-killing activity was equal to or higher than 90% at the concentration of 1.25 mg/L for the compounds 230, 234, 226, 227, 251, 252, 254, 255, 259, 301, 302, 305, 309, 326, 327, 401, 402, 409, 405, 547, 548, 549, 550, 553, 570, 579, 580, 585, 602, 771, 772, 780, 931, 932, 933, 940, 937, 963, 964 and 969; while the adult mite-killing activity of compounds 8-1, 8-2, 8-3, 8-4 disclosed in PCT patent application WO 01/68589 was less than 50% at a concentration of 1.25 mg/L.

According to the above method, parallel determination of adult mite-killing activity was performed for the compounds 226, 227, 230, 234, 251, 252, 254, 255, 301, 302, 547, 585, 771, 772, 931, 932 and 937 of the present invention and the compounds 8-1, 8-2, 8-3, 8-4 disclosed in PCT patent application WO01/68589. The results were shown in Table 5.

TABLE 5

| Compound | Concentration (mg/L) | Death rate (%) |
|---|---|---|
| 226 | 1.25 | 96 |
| 227 | 1.25 | 98 |
| 230 | 1.25 | 100 |
| 234 | 1.25 | 100 |
| 241 | 1.25 | 100 |
| 251 | 1.25 | 100 |
| 252 | 1.25 | 100 |
| 254 | 1.25 | 97 |
| 255 | 1.25 | 95 |
| 301 | 1.25 | 90 |
| 302 | 1.25 | 96 |
| 547 | 1.25 | 100 |
| 585 | 1.25 | 100 |
| 771 | 1.25 | 100 |
| 772 | 1.25 | 100 |
| 931 | 1.25 | 95 |
| 932 | 1.25 | 90 |
| 937 | 1.25 | 100 |
| 8-1 | 1.25 | 45 |
| 8-2 | 1.25 | 30 |
| 8-3 | 1.25 | 45 |
| 8-4 | 1.25 | 50 |

Example 8 Activity Assay of *Tetranychus cinnabarinus* Nymphs

According to the solubility of the test compound, the crude drug was dissolved in N, N-dimethylformamide, and then prepared into a test solution of the desired concentration with 1‰ Tween 80 aqueous solution. The content of N,N-dimethylformamide in the solution should not exceed 10%.

The broad bean leaves with petioles were cut and inserted into a small bottle with water. A certain number of brightly colored, active female adult mites were placed, 24h later, adult mites were removed, and leaves with insufficient eggs were removed. When eggs were hatched and grew into nymphs, spray treatment was performed. The experiment was repeated three times, and a blank control was set, and placed to an observation room (26±2° C., humidity 70%~80%, 16h light per day) for culture. 48 h later, the results were investigated. The nymphs were gently touched during investigation, and if no response, they were regarded as deaths.

According to the above method, the activity assay found that the nymph-killing activity was equal to or higher than 95% at the concentration of 2.5 mg/L for the compounds 1-17 26-72, 76-92, 101-117, 151-167, 176-192, 226-242, 251-267, 301-317, 326-342, 376-392, 401-417, 451-454, 456, 457, 458, 460, 467, 468, 471, 474, 476, 477, 480, 481, 483, 486, 488, 489, 490, 492, 494, 499 500 503, 506, 508, 509, 512, 513, 574-548, 549, 550, 552, 553, 554, 556, 558, 563, 564, 567, 570, 572, 573, 576, 577, 579-582, 584, 585, 586, 588, 590, 595, 596, 599, 606, 602, 604, 606, 608, 609, 643-646, 648, 649, 650, 652, 654, 659, 660, 663, 666, 668, 669, 972, 673, 675-678, 680, 681, 682, 684, 691, 692, 695, 698, 700, 701, 704, 705, 739-742, 744, 745, 746, 748, 750, 755, 757, 759, 762, 764, 765, 768, 769, 771-774, 776, 777, 778, 780, 782, 787, 788, 791, 794, 796, 797, 801, 835-838, 840, 841, 842, 844, 846, 851, 853, 855, 858, 860, 862, 864, 865, 867-870, 872, 873, 874, 876, 878, 883, 884, 887, 890, 892, 894, 896, 897, 931-934, 936, 937, 938, 940, 942, 947, 948, 951, 956, 958, 961, 960, 963-966, 968, 969, 970, 972, 974, 978, 980, 986, 988, 983, 989, 992, 993, 1158, 1172, 1293, 1318, 1323, 1468, while the nymph-killing activity of compounds 8-1, 8-2, 8-3, 8-4 disclosed in PCT patent application WO01/68589 was less than 80% at a concentration of 2.5 mg/L.

According to the above method, the activity assay found that the nymph-killing activity was equal to or higher than 90% at the concentration of 2 mg/L for the compounds 230, 234. 226, 227, 251, 252, 254, 255, 259, 301, 302, 305, 309, 326, 327, 401, 402, 409, 405, 547, 548, 549, 550, 553, 570, 579, 580, 585, 602, 771, 772, 780, 931, 932, 933, 940, 937, 963, 964 and 969 while the nymph-killing activity of compounds 8-1, 8-2, 8-3, 8-4 disclosed in PCT patent application WO01/68589 was less than 30% at a concentration of 0.5 mg/L.

According to the above method, parallel determination of nymph-killing activity was performed for the compounds 226, 227, 230, 234, 251, 252, 254, 255, 301, 302, 547, 585, 771, 772, 931, 932 and 937 of the present invention and the compounds 8-1, 8-2, 8-3, 8-4 disclosed in PCT patent application WO01/68589. The results were shown in Table 6.

TABLE 6

| Compound | Concentration (mg/L) | Death rate (%) |
|---|---|---|
| 226 | 0.5 | 90 |
| 227 | 0.5 | 94 |
| 230 | 0.5 | 98 |
| 234 | 0.5 | 96 |
| 241 | 0.5 | 100 |
| 251 | 0.5 | 100 |
| 252 | 0.5 | 100 |
| 254 | 0.5 | 96 |
| 255 | 0.5 | 95 |
| 301 | 0.5 | 90 |
| 302 | 0.5 | 96 |
| 547 | 0.5 | 93 |
| 585 | 0.5 | 96 |
| 675 | 0.5 | 675 |
| 771 | 0.5 | 95 |
| 772 | 0.5 | 90 |
| 931 | 0.5 | 95 |
| 937 | 0.5 | 90 |
| 937 | 0.5 | 93 |
| 8-1 | 0.5 | 25 |
| 8-2 | 0.5 | 0 |
| 8-3 | 0.5 | 30 |
| 8-4 | 0.5 | 15 |

What is claimed is:
1. A pyrazole derivative having the following formula stru-1:

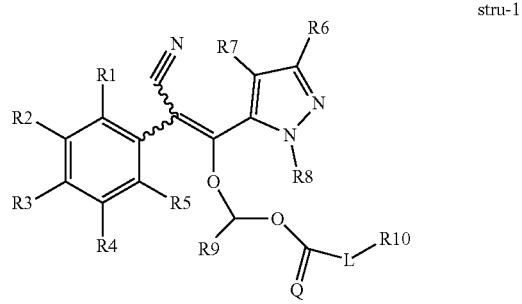

wherein:
R1, R2, R4, R5 are hydrogen;
R3 is t-butyl;
R6 is methyl;

R7 is selected from hydrogen, chlorine, and methyl;
R8 is ethyl;
R9 is selected from hydrogen, and methyl;
L is oxygen;
Q is oxygen;
R10 is selected from $C_1$-$C_6$ alkyl, $C_3$-$C_6$ cycloalkyl, and $C_2$-$C_6$ alkenyl.

2. The pyrazole derivative according to claim 1, wherein the pyrazole derivative is selected from at least one of the compounds represented by the following structural formula:

547
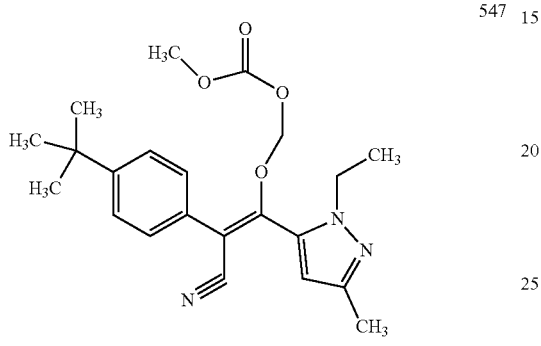

548
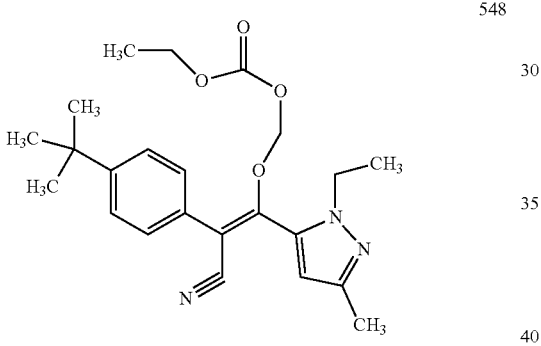

549
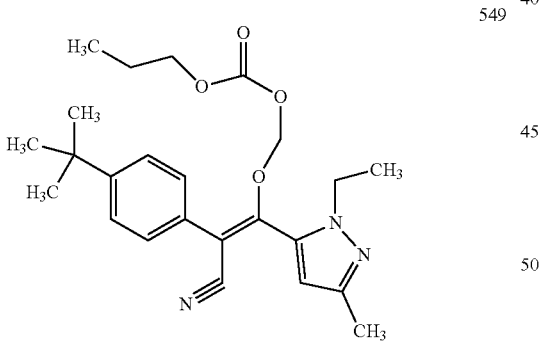

550
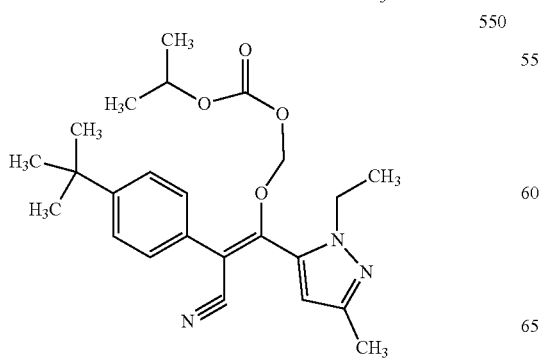

553
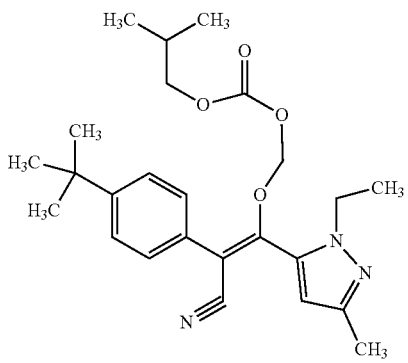

570
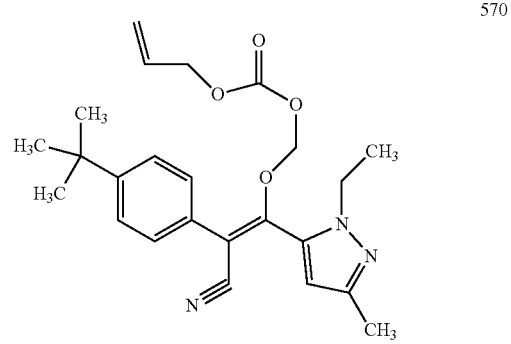

579
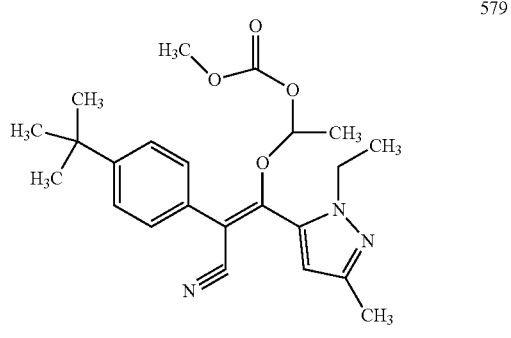

580
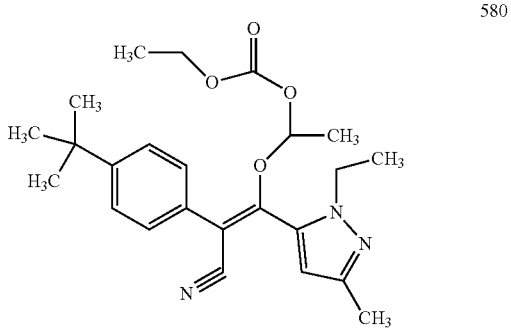

585 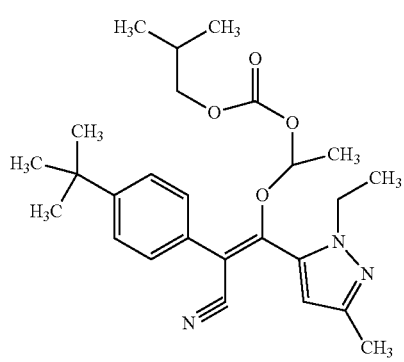
602 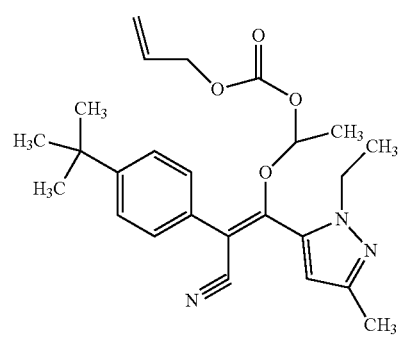
771 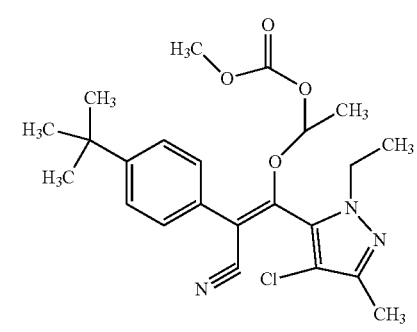
772 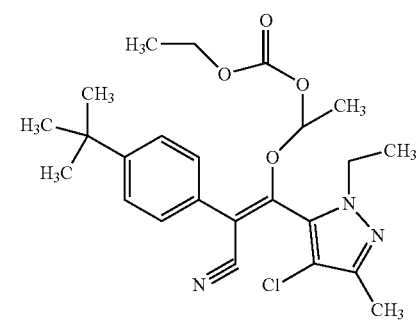
780 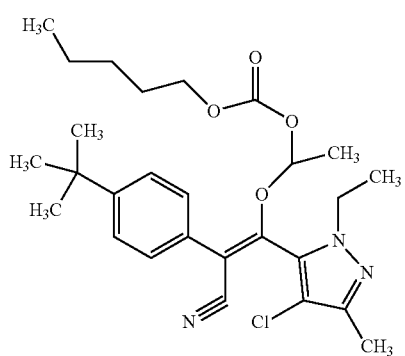
931 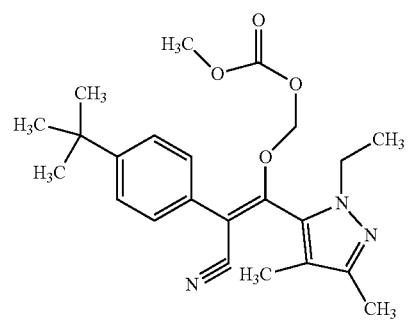
932 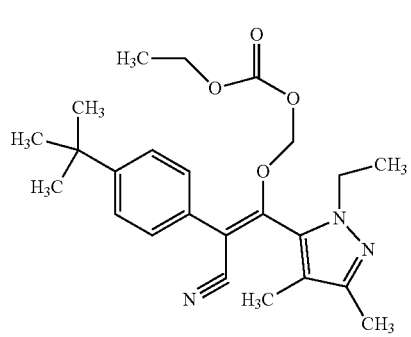
933 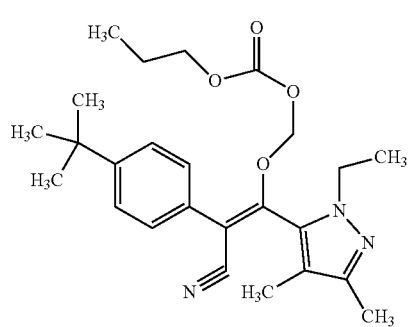

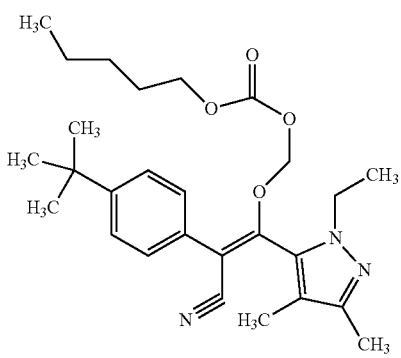

940

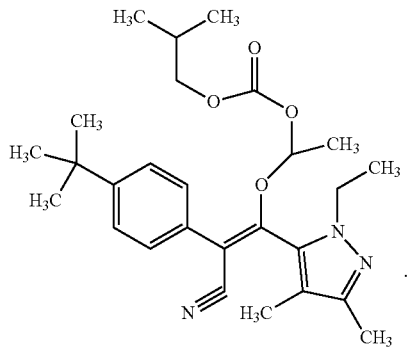

969

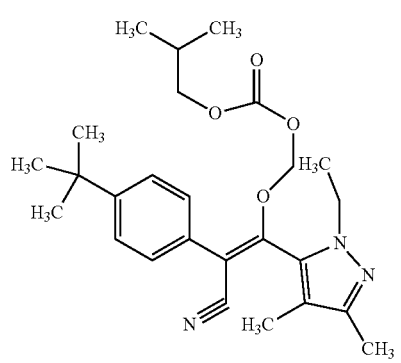

937

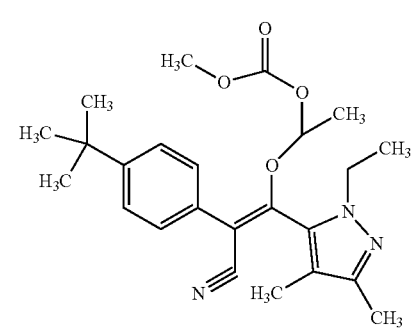

963

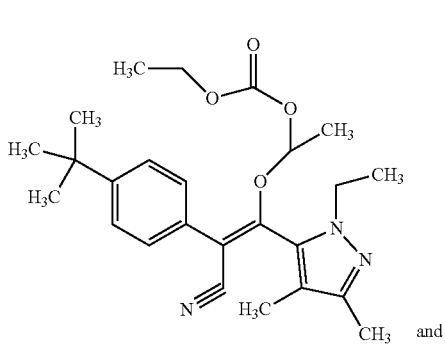

and

964

3. The pyrazole derivative according to claim 1, wherein the pyrazole derivative represented by the formula stru-1 comprises at least one selected from the group consisting of an E-type pyrazole derivative and a Z-type pyrazole derivative.

4. A preparation method of a pyrazole derivative represented by the formula stru-1 of claim 1, comprising:

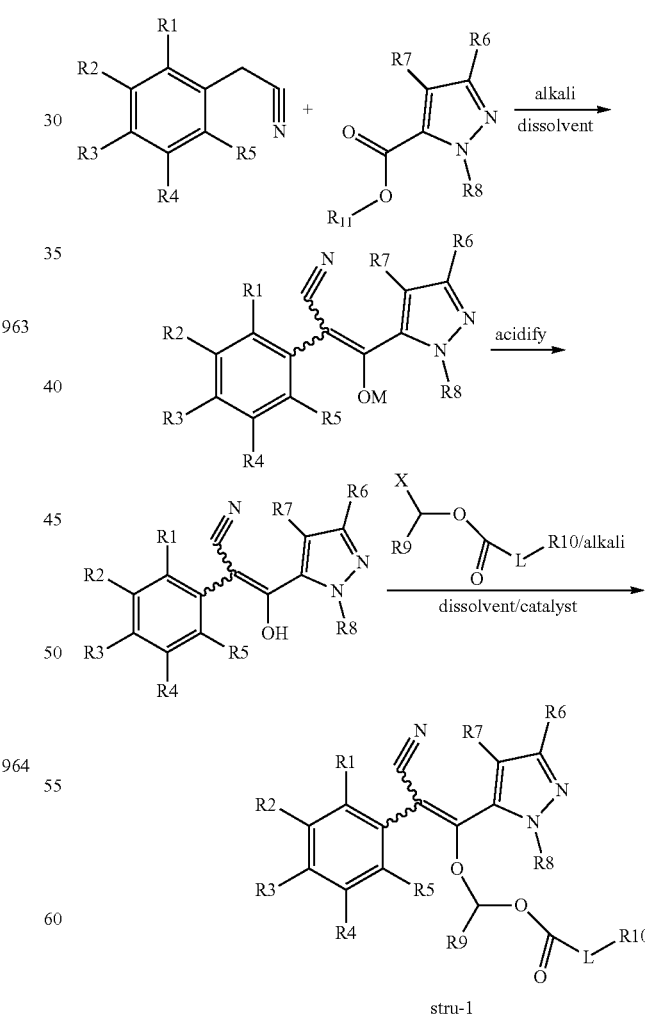

stru-1 wherein the X is selected from halogen, R11 is ethyl, M is the metal ion from a base, the base is at least one selected from sodium carbonate, potassium carbonate, sodium bicarbonate, potassium bicarbonate, sodium oxide, potassium hydroxide, sodium hydride, sodium alkoxide and potassium alkoxide.

5. The preparation method according to claim 4, wherein:

an acid is at least one selected from an organic acid and an inorganic acid, a solvent is at least one independently selected from a protic solvent and an aprotic solvent, and the catalyst is at least one selected from potassium iodide, sodium iodide, and a phase transfer catalyst.

6. The preparation method according to claim 5, wherein:

the X is selected from chlorine, bromine or iodine, the acid is at least one selected from hydrochloric acid, sulfuric acid and acetic acid, and the solvent is at least one independently selected from acetone, methyl ethyl ketone, tetrahydrofuran, acetonitrile, N, N-dimethylformamide, toluene and chlorobenzene.

7. An agricultural insecticide and acaricide, wherein the insecticide and acaricide contain a compound represented by the formula stru-1 of claim 1 with a mass percentage of 0.1~99%.

8. The pyrazole derivative according to claim 2, comprising at least one selected from the group consisting of an E-type pyrazole derivative and a Z-type pyrazole derivative.

9. An agricultural insecticide and acaricide, wherein the insecticide and acaricide contain a compound represented by the formula stru-1 of claim 2 with a mass percentage of 0.1~99%.

10. A pyrazole derivative, wherein the pyrazole derivative is selected from the compounds represented by the following structural formula:

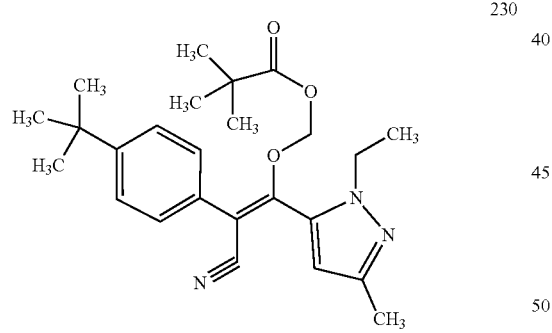
230

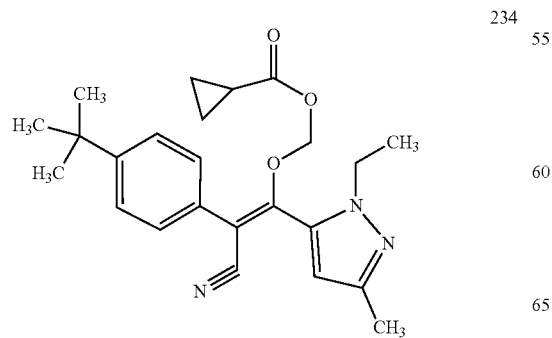
234

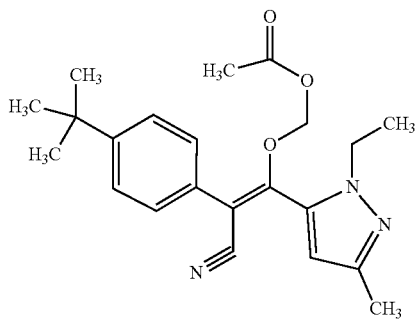
226

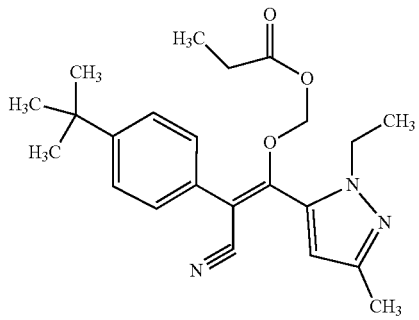
227

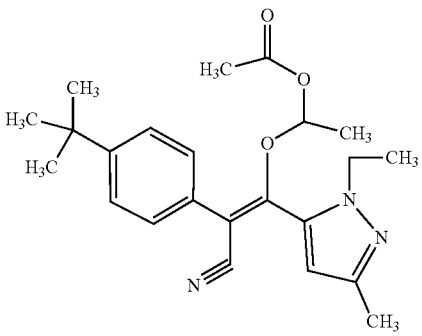
251

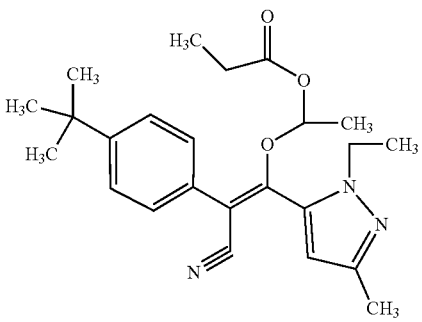
252

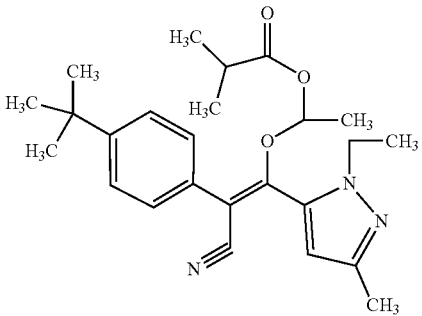
254

| 217 -continued | | 218 -continued | |
|---|---|---|---|
| 255 | 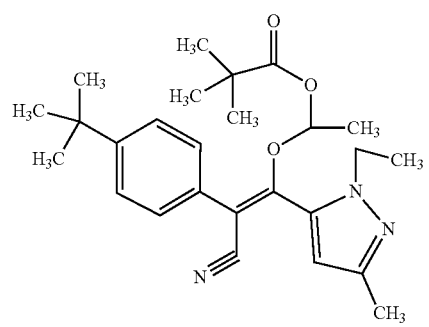 | 309 | 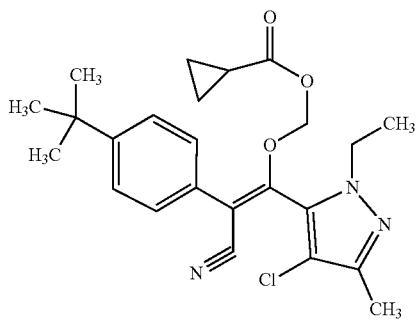 |
| 259 | 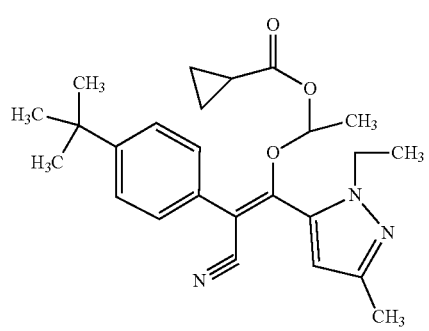 | 326 | 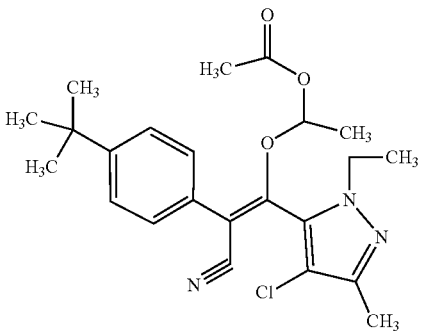 |
| 301 | 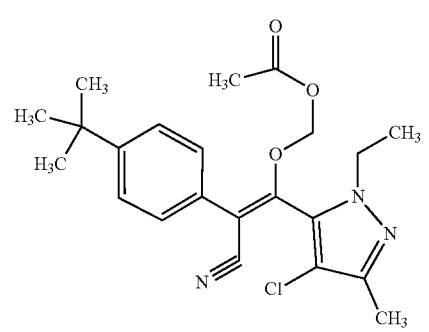 | 327 | 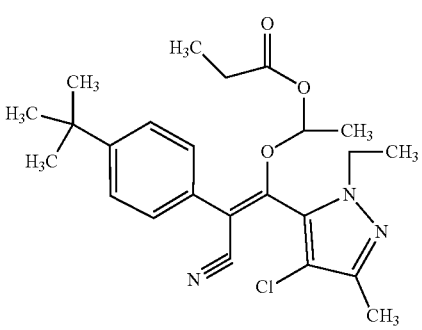 |
| 302 | 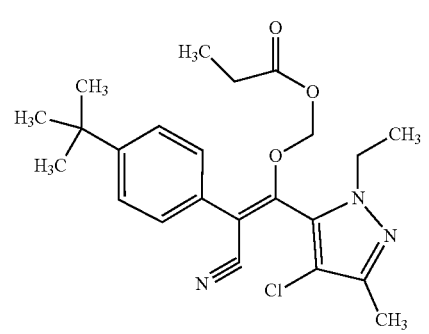 | 401 | 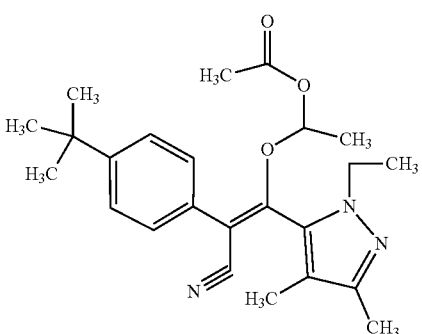 |
| 305 | 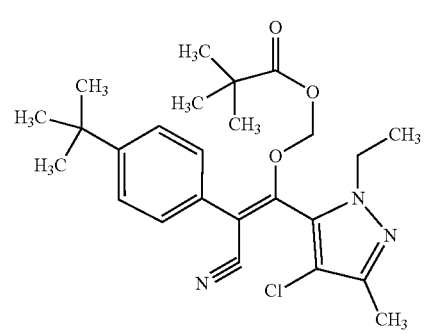 | 402 | 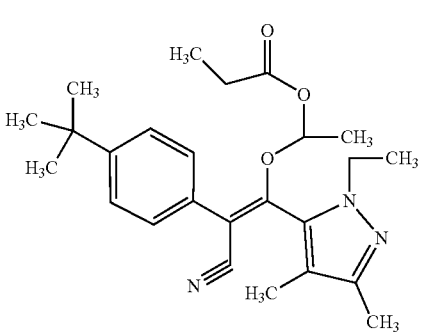 |

-continued
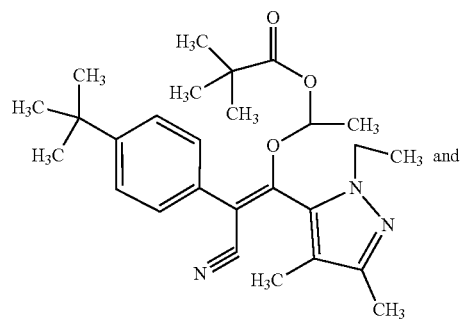
405
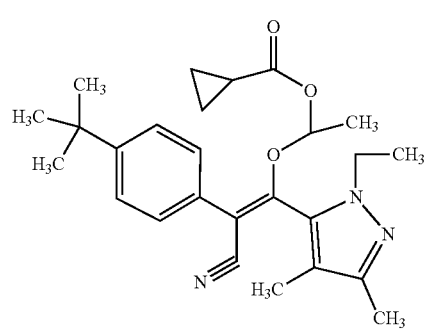
409
11. An agricultural insecticide and acaricide, wherein the insecticide and acaricide contain a pyrazole derivative of claim 10 with a mass percentage of 0.1~99%.
* * * * *